US011162114B2

(12) United States Patent
Crawley et al.

(10) Patent No.: US 11,162,114 B2
(45) Date of Patent: Nov. 2, 2021

(54) RNA-GUIDED NUCLEASES AND ACTIVE FRAGMENTS AND VARIANTS THEREOF AND METHODS OF USE

(71) Applicant: LifeEDIT Therapeutics, Inc., Research Triangle Park, NC (US)

(72) Inventors: Alexandra Briner Crawley, Cary, NC (US); Rodolphe Barrangou, Raleigh, NC (US); Tyson D. Bowen, Morrisville, NC (US); Michael Coyle, Chapel Hill, NC (US); Tedd D. Elich, Durham, NC (US)

(73) Assignee: LifeEDIT Therapeutics, Inc., Research Triangle Park, NC (US)

( * ) Notice: Subject to any disclaimer, the term of this patent is extended or adjusted under 35 U.S.C. 154(b) by 384 days.

(21) Appl. No.: 16/432,321

(22) Filed: Jun. 5, 2019

(65) Prior Publication Data

US 2019/0367949 A1    Dec. 5, 2019

Related U.S. Application Data

(60) Provisional application No. 62/680,845, filed on Jun. 5, 2018, provisional application No. 62/680,846, filed on Jun. 5, 2018, provisional application No. 62/680,853, filed on Jun. 5, 2018, provisional application No. 62/680,859, filed on Jun. 5, 2018, provisional application No. 62/680,862, filed on Jun. 5, 2018, provisional application No. 62/680,863, filed on Jun. 5, 2018, provisional application No. 62/686,901, filed on Jun. 19, 2018, provisional application No. 62/805,041, filed on Feb. 13, 2019, provisional application No. 62/805,045, filed on Feb. 13, 2019.

(51) Int. Cl.
| | | |
|---|---|---|
| *C12N 15/90* | (2006.01) | |
| *C12N 9/22* | (2006.01) | |
| *C12N 15/11* | (2006.01) | |
| *C12N 15/113* | (2010.01) | |

(52) U.S. Cl.
CPC ............. *C12N 15/907* (2013.01); *C12N 9/22* (2013.01); *C12N 15/11* (2013.01); *C12N 15/902* (2013.01); *C12N 2310/20* (2017.05); *C12N 2800/80* (2013.01)

(58) Field of Classification Search
None
See application file for complete search history.

(56) References Cited

FOREIGN PATENT DOCUMENTS

| | | |
|---|---|---|
| WO | WO 2013/176772 A1 | 11/2013 |
| WO | WO 2015/071474 A2 | 5/2015 |
| WO | WO 2016/186946 A1 | 11/2016 |
| WO | WO 2017/155714 A1 | 9/2017 |
| WO | WO 2017/155717 A1 | 9/2017 |
| WO | WO 2017/222773 A1 | 12/2017 |

OTHER PUBLICATIONS

Jiang. F., et anon., "CRISPR-Cas9 Structures and Mechanisms," *Annu. Rev. Biophys.*, 2017, vol. 46(1), pp. 505-529.
Van Erp, P., et al., "The history and market impact of CRISPR RNA-guided nucleases," *Current Opinion in Virology*, 2015, vol. 12, pp. 85-90.

*Primary Examiner* — Suzanne M Noakes
*Assistant Examiner* — Jae W Lee
(74) *Attorney, Agent, or Firm* — Womble Bond Dickinson (US) LLP

(57) ABSTRACT

Compositions and methods for binding to a target sequence of interest are provided. The compositions find use in cleaving or modifying a target sequence of interest, visualization of a target sequence of interest, and modifying the expression of a sequence of interest. Compositions comprise RNA-guided nuclease polypeptides, CRISPR RNAs, trans-activating CRISPR RNAs, guide RNAs, and nucleic acid molecules encoding the same. Vectors and host cells comprising the nucleic acid molecules are also provided. Further provided are CRISPR systems for binding a target sequence of interest, wherein the CRISPR system comprises an RNA-guided nuclease polypeptide and one or more guide RNAs.

19 Claims, No Drawings
Specification includes a Sequence Listing.

RNA-GUIDED NUCLEASES AND ACTIVE FRAGMENTS AND VARIANTS THEREOF AND METHODS OF USE

CROSS-REFERENCE TO RELATED APPLICATIONS

This application claims the benefit of U.S. Provisional Application Nos. 62/805,041, filed Feb. 13, 2019, 62/805,045, filed Feb. 13, 2019, 62/686,901, filed Jun. 19, 2018, 62/680,845, filed Jun. 5, 2018, 62/680,846, filed Jun. 5, 2018, 62/680,853, filed Jun. 5, 2018, 62/680,859, filed Jun. 5, 2018, 62/680,862, filed Jun. 5, 2018, and 62/680,863, filed Jun. 5, 2018, each of which is incorporated by reference herein in its entirety.

REFERENCE TO A SEQUENCE LISTING SUBMITTED ELECTRONICALLY AS A TEXT FILE

The instant application contains a Sequence Listing which has been submitted in ASCII format via EFS-Web and is hereby incorporated by reference in its entirety. Said ASCII copy, created on Jun. 5, 2019, is named L103438_1160US_0032_8_Sequence_List.txt, and is 451334 bytes in size.

FIELD OF THE INVENTION

The present invention relates to the field of molecular biology and gene editing.

BACKGROUND OF THE INVENTION

Targeted genome editing or modification is rapidly becoming an important tool for basic and applied research. Initial methods involved engineering nucleases such as meganucleases, zinc finger fusion proteins or TALENs, requiring the generation of chimeric nucleases with engineered, programmable, sequence-specific DNA-binding domains specific for each particular target sequence. RNA-guided nucleases, such as the Clustered Regularly Interspaced Short Palindromic Repeats (CRISPR)-associated (cas) proteins of the CRISPR-cas bacterial system, allow for the targeting of specific sequences by complexing the nucleases with guide RNA that specifically hybridizes with a particular target sequence. Producing target-specific guide RNAs is less costly and more efficient than generating chimeric nucleases for each target sequence. Such RNA-guided nucleases can be used to edit genomes through the introduction of a sequence-specific, double-stranded break that is repaired via error-prone non-homologous end-joining (NHEJ) to introduce a mutation at a specific genomic location. Alternatively, heterologous DNA may be introduced into the genomic site via homology-directed repair.

BRIEF SUMMARY OF THE INVENTION

Compositions and methods for binding a target sequence of interest are provided. The compositions find use in cleaving or modifying a target sequence of interest, detection of a target sequence of interest, and modifying the expression of a sequence of interest. Compositions comprise RNA-guided nuclease (RGN) polypeptides, CRISPR RNAs (crRNAs), trans-activating CRISPR RNAs (tracrRNAs), guide RNAs (gRNAs), nucleic acid molecules encoding the same, and vectors and host cells comprising the nucleic acid molecules. Also provided are CRISPR systems for binding a target sequence of interest, wherein the CRISPR system comprises an RNA-guided nuclease polypeptide and one or more guide RNAs. Thus, methods disclosed herein are drawn to binding a target sequence of interest, and in some embodiments, cleaving or modifying the target sequence of interest. The target sequence of interest can be modified, for example, as a result of non-homologous end joining or homology-directed repair with an introduced donor sequence.

DETAILED DESCRIPTION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended embodiments. Although specific terms are employed herein, they are used in a generic and descriptive sense only and not for purposes of limitation.

I. Overview

RNA-guided nucleases (RGNs) allow for the targeted manipulation of a single site within a genome and are useful in the context of gene targeting for therapeutic and research applications. In a variety of organisms, including mammals, RNA-guided nucleases have been used for genome engineering by stimulating non-homologous end joining and homologous recombination, for example. The compositions and methods described herein are useful for creating single- or double-stranded breaks in polynucleotides, modifying polynucleotides, detecting a particular site within a polynucleotide, or modifying the expression of a particular gene.

The RNA-guided nucleases disclosed herein can alter gene expression by modifying a target sequence. In specific embodiments, the RNA-guided nucleases are directed to the target sequence by a guide RNA (gRNA) as part of a Clustered Regularly Interspaced Short Palindromic Repeats (CRISPR) RNA-guided nuclease system. Guide RNAs form a complex with the RNA-guided nucleases to direct the RNA-guided nuclease to bind to a target sequence and in some embodiments, introduce a single-stranded or double-stranded break at the target sequence. After the target sequence has been cleaved, the break can be repaired such that the DNA sequence of the target sequence is modified during the repair process. Thus, provided herein are methods for using the RNA-guided nucleases to modify a target sequence in the DNA of host cells. For example, RNA-guided nucleases can be used to modify a target sequence at a genomic locus of eukaryotic cells or prokaryotic cells.

II. RNA-Guided Nucleases

Provided herein are RNA-guided nucleases. The term RNA-guided nuclease (RGN) refers to a polypeptide that binds to a particular target nucleotide sequence in a sequence-specific manner and is directed to the target nucleotide sequence by a guide RNA molecule that is complexed with the polypeptide and hybridizes with the target sequence. Although an RNA-guided nuclease can be capable of cleaving the target sequence upon binding, the term RNA-guided nuclease also encompasses nuclease-dead RNA-guided nucleases that are capable of binding to, but not cleaving, a target sequence. Cleavage of a target sequence by an RNA-guided nuclease can result in a single- or double-stranded break. RNA-guided nucleases only capable of cleaving a single strand of a double-stranded nucleic acid molecule are referred to herein as nickases.

The RNA-guided nucleases disclosed herein include the APG05083.1, APG07433.1, APG07513.1, APG08290.1, APG05459.1, APG04583.1, and APG1688.1 RNA-guided nucleases, the amino acid sequences of which are set forth, respectively, as SEQ ID NOs: 1, 11, 19, 27, 36, 45, or 54, and active fragments or variants thereof that retain the ability to bind to a target nucleotide sequence in an RNA-guided sequence-specific manner. In some of these embodiments, the active fragment or variant of the APG05083.1, APG07433.1, APG07513.1, APG08290.1, APG05459.1, APG04583.1, and APG1688.1 RGN is capable of cleaving a single- or double-stranded target sequence. In some embodiments, an active variant of the APG05083.1, APG07433.1, APG07513.1, APG08290.1, APG05459.1, APG04583.1, or APG1688.1 RGN comprises an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence set forth as SEQ ID NOs: 1, 11, 19, 27, 36, 45, or 54. In certain embodiments, an active fragment of the APG05083.1, APG07433.1, APG07513.1, APG08290.1, APG05459.1, APG04583.1, or APG1688.1 RGN comprises at least 50, 100, 150, 200, 250, 300, 350, 400, 450, 500, 550, 600, 650, 700, 750, 800, 850, 900, 950, 1000, 1050 or more contiguous amino acid residues of the amino acid sequence set forth as SEQ ID NOs: 1, 11, 19, 27, 36, 45, or 54. RNA-guided nucleases provided herein can comprise at least one nuclease domain (e.g., DNase, RNase domain) and at least one RNA recognition and/or RNA binding domain to interact with guide RNAs. Further domains that can be found in RNA-guided nucleases provided herein include, but are not limited to: DNA binding domains, helicase domains, protein-protein interaction domains, and dimerization domains. In specific embodiments, the RNA-guided nucleases provided herein can comprise at least 70%, 75%, 80%, 85%, 90%, 91%, 92%, 93%, 94%, 95%, 96%, 97%, 98%, 99% to one or more of a DNA binding domains, helicase domains, protein-protein interaction domains, and dimerization domains.

A target nucleotide sequence is bound by an RNA-guided nuclease provided herein and hybridizes with the guide RNA associated with the RNA-guided nuclease. The target sequence can then be subsequently cleaved by the RNA-guided nuclease if the polypeptide possesses nuclease activity. The terms "cleave" or "cleavage" refer to the hydrolysis of at least one phosphodiester bond within the backbone of a target nucleotide sequence that can result in either single-stranded or double-stranded breaks within the target sequence. The presently disclosed RGNs can cleave nucleotides within a polynucleotide, functioning as an endonuclease or can be an exonuclease, removing successive nucleotides from the end (the 5' and/or the 3' end) of a polynucleotide. In other embodiments, the disclosed RGNs can cleave nucleotides of a target sequence within any position of a polynucleotide and thus function as both an endonuclease and exonuclease. The cleavage of a target polynucleotide by the presently disclosed RGNs can result in staggered breaks or blunt ends.

The presently disclosed RNA-guided nucleases can be wild-type sequences derived from bacterial or archaeal species. Alternatively, the RNA-guided nucleases can be variants or fragments of wild-type polypeptides. The wild-type RGN can be modified to alter nuclease activity or alter PAM specificity, for example. In some embodiments, the RNA-guided nuclease is not naturally-occurring.

In certain embodiments, the RNA-guided nuclease functions as a nickase, only cleaving a single strand of the target nucleotide sequence. Such RNA-guided nucleases have a single functioning nuclease domain. In some of these embodiments, additional nuclease domains have been mutated such that the nuclease activity is reduced or eliminated.

In other embodiments, the RNA-guided nuclease lacks nuclease activity altogether or exhibits reduced nuclease activity, and is referred to herein as nuclease-dead. Any method known in the art for introducing mutations into an amino acid sequence, such as PCR-mediated mutagenesis and site-directed mutagenesis, can be used for generating nickases or nuclease-dead RGNs. See, e.g., U.S. Publ. No. 2014/0068797 and U.S. Pat. No. 9,790,490; each of which is incorporated by reference in its entirety.

RNA-guided nucleases that lack nuclease activity can be used to deliver a fused polypeptide, polynucleotide, or small molecule payload to a particular genomic location. In some of these embodiments, the RGN polypeptide or guide RNA can be fused to a detectable label to allow for detection of a particular sequence. As a non-limiting example, a nuclease-dead RGN can be fused to a detectable label (e.g., fluorescent protein) and targeted to a particular sequence associated with a disease to allow for detection of the disease-associated sequence.

Alternatively, nuclease-dead RGNs can be targeted to particular genomic locations to alter the expression of a desired sequence. In some embodiments, the binding of a nuclease-dead RNA-guided nuclease to a target sequence results in the repression of expression of the target sequence or a gene under transcriptional control by the target sequence by interfering with the binding of RNA polymerase or transcription factors within the targeted genomic region. In other embodiments, the RGN (e.g., a nuclease-dead RGN) or its complexed guide RNA further comprises an expression modulator that, upon binding to a target sequence, serves to either repress or activate the expression of the target sequence or a gene under transcriptional control by the target sequence. In some of these embodiments, the expression modulator modulates the expression of the target sequence or regulated gene through epigenetic mechanisms.

In other embodiments, the nuclease-dead RGNs or a RGN with only nickase activity can be targeted to particular genomic locations to modify the sequence of a target polynucleotide through fusion to a base-editing polypeptide, for example a deaminase polypeptide or active variant or fragment thereof that deaminates a nucleotide base, resulting in conversion from one nucleotide base to another. The base-editing polypeptide can be fused to the RGN at its N-terminal or C-terminal end. Additionally, the base-editing polypeptide may be fused to the RGN via a peptide linker. A non-limiting example of a deaminase polypeptide that is useful for such compositions and methods include cytidine deaminase or the adenosine deaminase base editor described in Gaudelli et al. (2017) *Nature* 551:464-471, U.S. Publ. Nos. 2017/0121693 and 2018/0073012, and International Publ. No. WO/2018/027078, each of which is herein incorporated by reference in its entirety.

RNA-guided nucleases that are fused to a polypeptide or domain can be separated or joined by a linker. The term "linker," as used herein, refers to a chemical group or a molecule linking two molecules or moieties, e.g., a binding domain and a cleavage domain of a nuclease. In some embodiments, a linker joins a gRNA binding domain of an RNA guided nuclease and a base-editing polypeptide, such as a deaminase. In some embodiments, a linker joins a nuclease-dead RGN and a deaminase. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

The presently disclosed RNA-guided nucleases can comprise at least one nuclear localization signal (NLS) to enhance transport of the RGN to the nucleus of a cell. Nuclear localization signals are known in the art and generally comprise a stretch of basic amino acids (see, e.g., Lange et al., *J. Biol. Chem.* (2007) 282:5101-5105). In particular embodiments, the RGN comprises 2, 3, 4, 5, 6 or more nuclear localization signals. The nuclear localization signal(s) can be a heterologous NLS. Non-limiting examples of nuclear localization signals useful for the presently disclosed RGNs are the nuclear localization signals of SV40 Large T-antigen, nucleopasmin, and c-Myc (see, e.g., Ray et al. (2015) *Bioconjug Chem* 26(6): 1004-7). In particular embodiments, the RGN comprises the NLS sequence set forth as SEQ ID NO: 67. The RGN can comprise one or more NLS sequences at its N-terminus, C-terminus, or both the N-terminus and C-terminus. For example, the RGN can comprise two NLS sequences at the N-terminal region and four NLS sequences at the C-terminal region.

Other localization signal sequences known in the art that localize polypeptides to particular subcellular location(s) can also be used to target the RGNs, including, but not limited to, plastid localization sequences, mitochondrial localization sequences, and dual-targeting signal sequences that target to both the plastid and mitochondria (see, e.g., Nassoury and Morse (2005) *Biochim Biophys Acta* 1743:5-19; Kunze and Berger (2015) Front Physiol dx.doi.org/10.3389/fphys.2015.00259; Herrmann and Neupert (2003) *IUBMB Life* 55:219-225; Soll (2002) *Curr Opin Plant Biol* 5:529-535; Carrie and Small (2013) *Biochim Biophys Acta* 1833:253-259; Carrie et al. (2009) *FEBS J* 276:1187-1195; Silva-Filho (2003) *Curr Opin Plant Biol* 6:589-595; Peeters and Small (2001) *Biochim Biophys Acta* 1541:54-63; Murcha et al. (2014) *J Exp Bot* 65:6301-6335; Mackenzie (2005) *Trends Cell Biol* 15:548-554; Glaser et al. (1998) *Plant Mol Biol* 38:311-338).

In certain embodiments, the presently disclosed RNA-guided nucleases comprise at least one cell-penetrating domain that facilitates cellular uptake of the RGN. Cell-penetrating domains are known in the art and generally comprise stretches of positively charged amino acid residues (i.e., polycationic cell-penetrating domains), alternating polar amino acid residues and non-polar amino acid residues (i.e., amphipathic cell-penetrating domains), or hydrophobic amino acid residues (i.e., hydrophobic cell-penetrating domains) (see, e.g., Milletti F. (2012) *Drug Discov Today* 17:850-860). A non-limiting example of a cell-penetrating domain is the trans-activating transcriptional activator (TAT) from the human immunodeficiency virus 1.

The nuclear localization signal, plastid localization signal, mitochondrial localization signal, dual-targeting localization signal, and/or cell-penetrating domain can be located at the amino-terminus (N-terminus), the carboxyl-terminus (C-terminus), or in an internal location of the RNA-guided nuclease.

The presently disclosed RGNs can be fused to an effector domain, such as a cleavage domain, a deaminase domain, or an expression modulator domain, either directly or indirectly via a linker peptide. Such a domain can be located at the N-terminus, the C-terminus, or an internal location of the RNA-guided nuclease. In some of these embodiments, the RGN component of the fusion protein is a nuclease-dead RGN.

In some embodiments, the RGN fusion protein comprises a cleavage domain, which is any domain that is capable of cleaving a polynucleotide (i.e., RNA, DNA, or RNA/DNA hybrid) and includes, but is not limited to, restriction endonucleases and homing endonucleases, such as Type IIS endonucleases (e.g., FokI) (see, e.g., Belfort et al. (1997) *Nucleic Acids Res.* 25:3379-3388; Linn et al. (eds.) Nucleases, Cold Spring Harbor Laboratory Press, 1993).

In other embodiments, the RGN fusion protein comprises a deaminase domain that deaminates a nucleotide base, resulting in conversion from one nucleotide base to another, and includes, but is not limited to, a cytidine deaminase or an adenosine deaminase base editor (see, e.g., Gaudelli et al. (2017) *Nature* 551:464-471, U.S. Publ. Nos. 2017/0121693 and 2018/0073012, U.S. Pat. No. 9,840,699, and International Publ. No. WO/2018/027078).

In some embodiments, the effector domain of the RGN fusion protein can be an expression modulator domain, which is a domain that either serves to upregulate or downregulate transcription. The expression modulator domain can be an epigenetic modification domain, a transcriptional repressor domain or a transcriptional activation domain.

In some of these embodiments, the expression modulator of the RGN fusion protein comprises an epigenetic modification domain that covalently modifies DNA or histone proteins to alter histone structure and/or chromosomal structure without altering the DNA sequence, leading to changes in gene expression (i.e., upregulation or downregulation). Non-limiting examples of epigenetic modifications include acetylation or methylation of lysine residues, arginine methylation, serine and threonine phosphorylation, and lysine ubiquitination and sumoylation of histone proteins, and methylation and hydroxymethylation of cytosine residues in DNA. Non-limiting examples of epigenetic modification domains include histone acetyltransferase domains, histone deacetylase domains, histone methyltransferase domains, histone demethylase domains, DNA methyltransferase domains, and DNA demethylase domains.

In other embodiments, the expression modulator of the fusion protein comprises a transcriptional repressor domain, which interacts with transcriptional control elements and/or transcriptional regulatory proteins, such as RNA polymerases and transcription factors, to reduce or terminate transcription of at least one gene. Transcriptional repressor domains are known in the art and include, but are not limited to, Spl-like repressors, IKB, and Kruippel associated box (KRAB) domains.

In yet other embodiments, the expression modulator of the fusion protein comprises a transcriptional activation domain, which interacts with transcriptional control elements and/or transcriptional regulatory proteins, such as RNA polymerases and transcription factors, to increase or activate transcription of at least one gene. Transcriptional activation domains are known in the art and include, but are not limited to, a herpes simplex virus VP16 activation domain and an NFAT activation domain.

The presently disclosed RGN polypeptides can comprise a detectable label or a purification tag. The detectable label or purification tag can be located at the N-terminus, the C-terminus, or an internal location of the RNA-guided nuclease, either directly or indirectly via a linker peptide. In some of these embodiments, the RGN component of the fusion protein is a nuclease-dead RGN. In other embodiments, the RGN component of the fusion protein is a RGN with nickase activity.

A detectable label is a molecule that can be visualized or otherwise observed. The detectable label may be fused to the RGN as a fusion protein (e.g., fluorescent protein) or may be a small molecule conjugated to the RGN polypeptide that can be detected visually or by other means. Detectable labels that can be fused to the presently disclosed RGNs as a fusion protein include any detectable protein domain, including but not limited to, a fluorescent protein or a protein domain that can be detected with a specific antibody. Non-limiting examples of fluorescent proteins include green fluorescent proteins (e.g., GFP, EGFP, ZsGreen1) and yellow fluorescent proteins (e.g., YFP, EYFP, ZsYellow1). Non-limiting examples of small molecule detectable labels include radioactive labels, such as $^3$H and $^{35}$S.

RGN polypeptides can also comprise a purification tag, which is any molecule that can be utilized to isolate a protein or fused protein from a mixture (e.g., biological sample, culture medium). Non-limiting examples of purification tags include biotin, myc, maltose binding protein (MBP), and glutathione-S-transferase (GST).

II. Guide RNA

The present disclosure provides guide RNAs and polynucleotides encoding the same. The term "guide RNA" refers to a nucleotide sequence having sufficient complementarity with a target nucleotide sequence to hybridize with the target sequence and direct sequence-specific binding of an associated RNA-guided nuclease to the target nucleotide sequence. Thus, a RGN's respective guide RNA is one or more RNA molecules (generally, one or two), that can bind to the RGN and guide the RGN to bind to a particular target nucleotide sequence, and in those instances wherein the RGN has nickase or nuclease activity, also cleave the target nucleotide sequence. In general, a guide RNA comprises a CRISPR RNA (crRNA) and a trans-activating CRISPR RNA (tracrRNA). Native guide RNAs that comprise both a crRNA and a tracrRNA generally comprise two separate RNA molecules that hybridize to each other through the repeat sequence of the crRNA and the anti-repeat sequence of the tracrRNA.

Native direct repeat sequences within a CRISPR array generally range in length from 28 to 37 base pairs, although the length can vary between about 23 bp to about 55 bp. Spacer sequences within a CRISPR array generally range from about 32 to about 38 bp in length, although the length can be between about 21 bp to about 72 bp. Each CRISPR array generally comprises less than 50 units of the CRISPR repeat-spacer sequence. The CRISPRs are transcribed as part of a long transcript termed the primary CRISPR transcript, which comprises much of the CRISPR array. The primary CRISPR transcript is cleaved by Cas proteins to produce crRNAs or in some cases, to produce pre-crRNAs that are further processed by additional Cas proteins into mature crRNAs. Mature crRNAs comprise a spacer sequence and a CRISPR repeat sequence. In some embodiments in which pre-crRNAs are processed into mature (or processed) crRNAs, maturation involves the removal of about one to about six or more 5', 3', or 5' and 3' nucleotides. For the purposes of genome editing or targeting a particular target nucleotide sequence of interest, these nucleotides that are removed during maturation of the pre-crRNA molecule are not necessary for generating or designing a guide RNA.

A CRISPR RNA (crRNA) comprises a spacer sequence and a CRISPR repeat sequence. The "spacer sequence" is the nucleotide sequence that directly hybridizes with the target nucleotide sequence of interest. The spacer sequence is engineered to be fully or partially complementary with the target sequence of interest. In various embodiments, the spacer sequence can comprise from about 8 nucleotides to about 30 nucleotides, or more. For example, the spacer sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In some embodiments, the spacer sequence is about 10 to about 26 nucleotides in length, or about 12 to about 30 nucleotides in length. In particular embodiments, the spacer sequence is about 30 nucleotides in length. In some embodiments, the degree of complementarity between a spacer sequence and its corresponding target sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more. In particular embodiments, the spacer sequence is free of secondary structure, which can be predicted using any suitable polynucleotide folding algorithm known in the art, including but not limited to mFold (see, e.g., Zuker and Stiegler (1981) *Nucleic Acids Res.* 9:133-148) and RNAfold (see, e.g., Gruber et al. (2008) *Cell* 106(1):23-24).

RGN proteins can have varying sensitivity to mismatches between a spacer sequence in a gRNA and its target sequence that affects the efficiency of cleavage. As discussed in Example 5, APG05459.1 RGN has an unusual sensitivity to mismatches between the spacer sequence and target sequence, extending at least 15 nucleotides 5' of the PAM site. Thus, APG05459.1 has the potential to more finely (i.e., specifically) target particular sequences with greater precision than other RGNs with less sensitivity to mismatches between the spacer sequence and target sequence.

The CRISPR RNA repeat sequence comprises a nucleotide sequence that comprises a region with sufficient complementarity to hybridize to a tracrRNA. In various embodiments, the CRISPR RNA repeat sequence can comprise from about 8 nucleotides to about 30 nucleotides, or more. For example, the CRISPR repeat sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In some embodiments, the CRISPR repeat sequence is about 21 nucleotides in length. In some embodiments, the degree of complementarity between a CRISPR repeat sequence and its corresponding tracrRNA sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more. In particular embodiments, the CRISPR repeat sequence comprises the nucleotide sequence of SEQ ID NOs: 2, 12, 20, 28, 37, 46, or 55, or an active variant or fragment thereof that when comprised within a guide RNA, is capable of directing the sequence-specific binding of an associated RNA-guided nuclease provided herein to a target sequence of interest. In certain embodiments, an active CRISPR repeat sequence variant of a wild-type sequence comprises a nucleotide sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the nucleotide sequence set forth as SEQ ID NOs: 2, 12, 20, 28, 37, 46, or 55. In certain embodiments, an active CRISPR repeat sequence fragment of a wild-type sequence comprises at least 5, 6, 7, 8, 9, 10, 11, 12, 13, 14, 15, 16, 17, 18, 19, or 20 contiguous nucleotides of the nucleotide sequence set forth as SEQ ID NOs: 2, 12, 20, 28, 37, 46, or 55.

In certain embodiments, the crRNA is not naturally-occurring. In some of these embodiments, the specific CRISPR repeat sequence is not linked to the engineered spacer sequence in nature and the CRISPR repeat sequence is considered heterologous to the spacer sequence. In certain embodiments, the spacer sequence is an engineered sequence that is not naturally occurring.

A trans-activating CRISPR RNA or tracrRNA molecule comprises a nucleotide sequence comprising a region that has sufficient complementarity to hybridize to a CRISPR repeat sequence of a crRNA, which is referred to herein as the anti-repeat region. In some embodiments, the tracrRNA molecule further comprises a region with secondary structure (e.g., stem-loop) or forms secondary structure upon hybridizing with its corresponding crRNA. In particular embodiments, the region of the tracrRNA that is fully or partially complementary to a CRISPR repeat sequence is at the 5' end of the molecule and the 3' end of the tracrRNA comprises secondary structure. This region of secondary structure generally comprises several hairpin structures, including the nexus hairpin, which is found adjacent to the anti-repeat sequence. The nexus hairpin often has a conserved nucleotide sequence in the base of the hairpin stem, with the motif UNANNG, UNANNU, or UNANNA (SEQ ID NOs: 68, 557, and 558, respectively) found in many nexus hairpins in tracrRNAs. There are often terminal hairpins at the 3' end of the tracrRNA that can vary in structure and number, but often comprise a GC-rich Rho-independent transcriptional terminator hairpin followed by a string of U's at the 3' end. See, for example, Briner et al. (2014) *Molecular Cell* 56:333-339, Briner and Barrangou (2016) *Cold Spring Harb Protoc*; doi: 10.1101/pdb.top090902, and U.S. Publication No. 2017/0275648, each of which is herein incorporated by reference in its entirety.

In various embodiments, the anti-repeat region of the tracrRNA that is fully or partially complementary to the CRISPR repeat sequence comprises from about 8 nucleotides to about 30 nucleotides, or more. For example, the region of base pairing between the tracrRNA anti-repeat sequence and the CRISPR repeat sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In particular embodiments, the anti-repeat region of the tracrRNA that is fully or partially complementary to a CRISPR repeat sequence is about 20 nucleotides in length. In some embodiments, the degree of complementarity between a CRISPR repeat sequence and its corresponding tracrRNA anti-repeat sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more.

In various embodiments, the entire tracrRNA can comprise from about 60 nucleotides to more than about 140 nucleotides. For example, the tracrRNA can be about 60, about 65, about 70, about 75, about 80, about 85, about 90, about 95, about 100, about 105, about 110, about 115, about 120, about 125, about 130, about 135, about 140, or more nucleotides in length. In particular embodiments, the tracrRNA is about 80 to about 90 nucleotides in length, including about 80, about 81, about 82, about 83, about 84, about 85, about 86, about 87, about 88, about 89, and about 90 nucleotides in length. In certain embodiments, the tracrRNA is about 85 nucleotides in length.

In particular embodiments, the tracrRNA comprises the nucleotide sequence of SEQ ID NOs: 3, 13, 21, 29, 38, 47, or 56, or an active variant or fragment thereof that when comprised within a guide RNA is capable of directing the sequence-specific binding of an associated RNA-guided nuclease provided herein to a target sequence of interest. In certain embodiments, an active tracrRNA sequence variant of a wild-type sequence comprises a nucleotide sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the nucleotide sequence set forth as SEQ ID NOs: 3, 13, 21, 29, 38, 47, or 56. In certain embodiments, an active tracrRNA sequence fragment of a wild-type sequence comprises at least 5, 10, 15, 20, 25, 30, 35, 40, 45, 50, 55, 60, 65, 70, 75, 80, or more contiguous nucleotides of the nucleotide sequence set forth as SEQ ID NOs: 3, 13, 21, 29, 38, 47, or 56.

Two polynucleotide sequences can be considered to be substantially complementary when the two sequences hybridize to each other under stringent conditions. Likewise, an RGN is considered to bind to a particular target sequence within a sequence-specific manner if the guide RNA bound to the RGN binds to the target sequence under stringent conditions. By "stringent conditions" or "stringent hybridization conditions" is intended conditions under which the two polynucleotide sequences will hybridize to each other to a detectably greater degree than to other sequences (e.g., at least 2-fold over background). Stringent conditions are sequence-dependent and will be different in different circumstances. Typically, stringent conditions will be those in which the salt concentration is less than about 1.5 M Na ion, typically about 0.01 to 1.0 M Na ion concentration (or other salts) at pH 7.0 to 8.3, and the temperature is at least about 30° C. for short sequences (e.g., 10 to 50 nucleotides) and at least about 60° C. for long sequences (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The Tm is the temperature (under defined ionic strength and pH) at which 50% of a complementary target sequence hybridizes to a perfectly matched sequence. For DNA-DNA hybrids, the Tm can be approximated from the equation of Meinkoth and Wahl (1984) Anal. Biochem. 138:267-284: Tm=81.5° C.+16.6 (log M)+0.41 (% GC)–0.61 (% form)– 500/L; where M is the molarity of monovalent cations, % GC is the percentage of guanosine and cytosine nucleotides in the DNA, % form is the percentage of formamide in the hybridization solution, and L is the length of the hybrid in base pairs. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. An extensive guide to the hybridization of nucleic acids is found in Tijssen (1993) Laboratory Techniques in Biochemistry and Molecular Biology-Hybridization with Nucleic Acid Probes, Part I, Chapter 2 (Elsevier, New York); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, N.Y.).

The guide RNA can be a single guide RNA or a dual-guide RNA system. A single guide RNA comprises the crRNA and tracrRNA on a single molecule of RNA, whereas a dual-guide RNA system comprises a crRNA and a tracrRNA present on two distinct RNA molecules, hybridized to one another through at least a portion of the CRISPR repeat sequence of the crRNA and at least a portion of the tracrRNA, which may be fully or partially complementary to the CRISPR repeat sequence of the crRNA. In some of those embodiments wherein the guide RNA is a single guide RNA, the crRNA and tracrRNA are separated by a linker nucleotide sequence. In general, the linker nucleotide sequence is one that does not include complementary bases in order to avoid the formation of secondary structure within or comprising nucleotides of the linker nucleotide sequence. In some embodiments, the linker nucleotide sequence between the crRNA and tracrRNA is at least 3, at least 4, at least 5, at least 6, at least 7, at least 8, at least 9, at least 10, at least 11, at least 12, or more nucleotides in length. In particular embodiments, the linker nucleotide sequence of a single guide RNA is at least 4 nucleotides in length. In certain embodiments, the linker nucleotide sequence is the nucleotide sequence set forth as SEQ ID NO: 63, 64, or 65. In other embodiments, the linker nucleotide sequence is at least 6 nucleotides in length. In certain embodiments, the linker nucleotide sequence is the nucleotide sequence set forth as SEQ ID NO: 65.

The single guide RNA or dual-guide RNA can be synthesized chemically or via in vitro transcription. Assays for determining sequence-specific binding between a RGN and a guide RNA are known in the art and include, but are not limited to, in vitro binding assays between an expressed RGN and the guide RNA, which can be tagged with a detectable label (e.g., biotin) and used in a pull-down detection assay in which the guide RNA:RGN complex is captured via the detectable label (e.g., with streptavidin beads). A control guide RNA with an unrelated sequence or structure to the guide RNA can be used as a negative control for non-specific binding of the RGN to RNA. In certain embodiments, the guide RNA is SEQ ID NO: 10, 18, 26, 35, 44, 53, or 62, wherein the spacer sequence can be any sequence and is indicated as a poly-N sequence.

As described in Example 8, certain RGNs of the invention can share certain guide RNAs. APG05083.1, APG07433.1, APG07513.1, and APG08290.1 can each function using guide RNAs comprising a crRNA comprising the nucleotide sequence of SEQ ID NOs: 2, 12, 20, or 28, with the corresponding tracrRNA comprising the nucleotide sequence of SEQ ID NOs: 3, 13, 21, or 29, respectively. Further, APG04583.1 and APG01688.1 can each function using guide RNAs comprising a crRNA comprising the nucleotide sequence of SEQ ID NOs: 46 or 55, with the corresponding tracrRNA comprising the nucleotide sequence of SEQ 47 or 56, respectively.

In certain embodiments, the guide RNA can be introduced into a target cell, organelle, or embryo as an RNA molecule. The guide RNA can be transcribed in vitro or chemically synthesized. In other embodiments, a nucleotide sequence encoding the guide RNA is introduced into the cell, organelle, or embryo. In some of these embodiments, the nucleotide sequence encoding the guide RNA is operably linked to a promoter (e.g., an RNA polymerase III promoter). The promoter can be a native promoter or heterologous to the guide RNA-encoding nucleotide sequence.

In various embodiments, the guide RNA can be introduced into a target cell, organelle, or embryo as a ribonucleoprotein complex, as described herein, wherein the guide RNA is bound to an RNA-guided nuclease polypeptide.

The guide RNA directs an associated RNA-guided nuclease to a particular target nucleotide sequence of interest through hybridization of the guide RNA to the target nucleotide sequence. A target nucleotide sequence can comprise DNA, RNA, or a combination of both and can be single-stranded or double-stranded. A target nucleotide sequence can be genomic DNA (i.e., chromosomal DNA), plasmid DNA, or an RNA molecule (e.g., messenger RNA, ribosomal RNA, transfer RNA, micro RNA, small interfering RNA). The target nucleotide sequence can be bound (and in some embodiments, cleaved) by an RNA-guided nuclease in vitro or in a cell. The chromosomal sequence targeted by the RGN can be a nuclear, plastid or mitochondrial chromosomal sequence. In some embodiments, the target nucleotide sequence is unique in the target genome.

The target nucleotide sequence is adjacent to a protospacer adjacent motif (PAM). A protospacer adjacent motif is generally within about 1 to about 10 nucleotides from the target nucleotide sequence, including about 1, about 2, about 3, about 4, about 5, about 6, about 7, about 8, about 9, or about 10 nucleotides from the target nucleotide sequence. The PAM can be 5' or 3' of the target sequence. In some embodiments, the PAM is 3' of the target sequence for the presently disclosed RGNs. Generally, the PAM is a consensus sequence of about 3-4 nucleotides, but in particular embodiments, can be 2, 3, 4, 5, 6, 7, 8, 9, or more nucleotides in length. In various embodiments, the PAM sequence recognized by the presently disclosed RGNs comprises the consensus sequence set forth as SEQ ID NOs: 6, 32, 41, 50, or 59. Non-limiting exemplary PAM sequences are the nucleotide sequences set forth as SEQ ID NO: 7, 69, 70, 71, and 72.

In particular embodiments, an RNA-guided nuclease having SEQ ID NOs: 1, 11, 19, 27, 36, 45, or 54 or an active variant or fragment thereof binds respectively a target nucleotide sequence adjacent to a PAM sequence set forth as SEQ ID NOs: 6, 32, 41, 50, 59, or 7. In some of these embodiments, the RGN binds to a guide sequence comprising a CRISPR repeat sequence set forth in SEQ ID NOs: 2, 12, 20, 28, 37, 46, or 55, respectively, or an active variant or fragment thereof, and a tracrRNA sequence set forth in SEQ ID NOs: 3, 13, 21, 29, 38, 47, or 56, respectively, or an active variant or fragment thereof. The RGN systems are described further in Example 1 and Table 1 of the present specification.

It is well-known in the art that PAM sequence specificity for a given nuclease enzyme is affected by enzyme concentration (see, e.g., Karvelis et al. (2015) *Genome Biol* 16:253), which may be modified by altering the promoter used to express the RGN, or the amount of ribonucleoprotein complex delivered to the cell, organelle, or embryo.

Upon recognizing its corresponding PAM sequence, the RGN can cleave the target nucleotide sequence at a specific cleavage site. As used herein, a cleavage site is made up of the two particular nucleotides within a target nucleotide sequence between which the nucleotide sequence is cleaved by an RGN. The cleavage site can comprise the $1^{st}$ and $2^{nd}$, $2^{nd}$ and $3^{rd}$, $3^{rd}$ and 4th, 4th and $5^{th}$, $5^{th}$ and $6^{th}$, $7^{th}$ and $8^{th}$, or $8^{th}$ and $9^{th}$ nucleotides from the PAM in either the 5' or 3' direction. In some embodiments, the cleavage site may be over 10, 11, 12, 13, 14, 15, 16, 17, 18, 19, or 20 nucleotides from the PAM in either the 5' or 3' direction. In some embodiments, the cleavage site is 4 nucleotides away from the PAM. In other embodiments, the cleavage site is at least 15 nucleotides away from the PAM. As RGNs can cleave a target nucleotide sequence resulting in staggered ends, in some embodiments, the cleavage site is defined based on the distance of the two nucleotides from the PAM on the positive (+) strand of the polynucleotide and the distance of the two nucleotides from the PAM on the negative (−) strand of the polynucleotide.

III. Nucleotides Encoding RNA-Guided Nucleases, CRISPR RNA, and/or tracrRNA

The present disclosure provides polynucleotides comprising the presently disclosed CRISPR RNAs, tracrRNAs, and/or sgRNAs and polynucleotides comprising a nucleotide sequence encoding the presently disclosed RNA-guided nucleases, CRISPR RNAs, tracrRNAs, and/or sgRNAs. Presently disclosed polynucleotides include those comprising or encoding a CRISPR repeat sequence comprising the nucleotide sequence of SEQ ID NOs: 2, 12, 20, 28, 37, 46, or 55, or an active variant or fragment thereof that when comprised within a guide RNA is capable of directing the sequence-specific binding of an associated RNA-guided nuclease to a target sequence of interest. Also disclosed are polynucleotides comprising or encoding a tracrRNA comprising the nucleotide sequence of SEQ ID NOs: 3, 13, 21, 29, 38, 47, or 56, or an active variant or fragment thereof that when comprised within a guide RNA is capable of directing the sequence-specific binding of an associated RNA-guided nuclease to a target sequence of interest. Polynucleotides are also provided that encode an RNA-guided nuclease comprising the amino acid sequence set forth as SEQ ID NOs: 1, 11, 19, 27, 36, 45, or 54, and active fragments or variants thereof that retain the ability to bind to a target nucleotide sequence in an RNA-guided sequence-specific manner.

The use of the term "polynucleotide" is not intended to limit the present disclosure to polynucleotides comprising DNA. Those of ordinary skill in the art will recognize that polynucleotides can comprise ribonucleotides (RNA) and combinations of ribonucleotides and deoxyribonucleotides. Such deoxyribonucleotides and ribonucleotides include both naturally occurring molecules and synthetic analogues. These include peptide nucleic acids (PNAs), PNA-DNA chimers, locked nucleic acids (LNAs), and phosphothiorate linked sequences. The polynucleotides disclosed herein also encompass all forms of sequences including, but not limited to, single-stranded forms, double-stranded forms, DNA-RNA hybrids, triplex structures, stem-and-loop structures, and the like.

The nucleic acid molecules encoding RGNs can be codon optimized for expression in an organism of interest. A "codon-optimized" coding sequence is a polynucleotide coding sequence having its frequency of codon usage designed to mimic the frequency of preferred codon usage or transcription conditions of a particular host cell. Expression in the particular host cell or organism is enhanced as a result of the alteration of one or more codons at the nucleic acid level such that the translated amino acid sequence is not changed. Nucleic acid molecules can be codon optimized, either wholly or in part. Codon tables and other references providing preference information for a wide range of organisms are available in the art (see, e.g., Campbell and Gowri (1990) *Plant Physiol.* 92:1-11 for a discussion of plant-preferred codon usage). Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Polynucleotides encoding the RGNs, crRNAs, tracrRNAs, and/or sgRNAs provided herein can be provided in expression cassettes for in vitro expression or expression in a cell, organelle, embryo, or organism of interest. The cassette will include 5' and 3' regulatory sequences operably linked to a polynucleotide encoding an RGN, crRNA, tracrRNAs, and/or sgRNAs provided herein that allows for expression of the polynucleotide. The cassette may additionally contain at least one additional gene or genetic element to be cotransformed into the organism. Where additional genes or elements are included, the components are operably linked. The term "operably linked" is intended to mean a functional linkage between two or more elements. For example, an operable linkage between a promoter and a coding region of interest (e.g., region coding for an RGN, crRNA, tracrRNAs, and/or sgRNAs) is a functional link that allows for expression of the coding region of interest. Operably linked elements may be contiguous or non-contiguous. When used to refer to the joining of two protein coding regions, by operably linked is intended that the coding regions are in the same reading frame. Alternatively, the additional gene(s) or element(s) can be provided on multiple expression cassettes. For example, the nucleotide sequence encoding a presently disclosed RGN can be present on one expression cassette, whereas the nucleotide sequence encoding a crRNA, tracrRNA, or complete guide RNA can be on a separate expression cassette. Such an expression cassette is provided with a plurality of restriction sites and/or recombination sites for insertion of the polynucleotides to be under the transcriptional regulation of the regulatory regions. The expression cassette may additionally contain a selectable marker gene.

The expression cassette will include in the 5'-3' direction of transcription, a transcriptional (and, in some embodiments, translational) initiation region (i.e., a promoter), an RGN-, crRNA-, tracrRNA- and/or sgRNA-encoding polynucleotide of the invention, and a transcriptional (and in some embodiments, translational) termination region (i.e., termination region) functional in the organism of interest. The promoters of the invention are capable of directing or driving expression of a coding sequence in a host cell. The regulatory regions (e.g., promoters, transcriptional regulatory regions, and translational termination regions) may be endogenous or heterologous to the host cell or to each other. As used herein, "heterologous" in reference to a sequence is a sequence that originates from a foreign species, or, if from the same species, is substantially modified from its native form in composition and/or genomic locus by deliberate human intervention. As used herein, a chimeric gene comprises a coding sequence operably linked to a transcription initiation region that is heterologous to the coding sequence.

Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional regulatory signals include, but are not limited to, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (1992) Molecular Cloning: A Laboratory Manual, ed. Maniatis et al. (Cold Spring Harbor Laboratory Press, Cold Spring Harbor, N.Y.), hereinafter "Sambrook 11"; Davis et al., eds. (1980) Advanced Bacterial Genetics (Cold Spring Harbor Laboratory Press), Cold Spring Harbor, N.Y., and the references cited therein.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, inducible, growth stage-specific, cell type-specific, tissue-preferred, tissue-specific, or other promoters for expression in the organism of interest. See, for example, promoters set forth in WO 99/43838 and in U.S. Pat. Nos. 8,575,425; 7,790,846; 8,147,856; 8,586832; 7,772,369; 7,534,939; 6,072,050; 5,659,026; 5,608,149; 5,608,144; 5,604,121; 5,569,597; 5,466,785; 5,399,680; 5,268,463; 5,608,142; and 6,177,611; herein incorporated by reference.

For expression in plants, constitutive promoters also include CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); and MAS (Velten et al. (1984) *EMBO J.* 3:2723-2730).

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the Axig1 promoter which is auxin induced and tapetum specific but also active in callus (PCT US01/22169), the steroid-responsive promoters (see, for example, the ERE promoter which is estrogen induced, and the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-specific or tissue-preferred promoters can be utilized to target expression of an expression construct within a particular tissue. In certain embodiments, the tissue-specific or tissue-preferred promoters are active in plant tissue. Examples of promoters under developmental control in plants include promoters that initiate transcription preferentially in certain tissues, such as leaves, roots, fruit, seeds, or flowers. A "tissue specific" promoter is a promoter that initiates transcription only in certain tissues. Unlike constitutive expression of genes, tissue-specific expression is the result of several interacting levels of gene regulation. As such, promoters from homologous or closely related plant species can be preferable to use to achieve efficient and reliable expression of transgenes in particular tissues. In some embodiments, the expression comprises a tissue-preferred promoter. A "tissue preferred" promoter is a promoter that initiates transcription preferentially, but not necessarily entirely or solely in certain tissues.

In some embodiments, the nucleic acid molecules encoding a RGN, crRNA, and/or tracrRNA comprise a cell type-specific promoter. A "cell type specific" promoter is a promoter that primarily drives expression in certain cell types in one or more organs. Some examples of plant cells in which cell type specific promoters functional in plants may be primarily active include, for example, BETL cells, vascular cells in roots, leaves, stalk cells, and stem cells. The nucleic acid molecules can also include cell type preferred promoters. A "cell type preferred" promoter is a promoter that primarily drives expression mostly, but not necessarily entirely or solely in certain cell types in one or more organs. Some examples of plant cells in which cell type preferred promoters functional in plants may be preferentially active include, for example, BETL cells, vascular cells in roots, leaves, stalk cells, and stem cells.

The nucleic acid sequences encoding the RGNs, crRNAs, tracrRNAs, and/or sgRNAs can be operably linked to a promoter sequence that is recognized by a phage RNA polymerase for example, for in vitro mRNA synthesis. In such embodiments, the in vitro-transcribed RNA can be purified for use in the methods described herein. For example, the promoter sequence can be a T7, T3, or SP6 promoter sequence or a variation of a T7, T3, or SP6 promoter sequence. In such embodiments, the expressed protein and/or RNAs can be purified for use in the methods of genome modification described herein.

In certain embodiments, the polynucleotide encoding the RGN, crRNA, tracrRNA, and/or sgRNA also can be linked to a polyadenylation signal (e.g., SV40 polyA signal and other signals functional in plants) and/or at least one transcriptional termination sequence. Additionally, the sequence encoding the RGN also can be linked to sequence(s) encoding at least one nuclear localization signal, at least one cell-penetrating domain, and/or at least one signal peptide capable of trafficking proteins to particular subcellular locations, as described elsewhere herein.

The polynucleotide encoding the RGN, crRNA, tracrRNA, and/or sgRNA can be present in a vector or multiple vectors. A "vector" refers to a polynucleotide composition for transferring, delivering, or introducing a nucleic acid into a host cell. Suitable vectors include plasmid vectors, phagemids, cosmids, artificial/mini-chromosomes, transposons, and viral vectors (e.g., lentiviral vectors, adeno-associated viral vectors, baculoviral vector). The vector can comprise additional expression control sequences (e.g., enhancer sequences, Kozak sequences, polyadenylation sequences, transcriptional termination sequences), selectable marker sequences (e.g., antibiotic resistance genes), origins of replication, and the like. Additional information can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3rd edition, 2001.

The vector can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D).

In some embodiments, the expression cassette or vector comprising the sequence encoding the RGN polypeptide can further comprise a sequence encoding a crRNA and/or a tracrRNA, or the crRNA and tracrRNA combined to create a guide RNA. The sequence(s) encoding the crRNA and/or tracrRNA can be operably linked to at least one transcriptional control sequence for expression of the crRNA and/or tracrRNA in the organism or host cell of interest. For example, the polynucleotide encoding the crRNA and/or tracrRNA can be operably linked to a promoter sequence that is recognized by RNA polymerase III (Pol III). Examples of suitable Pol III promoters include, but are not limited to, mammalian U6, U3, H1, and 7SL RNA promoters and rice U6 and U3 promoters.

As indicated, expression constructs comprising nucleotide sequences encoding the RGNs, crRNA, tracrRNA, and/or sgRNA can be used to transform organisms of interest. Methods for transformation involve introducing a nucleotide construct into an organism of interest. By "introducing" is intended to introduce the nucleotide construct to the host cell in such a manner that the construct gains access to the interior of the host cell. The methods of the invention do not require a particular method for introducing a nucleotide construct to a host organism, only that the nucleotide construct gains access to the interior of at least one cell of the host organism. The host cell can be a eukaryotic or prokaryotic cell. In particular embodiments, the eukaryotic host cell is a plant cell, a mammalian cell, or an insect cell. Methods for introducing nucleotide constructs into plants and other host cells are known in the art including, but not limited to, stable transformation methods, transient transformation methods, and virus-mediated methods.

The methods result in a transformed organism, such as a plant, including whole plants, as well as plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic organisms" or "transformed organisms" or "stably transformed" organisms or cells or tissues refers to organisms that have incorporated or integrated a polynucleotide encoding a RGN, crRNA, and/or tracrRNA of the invention. It is recognized that other exogenous or endogenous nucleic acid sequences or DNA fragments may also be incorporated into the host cell. Agrobacterium- and biolistic-mediated transformation remain the two predominantly employed approaches for transformation of plant cells. However, transformation of a host cell may be performed by infection, transfection, microinjection, electroporation, microprojection, biolistics or particle bombardment, electroporation, silica/carbon fibers, ultrasound mediated, PEG mediated, calcium phosphate co-precipitation, polycation DMSO technique, DEAE dextran procedure, and viral mediated, liposome mediated and the like. Viral-mediated introduction of a polynucleotide encoding an RGN, crRNA, and/or tracrRNA includes retroviral, lentiviral, adenoviral, and adeno-associated viral mediated introduction and expression, as well as the use of Caulimoviruses, Geminiviruses, and RNA plant viruses.

Transformation protocols as well as protocols for introducing polypeptides or polynucleotide sequences into plants may vary depending on the type of host cell (e.g., monocot or dicot plant cell) targeted for transformation. Methods for transformation are known in the art and include those set forth in U.S. Pat. Nos. 8,575,425; 7,692,068; 8,802,934; 7,541,517; each of which is herein incorporated by reference. See, also, Rakoczy-Trojanowska, M. (2002) *Cell Mol Biol Lett.* 7:849-858; Jones et al. (2005) *Plant Methods* 1:5; Rivera et al. (2012) *Physics ofLife Reviews* 9:308-345; Bartlett et al. (2008) *Plant Methods* 4:1-12; Bates, G. W. (1999) *Methods in Molecular Biology* 111:359-366; Binns and Thomashow (1988) *Annual Reviews in Microbiology* 42:575-606; Christou, P. (1992) *The Plant Journal* 2:275-281; Christou, P. (1995) *Euphytica* 85:13-27; Tzfira et al. (2004) *TRENDS in Genetics* 20:375-383; Yao et al. (2006) *Journal of Experimental Botany* 57:3737-3746; Zupan and Zambryski (1995) *Plant Physiology* 107:1041-1047; Jones et al. (2005) *Plant Methods* 1:5;

Transformation may result in stable or transient incorporation of the nucleic acid into the cell. "Stable transformation" is intended to mean that the nucleotide construct introduced into a host cell integrates into the genome of the host cell and is capable of being inherited by the progeny thereof. "Transient transformation" is intended to mean that a polynucleotide is introduced into the host cell and does not integrate into the genome of the host cell.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into a transgenic organism, such as a plant, in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Alternatively, cells that have been transformed may be introduced into an organism. These cells could have originated from the organism, wherein the cells are transformed in an ex vivo approach.

The sequences provided herein may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides. Further provided is a processed plant product or byproduct that retains the sequences disclosed herein, including for example, soymeal.

The polynucleotides encoding the RGNs, crRNAs, and/or tracrRNAs can also be used to transform any prokaryotic species, including but not limited to, archaea and bacteria (e.g., *Bacillus* sp., *Klebsiella* sp. *Streptomyces* sp., *Rhizobium* sp., *Escherichia* sp., *Pseudomonas* sp., *Salmonella* sp., *Shigella* sp., *Vibrio* sp., *Yersinia* sp., *Mycoplasma* sp., *Agrobacterium, Lactobacillus* sp.).

The polynucleotides encoding the RGNs, crRNAs, and/or tracrRNAs can be used to transform any eukaryotic species, including but not limited to animals (e.g., mammals, insects, fish, birds, and reptiles), fungi, amoeba, algae, and yeast.

Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256: 808-813 (1992); Nabel & Feigner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10): 1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology, Doerfler and Bohm (eds) (1995); and Yu et al., Gene Therapy 1:13-26 (1994).

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024.

Delivery can be to cells (e.g. in vitro or ex vivo administration) or target tissues (e.g. in vivo administration). The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Viral. 66:2731-2739 (1992); Johann et al., J. Viral. 66:1635-1640 (1992); Sommnerfelt et al., Viral. 176:58-59 (1990); Wilson et al., J. Viral. 63:2374-2378 (1989); Miller et al., 1. Viral. 65:2220-2224 (1991); PCT/US94/05700).

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Katin, Human Gene Therapy 5:793-801 (1994); Muzyczka, I. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., 1. Viral. 63:03822-3828 (1989). Packaging cells are typically used to form virus particles that are capable of infecting a host cell. Such cells include 293 cells, which package adenovirus, and ψJ2 cells or PA317 cells, which package retrovirus.

Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences.

The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLaS3, Huhl, Huh4, Huh7, HUVEC, HASMC, HEKn, HEKa, MiaPaCell, Panel, PC-3, TF1, CTLL-2, CIR, Rat6, CVI, RPTE, AlO, T24, 182, A375, ARH-77, Calul, SW480, SW620, SKOV3, SK-UT, CaCo2, P388D1, SEM-K2, WEHI-231, HB56, TIB55, lurkat, 145.01, LRMB, Bcl-1, BC-3, IC21, DLD2, Raw264.7, NRK, NRK-52E, MRC5, MEF, Hep G2, HeLa B, HeLa T4. COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-I cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr–/–, COR-L23, COR-L23/CPR, COR-L235010, CORL23/R23, COS-7, COV-434, CML Tl, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepalclc7, HL-60, HMEC, HT-29, lurkat, lY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCKII, MDCKII, MOR/0.2R, MONO-MAC 6, MTD-1A, MyEnd, NCI-H69/CPR, NCI-H69/LX 10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)).

In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit.

IV. Variants and Fragments of Polypeptides and Polynucleotides

The present disclosure provides active variants and fragments of a naturally-occurring (i.e., wild-type) RNA-guided nuclease, the amino acid sequence of which is set forth as SEQ ID NOs: 1, 11, 19, 27, 36, 45, or 54, as well as active variants and fragments of naturally-occurring CRISPR repeats, such as the sequence set forth as SEQ ID NOs: 2, 12, 20, 28, 37, 46, or 55, and active variant and fragments of naturally-occurring tracrRNAs, such as the sequence set forth as SEQ ID NOs: 3, 13, 21, 29, 38, 47, or 56, and polynucleotides encoding the same.

While the activity of a variant or fragment may be altered compared to the polynucleotide or polypeptide of interest, the variant and fragment should retain the functionality of the polynucleotide or polypeptide of interest. For example, a variant or fragment may have increased activity, decreased activity, different spectrum of activity or any other alteration in activity when compared to the polynucleotide or polypeptide of interest.

Fragments and variants of naturally-occurring RGN polypeptides, such as those disclosed herein, will retain sequence-specific, RNA-guided DNA-binding activity. In particular embodiments, fragments and variants of naturally-occurring RGN polypeptides, such as those disclosed herein, will retain nuclease activity (single-stranded or double-stranded).

Fragments and variants of naturally-occurring CRISPR repeats, such as those disclosed herein, will retain the ability, when part of a guide RNA (comprising a tracrRNA), to bind to and guide an RNA-guided nuclease (complexed with the guide RNA) to a target nucleotide sequence in a sequence-specific manner.

Fragments and variants of naturally-occurring tracrRNAs, such as those disclosed herein, will retain the ability, when part of a guide RNA (comprising a CRISPR RNA), to guide an RNA-guided nuclease (complexed with the guide RNA) to a target nucleotide sequence in a sequence-specific manner.

The term "fragment" refers to a portion of a polynucleotide or polypeptide sequence of the invention. "Fragments" or "biologically active portions" include polynucleotides comprising a sufficient number of contiguous nucleotides to retain the biological activity (i.e., binding to and directing an RGN in a sequence-specific manner to a target nucleotide sequence when comprised within a guideRNA). "Fragments" or "biologically active portions" include polypeptides comprising a sufficient number of contiguous amino acid residues to retain the biological activity (i.e., binding to a target nucleotide sequence in a sequence-specific manner when complexed with a guide RNA). Fragments of the RGN proteins include those that are shorter than the full-length sequences due to the use of an alternate downstream start site. A biologically active portion of an RGN protein can be a polypeptide that comprises, for example, 10, 25, 50, 100, 150, 200, 250, 300, 350, 400, 450, 500, 550, 600, 650, 700, 750, 800, 850, 900, 950, 1000, 1050 or more contiguous amino acid residues of SEQ ID NOs: 1, 11, 19, 27, 36, 45, or 54. Such biologically active portions can be prepared by recombinant techniques and evaluated for sequence-specific, RNA-guided DNA-binding activity. A biologically active fragment of a CRISPR repeat sequence can comprise at least 8 contiguous amino acids of SEQ ID NOs: 2, 12, 20, 28, 37, 46, or 55. A biologically active portion of a CRISPR repeat sequence can be a polynucleotide that comprises, for example, 8, 9, 10, 11, 12, 13, 14, 15, 16, 17, 18, 19, or 20 contiguous nucleotides of SEQ ID NOs: 2, 12, 20, 28, 37, 46, or 55. A biologically active portion of a tracrRNA can be a polynucleotide that comprises, for example, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80 or more contiguous nucleotides of SEQ ID NOs: 3, 13, 21, 29, 38, 47, or 56.

In general, "variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" or "wild type" polynucleotide or polypeptide comprises a naturally occurring nucleotide sequence or amino acid sequence, respectively. For polynucleotides, conservative variants include those sequences that, because of the degeneracy of the genetic code, encode the native amino acid sequence of the gene of interest. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode the polypeptide or the polynucleotide of interest. Generally, variants of a particular polynucleotide disclosed herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide disclosed herein (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides disclosed herein is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

In particular embodiments, the presently disclosed polynucleotides encode an RNA-guided nuclease polypeptide comprising an amino acid sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to an amino acid sequence of SEQ ID NOs: 1, 11, 19, 27, 36, 45, or 54.

A biologically active variant of an RGN polypeptide of the invention may differ by as few as about 1-15 amino acid residues, as few as about 1-10, such as about 6-10, as few as 5, as few as 4, as few as 3, as few as 2, or as few as 1 amino acid residue. In specific embodiments, the polypeptides can comprise an N-terminal or a C-terminal truncation, which can comprise at least a deletion of 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050 amino acids or more from either the N or C terminus of the polypeptide.

In certain embodiments, the presently disclosed polynucleotides comprise or encode a CRISPR repeat comprising a nucleotide sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to the nucleotide sequence set forth as SEQ ID NOs: 2, 12, 20, 28, 37, 46, or 55.

The presently disclosed polynucleotides can comprise or encode a tracrRNA comprising a nucleotide sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to the nucleotide sequence set forth as SEQ ID NOs: 3, 13, 21, 29, 38, 47, or 56.

Biologically active variants of a CRISPR repeat or tracrRNA of the invention may differ by as few as about 1-15 nucleotides, as few as about 1-10, such as about 6-10, as few as 5, as few as 4, as few as 3, as few as 2, or as few as 1 nucleotides. In specific embodiments, the polynucleotides can comprise a 5' or 3' truncation, which can comprise at least a deletion of 10, 15, 20, 25, 30, 35, 40, 45, 50, 55, 60, 65, 70, 75, 80 nucleotides or more from either the 5' or 3' end of the polynucleotide.

It is recognized that modifications may be made to the RGN polypeptides, CRISPR repeats, and tracrRNAs provided herein creating variant proteins and polynucleotides. Changes designed by man may be introduced through the application of site-directed mutagenesis techniques. Alternatively, native, as yet-unknown or as yet unidentified polynucleotides and/or polypeptides structurally and/or functionally-related to the sequences disclosed herein may also be identified that fall within the scope of the present invention. Conservative amino acid substitutions may be made in nonconserved regions that do not alter the function of the RGN proteins. Alternatively, modifications may be made that improve the activity of the RGN.

Variant polynucleotides and proteins also encompass sequences and proteins derived from a mutagenic and recombinogenic procedure such as DNA shuffling. With such a procedure, one or more different RGN proteins disclosed herein (e.g., SEQ ID NOs: 1, 11, 19, 27, 36, 45, or 54) is manipulated to create a new RGN protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the RGN sequences provided herein and other known RGN genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458. A "shuffled" nucleic acid is a nucleic acid produced by a shuffling procedure such as any shuffling procedure set forth herein. Shuffled nucleic acids are produced by recombining (physically or virtually) two or more nucleic acids (or character strings), for example in an artificial, and optionally recursive, fashion. Generally, one or more screening steps are used in shuffling processes to identify nucleic acids of interest; this screening step can be performed before or after any recombination step. In some (but not all) shuffling embodiments, it is desirable to perform multiple rounds of recombination prior to selection to increase the diversity of the pool to be screened. The overall process of recombination and selection are optionally repeated recursively. Depending on context, shuffling can refer to an overall process of recombination and selection, or, alternately, can simply refer to the recombinational portions of the overall process.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins." In "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Natl. Acad. Sci. USA 89:10915-10919. The BLOSUM62 matrix is often used as a default scoring substitution matrix in sequence alignment protocols. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al. (1997) *Nucleic Acids Res.* 25:3389-3402, and made available to the public at the National Center for Biotechnology Information Website (www.ncbi.nlm.nih.gov). Optimal alignments, including multiple alignments, can be prepared using, e.g., PSI-BLAST, available through www.ncbi.nlm.nih.gov and described by Altschul et al. (1997) *Nucleic Acids Res.* 25:3389-3402.

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

V. Antibodies

Antibodies to the RGN polypeptides or ribonucleoproteins comprising the RGN polypeptides of the present invention, including those having the amino acid sequence set forth as SEQ ID NOs: 1, 11, 19, 27, 36, 45, or 54 or active variants or fragments thereof, are also encompassed. Methods for producing antibodies are well known in the art (see, for example, Harlow and Lane (1988) Antibodies: A Laboratory Manual, Cold Spring Harbor Laboratory, Cold Spring Harbor, N.Y.; and U.S. Pat. No. 4,196,265). These antibodies can be used in kits for the detection and isolation of RGN polypeptides or ribonucleoproteins. Thus, this disclosure provides kits comprising antibodies that specifically bind to the polypeptides or ribonucleoproteins described herein, including, for example, polypeptides having the sequence of SEQ ID NOs: 1, 11, 19, 27, 36, 45, or 54.

VI. Systems and Ribonucleoprotein Complexes for Binding a Target Sequence of Interest and Methods of Making the Same The present disclosure provides a system for binding a target sequence of interest, wherein the system comprises at least one guide RNA or a nucleotide sequence encoding the same, and at least one RNA-guided nuclease or a nucleotide sequence encoding the same. The guide RNA hybridizes to the target sequence of interest and also forms a complex with the RGN polypeptide, thereby directing the RGN polypeptide to bind to the target sequence. In some of these embodiments, the RGN comprises an amino acid sequence of SEQ ID NOs: 1, 11, 19, 27, 36, 45, or 54, or an active variant or fragment thereof.

In various embodiments, the guide RNA comprises a CRISPR repeat sequence comprising the nucleotide sequence of SEQ ID NOs: 2, 12, 20, 28, 37, 46, or 55, or an active variant or fragment thereof. In particular embodiments, the guide RNA comprises a tracrRNA comprising a nucleotide sequence of SEQ ID NOs: 3, 13, 21, 29, 38, 47, or 56, or an active variant or fragment thereof. The guide RNA of the system can be a single guide RNA or a dual-guide RNA. In particular embodiments, the system comprises a RNA-guided nuclease that is heterologous to the guideRNA, wherein the RGN and guideRNA are not naturally complexed in nature.

The system for binding a target sequence of interest provided herein can be a ribonucleoprotein complex, which is at least one molecule of an RNA bound to at least one protein. The ribonucleoprotein complexes provided herein comprise at least one guide RNA as the RNA component and an RNA-guided nuclease as the protein component. Such ribonucleoprotein complexes can be purified from a cell or organism that naturally expresses an RGN polypeptide and has been engineered to express a particular guide RNA that is specific for a target sequence of interest. Alternatively, the ribonucleoprotein complex can be purified from a cell or organism that has been transformed with polynucleotides that encode an RGN polypeptide and a guide RNA and cultured under conditions to allow for the expression of the RGN polypeptide and guide RNA. Thus, methods are provided for making an RGN polypeptide or an RGN ribonucleoprotein complex. Such methods comprise culturing a cell comprising a nucleotide sequence encoding an RGN polypeptide, and in some embodiments a nucleotide sequence encoding a guide RNA, under conditions in which the RGN polypeptide (and in some embodiments, the guide RNA) is expressed. The RGN polypeptide or RGN ribonucleoprotein can then be purified from a lysate of the cultured cells.

Methods for purifying an RGN polypeptide or RGN ribonucleoprotein complex from a lysate of a biological sample are known in the art (e.g., size exclusion and/or affinity chromatography, 2D-PAGE, HPLC, reversed-phase chromatography, immunoprecipitation). In particular methods, the RGN polypeptide is recombinantly produced and comprises a purification tag to aid in its purification, including but not limited to, glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6×His, 10×His, biotin carboxyl carrier protein (BCCP), and calmodulin. Generally, the tagged RGN polypeptide or RGN ribonucleoprotein complex is purified using immobilized metal affinity chromatography. It will be appreciated that other similar methods known in the art may be used, including other forms of chromatography or for example immunoprecipitation, either alone or in combination.

An "isolated" or "purified" polypeptide, or biologically active portion thereof, is substantially or essentially free from components that normally accompany or interact with the polypeptide as found in its naturally occurring environment. Thus, an isolated or purified polypeptide is substantially free of other cellular material, or culture medium when produced by recombinant techniques, or substantially free of chemical precursors or other chemicals when chemically synthesized. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Particular methods provided herein for binding and/or cleaving a target sequence of interest involve the use of an in vitro assembled RGN ribonucleoprotein complex. In vitro assembly of an RGN ribonucleoprotein complex can be performed using any method known in the art in which an RGN polypeptide is contacted with a guide RNA under conditions to allow for binding of the RGN polypeptide to the guide RNA. As used herein, "contact", "contacting", "contacted," refer to placing the components of a desired reaction together under conditions suitable for carrying out the desired reaction. The RGN polypeptide can be purified from a biological sample, cell lysate, or culture medium, produced via in vitro translation, or chemically synthesized. The guide RNA can be purified from a biological sample, cell lysate, or culture medium, transcribed in vitro, or chemically synthesized. The RGN polypeptide and guide RNA can be brought into contact in solution (e.g., buffered saline solution) to allow for in vitro assembly of the RGN ribonucleoprotein complex.

VII. Methods of Binding, Cleaving, or Modifying a Target Sequence

The present disclosure provides methods for binding, cleaving, and/or modifying a target nucleotide sequence of interest. The methods include delivering a system comprising at least one guide RNA or a polynucleotide encoding the same, and at least one RGN polypeptide or a polynucleotide encoding the same to the target sequence or a cell, organelle, or embryo comprising the target sequence. In some of these embodiments, the RGN comprises the amino acid sequence of SEQ ID NOs: 1, 11, 19, 27, 36, 45, or 54, or an active variant or fragment thereof. In various embodiments, the guide RNA comprises a CRISPR repeat sequence comprising the nucleotide sequence of SEQ ID NOs: 2, 12, 20, 28, 37, 46, or 55, or an active variant or fragment thereof. In particular embodiments, the guide RNA comprises a tracrRNA comprising the nucleotide sequence of SEQ ID NOs: 3, 13, 21, 29, 38, 47, or 56, or an active variant or fragment thereof. The guide RNA of the system can be a single guide RNA or a dual-guide RNA. The RGN of the system may be nuclease dead RGN, have nickase activity, or may be a fusion polypeptide. In some embodiments, the fusion polypeptide comprises a base-editing polypeptide, for example a cytidine deaminase or an adenosine deaminase. In particular embodiments, the RGN and/or guide RNA is heterologous to the cell, organelle, or embryo to which the RGN and/or guide RNA (or polynucleotide(s) encoding at least one of the RGN and guide RNA) are introduced.

In those embodiments wherein the method comprises delivering a polynucleotide encoding a guide RNA and/or an RGN polypeptide, the cell or embryo can then be cultured under conditions in which the guide RNA and/or RGN polypeptide are expressed. In various embodiments, the method comprises contacting a target sequence with an RGN ribonucleoprotein complex. The RGN ribonucleoprotein complex may comprise an RGN that is nuclease dead or has nickase activity. In some embodiments, the RGN of the ribonucleoprotein complex is a fusion polypeptide comprising a base-editing polypeptide. In certain embodiments, the method comprises introducing into a cell, organelle, or embryo comprising a target sequence an RGN ribonucleoprotein complex. The RGN ribonucleoprotein complex can be one that has been purified from a biological sample, recombinantly produced and subsequently purified, or in vitro-assembled as described herein. In those embodiments wherein the RGN ribonucleoprotein complex that is contacted with the target sequence or a cell organelle, or embryo has been assembled in vitro, the method can further comprise the in vitro assembly of the complex prior to contact with the target sequence, cell, organelle, or embryo.

A purified or in vitro assembled RGN ribonucleoprotein complex can be introduced into a cell, organelle, or embryo using any method known in the art, including, but not limited to electroporation. Alternatively, an RGN polypeptide and/or polynucleotide encoding or comprising the guide RNA can be introduced into a cell, organelle, or embryo using any method known in the art (e.g., electroporation).

Upon delivery to or contact with the target sequence or cell, organelle, or embryo comprising the target sequence, the guide RNA directs the RGN to bind to the target sequence in a sequence-specific manner. In those embodiments wherein the RGN has nuclease activity, the RGN polypeptide cleaves the target sequence of interest upon binding. The target sequence can subsequently be modified via endogenous repair mechanisms, such as non-homologous end joining, or homology-directed repair with a provided donor polynucleotide.

Methods to measure binding of an RGN polypeptide to a target sequence are known in the art and include chromatin immunoprecipitation assays, gel mobility shift assays, DNA pull-down assays, reporter assays, microplate capture and detection assays. Likewise, methods to measure cleavage or modification of a target sequence are known in the art and include in vitro or in vivo cleavage assays wherein cleavage is confirmed using PCR, sequencing, or gel electrophoresis, with or without the attachment of an appropriate label (e.g., radioisotope, fluorescent substance) to the target sequence to facilitate detection of degradation products. Alternatively, the nicking triggered exponential amplification reaction (NTEXPAR) assay can be used (see, e.g., Zhang et al. (2016) *Chem. Sci.* 7:4951-4957). In vivo cleavage can be evaluated using the Surveyor assay (Guschin et al. (2010) *Methods Mol Biol* 649:247-256).

In some embodiments, the methods involve the use of a single type of RGN complexed with more than one guide RNA. The more than one guide RNA can target different regions of a single gene or can target multiple genes.

In those embodiments wherein a donor polynucleotide is not provided, a double-stranded break introduced by an RGN polypeptide can be repaired by a non-homologous end-joining (NHEJ) repair process. Due to the error-prone nature of NHEJ, repair of the double-stranded break can result in a modification to the target sequence. As used herein, a "modification" in reference to a nucleic acid molecule refers to a change in the nucleotide sequence of the nucleic acid molecule, which can be a deletion, insertion, or substitution of one or more nucleotides, or a combination thereof. Modification of the target sequence can result in the expression of an altered protein product or inactivation of a coding sequence.

In those embodiments wherein a donor polynucleotide is present, the donor sequence in the donor polynucleotide can be integrated into or exchanged with the target nucleotide sequence during the course of repair of the introduced double-stranded break, resulting in the introduction of the exogenous donor sequence. A donor polynucleotide thus comprises a donor sequence that is desired to be introduced into a target sequence of interest. In some embodiments, the donor sequence alters the original target nucleotide sequence such that the newly integrated donor sequence will not be recognized and cleaved by the RGN. Integration of the donor sequence can be enhanced by the inclusion within the donor polynucleotide of flanking sequences that have substantial sequence identity with the sequences flanking the target nucleotide sequence, allowing for a homology-directed repair process. In those embodiments wherein the RGN polypeptide introduces double-stranded staggered breaks, the donor polynucleotide can comprise a donor sequence flanked by compatible overhangs, allowing for direct ligation of the donor sequence to the cleaved target nucleotide sequence comprising overhangs by a non-homologous repair process during repair of the double-stranded break.

In those embodiments wherein the method involves the use of an RGN that is a nickase (i.e., is only able to cleave a single strand of a double-stranded polynucleotide), the method can comprise introducing two RGN nickases that target identical or overlapping target sequences and cleave different strands of the polynucleotide. For example, an RGN nickase that only cleaves the positive (+) strand of a double-stranded polynucleotide can be introduced along with a second RGN nickase that only cleaves the negative (−) strand of a double-stranded polynucleotide.

In various embodiments, a method is provided for binding a target nucleotide sequence and detecting the target sequence, wherein the method comprises introducing into a cell, organelle, or embryo at least one guide RNA or a polynucleotide encoding the same, and at least one RGN polypeptide or a polynucleotide encoding the same, expressing the guide RNA and/or RGN polypeptide (if coding sequences are introduced), wherein the RGN polypeptide is a nuclease-dead RGN and further comprises a detectable label, and the method further comprises detecting the detectable label. The detectable label may be fused to the RGN as a fusion protein (e.g., fluorescent protein) or may be a small molecule conjugated to or incorporated within the RGN polypeptide that can be detected visually or by other means.

Also provided herein are methods for modulating the expression of a target sequence or a gene of interest under the regulation of a target sequence. The methods comprise introducing into a cell, organelle, or embryo at least one guide RNA or a polynucleotide encoding the same, and at least one RGN polypeptide or a polynucleotide encoding the same, expressing the guide RNA and/or RGN polypeptide (if coding sequences are introduced), wherein the RGN polypeptide is a nuclease-dead RGN. In some of these embodiments, the nuclease-dead RGN is a fusion protein comprising an expression modulator domain (i.e., epigenetic modification domain, transcriptional activation domain or a transcriptional repressor domain) as described herein.

The present disclosure also provides methods for binding and/or modifying a target nucleotide sequence of interest. The methods include delivering a system comprising at least one guide RNA or a polynucleotide encoding the same, and at least one fusion polypeptide comprises an RGN of the invention and a base-editing polypeptide, for example a cytidine deaminase or an adenosine deaminase, or a polynucleotide encoding the fusion polypeptide, to the target sequence or a cell, organelle, or embryo comprising the target sequence.

One of ordinary skill in the art will appreciate that any of the presently disclosed methods can be used to target a single target sequence or multiple target sequences. Thus, methods comprise the use of a single RGN polypeptide in combination with multiple, distinct guide RNAs, which can target multiple, distinct sequences within a single gene and/or multiple genes. Also encompassed herein are methods wherein multiple, distinct guide RNAs are introduced in combination with multiple, distinct RGN polypeptides. These guide RNAs and guide RNA/RGN polypeptide systems can target multiple, distinct sequences within a single gene and/or multiple genes.

In one aspect, the invention provides kits containing any one or more of the elements disclosed in the above methods and compositions. In some embodiments, the kit comprises a vector system and instructions for using the kit. In some embodiments, the vector system comprises (a) a first regulatory element operably linked to a tracr mate sequence and one or more insertion sites for inserting a guide sequence upstream of the tracr mate sequence, wherein when expressed, the guide sequence directs sequence-specific binding of a CRISPR complex to a target sequence in a eukaryotic cell, wherein the CRISPR complex comprises a CRIS PR enzyme complexed with (1) the guide sequence that is hybridized to the target sequence, and (2) the tracr mate sequence that is hybridized to the tracr sequence; and/or (b) a second regulatory element operably linked to an enzyme coding sequence encoding said CRISPR enzyme comprising a nuclear localization sequence. Elements may be provided individually or in combinations, and may be provided in any suitable container, such as a vial, a bottle, or a tube.

In some embodiments, the kit includes instructions in one or more languages. In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10.

In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide.

VIII. Target Polynucleotides

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including microalgae) and modifying the cell or cells. Culturing may occur at any stage ex vivo. The cell or cells may even be re-introduced into the non-human animal or plant (including micro-algae).

Using natural variability, plant breeders combine most useful genes for desirable qualities, such as yield, quality, uniformity, hardiness, and resistance against pests. These desirable qualities also include growth, day length preferences, temperature requirements, initiation date of floral or reproductive development, fatty acid content, insect resistance, disease resistance, nematode resistance, fungal resistance, herbicide resistance, tolerance to various environmental factors including drought, heat, wet, cold, wind, and adverse soil conditions including high salinity The sources of these useful genes include native or foreign varieties, heirloom varieties, wild plant relatives, and induced mutations, e.g., treating plant material with mutagenic agents. Using the present invention, plant breeders are provided with a new tool to induce mutations. Accordingly, one skilled in the art can analyze the genome for sources of useful genes, and in varieties having desired characteristics or traits employ the present invention to induce the rise of useful genes, with more precision than previous mutagenic agents and hence accelerate and improve plant breeding programs.

The target polynucleotide of an RGN system can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence).

The target polynucleotide of a CRISPR complex may include a number of disease-associated genes and polynucleotides as well as signaling biochemical pathway-associated genes and polynucleotides. Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non-disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease (e.g., a causal mutation). The transcribed or translated products may be known or unknown, and further may be at a normal or abnormal level. Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web.

Although CRISPR systems are particularly useful for their relative ease in targeting to genomic sequences of interest, there still remains an issue of what the RGN can do to address a causal mutation. One approach is to produce a fusion protein between an RGN (preferably an inactive or nickase variant of the RGN) and a base-editing enzyme or the active domain of a base editing enzyme, such as an cytidine deaminase or an adenosine deaminase base editor (U.S. Pat. No. 9,840,699, herein incorporated by reference). In some embodiments, the methods comprise contacting a DNA molecule with (a) a fusion protein comprising an RGN of the invention and a base-editing polypeptide such as a deaminase; and (b) a gRNA targeting the fusion protein of (a) to a target nucleotide sequence of the DNA strand; wherein the DNA molecule is contacted with the fusion protein and the gRNA in an amount effective and under conditions suitable for the deamination of a nucleotide base. In some embodiments, the target DNA sequence comprises a sequence associated with a disease or disorder, and wherein the deamination of the nucleotide base results in a sequence that is not associated with a disease or disorder. In some embodiments, the target DNA sequence resides in an allele of a crop plant, wherein the particular allele of the trait of interest results in a plant of lesser agronomic value. The deamination of the nucleotide base results in an allele that improves the trait and increases the agronomic value of the plant.

In some embodiments, the DNA sequence comprises a T-C or A-G point mutation associated with a disease or disorder, and wherein the deamination of the mutant C or G base results in a sequence that is not associated with a disease or disorder. In some embodiments, the deamination corrects a point mutation in the sequence associated with the disease or disorder.

In some embodiments, the sequence associated with the disease or disorder encodes a protein, and wherein the deamination introduces a stop codon into the sequence associated with the disease or disorder, resulting in a truncation of the encoded protein. In some embodiments, the contacting is performed in vivo in a subject susceptible to having, having, or diagnosed with the disease or disorder. In some embodiments, the disease or disorder is a disease associated with a point mutation, or a single-base mutation, in the genome. In some embodiments, the disease is a genetic disease, a cancer, a metabolic disease, or a lysosomal storage disease.

Further examples of loci which are causal for certain genetic diseases, particularly loci which can be readily targeted by RGNs or RGN-base editor fusion proteins of the invention, can be found in Example 9 and corresponding Table 12.

Hurler Syndrome

An example of a genetically inherited disease which could be corrected using an approach that relies on an RGN-base editor fusion protein of the invention is Hurler Syndrome. Hurler Syndrome, also known as MPS-1, is the result of a deficiency of α-L-iduronidase (IDUA) resulting in a lysosomal storage disease characterized at the molecular level by the accumulation of dermatan sulfate and heparan sulfate in lysosomes. This disease is generally an inherited genetic disorder caused by mutations in the IDUA gene encoding α-L-iduronidase. Common IDUA mutations are W402X and Q70X, both nonsense mutations resulting in premature termination of translation. Such mutations are well addressed by precise genome editing (PGE) approaches, since reversion of a single nucleotide, for example by a base-editing approach, would restore the wild-type coding sequence and result in protein expression controlled by the endogenous regulatory mechanisms of the genetic locus. Additionally, since heterozygotes are known to be asymptomatic, a PGE therapy that targets one of these mutations would be useful to a large proportion of patients with this disease, as only one of the mutated alleles needs to be corrected (Bunge et al. (1994) Hum. Mol. Genet. 3(6): 861-866, herein incorporated by reference).

Current treatments for Hurler Syndrome include enzyme replacement therapy and bone marrow transplants (Vellodi et al. (1997) Arch. Dis. Child. 76(2): 92-99; Peters et al. (1998) Blood 91(7): 2601-2608, herein incorporated by reference). While enzyme replacement therapy has had a dramatic effect on the survival and quality of life of Hurler Syndrome patients, this approach requires costly and time-consuming weekly infusions. Additional approaches include the delivery of the IDUA gene on an expression vector or the insertion of the gene into a highly expressed locus such as that of serum albumin (U.S. Pat. No. 9,956,247, herein incorporated by reference). However, these approaches do not restore the original IDUA locus to the correct coding sequence. A genome-editing strategy would have a number of advantages, most notably that regulation of gene expression would be controlled by the natural mechanisms present in healthy individuals. Additionally, using base editing does not necessitate causing a double stranded DNA breaks, which could lead to large chromosomal rearrangements, cell death, or oncogenecity by the disruption of tumor suppression mechanisms. An enabling description of a method to correct the causal mutation of this disease is provided in Example 10. The described methods are an example of a general strategy directed toward using RGN-base editor fusion proteins of the invention to target and correct certain disease-causing mutations in the human genome. It will be appreciated that similar approaches to target diseases such as those described in Table 12 may also be pursued. It will be further appreciated that similar approaches to target disease-causing mutations in other species, particularly common household pets or livestock, can also be deployed using the RGNs of the invention. Common household pets and livestock include dogs, cats, horses, pigs, cows, sheep, chickens, donkeys, snakes, ferrets, fish including salmon, and shrimp.

Friedreich's Ataxia

RGNs of the invention could also be useful in human therapeutic approaches where the causal mutation is more complicated. For example, some diseases such as Friedreich's Ataxia and Huntington's Disease are the result of a significant increase in repeats of a three nucleotide motif at a particular region of a gene, which affects the ability of the expressed protein to function or to be expressed. Friedreich's Ataxia (FRDA) is an autosomal recessive disease resulting in progressive degeneration of nervous tissue in the spinal cord. Reduced levels of the frataxin (FXN) protein in the mitochondria cause oxidative damages and iron deficiencies at the cellular level. The reduced FXN expression has been linked to a GAA triplet expansion within the intron 1 of the somatic and germline FXN gene. In FRDA patients, the GAA repeat frequently consists of more than 70, sometimes even more than 1000 (most commonly 600-900) triplets, whereas unaffected individuals have about 40 repeats or less (Pandolfo et al. (2012) Handbook of Clinical Neurology 103: 275-294; Campuzano et al. (1996) Science 271: 1423-1427; Pandolfo (2002) Adv. Exp. Med. Biol. 516: 99-118; all herein incorporated by reference).

The expansion of the trinucleotide repeat sequence causing Friedreich's Ataxia (FRDA) occurs in a defined genetic locus within the FXN gene, referred to as the FRDA instability region. RNA guided nucleases (RGNs) may be used for excising the instability region in FRDA patient cells. This approach requires 1) an RGN and guide RNA sequence that can be programmed to target the allele in the human genome; and 2) a delivery approach for the RGN and guide sequence. Many nucleases used for genome editing, such as the commonly used Cas9 nuclease from $S.$ $pyogenes$ (SpCas9), are too large to be packaged into adeno-associated viral (AAV) vectors, especially when considering the length of the SpCas9 gene and the guide RNA in addition to other genetic elements required for functional expression cassettes. This makes an approach using SpCas9 more difficult.

The compact RNA guided nucleases of the invention, particularly APG07433.1 and APG08290.1, are uniquely well suited for the excision of the FRDA instability region. Each RGN has a PAM requirement that is in the vicinity of the FRDA instability region. Additionally, each of these RGNs can be packaged into an AAV vector along with a guide RNA. Packing two guide RNAs would likely require a second vector, but this approach still compares favorably to what would be required of a larger nuclease such as SpCas9, which may require splitting the protein sequence between two vectors. An enabling description of a method to correct the causal mutation of this disease is provided in Example 11. The described methods encompass a strategy using RGNs of the invention in which a region of genomic instability is removed. Such a strategy is applicable to other diseases and disorders which have a similar genetic basis, such as Huntington's Disease. Similar strategies using RGNs of the invention may also be applicable to similar diseases and disorders in non-human animals of agronomic or economic importance, including dogs, cats, horses, pigs, cows, sheep, chickens, donkeys, snakes, ferrets, fish including salmon, and shrimp Hemoglobinopathies RGNs of the invention could also be to introduce disruptive mutations that may result in a beneficial effect. Genetic defects in the genes encoding hemoglobin, particularly the beta globin chain (the HBB gene), can be responsible for a number of diseases known as hemoglobinopathies, including sickle cell anemia and thalassemias.

In adult humans, hemoglobin is a heterotetramer comprising two alpha (α)-like globin chains and two beta (β)-like globin chains and 4 heme groups. In adults the a2β2 tetramer is referred to as Hemoglobin A (HbA) or adult hemoglobin. Typically, the alpha and beta globin chains are synthesized in an approximate 1:1 ratio and this ratio seems to be critical in terms of hemoglobin and red blood cell (RBC) stabilization. In a developing fetus, a different form of hemoglobin, fetal hemoglobin (HbF), is produced which has a higher binding affinity for oxygen than Hemoglobin A such that oxygen can be delivered to the baby's system via the mother's blood stream. Fetal hemoglobin also contains two a globin chains, but in place of the adult β-globin chains, it has two fetal gamma (γ)-globin chains (i.e., fetal hemoglobin is α2γ2). The regulation of the switch from production of gamma- to beta-globin is quite complex, and primarily involves a down-regulation of gamma globin transcription with a simultaneous up-regulation of beta globin transcription. At approximately 30 weeks of gestation, the synthesis of gamma globin in the fetus starts to drop while the production of beta globin increases. By approximately 10 months of age, the newborn's hemoglobin is nearly all α2β2 although some HbF persists into adulthood (approximately 1-3% of total hemoglobin). In the majority of patients with hemoglobinopathies, the genes encoding gamma globin remain present, but expression is relatively low due to normal gene repression occurring around parturition as described above.

Sickle cell disease is caused by a V6E mutation in the 3 globin gene (HBB) (a GAG to GTG at the DNA level), where the resultant hemoglobin is referred to as "hemoglobinS" or "HbS." Under lower oxygen conditions, HbS molecules aggregate and form fibrous precipitates. These aggregates cause the abnormality or 'sickling' of the RBCs, resulting in a loss of flexibility of the cells. The sickling RBCs are no longer able to squeeze into the capillary beds and can result in vaso-occlusive crisis in sickle cell patients. In addition, sickled RBCs are more fragile than normal RBCs, and tend towards hemolysis, eventually leading to anemia in the patient.

Treatment and management of sickle cell patients is a life-long proposition involving antibiotic treatment, pain management and transfusions during acute episodes. One approach is the use of hydroxyurea, which exerts its effects in part by increasing the production of gamma globin. Long term side effects of chronic hydroxyurea therapy are still unknown, however, and treatment gives unwanted side effects and can have variable efficacy from patient to patient. Despite an increase in the efficacy of sickle cell treatments, the life expectancy of patients is still only in the mid to late 50's and the associated morbidities of the disease have a profound impact on a patient's quality of life.

Thalassemias (alpha thalassemias and beta thalassemia) are also diseases relating to hemoglobin and typically involve a reduced expression of globin chains. This can occur through mutations in the regulatory regions of the genes or from a mutation in a globin coding sequence that results in reduced expression or reduced levels or functional globin protein. Treatment of thalassemias usually involves blood transfusions and iron chelation therapy. Bone marrow transplants are also being used for treatment of people with severe thalassemias if an appropriate donor can be identified, but this procedure can have significant risks.

One approach that has been proposed for the treatment of both SCD and beta thalassemias is to increase the expression of gamma globin so that HbF functionally replaces the aberrant adult hemoglobin As mentioned above, treatment of SCD patients with hydroxyurea is thought to be successful in part due to its effect on increasing gamma globin expression (DeSimone (1982) Proc Nat'l Acad Sci USA 79(14): 4428-31; Ley, et al., (1982) N. Engl. J. Medicine, 307: 1469-1475; Ley, et al., (1983) Blood 62: 370-380; Constantoulakis et al., (1988) Blood 72(6):1961-1967, all herein incorporated by reference). Increasing the expression of HbF involves identification of genes whose products play a role in the regulation of gamma globin expression. One such gene is BCL11A. BCL11A encodes a zinc finger protein that is expressed in adult erythroid precursor cells, and down-regulation of its expression leads to an increase in gamma globin expression (Sankaran et at (2008) Science 322: 1839, herein incorporated by reference). Use of an inhibitory RNA targeted to the BCL11A gene has been proposed (e.g., U.S. Patent Publication 2011/0182867, herein incorporated by reference) but this technology has several potential drawbacks, including that complete knock down may not be achieved, delivery of such RNAs may be problematic, and the RNAs must be present continuously, requiring multiple treatments for life.

RGNs of the invention may be used to target the BCL11A enhancer region to disrupt expression of BCL 11A, thereby increasing gamma globin expression. This targeted disruption can be achieved by non-homologous end joining (NHEJ), whereby an RGN of the invention targets to a particular sequence within the BCL11A enhancer region, makes a double-stranded break, and the cell's machinery repairs the break, typically simultaneously introducing deleterious mutations. Similar to what is described for other disease targets, the RGNs of the invention have advantages over other known RGNs due to their relatively small size, which enables packaging expression cassettes for the RGN and its guide RNA into a single AAV vector for in vivo delivery. An enabling description of this method is provided in Example 12. Similar strategies using RGNs of the invention may also be applicable to similar diseases and disorders in both humans and in non-human animals of agronomic or economic importance.

IX. Cells Comprising a Polynucleotide Genetic Modification

Provided herein are cells and organisms comprising a target sequence of interest that has been modified using a process mediated by an RGN, crRNA, and/or tracrRNA as described herein. In some of these embodiments, the RGN comprises the amino acid sequence of SEQ ID NOs: 1, 11, 19, 27, 36, 45, or 54, or an active variant or fragment thereof. In various embodiments, the guide RNA comprises a CRISPR repeat sequence comprising the nucleotide sequence of SEQ ID NOs: 2, 12, 20, 28, 37, 46, or 55, or an active variant or fragment thereof. In particular embodiments, the guide RNA comprises a tracrRNA comprising the nucleotide sequence of SEQ ID NOs: 3, 13, 21, 29, 38, 47, or 56, or an active variant or fragment thereof. The guide RNA of the system can be a single guide RNA or a dual-guide RNA.

The modified cells can be eukaryotic (e.g., mammalian, plant, insect cell) or prokaryotic. Also provided are organelles and embryos comprising at least one nucleotide sequence that has been modified by a process utilizing an RGN, crRNA, and/or tracrRNA as described herein. The genetically modified cells, organisms, organelles, and embryos can be heterozygous or homozygous for the modified nucleotide sequence.

The chromosomal modification of the cell, organism, organelle, or embryo can result in altered expression (up-regulation or down-regulation), inactivation, or the expression of an altered protein product or an integrated sequence. In those instances wherein the chromosomal modification results in either the inactivation of a gene or the expression of a non-functional protein product, the genetically modified cell, organism, organelle, or embryo is referred to as a "knock out". The knock out phenotype can be the result of a deletion mutation (i.e., deletion of at least one nucleotide), an insertion mutation (i.e., insertion of at least one nucleotide), or a nonsense mutation (i.e., substitution of at least one nucleotide such that a stop codon is introduced).

Alternatively, the chromosomal modification of a cell, organism, organelle, or embryo can produce a "knock in", which results from the chromosomal integration of a nucleotide sequence that encodes a protein. In some of these embodiments, the coding sequence is integrated into the chromosome such that the chromosomal sequence encoding the wild-type protein is inactivated, but the exogenously introduced protein is expressed.

In other embodiments, the chromosomal modification results in the production of a variant protein product. The expressed variant protein product can have at least one amino acid substitution and/or the addition or deletion of at least one amino acid. The variant protein product encoded by the altered chromosomal sequence can exhibit modified characteristics or activities when compared to the wild-type protein, including but not limited to altered enzymatic activity or substrate specificity.

In yet other embodiments, the chromosomal modification can result in an altered expression pattern of a protein. As a non-limiting example, chromosomal alterations in the regulatory regions controlling the expression of a protein product can result in the overexpression or downregulation of the protein product or an altered tissue or temporal expression pattern.

The article "a" and "an" are used herein to refer to one or more than one (i.e., to at least one) of the grammatical object of the article. By way of example, "a polypeptide" means one or more polypeptides.

All publications and patent applications mentioned in the specification are indicative of the level of those skilled in the art to which this disclosure pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended embodiments.

Non-Limiting Embodiments Include

1. A nucleic acid molecule comprising a polynucleotide encoding an RNA-guided nuclease (RGN) polypeptide, wherein said polynucleotide comprises a nucleotide sequence encoding an RGN polypeptide comprising an amino acid sequence having at least 95% sequence identity to SEQ ID NOs: 1, 11, 19, 27, 36, 45, or 54; wherein said RGN polypeptide binds a target DNA sequence in an RNA-guided sequence specific manner when bound to a guide RNA (gRNA) capable of hybridizing to said target DNA sequence, and
wherein said polynucleotide encoding an RGN polypeptide is operably linked to a promoter heterologous to said polynucleotide.

2. The nucleic acid molecule of embodiment 1, wherein said RGN polypeptide is capable of cleaving said target DNA sequence upon binding.

3. The nucleic acid molecule of embodiment 2, wherein cleavage by said RGN polypeptide generates a double-stranded break.

4. The nucleic acid molecule of embodiment 2, wherein cleavage by said RGN polypeptide generates a single-stranded break.

5. The nucleic acid molecule of any one of embodiments 1-4, wherein the RGN polypeptide is operably fused to a base-editing polypeptide.

6. The nucleic acid molecule of any one of embodiments 1-5, wherein the RGN polypeptide comprises one or more nuclear localization signals.

7. The nucleic acid molecule of any one of embodiments 1-6, wherein the RGN polypeptide is codon optimized for expression in a eukaryotic cell.

8. The nucleic acid molecule of any one of embodiments 1-7, wherein said target DNA sequence is located adjacent to a protospacer adjacent motif (PAM).

9. A vector comprising the nucleic acid molecule of any one of embodiments 1-8.

10. The vector of embodiment 9, further comprising at least one nucleotide sequence encoding said gRNA capable of hybridizing to said target DNA sequence.

11. The vector of embodiment 10, where said gRNA is a single guide RNA.

12. The vector of embodiment 10, wherein said gRNA is a dual-guide RNA.

13. The vector of any one of embodiments 10-12, wherein the guide RNA comprises a CRISPR RNA comprising a CRISPR repeat sequence having at least 95% sequence identity to SEQ ID NOs: 2, 12, 20, 28, 37, 46, or 55.

14. The vector of any one of embodiments 10-13, wherein the guide RNA comprises a tracrRNA having at least 95% sequence identity to SEQ ID NOs: 3, 13, 21, 29, 38, 47, or 56.

15. A cell comprising the nucleic acid molecule of any one of embodiments 1-8 or the vector of any one of embodiments 9-14.

16. A method for making an RGN polypeptide comprising culturing the cell of embodiment 15 under conditions in which the RGN polypeptide is expressed.

17. A method for making an RGN polypeptide comprising introducing into a cell a heterologous nucleic acid molecule comprising a nucleotide sequence encoding an RNA-guided nuclease (RGN) polypeptide comprising an amino acid sequence having at least 95% sequence identity to SEQ ID NOs: 1, 11, 19, 27, 36, 45, or 54;
wherein said RGN polypeptide binds a target DNA sequence in an RNA-guided sequence specific manner when bound to a guide RNA (gRNA) capable of hybridizing to said target DNA sequence;
and culturing said cell under conditions in which the RGN polypeptide is expressed.

18. The method of embodiment 16 or 17, further comprising purifying said RGN polypeptide.

19. The method of embodiment 16 or 17, wherein said cell further expresses one or more guide RNAs that binds to said RGN polypeptide to form an RGN ribonucleoprotein complex.

20. The method of embodiment 19, further comprising purifying said RGN ribonucleoprotein complex.

21. A nucleic acid molecule comprising a polynucleotide encoding a CRISPR RNA (crRNA), wherein said crRNA comprises a spacer sequence and a CRISPR repeat sequence, wherein said CRISPR repeat sequence comprises a nucleotide sequence having at least 95% sequence identity to SEQ ID NOs: 2, 12, 20, 28, 37, 46, or 55;
wherein a guide RNA comprising:
a) said crRNA; and
b) a trans-activating CRISPR RNA (tracrRNA) hybridized to said CRISPR repeat sequence of said crRNA;
is capable of hybridizing to a target DNA sequence in a sequence specific manner through the spacer sequence of said crRNA when said guide RNA is bound to an RNA-guided nuclease (RGN) polypeptide, and
wherein said polynucleotide encoding a crRNA is operably linked to a promoter heterologous to said polynucleotide.

22. A vector comprising the nucleic acid molecule of embodiment 21.

23. The vector of embodiment 22, wherein said vector further comprises a polynucleotide encoding said tracrRNA.

24. The vector of embodiment 23, wherein said tracrRNA comprises a nucleotide sequence having at least 95% sequence identity to SEQ ID NOs: 3, 13, 21, 29, 38, 47, or 56.

25. The vector of embodiment 23 or 24, wherein said polynucleotide encoding said crRNA and said polynucleotide encoding said tracrRNA are operably linked to the same promoter and are encoded as a single guide RNA.

26. The vector of embodiment 23 or 24, wherein said polynucleotide encoding said crRNA and said polynucleotide encoding said tracrRNA are operably linked to separate promoters.

27. The vector of any one of embodiments 22-26, wherein said vector further comprises a polynucleotide encoding said RGN polypeptide, wherein said RGN polypeptide comprises an amino acid sequence having at least 95% sequence identity to SEQ ID NOs: 1, 11, 19, 27, 36, 45, or 54.

28. A nucleic acid molecule comprising a polynucleotide encoding a trans-activating CRISPR RNA (tracrRNA) comprising a nucleotide sequence having at least 95% sequence identity to SEQ ID NOs: 3, 13, 21, 29, 38, 47, or 56;
wherein a guide RNA comprising:
a) said tracrRNA; and
b) a crRNA comprising a spacer sequence and a CRISPR repeat sequence, wherein said tracrRNA hybridizes with said CRISPR repeat sequence of said crRNA;
is capable of hybridizing to a target DNA sequence in a sequence specific manner through the spacer sequence of said crRNA when said guide RNA is bound to an RNA-guided nuclease (RGN) polypeptide, and
wherein said polynucleotide encoding a tracrRNA is operably linked to a promoter heterologous to said polynucleotide.

29. A vector comprising the nucleic acid molecule of embodiment 28.

30. The vector of embodiment 29, wherein said vector further comprises a polynucleotide encoding said crRNA.

31. The vector of embodiment 30, wherein the CRISPR repeat sequence of said crRNA comprises a nucleotide sequence having at least 95% sequence identity to SEQ ID NOs: 2, 12, 20, 28, 37, 46, or 55.

32. The vector of embodiment 30 or 31, wherein said polynucleotide encoding said crRNA and said polynucleotide encoding said tracrRNA are operably linked to the same promoter and are encoded as a single guide RNA.

33. The vector of embodiment 30 or 31, wherein said polynucleotide encoding said crRNA and said polynucleotide encoding said tracrRNA are operably linked to separate promoters.

34. The vector of any one of embodiments 29-33, wherein said vector further comprises a polynucleotide encoding said RGN polypeptide, wherein said RGN polypeptide comprises an amino acid sequence having at least 95% sequence identity to SEQ ID NOs: 1, 11, 19, 27, 36, 45, or 54.

35. A system for binding a target DNA sequence, said system comprising:
a) one or more guide RNAs capable of hybridizing to said target DNA sequence or one or more nucleotide sequences encoding the one or more guide RNAs (gRNAs); and
b) an RNA-guided nuclease (RGN) polypeptide comprising an amino acid sequence having at least 95% sequence identity to SEQ ID NOs: 1, 11, 19, 27, 36, 45, or 54 or a nucleotide sequence encoding the RGN polypeptide;
wherein said nucleotide sequences encoding the one or more guide RNAs and encoding the RGN polypeptide are each operably linked to a promoter heterologous to said nucleotide sequence;
wherein the one or more guide RNAs hybridize to the target DNA sequence, and
wherein the one or more guide RNAs form a complex with the RGN polypeptide, thereby directing said RGN polypeptide to bind to said target DNA sequence.

36. The system of embodiment 35, wherein said gRNA is a single guide RNA (sgRNA).

37. The system of embodiment 35, wherein said gRNA is a dual-guide RNA.

38. The system of any one of embodiments 35-37, wherein said gRNA comprises a CRISPR repeat sequence comprising a nucleotide sequence having at least 95% sequence identity to SEQ ID NOs: 2, 12, 20, 28, 37, 46, or 55.

39. The system of any one of embodiments 35-38, wherein said gRNA comprises a tracrRNA comprising a nucleotide sequence having at least 95% sequence identity to SEQ ID NOs: 3, 13, 21, 29, 38, 47, or 56.

40. The system of any one of embodiments 35-39, wherein said target DNA sequence is located adjacent to a protospacer adjacent motif (PAM).

41. The system of any one of embodiments 35-40, wherein the target DNA sequence is within a cell.

42. The system of embodiment 41, wherein the cell is a eukaryotic cell.

43. The system of embodiment 42, wherein the eukaryotic cell is a plant cell.

44. The system of embodiment 42, wherein the eukaryotic cell is a mammalian cell.

45. The system of embodiment 42, wherein the eukaryotic cell is an insect cell.

46. The system of embodiment 41, wherein the cell is a prokaryotic cell.

47. The system of any one of embodiments 35-46, wherein when transcribed the one or more guide RNAs hybridize to the target DNA sequence and the guide RNA forms a complex with the RGN polypeptide which causes cleavage of the target DNA sequence.

48. The system of embodiment 47, wherein the cleavage generates a double-stranded break.

49. The system of embodiment 47, wherein cleavage by said RGN polypeptide generates a single-stranded break.

50. The system of any one of embodiments 35-49, wherein the RGN polypeptide is operably linked to a base-editing polypeptide.

51. The system of any one of embodiments 35-50, wherein the RGN polypeptide comprises one or more nuclear localization signals.

52. The system of any one of embodiments 35-51, wherein the RGN polypeptide is codon optimized for expression in a eukaryotic cell.

53. The system of any one of embodiments 35-52, wherein nucleotide sequences encoding the one or more guide RNAs and the nucleotide sequence encoding an RGN polypeptide are located on one vector.

54. The system of any one of embodiments 35-53, wherein said system further comprises one or more donor polynucleotides or one or more nucleotide sequences encoding the one or more donor polynucleotides.

55. A method for binding a target DNA sequence comprising delivering a system according to any one of embodiments 35-54, to said target DNA sequence or a cell comprising the target DNA sequence.

56. The method of embodiment 55, wherein said RGN polypeptide or said guide RNA further comprises a detectable label, thereby allowing for detection of said target DNA sequence.

57. The method of embodiment 55, wherein said guide RNA or said RGN polypeptide further comprises an expression modulator, thereby modulating expression of said target DNA sequence or a gene under transcriptional control by said target DNA sequence.

58. A method for cleaving or modifying a target DNA sequence comprising delivering a system according to any one of embodiments 35-54, to said target DNA sequence or a cell comprising the target DNA sequence.

59. The method of embodiment 58, wherein said modified target DNA sequence comprises insertion of heterologous DNA into the target DNA sequence.

60. The method of embodiment 58, wherein said modified target DNA sequence comprises deletion of at least one nucleotide from the target DNA sequence.

61. The method of embodiment 58, wherein said modified target DNA sequence comprises mutation of at least one nucleotide in the target DNA sequence.

62. A method for binding a target DNA sequence comprising:
a) assembling a RNA-guided nuclease (RGN) ribonucleotide complex in vitro by combining:
i) one or more guide RNAs capable of hybridizing to the target DNA sequence; and
ii) an RGN polypeptide comprising an amino acid sequence having at least 95% sequence identity to SEQ ID NOs: 1, 11, 19, 27, 36, 45, or 54;
under conditions suitable for formation of the RGN ribonucleotide complex; and
b) contacting said target DNA sequence or a cell comprising said target DNA sequence with the in vitro-assembled RGN ribonucleotide complex;
wherein the one or more guide RNAs hybridize to the target DNA sequence, thereby directing said RGN polypeptide to bind to said target DNA sequence.

63. The method of embodiment 62, wherein said RGN polypeptide or said guide RNA further comprises a detectable label, thereby allowing for detection of said target DNA sequence.

64. The method of embodiment 62, wherein said guide RNA or said RGN polypeptide further comprises an expression modulator, thereby allowing for the modulation of expression of said target DNA sequence.

65. A method for cleaving and/or modifying a target DNA sequence, comprising contacting the DNA molecule with:
a) an RNA-guided nuclease (RGN) polypeptide, wherein said RGN comprises an amino acid sequence having at least 95% sequence identity to SEQ ID NOs: 1, 11, 19, 27, 36, 45 or 54; and
b) one or more guide RNAs capable of targeting the RGN of (a) to the target DNA sequence;
wherein the one or more guide RNAs hybridize to the target DNA sequence, thereby directing said RGN polypeptide to bind to said target DNA sequence and cleavage and/or modification of said target DNA sequence occurs.

66. The method of embodiment 65, wherein said modified target DNA sequence comprises insertion of heterologous DNA into the target DNA sequence.

67. The method of embodiment 65, wherein said modified target DNA sequence comprises deletion of at least one nucleotide from the target DNA sequence.

68. The method of embodiment 65, wherein said modified target DNA sequence comprises mutation of at least one nucleotide in the target DNA sequence.

69. The method of any one of embodiments 62-68, wherein said gRNA is a single guide RNA (sgRNA).

70. The method of any one of embodiments 62-68, wherein said gRNA is a dual-guide RNA.

71. The method of any one of embodiments 62-70, wherein said gRNA comprises a CRISPR repeat sequence comprising a nucleotide sequence having at least 95% sequence identity to SEQ ID NOs: 2, 12, 20, 28, 37, 46, or 55.

72. The method of any one of embodiments 62-71, wherein said gRNA comprises a tracrRNA comprising a nucleotide sequence having at least 95% sequence identity to SEQ ID NOs: 3, 13, 21, 29, 38, 47, or 56.

73. The method of any one of embodiments 62-72, wherein said target DNA sequence is located adjacent to a protospacer adjacent motif (PAM).

74. The method of any one of embodiments 55-73, wherein the target DNA sequence is within a cell.

75. The method of embodiment 74, wherein the cell is a eukaryotic cell.

76. The method of embodiment 75, wherein the eukaryotic cell is a plant cell.

77. The method of embodiment 75, wherein the eukaryotic cell is a mammalian cell.

78. The method of embodiment 75, wherein the eukaryotic cell is an insect cell.

79. The method of embodiment 74, wherein the cell is a prokaryotic cell.

80. The method of any one of embodiments 74-79, further comprising culturing the cell under conditions in which the RGN polypeptide is expressed and cleaves the target DNA sequence to produce a modified DNA sequence; and selecting a cell comprising said modified DNA sequence.

81. A cell comprising a modified target DNA sequence according to the method of embodiment 80.

82. The cell of embodiment 81, wherein the cell is a eukaryotic cell.

83. The cell of embodiment 82, wherein the eukaryotic cell is a plant cell.

84. A plant comprising the cell of embodiment 83.

85. A seed comprising the cell of embodiment 83.

86. The cell of embodiment 82, wherein the eukaryotic cell is a mammalian cell.

87. The cell of embodiment 82, wherein the eukaryotic cell is an insect cell.

88. The cell of embodiment 81, wherein the cell is a prokaryotic cell.

89. A method for producing a genetically modified cell with a correction in a causal mutation for a genetically inherited disease, the method comprising introducing into the cell:
a) an RNA-guided nuclease (RGN) polypeptide, wherein the RGN polypeptide comprises an amino acid sequence having at least 95% sequence identity to SEQ ID NOs: 1, 11, 19, 27, 36, 45, or 54, or a polynucleotide encoding said RGN polypeptide, wherein said polynucleotide encoding the RGN polypeptide is operably linked to a promoter to enable expression of the RGN polypeptide in the cell; and
b) a guide RNA (gRNA), wherein the gRNA comprises a CRISPR repeat sequence comprising a nucleotide sequence having at least 95% sequence identity to SEQ ID NOs: 2, 12, 20, 28, 37, 46, or 55, or a polynucleotide encoding said gRNA, wherein said polynucleotide encoding the gRNA is operably linked to a promoter to enable expression of the gRNA in the cell
whereby the RGN and gRNA target to the genomic location of the causal mutation and modify the genomic sequence to remove the causal mutation.

90. The method of embodiment 89, wherein the RGN is fused to a polypeptide which has base-editing activity.

91. The method of embodiment 90, wherein the polypeptide with base-editing activity is a cytidine deaminase or an adenosine deaminase.

92. The method of embodiment 89, wherein the cell is an animal cell.

93. The method of embodiment 89, wherein the cell is a mammalian cell.

94. The method of embodiment 92, wherein the cell is derived from a dog, cat, mouse, rat, rabbit, horse, cow, pig, or human.

95. The method of embodiment 92, wherein the genetically inherited disease is a disease listed in Table 12.

96. The method of embodiment 92, wherein the genetically inherited disease is Hurler Syndrome.

97. The method of embodiment 96, wherein the gRNA further comprises a spacer sequence that targets SEQ ID NO: 453, 454, or 455.

98. A method for producing a genetically modified cell with a deletion in a disease-causing genomic region of instability, the method comprising introducing into the cell:

a) an RNA-guided nuclease (RGN) polypeptide, wherein the RGN polypeptide comprises an amino acid sequence having at least 95% sequence identity to SEQ ID NOs: 1, 11, 19, 27, 36, 45, or 54, or a polynucleotide encoding said RGN polypeptide, wherein said polynucleotide encoding the RGN polypeptide is operably linked to a promoter to enable expression of the RGN polypeptide in the cell; and b) a guide RNA (gRNA), wherein the gRNA comprises a CRISPR repeat sequence comprising a nucleotide sequence having at least 95% sequence identity to SEQ ID NOs: 2, 12, 20, 28, 37, 46, or 55, or a polynucleotide encoding said gRNA, wherein said polynucleotide encoding the gRNA is operably linked to a promoter to enable expression of the gRNA in the cell, and further wherein the gRNA comprises a spacer sequence that targets the 5'flank of the genomic region of instability; and c) a second guide RNA (gRNA), wherein the gRNA comprises a CRISPR repeat sequence comprising a nucleotide sequence having at least 95% sequence identity to SEQ ID NOs: 2, 12, 20, 28, 37, 46, or 55, or a polynucleotide encoding said gRNA, wherein said polynucleotide encoding the gRNA is operably linked to a promoter to enable expression of the gRNA in the cell, and further wherein said second gRNA comprises a spacer sequence that targets the 3'flank of the genomic region of instability;

whereby the RGN and the two gRNAs target to the genomic region of instability and at least a portion of the genomic region of instability is removed.

99. The method of embodiment 98, wherein the cell is an animal cell.

100. The method of embodiment 98, wherein the cell is a mammalian cell.

101. The method of embodiment 100, wherein the cell is derived from a dog, cat, mouse, rat, rabbit, horse, cow, pig, or human.

102. The method of embodiment 99, wherein the genetically inherited disease is Friedrich's Ataxia or Huntington's Disease.

103. The method of embodiment 102, wherein the first gRNA further comprises a spacer sequence that targets SEQ ID NO: 468, 469, or 470.

104. The method of embodiment 103, wherein the second gRNA further comprises a spacer sequence that targets SEQ ID NO: 471.

105. A method for producing a genetically modified mammalian hematopoietic progenitor cell having decreased BCL11A mRNA and protein expression, the method comprising introducing into an isolated human hematopoietic progenitor cell:

a) an RNA-guided nuclease (RGN) polypeptide, wherein the RGN polypeptide comprises an amino acid sequence having at least 95% sequence identity to SEQ ID NOs: 1, 11, 19, 27, 36, 45, or 54, or a polynucleotide encoding said RGN polypeptide, wherein said polynucleotide encoding the RGN polypeptide is operably linked to a promoter to enable expression of the RGN polypeptide in the cell; and b) a guide RNA (gRNA), wherein the gRNA comprises a CRISPR repeat sequence comprising a nucleotide sequence having at least 95% sequence identity to SEQ ID NOs: 2, 12, 20, 28, 37, 46, or 55, or a polynucleotide encoding said gRNA, wherein said polynucleotide encoding the gRNA is operably linked to a promoter to enable expression of the gRNA in the cell, whereby the RGN and gRNA are expressed in the cell and cleave at the BCL11A enhancer region, resulting in genetic modification of the human hematopoietic progenitor cell and reducing the mRNA and/or protein expression of BCL11A.

106. The method of embodiment 105, wherein the gRNA further comprises a spacer sequence that targets SEQ ID NO: 473, 474, 475, 476, 477, or 478.

107. A system for binding a target DNA sequence, said system comprising:

a) one or more guide RNAs capable of hybridizing to said target DNA sequence or one or more nucleotide sequences encoding the one or more guide RNAs (gRNAs); and b) an RNA-guided nuclease (RGN) polypeptide comprising an amino acid sequence having at least 95% sequence identity to SEQ ID NOs: 1, 11, 19, 27, 36, 45, or 54;

wherein the one or more guide RNAs hybridize to the target DNA sequence, and wherein the one or more guide RNAs forms a complex with the RGN polypeptide, thereby directing said RGN polypeptide to bind to said target DNA sequence.

108. The system of embodiment 107, wherein said RGN polypeptide is nuclease dead or functions as a nickase.

109. The system of embodiment 107 or 108, wherein said RGN polypeptide is operably fused to a base-editing polypeptide.

110. The system of embodiment 109, wherein the base-editing polypeptide is a deaminase.

111. The system of embodiment 110, wherein the deaminase is a cytidine deaminase or an adenosine deaminase.

The following examples are offered by way of illustration and not by way of limitation.

EXPERIMENTAL

Example 1. Identification of RNA-Guided Nuclease

Seven distinct CRISPR-associated RNA-guided nucleases (RGN's) were identified and are described in Table 1 below. Table 1 provides the name of each RGN, its amino acid sequence, the source from which it was derived, and processed crRNA and tracrRNA sequences. Table 1 further provides a generic single guide RNA (sgRNA) sequence, where the poly-N indicates the location of the spacer sequence which determines the nucleic acid target sequence of the sgRNA. RGN systems APG systems APG05083.1, APG07433.1, APG08290.1, and APG08290.1 had a conserved sequence in the base of the hairpin stem of the tracrRNA, UNANNG (SEQ ID NO: 68). For the AP05459.1 system, the sequence in the same location is UNANNU (SEQ ID NO: 557). For APG04583.1 and APG01688.1 systems, the sequence is UNANNA (SEQ ID NO: 558).

TABLE 1

Summary of SEQ IDs and CRISPR associated systems

| RGN ID | SEQ ID NO. | Source | crRNA repeat seq (SEQ ID NO.) | tracrRNA (SEQ ID NO.) | sgRNA (SEQ ID NO) |
|---|---|---|---|---|---|
| APG05083.1 | 1 | Bacillus sp. | 2 | 3 | 10 |
| APG07433.1 | 10 | Bacillus sp. | 12 | 13 | 18 |
| APG07513.1 | 18 | Bacillus sp. | 20 | 21 | 26 |
| APG08290.1 | 26 | Bacillus sp. | 28 | 29 | 35 |
| APG05459.1 | 34 | Enterococcus sp. | 37 | 38 | 44 |
| APG04583.1 | 42 | Enterococcus sp. | 46 | 47 | 53 |
| APG01688.1 | 50 | Empedobacter sp. | 55 | 56 | 62 |

Example 2: Guide RNA Identification and sgRNA Construction

Cultures of bacteria that natively express the RNA-guided nuclease system under investigation were grown to mid-log phase (OD600 of ~0.600), pelleted, and flash frozen. RNA was isolated from the pellets using a mirVANA miRNA Isolation Kit (Life Technologies, Carlsbad, Calif.), and sequencing libraries were prepared from the isolated RNA using an NEBNext Small RNA Library Prep kit (NEB, Beverly, Mass.). The library prep was fractionated on a 6% polyacrylamide gel into 2 size fractions corresponding to 18-65 nt and 90-200 nt RNA species to detect crRNAs and tracrRNAs, respectively. Deep sequencing (40 bp paired-end for the smaller fraction and 80 bp paired-end for the larger fraction) was performed on a Next Seq 500 (High Output kit) by a service provider (MoGene, St. Louis, Mo.). Reads were quality trimmed using Cutadapt and mapped to reference genomes using Bowtie2. A custom RNAseq pipeline was written in python to detect the crRNA and tracrRNA transcripts. Processed crRNA boundaries were determined by sequence coverage of the native repeat spacer array. The anti-repeat portion of the tracrRNA was identified using permissive BLASTn parameters. RNA sequencing depth confirmed the boundaries of the processed tracrRNA by identifying the transcript containing the anti-repeat. Manual curation of RNAs was performed using secondary structure prediction by NUPACK, an RNA folding software. sgRNA cassettes were prepared by DNA synthesis and were generally designed as follows (5'->3'): 20-30 bp spacer sequence—processed repeat portion of the crRNA—4 bp noncomplementary linker (AAAG; SEQ ID NO: 63)—processed tracrRNA. Other 4 bp noncomplementary linkers may also be used, for example GAAA (SEQ ID NO: 64) or ACUU (SEQ ID NO: 65). In some instances, a 6 bp nucleotide linker may be used, for example CAAAGG (SEQ ID NO: 66). For in vitro assays, sgRNAs were synthesized by in vitro transcription of the sgRNA cassettes with a GeneArt™ Precision gRNA Synthesis Kit (ThermoFisher). Processed crRNA and tracrRNA sequences for each of the RGN polypeptides are identified and are set forth in Table 1. See below for the sgRNAs constructed for PAM libraries 1 and 2.

Example 3: Determination of PAM Requirements for Each RGN

PAM requirements for each RGN were determined using a PAM depletion assay essentially adapted from Kleinstiver et al. (2015) Nature 523:481-485 and Zetsche et al. (2015) Cell 163:759-771. Briefly, two plasmid libraries (L1 and L2) were generated in a pUC18 backbone (ampR), with each containing a distinct 30 bp protospacer (target) sequence flanked by 8 random nucleotides (i.e., the PAM region). The target sequence and flanking PAM region of library 1 and library 2 for each RGN are set forth in Table 2.

The libraries were separately electroporated into E. coli BL21(DE3) cells harboring pRSF-1b expression vectors containing an RGN of the invention (codon optimized for E. coli) along with a cognate sgRNA containing a spacer sequence corresponding to the protospacer in L1 or L2. Sufficient library plasmid was used in the transformation reaction to obtain >10^6 cfu. Both the RGN and sgRNA in the pRSF-1b backbone were under the control of T7 promoters. The transformation reaction was allowed to recover for 1 hr after which it was diluted into LB media containing carbenicillin and kanamycin and grown overnight. The following day the mixture was diluted into self-inducing Overnight Express™ Instant TB Medium (Millipore Sigma) to allow expression of the RGN and sgRNA, and grown for an additional 4h or 20h after which the cells were spun down and plasmid DNA was isolated with a Mini-prep kit (Qiagen, Germantown, Md.). In the presence of the appropriate sgRNA, plasmids containing a PAM that is recognizable by the RGN will be cleaved resulting in their removal from the population. Plasmids containing PAMs that are not recognizable by the RGN, or that are transformed into bacteria not containing an appropriate sgRNA, will survive and replicate. The PAM and protospacer regions of uncleaved plasmids were PCR-amplified and prepared for sequencing following published protocols (16s-metagenomic library prep guide 15044223B, Illumina, San Diego, Calif.). Deep sequencing (80 bp single end reads) was performed on a MiSeq (Illumina) by a service provider (MoGene, St. Louis, Mo.). Typically, 1-4M reads were obtained per amplicon. PAM regions were extracted, counted, and normalized to total reads for each sample. PAMs that lead to plasmid cleavage were identified by being underrepresented when compared to controls (i.e., when the library is transformed into E. coli containing the RGN but lacking an appropriate sgRNA). To represent PAM requirements for a novel RGN, the depletion ratios (frequency in sample/frequency in control) for all sequences in the region in question were converted to enrichment values with a −log base 2 transformation. Sufficient PAMs were defined as those with enrichment values>2.3 (which corresponds to depletion ratios<−0.2). PAMs above this threshold in both libraries were collected and used to generate web logos, which for example can be generated using a web-based service on the internet known as "weblogo". PAM sequences were identified and reported when there was a consistent pattern in the top enriched PAMs. A PAM (having an enrichment factor (EF)>2.3) for each RGN is provided in Table 2. For some RGNs, non-limiting exemplary PAMs (having an EF>3.3) were also identified. For APG005083.1, the exemplary PAM is NNRNCC (SEQ ID NO: 69). For APG007433.1, the exemplary PAM is NNNNCCR (SEQ ID NO: 70). For APG007513.1, the exemplary PAM is NNRNCC (SEQ ID NO: 71). For APG001688.1, the exemplary PAM is NNRANC (SEQ ID NO: 72).

TABLE 2

PAM determination

| RGN ID | sgRNA L1 (SEQ ID NO.) | sgRNA L2 (SEQ ID NO.) | PAM (SEQ ID NO.) | Target seq and PAM region of plasmid library 1 (SEQ ID NO.) | Target seq and PAM region of plasmid library 2 (SEQ ID NO.) |
|---|---|---|---|---|---|
| APG05083.1 | 4 | 5 | 6 | 8 | 9 |
| APG07433.1 | 13 | 14 | 6 | 16 | 17 |
| APG07513.1 | 21 | 22 | 6 | 24 | 25 |
| APG08290.1 | 29 | 30 | 32 | 33 | 34 |
| APG05459.1 | 37 | 38 | 41 | 42 | 43 |
| APG04583.1 | 45 | 46 | 50 | 51 | 52 |
| APG01688.1 | 53 | 54 | 59 | 60 | 61 |

Example 4: Cleavage Determination

Cleavage sites were determined from in vitro cleavage reactions using RNPs (ribonucleoproteins). Expression plasmids containing an RGN fused to a His6 or a His 10 tag were constructed and transformed into BL21 (DE3) strains of *E. coli*. Expression was performed using self-inducing media or with IPTG induction. After lysis and clarification, the proteins were purified by immobilized metal affinity chromatography.

Ribonucleoprotein complexes (comprising nuclease and an sgRNA or a crRNA and tracrRNA duplex) were formed by incubation of nuclease and the RNA in a buffered solution for 20 min at room temperature. The complex was transferred to a tube containing digestion buffer and a PCR amplified target, referred to as "Sequence 1". Sequence 1 comprised a nucleotide sequence (SEQ ID NO: 73) directly linked at its 3' end to the corresponding PAM sequence for each RGN. Each RGN as a ribonucleoprotein complex was incubated with its respective target polynucleotide at 25° C. (APG04583.1) or 37° C. (all others) for 30 min or 60 min (APG05459.1 and APG01688.1 only). The digestion reaction was heat inactivated and run on an agarose gel. The cleavage product bands were excised from the gel and sequenced using Sanger sequencing. Cleavage sites were identified by aligning the sequencing results with the expected sequence of the PCR product. Results are shown in Table 3. As shown in Table 3, RGN APG007433.1 may also produce a blunt cut with a different target sequence.

The cleavage site for Sequence 2 (SEQ ID NO: 559, operably fused at its 3'end to a PAM sequence for RGN APG0733.1) was determined by the following approach for the nuclease APG07433.1. After digestion, the gel purified DNA products were treated with a DNA end repair kit (Thermo Scientific K0771), ligated into linearized blunt vector, and the resulting circular DNA was transformed into *E. coli* competent cells. A staggered cut with a 5' overhang would result in detection of overlapping sequences in the clones from both cleavage products. A 3' overhang would result in missing sequence, and a blunt cut would result in all of the original sequence being detected with no overlap. This experiment also verified the finding from the above described method for sequence 1—most of the clones were detected as having originated from a cut with a 5' overlap, so it is not expected that the finding of a blunt cut is an artifact of utilizing this method.

TABLE 3

RGN cleavage sites

| | Sequence 1 | | | Sequence 2 | | |
|---|---|---|---|---|---|---|
| | Distance from PAM | | | Distance from PAM | | |
| Nuclease | NTS cut site | TS cut site | Overhang | NTS cut site | TS cut site | Overhang |
| APG07433.1 | 4 | 3 | 1 nt, 5' | 3 | 3 | None |
| APG08290.1 | 4 | 3 | 1 nt, 5' | 3 | Not determined | |
| APG05459.1 | 3 | 3 | None | 3 | Not determined | |
| APG04583.1 | 3 | 3 | None | 3 | Not determined | |
| APG01688.1 | 3 | 3 | None | 3 | Not determined | |

NTS = non-target strand;
TS = target strand

Example 5: Mismatch Sensitivity Assay

Plasmids were designed and obtained with a target sequence (SEQ ID NO: 73) immediately 5' to a suitable PAM motif for the nuclease being evaluated. Single mismatch sequences were also generated with an altered sequence at the position indicated (Table 4). RNP complexes of purified nuclease (APG08290.1 or APG05459. 1) and guide RNA were formed and incubated with PCR amplified linear DNA from the designed plasmids. After incubation for a designated period of time and nuclease inactivation, the samples were analyzed by agarose gel electrophoresis to determine the fraction of the linear PCR product remaining. The percentage of the intact band cleaved is shown in Table 5 for mismatches in each position.

TABLE 4

Sequences tested for the mismatch sensitivity assay for APG08290.1 and APG05459.1

| Protospacer sequence | SEQ ID NO. | Mismatch position |
|---|---|---|
| GAGCGGACAGCAGCTTCCTATATCTCGTAC | 73 | None |
| GAGCGGACAGCAGCTTCCTATATCTCGTAG | 74 | 1 |

TABLE 4-continued

Sequences tested for the mismatch sensitivity assay for APG08290.1 and APG05459.1

| Protospacer sequence | SEQ ID NO. | Mismatch position |
|---|---|---|
| GAGCGGACAGCAGCTTCCTATATCTCGTTC | 75 | 2 |
| GAGCGGACAGCAGCTTCCTATATCTCGAAC | 76 | 3 |
| GAGCGGACAGCAGCTTCCTATATCTCCTAC | 77 | 4 |
| GAGCGGACAGCAGCTTCCTATATCTGGTAC | 78 | 5 |
| GAGCGGACAGCAGCTTCCTATATCACGTAC | 79 | 6 |
| GAGCGGACAGCAGCTTCCTATATGTCGTAC | 80 | 7 |
| GAGCGGACAGCAGCTTCCTATAACTCGTAC | 81 | 8 |
| GAGCGGACAGCAGCTTCCTATTTCTCGTAC | 82 | 9 |
| GAGCGGACAGCAGCTTCCTAAATCTCGTAC | 83 | 10 |
| GAGCGGACAGCAGCTTCCTTTATCTCGTAC | 84 | 11 |
| GAGCGGACAGCAGCTTCCAATATCTCGTAC | 85 | 12 |
| GAGCGGACAGCAGCTTCGTATATCTCGTAC | 86 | 13 |
| GAGCGGACAGCAGCTTGCTATATCTCGTAC | 87 | 14 |
| GAGCGGACAGCAGCTACCTATATCTCGTAC | 88 | 15 |
| GAGCGGACAGCAGCATCCTATATCTCGTAC | 89 | 16 |
| GAGCGGACAGCAGGTTCCTATATCTCGTAC | 90 | 17 |
| GAGCGGACAGCACCTTCCTATATCTCGTAC | 91 | 18 |
| GAGCGGACAGCTGCTTCCTATATCTCGTAC | 92 | 19 |
| GAGCGGACAGGAGCTTCCTATATCTCGTAC | 93 | 20 |
| GAGCGGACACCAGCTTCCTATATCTCGTAC | 94 | 21 |
| GAGCGGACTGCAGCTTCCTATATCTCGTAC | 95 | 22 |
| GAGCGGAGAGCAGCTTCCTATATCTCGTAC | 96 | 23 |
| GAGCGGTCAGCAGCTTCCTATATCTCGTAC | 97 | 24 |
| GAGCGCACAGCAGCTTCCTATATCTCGTAC | 98 | 25 |
| GAGCCGACAGCAGCTTCCTATATCTCGTAC | 99 | 26 |
| GAGGGGACAGCAGCTTCCTATATCTCGTAC | 100 | 27 |
| GACCGGACAGCAGCTTCCTATATCTCGTAC | 101 | 28 |
| GTGCGGACAGCAGCTTCCTATATCTCGTAC | 102 | 29 |
| CAGCGGACAGCAGCTTCCTATATCTCGTAC | 103 | 30 |

TABLE 5

Mismatch sensitivity for RGN APG08290.1 and RGN APG05459.1

| Mismatch position | % cleaved APG08290.1 | % cleaved APG05459.1 |
|---|---|---|
| Incompatible PAM, no mismatch | 0 | 0 |
| No mismatch | 95 | 67 |
| 1 | 0 | 0 |
| 2 | 0 | 74 |
| 3 | 73 | 3 |
| 4 | 0 | 0 |
| 5 | 0 | 0 |
| 6 | 31 | 30 |
| 7 | 0 | 12 |
| 8 | 0 | 51 |
| 9 | 0 | 0 |
| 10 | 75 | 52 |
| 11 | 77 | 5 |
| 12 | 79 | 62 |
| 13 | 28 | 18 |
| 14 | 8 | 5 |
| 15 | 90 | 6 |
| 16 | 85 | 5 |
| 17 | 81 | 4 |
| 18 | 100 | 0 |
| 19 | 100 | 0 |
| 20 | 100 | 2 |
| 21 | 100 | 30 |
| 22 | 100 | 48 |
| 23 | 100 | 40 |
| 24 | 100 | 45 |
| 25 | 100 | 29 |
| 26 | 100 | 33 |
| 27 | 100 | 73 |
| 28 | 100 | 46 |
| 29 | 100 | 59 |
| 30 | 100 | 57 |

A similar mismatch sensitivity experiment was performed for RGN APG07433.1. This experiment was similar to the one described above, except that the alternative base was introduced into the RNA guide rather than the DNA target. DNA sequences for mismatched sgRNA synthesis are shown in Table 6. Results of the mismatch sensitivity assay are shown in Table 7.

TABLE 6

Sequences tested for the mismatch sensitivity assay for RGN APG07433.1

| DNA template for sgRNA synthesis | SEQ ID NO. | Mismatch position |
|---|---|---|
| GAGCGGACAGCAGCTTCCTATATCTCGTAC | 73 | None |
| GAGCGGACAGCAGCTTCCTATATCTCGTAT | 104 | 1 |
| GAGCGGACAGCAGCTTCCTATATCTCGTGC | 105 | 2 |
| GAGCGGACAGCAGCTTCCTATATCTCGCAC | 106 | 3 |
| GAGCGGACAGCAGCTTCCTATATCTCATAC | 107 | 4 |
| GAGCGGACAGCAGCTTCCTATATCTTGTAC | 108 | 5 |
| GAGCGGACAGCAGCTTCCTATATCCCGTAC | 109 | 6 |
| GAGCGGACAGCAGCTTCCTATATTTCGTAC | 110 | 7 |
| GAGCGGACAGCAGCTTCCTATACCTCGTAC | 111 | 8 |
| GAGCGGACAGCAGCTTCCTATGTCTCGTAC | 112 | 9 |
| GAGCGGACAGCAGCTTCCTACATCTCGTAC | 113 | 10 |
| GAGCGGACAGCAGCTTCCTGTATCTCGTAC | 114 | 11 |

TABLE 6-continued

Sequences tested for the mismatch sensitivity assay for RGN APG07433.1

| DNA template for sgRNA synthesis | SEQ ID NO. | Mismatch position |
|---|---|---|
| GAGCGGACAGCAGCTTCCCATATCTCGTAC | 115 | 12 |
| GAGCGGACAGCAGCTTCTTATATCTCGTAC | 116 | 13 |
| GAGCGGACAGCAGCTTTCTATATCTCGTAC | 117 | 14 |
| GAGCGGACAGCAGCTCCCTATATCTCGTAC | 118 | 15 |
| GAGCGGACAGCAGCCTCCTATATCTCGTAC | 119 | 16 |
| GAGCGGACAGCAGTTTCCTATATCTCGTAC | 120 | 17 |
| GAGCGGACAGCAACTTCCTATATCTCGTAC | 121 | 18 |
| GAGCGGACAGCGGCTTCCTATATCTCGTAC | 122 | 19 |
| GAGCGGACAGTAGCTTCCTATATCTCGTAC | 123 | 20 |
| GAGCGGACAACAGCTTCCTATATCTCGTAC | 124 | 21 |
| GAGCGGACGGCAGCTTCCTATATCTCGTAC | 125 | 22 |
| GAGCGGATAGCAGCTTCCTATATCTCGTAC | 126 | 23 |

TABLE 7

Mismatch sensitivity for RGN APG07433.1

| Mismatch position | % cleaved APG07433.1 |
|---|---|
| No mismatch | 86 |
| 1 | 6 |
| 2 | 21 |
| 3 | -2 |
| 4 | 1 |
| 5 | -1 |
| 6 | 0 |
| 7 | 7 |
| 8 | 24 |
| 9 | 14 |
| 10 | -1 |
| 11 | 72 |
| 12 | 44 |
| 13 | 54 |
| 14 | 60 |
| 16 | 65 |
| 17 | 76 |
| 18 | 84 |
| 19 | 86 |
| 20 | 83 |
| 21 | 83 |
| 22 | 93 |
| 23 | 80 |

RGNs APG07433.1 and APG08290.1 show significant sensitivity to mismatches in positions 1-10 5' from the PAM with a few exceptions (Table 5 and Table 7). RGN APG05459.1 is sensitive as well to mismatches in this region, but its ability to cleave dsDNA is also heavily abrogated by mismatches distant from the PAM site (Table 5). The total number of sites with a significant influence on whether or not cleavage occurs is at least 15 positions in the spacer sequence. This compares favorably to other genome editing tools, such as the well-studied Cas9 nuclease from *S. pyogenes*, which is generally sensitive to between 10-13 base pairs (Hsu et al., Nat Biotechnol (2013) 31(9): 827-832). Additionally, many of the critical sites abrogating RGN APG05459.1 mediated cleavage are very far from the PAM sequence, notably in the range of 13-20 bp, where many other nucleases show little if any sensitivity to mismatches. This property could be extraordinarily useful in targeting genetic loci that have close sequence similarity to other sites in the organism of interest.

Example 6: Demonstration of Gene Editing Activity in Mammalian Cells

RGN expression cassettes were produced and introduced into vectors for mammalian expression. Each RGN was codon-optimized for human expression (SEQ ID NOs 127-133), and operably fused at the 5'end to an SV40 nuclear localization sequence (NLS; SEQ ID NO 134) and to 3×FLAG tags (SEQ ID NO: 135), and operably fused at the 3'end to nucleoplasmin NLS sequences (SEQ ID NO: 136). Each expression cassette was under control of a cytomegalovirus (CMV) promoter (SEQ ID NO: 137). It is known in the art that the CMV transcription enhancer (SEQ ID NO: 138) may also be included in constructs comprising the CMV promoter. Guide RNA expression constructs encoding a single gRNA each under the control of a human RNA polymerase III U6 promoter (SEQ ID NO. 139) were produced and introduced into the pTwist High Copy Amp vector. Sequences for the target sequences for each guide are in Table 9.

The constructs described above were introduced into mammalian cells. One day prior to transfection, 1×10$^5$ HEK293T cells/well (Sigma) were plated in 24-well dishes in Dulbecco's modified Eagle medium (DMEM) plus 10% (vol/vol) fetal bovine serum (Gibco) and 1% Penicillin-Streptomycin (Gibco). The next day when the cells were at 50-60% confluency, 500 ng of a RGN expression plasmid plus 500 ng of a single gRNA expression plasmid were co-transfected using 1.5 μL of Lipofectamine 3000 (Thermo Scientific) per well, following the manufacturer's instructions. After 48 hours of growth, total genomic DNA was harvested using a genomic DNA isolation kit (Machery-Nagel) according to the manufacturer's instructions.

The total genomic DNA was then analyzed to determine the rate of editing for each RGN for each genomic target. First, oligonucleotides were produced to be used for PCR amplification and subsequent analysis of the amplified genomic target site. Oligonucleotide sequences used are listed in Tables 8.1 to 8.5.

All PCR reactions were performed using 10 μL of 2× Master Mix Phusion High-Fidelity DNA polymerase (Thermo Scientific) in a 20 μL reaction including 0.5 μM of each primer. Large genomic regions encompassing each target gene were first amplified using PCR#1 primers, using a program of: 98° C., 1 min; 30 cycles of [98° C., 10 sec; 62° C., 15 sec; 72° C., 5 min]; 72° C., 5 min; 12° C., forever. One microliter of this PCR reaction was then further amplified using primers specific for each guide (PCR#2 primers), using a program of: 98° C., 1 min; 35 cycles of [98° C., 10 sec; 67° C., 15 sec; 72° C., 30 sec]; 72° C., 5 min; 12° C., forever. Primers for PCR#2 include Nextera Read 1 and Read 2 Transposase Adapter overhang sequences for Illumina sequencing.

TABLE 8.1

Oligonucleotides for detection of gene editing activity in mammalian cells, PCR#1

| Description | Sequence | SEQ ID NO |
|---|---|---|
| RelA FWD | 5'-CTT AGT TTC ACC GCA GGT TCT A-3' | 479 |
| RelA REV | 5'-CTG TGC ACT CAA CAC TGA TCT A-3' | 480 |
| AurkB FWD | 5'-CCC AGC CCT AGG TTG TTT ATT-3' | 481 |
| AurkB REV | 5'-CTG GCT ACA TCT TCC TTG ACT AC-3' | 482 |
| HPRT1 FWD | 5'-GTG GCA GAA GCA GTG AGT AA-3' | 483 |
| HPRT1 REV | 5'-TCC CAT CTA GGC ACT AGG TAA A-3' | 484 |

TABLE 8.2

Oligonucleotides for detection of gene editing activity in mammalian cells, PCR#2 for APG05083.1, APG07433.1, APG07513.1, and APG08290.1

| Description | SEQ ID NO. |
|---|---|
| FWD_Guide 134, Guide 135, Guide 136, Guide 137 | 485 |
| REV_Guide 134, Guide 135, Guide 136, Guide 137 | 486 |
| FWD_Guide 138, Guide 139, Guide 140, Guide 141 | 487 |
| REV_Guide 138, Guide 139, Guide 140, Guide 141 | 488 |
| REV_Guide 142, Guide 143, Guide 144, Guide 145 | 489 |
| FWD_Guide 142, Guide 143, Guide 144, Guide 145 | 490 |
| REV_Guide 164, Guide 165, Guide 166, Guide 167 | 491 |
| FWD_Guide 164, Guide 165, Guide 166, Guide 167 | 492 |
| REV_Guide 168, Guide 169, Guide 170, Guide 171 | 493 |
| FWD_Guide 168, Guide 169, Guide 170, Guide 171 | 494 |
| REV_Guide 172, Guide 173, Guide 174, Guide 175 | 495 |
| FWD_Guide 172, Guide 173, Guide 174, Guide 175 | 496 |
| REV_Guide 185, Guide 186, Guide 187, Guide 188 | 497 |
| FWD_Guide 185, Guide 186, Guide 187, Guide 188 | 498 |
| REV_Guide 189, Guide 190, Guide 191, Guide 192 | 499 |
| FWD_Guide 189, Guide 190, Guide 191, Guide 192 | 500 |
| REV_Guide 193, Guide 194, Guide 195, Guide 196 | 501 |
| FWD_Guide 193, Guide 194, Guide 195, Guide 196 | 502 |

TABLE 8.3

Oligonucleotides for detection of gene editing activity in mammalian cells, PCR#2 for APG005459.1

| Description | SEQ ID NO. |
|---|---|
| FWD_Guide 146 | 503 |
| REV_Guide 146 | 504 |
| FWD_Guide 147 | 505 |
| REV_Guide 147 | 506 |
| REV_Guide 148 | 507 |
| FWD_Guide 148 | 508 |
| REV_Guide 176 | 509 |
| FWD_Guide 176 | 510 |
| REV_Guide 177 | 511 |
| FWD_Guide 177 | 512 |
| REV_Guide 209 | 513 |
| FWD_Guide 209 | 514 |
| REV_Guide 197 | 515 |
| FWD_Guide 197 | 516 |
| REV_Guide 198 | 517 |
| FWD_Guide 198 | 518 |

TABLE 8.3-continued

Oligonucleotides for detection of gene editing activity in mammalian cells, PCR#2 for APG005459.1

| Description | SEQ ID NO. |
|---|---|
| REV_Guide 199 | 519 |
| FWD_Guide 199 | 520 |

TABLE 8.4

Oligonucleotides for detection of gene editing activity in mammalian cells, PCR#2 for APG004583.1

| Description | SEQ ID NO. |
|---|---|
| FWD_Guide 149 | 521 |
| REV_Guide 149 | 522 |
| FWD_Guide 150 | 523 |
| REV_Guide 150 | 524 |
| REV_Guide 151 | 525 |
| FWD_Guide 151 | 526 |
| REV_Guide 179 | 527 |
| FWD_Guide 179 | 528 |
| REV_Guide 180 | 529 |
| FWD_Guide 180 | 530 |
| REV_Guide 181 | 531 |
| FWD_Guide 181 | 532 |
| REV_Guide 200 | 533 |
| FWD_Guide 200 | 534 |
| REV_Guide 201 | 535 |
| FWD_Guide 201 | 536 |
| REV_Guide 202 | 537 |
| FWD_Guide 202 | 538 |

TABLE 8.5

Oligonucleotides for detection of gene editing activity in mammalian cells, PCR#2 for APG01988.1

| Description | SEQ ID NO. |
|---|---|
| FWD_Guide 152 | 539 |
| REV_Guide 152 | 540 |
| FWD_Guide 153 | 541 |
| REV_Guide 153 | 542 |
| FWD_Guide 154 | 543 |
| REV_Guide 154 | 544 |
| FWD_Guide 182 | 545 |
| REV_Guide 182 | 546 |
| FWD_Guide 183 | 547 |
| REV_Guide 183 | 548 |
| FWD_Guide 184 | 549 |
| REV_Guide 184 | 550 |
| FWD_Guide 203 | 551 |
| REV_Guide 203 | 552 |
| FWD_Guide 204 | 553 |
| REV_Guide 204 | 554 |
| FWD_Guide 205 | 555 |
| REV_Guide 205 | 556 |

Purified genomic DNA was subjected to PCR#1 and PCR#2 as above. Following the second PCR amplification DNA was cleaned using a PCR cleanup kit (Zymo) according to the manufacturer's instructions and eluted in water. 200-500 ng of purified PCR#2 product was combined with 2 μL of 10×NEB Buffer 2 and water in a 20 μL reaction and annealed to form heteroduplex DNA using a program of: 95° C., 5 min; 95-85° C., cooled at a rate of 2° C./sec; 85-25° C., cooled at a rate of 0.1° C./sec.; 12° C., forever. Following annealing 5 μL of DNA was removed as a no enzyme control, and 1 μL of T7 Endonuclease I (NEB) was added and the reaction incubated at 37° C. for 1 hr. After incubation 5× FlashGel loading dye (Lonza) was added and 5 μL of each reaction and controls were analyzed by a 2.2% agarose FlashGel (Lonza) using gel electrophoresis. Following visualization of the gel, the percentage of non-homologous end joining (NHEJ) was determined using the following equation: % NHEJ events=100×[1−(1−fraction cleaved)^(½)], where (fraction cleaved) is defined as: (density of digested products)/(density of digested products+undigested parental band).

For some samples, SURVEYOR® was used to analyze the results following expression in mammalian cells. Cells were incubated at 37° C. for 72 h post-transfection before genomic DNA extraction. Genomic DNA was extracted using the QuickExtract DNA Extraction Solution (Epicentre) following the manufacturer's protocol. The genomic region flanking the RGN target site was PCR amplified, and products were purified using QiaQuick Spin Column (Qiagen) following the manufacturer's protocol. 200-500 ng total of the purified PCR products were mixed with 1 µl 10× Taq DNA Polymerase PCR buffer (Enzymatics) and ultrapure water to a final volume of 10 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 min.

After reannealing, products were treated with SURVEYOR® nuclease and SURVEYOR® enhancer S (Integrated DNA Technologies) following the manufacturer's recommended protocol and analyzed on 4-20% Novex TBE polyacrylamide gels (Life Technologies). Gels were stained with SYBR Gold DNA stain (Life Technologies) for 10 min and imaged with a Gel Doc gel imaging system (Bio-rad). Quantification was based on relative band intensities. Indel percentage was determined by the formula, 100×(1−(1−(b+c)/(a+b+c))^½), where a is the integrated intensity of the undigested PCR product, and b and c are the integrated intensities of each cleavage product.

Additionally, products from PCR#2 containing Illumina overhang sequences underwent library preparation following the Illumina 16S Metagenomic Sequencing Library protocol. Deep sequencing was performed on an Illumina Mi-Seq platform by a service provider (MOGene). Typically 200,000 of 250 bp paired-end reads (2×100,000 reads) are generated per amplicon. The reads were analyzed using CRISPResso (Pinello, et al. 2016 Nature Biotech, 34:695-697) to calculate the rates of editing. Output alignments were hand-curated to confirm insertion and deletion sites as well as identify microhomology sites at the recombination sites. The rates of editing are shown in Table 9. All experiments were performed in human cells. The "target sequence" is the targeted sequence within the gene target. For each target sequence, the guide RNA comprised the complementary RNA target sequence and the appropriate sgRNA depending on the RGN used. A selected breakdown of experiments by guide RNA is shown in Tables 10.1-10.9.

TABLE 9

Overall rates of editing

| RGN | Guide RNA ID | Target Sequence (SEQ ID NO.) | Gene Target | Overall Editing Rate in Sample | Deletion Rate in Sample | Insertion Rate in Sample |
|---|---|---|---|---|---|---|
| APG05083.1 | 189 | 140 | RelA | 6.9% | | 100% |
| APG05083.1 | 185 | 141 | RelA | 8.2% | 79.9% | 20.1% |
| APG05083.1 | 168 | 142 | HPRT1 | 11.3% | 36.3% | 72.4% |
| APG07433.1 | 135 | 143 | AurkB | 1.7% | 88.3% | 11.7% |
| APG07433.1 | 139 | 144 | AurkB | 3.32% | 94.3% | 15.6% |
| APG07433.1 | 143 | 145 | AurkB | 2.2% | 35.1% | 64.9% |
| APG07433.1 | 190 | 146 | RelA | 60.5% | 94.8% | 5.2% |
| APG07433.1 | 194 | 147 | RelA | 6.2% | | 100% |
| APG07433.1 | 165 | 148 | HPRT1 | 3.5% | 68.0% | 32.0% |
| APG07433.1 | 169 | 149 | HPRT1 | 18.1% | 30.3% | 69.7% |
| APG07433.1 | 173 | 150 | HPRT1 | 26.6% | 91.9% | 10.0% |
| APG07513.1 | 144 | 151 | AurkB | 2.4% | 59.1% | 40.9% |
| APG07513.1 | 136 | 152 | AurkB | 0.9% | 80.5% | 19.5% |
| APG08290.1 | 145 | 153 | AurkB | 14.18% | 75.85% | 24.15% |
| APG08290.1 | 188 | 154 | RelA | 21.40% | 99.05% | 50.05% |
| APG08290.1 | 192 | 155 | RelA | 28.98% | 42.05% | 57.95% |
| APG08290.1 | 196 | 156 | RelA | 13.27% | 91.80% | 8.20% |
| APG08290.1 | 167 | 157 | HPRT1 | 14.14% | 65.98% | 34.02% |
| APG08290.1 | 171 | 158 | HPRT1 | 48.23% | 58.26% | 41.74% |
| APG08290.1 | 175 | 159 | HPRT1 | 13.60% | 74.18% | 25.82% |
| APG05459.1 | 197 | 160 | RelA | 12.95% | 92.16% | 7.84% |
| APG05459.1 | 199 | 161 | RelA | 5.19% | 100% | |
| APG05459.1 | 146 | 162 | AurkB | 1.12% | 61.50% | 38.50% |
| APG05459.1 | 148 | 163 | AurkB | 0.78% | 49.47% | 50.53% |
| APG05459.1 | 176 | 164 | HPRT1 | 6.20% | 48.91% | 51.09% |
| APG05459.1 | 177 | 165 | HPRT1 | 9.00% | 9.33% | 90.67% |
| APG05459.1 | 209 | 166 | HPRT1 | 2.50% | | 100% |
| APG04583.1 | 151 | 167 | AurkB | 0.0% | | |
| APG01688.1 | 152 | 168 | AurkB | 0.0% | | |

Specific insertions and deletions for respective guides are shown in Tables 10.1-10.7. In these tables, the target sequence is identified by bold upper case letters. The 8mer PAM regions are double underlined, with the main recognized nucleotides in bold. Insertions are identified by lowercase letters. Deletions are indicated with dashes (---). The INDEL location is calculated from the PAM proximal edge of the target sequence, with the edge being location 0. The location is positive (+) if the location is on the target side of the edge; the location is negative (−) if the location is on the PAM side of the edge.

TABLE 10.1

Specific insertions and deletions for Guide 139 using RGN APG07433.1

| Guide 139 (SEQ ID NO: 144) | # Reads | % Reads | % of INDELs | Type | INDEL Location | Size |
|---|---|---|---|---|---|---|
| CCTGGGTGTGAGGCTGGGCCATTAAAACCTCTCC | 82540 | 95.562 | | | | |
| CCTG------------------AAAACCTCTCC | 170 | 0.199 | 23.16 | Deletion | −6 | 19 |

TABLE 10.1-continued

Specific insertions and deletions for Guide 139 using RGN APG07433.1

| Guide 139 (SEQ ID NO: 144) | # Reads | % Reads | % of INDELs | Type | INDEL Location | Size |
|---|---|---|---|---|---|---|
| CCTGGGTGTGA-GCTGGGCCATTAAAACCTCTCC | 132 | 0.155 | 17.98 | Deletion | +1 | 1 |
| C------------CTGGGCCATTAAAACCTCTCC | 107 | 0.125 | 14.57 | Deletion | -9 | 12 |
| CCTGG----------------------CTCTCC | 101 | 0.118 | 13.76 | Deletion | -5 | 23 |
| C----------------GGGCCATTAAAACCTCTCC | 61 | 0.071 | 8.31 | Deletion | -9 | 14 |
| CCTGGGTGTGAGGccagacCTGGGCCATTAAAACCTCTCC | 49 | 0.057 | 6.67 | Insertion | +3 | 6 |
| CCTGGGTGTGAGGgggaagctgacgtcctttccatggctgctcgcctgtgttgccaccGCTGGGCCATTAAAACCTCTCC | 44 | 0.051 | 5.99 | Insertion | +2 | 45 |
| CCTGGGTGTGA-cCTGGGCCATTAAAACCTCTCC | 39 | 0.045 | 5.31 | Deletion & Mutation | +1 | 1 |
| CCTGGGTGTGAGGaCTGGGCCATTAAAACCTCTCC | 31 | 0.036 | 4.22 | Insertion | +3 | 1 |

TABLE 10.2

Specific insertions and deletions for Guide 143 using RGN APG07433.1

| Guide 143 (SEQ ID NO: 145) | # Reads | % Reads | % of INDELs | Type | INDEL Location | Size |
|---|---|---|---|---|---|---|
| AGTTGGCAGATGCTCTAATGTACTGCCATGGGAA | 84043 | 99.646 | | | | |
| AGTTGGCAGATGC---AATGTACTGCCATGGGAA | 126 | 0.149 | 42.281 | Deletion | +3 | 3 |
| AGTTGGCAGATGC----ATGTACTGCCATGGGAA | 81 | 0.096 | 27.181 | Deletion | +3 | 3 |
| AGTTGGCAGATGCT---ATGTACTGCCATGGGAA | 42 | 0.049 | 14.093 | Deletion | +4 | 3 |
| AGTTGGCAGATGC--TAATGTACTGCCATGGGAA | 34 | 0.040 | 11.409 | Deletion | +3 | 2 |
| AGTTGGCAGATGCT---ATGTAaTGCCATGGGAA | 8 | 0.009 | 2.684 | Deletion & Mutation | +4 | 3 |
| AGTTGGCAGATGCTCT-ATGTACTGCCATGGGAA | 7 | 0.008 | 2.348 | Deletion | +6 | 1 |

TABLE 10.3

Specific insertions and deletions for Guide 190 using RGN APG07433.1

| Guide 190 (SEQ ID NO: 146) | # Reads | % Reads | % of INDELs | Type | INDEL Location | Size |
|---|---|---|---|---|---|---|
| CGACCTGAATGCTGTGC-----------------------------------------------------GGCGCTCTGGCTTCATTCAATC | 64040 | 55.46 | 91.70 | Deletion | -164 | 170 |
| CGACCTGAATGCTGTGCGGCTCTGCTTCCAGGTGA | 45619 | 39.51 | | WT | | |
| CGACCTGAATGCTGTGCGGCaTCTGCTTCCAGGTGA | 3620 | 3.13 | 5.18 | Insertion | +3 | 1 |

TABLE 10.3-continued

Specific insertions and deletions for Guide 190 using RGN APG07433.1

| Guide 190 (SEQ ID NO: 146) | # Reads | % Reads | % of INDELs | Type | INDEL Location | Size |
|---|---|---|---|---|---|---|
| CGACCTGAATG----------CTGCTTCCAGGTGA | 1110 | 0.96 | 1.58 | Deletion | +2 | 10 |
| CGACCTGAATGCT-------TCTGCTTCCAGGTGA | 858 | 0.74 | 1.22 | Deletion | +3 | 7 |
| CGACCTGAA-------------TGCTTCCAGGTGA | 206 | 0.17 | 0.29 | Deletion | +1 | 13 |

TABLE 10.4

Specific insertions and deletions for Guide 194 using RGN APG07433.1

| Guide 194 (SEQ ID NO: 147) | # Reads | % Reads | % of INDELs | Type | INDEL Location | Size |
|---|---|---|---|---|---|---|
| GCGTGGGGACTACGACCTGAATGCTGTGCGGCTCT | 96635 | 97.318 | | | | |
| GCG-----------ACCTGAATGCTGTGCGGCTCT | 1194 | 1.202 | 44.836 | Deletion | -9 | 11 |
| GCGTGGGGACTACGA-------GCTGTGCGGCTCT | 547 | 0.550 | 20.540 | Deletion | +3 | 7 |
| GCGTGGGA-------CTGAATGCTGTGCGGCTCT | 473 | 0.476 | 17.761 | Deletion | -3 | 7 |
| GCGTGGGGACT----CCTGAATGCTGTGCGGCTCT | 270 | 0.271 | 10.138 | Deletion | -1 | 4 |
| GCGTGGGGACTACGAaCCTGAaTGCTGTGCGGCTCT | 88 | 0.088 | 3.304 | Insertion | +3 | 1 |
| GCGTGGGGACTACGA-----ATGCTGTGCGGCTCT | 41 | 0.041 | 1.539 | Deletion | +3 | 5 |
| GCGTGGGGACTAC---CTGAATGCTGTGCGGCTCT | 31 | 0.031 | 1.164 | Deletion | +2 | 3 |
| GCG--------------TGAATGCTGTGCGGCTCT | 9 | 0.009 | 0.337 | Deletion | -9 | 14 |
| GCG-----------ACCTGAcTGCTGTGCGGCTCT | 5 | 0.005 | 0.187 | Deletion & Mutation | -9 | 11 |
| GCGTGGGGACTACG-CCTGAATGCTGTGCGGCTCT | 5 | 0.005 | 0.187 | Deletion | +2 | 1 |

TABLE 10.5

Specific insertions and deletions for Guide 145 using RGN APG08290.1

| Guide 145 (SEQ ID NO: 153) | # Reads | % Reads | % of INDELs | Type | INDEL Location | Size |
|---|---|---|---|---|---|---|
| ATGGAGGAGTTGGCAGATGCTCTAATGTACTGCCATGGGAAG | 62618 | 95.889 | | | | |
| ATGGAGGAGTTGGCAGATGC-TAATGTACTGCCATGGGAAG | 976 | 1.494 | 36.363 | Deletion | +3 | 2 |
| ATGGAGGAGTTGGCAGATG--------TACTGCCATGGGAAG | 319 | 0.488 | 11.885 | Deletion | +2 | 8 |
| ATG-------------------TACTGCCATGGGAAG | 168 | 0.257 | 6.259 | Deletion | -14 | 24 |
| ATGGAGGAGTTGG------------TGTACTGCCATGGGAAG | 157 | 0.240 | 5.849 | Deletion | -4 | 12 |
| ATGGAGGAGTTGGCAGATGCTCTaAATGTACTGCCATGGGAAG | 147 | 0.225 | 5.476 | Insertion | +6 | 1 |
| ATGGAGGAGTTGGCAGATGCtctTCTAATGTACTGCCATGGGAAG | 123 | 0.188 | 4.582 | Insertion | +2 | 3 |
| ATGGAGGAGTTGGCAGATGccCTCTAATGTACTGCCATGGGAAG | 110 | 0.168 | 4.098 | Insertion | +2 | 2 |

TABLE 10.5-continued

Specific insertions and deletions for Guide 145 using RGN APG08290.1

| Guide 145 (SEQ ID NO: 153) | # Reads | % Reads | % of INDELs | Type | INDEL Location | Size |
|---|---|---|---|---|---|---|
| ATGGAGGAGTTGGCAGAT-----AATGTACTGC CATGGGAAGAAG | 103 | 0.157 | 3.837 | Deletion | +1 | 5 |
| ATGG---------------------cGTACTGC CATGGGAAGAAG | 96 | 0.147 | 3.57 | Deletion & Mutation | -7 | 21 |
| ATGGAGGAGTTGGCAGATGCtTCTAATGTACTG CCATGGGAAGAAG | 85 | 0.130 | 3.166 | Insertion | +3 | 1 |
| ATGGAGGAGTTGGCA-------------TCTGC CATGGGAAGAAG | 84 | 0.128 | 3.129 | Deletion | -2 | 13 |
| ATGGAGGAGTTGGCAGATGC---AATGTACTGC CATGGGAAGAAG | 79 | 0.120 | 2.943 | Deletion | +3 | 3 |
| ATGGAGGAGTTGGCAGATGCcaaactgaaaaac aaatcaaagcactcttattgagtgctggcgatc cccgacgccacgggccgaaacccttatcataga aaCTCTAATGTACTGCCATGGGAAG | 58 | 0.0884 | 2.160 | Insertion | +3 | 81 |
| ATGGAGGAGTTGGCAGATGCtgcttatatagac ctcccaccgtacacgcctaccgcccattTCTA ATGTACTGCCATGGGAAG | 53 | 0.081 | 1.974 | Insertion | +3 | 42 |
| ATGGAGGAGTTG-----------TCTAATGTACTGC CATGGGAAG | 47 | 0.071 | 1.751 | Deletion | -5 | 8 |
| ------------------------------CTGC CATGGGAAGAAG | 26 | 0.039 | 0.968 | Deletion | | |
| ATGGAGGAGTTGGCAGATGCgcggctgttcctg tacagaaccgtgggcgagatgtggatcaaggat gcTCTAATGTACTGCCATGGGAAG | 21 | 0.032 | 0.782 | Insertion | +3 | 48 |
| ATGGAGGAGTTGGCAGATGC-CTAATGTACTGC CATGGGAAG | 14 | 0.021 | 0.521 | Deletion | +3 | 1 |
| ATGGAGGAGTTGGCAGATGCtgtcatgatcttt ttccgctcgtcgtgggacttgctcagttctctg gccagctcgTCTAATGTACTGCCATGGGAAG | 10 | 0.015 | 0.372 | Insertion | +3 | 55 |
| ATGGAGGAGTTGGCAGATGCTCT-ATGTACTGC CATGGGAAG | 8 | 0.012 | 0.29 | Deletion | +6 | 1 |

TABLE 10.6

Specific insertions and deletions for Guide 188 using RGN APG08290.1

| Guide 188 (SEQ ID NO: 154) | # Reads | % Reads | % of INDELs | Type | INDEL Location | Size |
|---|---|---|---|---|---|---|
| CAGGGACAGTGCGCATCTCCCTGGTCACCAAG | 59686 | 97.000 | | | | |
| CAGGGACA---------------GTCACCAAG | 1286 | 2.089 | 69.664 | Deletion | 0 | 15 |
| CAGGGACAGTGCGCATCTC-CTGGTCACCAAG | 473 | 0.768 | 25.622 | Deletion | +3 | 1 |
| CAGGGACAGTGCGCATCT--CTGGTCACCAAG | 57 | 0.092 | 3.087 | Deletion | +3 | 2 |
| CAGGGACAGTGCGCATCTCCtCTGGTCACCAAG | 11 | 0.017 | 0.595 | Insertion | +3 | 1 |
| CAGGGACAGTGCGCATC---CTGGTCACCAAG | 7 | 0.011 | 0.379 | Deletion | +3 | 3 |
| CAGGGAC---------------GGTCACCAAG | 7 | 0.011 | 0.379 | Deletion | +2 | 15 |
| CGGGGACAGgGCGCATCTC-CTGGTCACCAAG | 5 | 0.008 | 0.270 | Deletion & Mutation | +3 | 1 |

TABLE 10.7

Specific insertions and deletions for Guide 192 using RGN APG08290.1

| Guide 192 (SEQ ID NO: 155) | # Reads | % Reads | % of INDELs | Type | INDEL Location | Size |
|---|---|---|---|---|---|---|
| CGACCTGAATGCTGTGCGGCTCT<u>GCTTCCAGG</u> | 62352 | 95.658 | | | | |
| CGACCTGAATGCTGTGCGGCaTCT<u>GCTTCCAGG</u> | 1262 | 1.936 | 44.593 | Insertion | +3 | 1 |
| CGACCTGAATGCTGTGCGGCtTCT<u>GCTTCCAGG</u> | 842 | 1.291 | 29.752 | Insertion | +3 | 1 |
| CGACCTGAATGCTGTG----TCT<u>GCTTCCAGG</u> | 686 | 1.052 | 24.240 | Deletion | +3 | 4 |
| CGACCTGcATGCTGTGCGGCaTCT<u>GCTTCCAGG</u> | 18 | 0.027 | 0.636 | Insertion & Mutation | +3 | 1 |
| CGACCTGcATGCTGTGCGGCtTCT<u>GCTTCCAGG</u> | 11 | 0.016 | 0.388 | Insertion & Mutation | +3 | 1 |
| CGACCTGcATGCTGTG----TCT<u>GCTTCCAGG</u> | 6 | 0.009 | 0.212 | Deletion & Mutation | +3 | 4 |
| CGACCTGAATGCTGTGCGaCaTCT<u>GCTTCCAGG</u> | 5 | 0.007 | 0.176 | Insertion & Mutation | +3 | 2 |

TABLE 10.8

Specific insertions and deletions for Guide 196 using RGN APG08290.1

| Guide 196 (SEQ ID NO: 156) | # Reads | % Reads | % of INDELs | Type | INDEL Location | Size |
|---|---|---|---|---|---|---|
| T<u>GGGGACTA</u>CGACCTGAATGCTGTGCGGCTCT | 37206 | 93.073 | | | | |
| T<u>GGGGACTA</u>CGA-----ATGCTGTGCGGCTCT | 1288 | 3.222 | 46.514 | Deletion | +3 | 5 |
| T<u>GGGGACTA</u>CGAgcaggcagaagtatgcaaagcatgcatctcaattCCTGAATGCTGTGCGGCTCT | 881 | 2.203 | 31.816 | Insertion | +3 | 34 |
| T<u>GGGGACTA</u>CGAagaaggcgatagaaggccatgcgctgcgaatcgggagcggCCTGAATGCTGTGCGGCTCT | 302 | 0.755 | 10.906 | Insertion | +3 | 40 |
| T<u>GGGGACTA</u>CGAtgactcgctgcgctcggtcgttcggctgcggcgagcggtatcagctcactcaaaggcggtaatacggCCTGAATGCTGTGCGGCTCT | 272 | 0.680 | 9.823 | Insertion | +3 | 67 |
| T<u>GGG</u>-----------------GTGCGGCTCT | 13 | 0.032 | 0.4694 | Deletion | -5 | 18 |
| T<u>GGGGACTA</u>CGAC-----TGCTGTGCGGCTCT | 13 | 0.032 | 0.469 | Deletion | +4 | 5 |

TABLE 10.9

Specific insertions and deletions for Guide 190 using RGN APG07433.1

| Guide 190 (SEQ ID NO: 146) | #Reads | % Reads | % of INDELs | Type | INDEL Location | Size |
|---|---|---|---|---|---|---|
| CGACCTGAATGCTGTGC------------------------------------------------------------------------------------------------------------------------GGCGCTCTGGCTTCATTCAATC | 64040 | 55.46 | 91.70 | Deletion | -164 | 170 |
| CGACCTGAATGCTGTGCGGCTCT<u>GCTTCCAGG</u>TGA | 45619 | 39.51 | | WT | | |
| CGACCTGAATGCTGTGCGGCaTCT<u>GCTTCCAGG</u>TGA | 3620 | 3.13 | 5.18 | Insertion | +3 | 1 |
| CGACCTGAATG----------CT<u>GCTTCCAGG</u>TGA | 1110 | 0.96 | 1.58 | Deletion | +2 | 10 |

TABLE 10.9-continued

Specific insertions and deletions for Guide 190 using RGN APG07433.1

| Guide 190 (SEQ ID NO: 146) | #Reads | % Reads | % of INDELs | Type | INDEL Location | Size |
|---|---|---|---|---|---|---|
| CGACCTGAATGCT-------TCTGCTTCCAGGTGA | 858 | 0.74 | 1.22 | Deletion | +3 | 7 |
| CGACCTGAA-------------TGCTTCCAGGTGA | 206 | 0.17 | 0.29 | Deletion | +1 | 13 |

Example 7: Demonstration of Gene Editing Activity in Plant Cells

RNA-guided nuclease activity of the RGNs of the invention is demonstrated in plant cells using protocols adapted from Li, et al. (2013) *Nat. Biotech.* 31:688-691. Briefly, plant codon optimized versions of each RGN (SEQ ID NOs: 169-182) containing an N-terminal SV40 nuclear localization signal are cloned behind the strong constitutive 35S promoter in a transient transformation vector. sgRNAs targeting one or more sites in the plant PDS gene that flank an appropriate PAM sequence are cloned behind a plant U6 promoter in a second transient expression vector. The expression vectors are introduced into *Nicotiana benthamiana* mesophyll protoplasts using PEG-mediated transformation. The transformed protoplasts are incubated in the dark for up to 36 hr. Genomic DNA is isolated from the protoplasts using a DNeasy Plant Mini Kit (Qiagen). The genomic region flanking the RGN target site is PCR amplified, and products are purified using QiaQuick Spin Column (Qiagen) following the manufacturer's protocol. 200-500 ng total of the purified PCR products are mixed with 1 µl 10× Taq DNA Polymerase PCR buffer (Enzymatics) and ultrapure water to a final volume of 10 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 min. After reannealing, products are treated with SURVEYOR nuclease and SURVEYOR enhancer S (Integrated DNA Technologies) following the manufacturer's recommended protocol and analyzed on 4-20% Novex TBE polyacrylamide gels (Life Technologies). Gels are stained with SYBR Gold DNA stain (Life Technologies) for 10 min and imaged with a Gel Doc gel imaging system (Bio-rad). Quantification is based on relative band intensities. Indel percentage is determined by the formula, $100\times(1-(1-(b+c)/(a+b+c))^{1/2})$, where a is the integrated intensity of the undigested PCR product, and b and c are the integrated intensities of each cleavage product.

Alternatively, PCR products derived from the targeted genomic sequence can be subjected to PCR similar to that described in Example 6, so that PCR products contain Illumina overhang sequences and can undergo library preparation and deep sequencing. This method allows determination of the rates of editing as shown in Table 9.

Example 8: Guide Cross-Compatibility

To determine the cross-compatibility of guide RNAs between RGNs, a two-plasmid interference experiment was performed (Esvelt et al (2013), Nat. Methods 10(11): 1116-21). The first plasmid contained the RGN with several targets containing defined PAMs on a kanamycin resistant backbone. These plasmids were transformed into *E. coli* BL21, and the transformed strains were made to be chemically competent. A second plasmid containing a guide RNA on an ampicillin resistance backbone was then introduced. Cells were plated on media containing both antibiotics. If an RGN is able to use the guide on the second plasmid, the kanamycin-resistance plasmid is cleaved and linearized, resulting in little or no colony formation. If an RGN is not able to use the guide on the second plasmid, the kanamycin-resistance plasmid is not be cleaved, resulting in high levels of colony formation. Guide RNAs for *Streptococcus pyogenes* Cas9 (SpyCas9) and *Staphylococcus aureus* Cas9 (SauCas9) were also included to determine cross-compatibility with those guide RNAs.

To calculate the depletion percentage, the number of colonies for each guide transformation is compared to the transformation efficiency using a positive control. Based on this comparison, if an RGN can use a guide, the depletion percentage should be 0, as no colonies are able to survive. If an RGN cannot use a guide, the depletion percentage should be 1 as all plasmids remain intact. Results are shown in Table 11 below. "sg" indicates the guide RNA for the recited RGN.

TABLE 11

Cross-compatibility assay

| | APG05083.1 | APG07513.1 | APG08290.1 | APG05459.1 | APG04583.1 | APG01688.1 |
|---|---|---|---|---|---|---|
| sgAPG05083.1 | 0 | 0 | 0 | 0.21 | 1 | 0.74 |
| sgAPG07433.1 | 0 | 0 | 0 | 0.16 | 0.78 | 0.33 |
| sgAPG07513.1 | 0 | 0.01 | 0 | 0.32 | 0.97 | 0.64 |
| sgAPG05459.1 | 0.24 | 0.53 | 0.26 | 0.09 | 1 | 0.49 |
| sgAPG04583.1 | 0.74 | 0.8 | 0.36 | 0.21 | 0 | 0 |
| sgAPG01688.1 | 0.12 | 0.26 | 0.18 | 0.43 | 0 | 0 |
| sgSauCas9 | 1 | 0.23 | 0.27 | 0.53 | 0.51 | 0.92 |
| sg Spy | 0.16 | 0.27 | 0.32 | 0.06 | 1 | 1 |

As Table 11 indicates, there are four groups of orthogonal systems. RGNs can recognize guides from other systems in their groups, but cannot use guides from other groups. The first group contains APG05083.1, APG07433.1, APG07513.1, and APG08290.1. The second group contains SpyCas9 and APG05459.1. The third group contains APG04583.1 and APG01688.1. The fourth group contains SauCas9.

Example 9: Identification of Disease Targets

A database of clinical variants was obtained from NCBI ClinVar database, which is available through the world wide web at the NCBI ClinVar website. Pathogenic Single Nucleotide Polymorphisms (SNPs) were identified from this list. Using the genomic locus information, CRISPR targets in the region overlapping and surrounding each SNP were identified. A selection of SNPs that can be corrected using base editing in combination with the RGNs of the invention to target the causal mutation is listed in Table 12. In Table 12, only one alias of each disease is listed. The "RS#" corresponds to the RS accession number through the SNP database at the NCBI website. The AlleleID corresponds to a causal allele accession number, and the Chromosome Accession number also provides accession reference information found through the NCBI website. Table 12 also provides genomic target sequence information suitable for the RGN listed for each disease. The target sequence information also provides protospacer sequence for the production of the necessary sgRNA for the corresponding RGN of the invention.

TABLE 12

Disease Targets for RGNs of the invention

| Disease | RS# (dbSNP) | RGN | Causal Mutation | Allele ID | ChromosomeAccession | Gene Symbol | Target Seq (SEQ ID NO) |
|---|---|---|---|---|---|---|---|
| Ataxia-telangiectasia syndrome | 1137887 | APG04583.1 | G > A | 18083 | NC_000011.10, NC_000011.9 | ATM | 197 |
| Very long chain acyl-CoA dehydrogenase deficiency | 2309689 | APG05459.1 | G > A | 33868 | NC_000017.10, NC_000017.11 | ACADVL | 198 |
| Abnormality of T cell physiology | 3218716 | APG01688.1 | G > A | 52071 | NC_000014.8, NC_000014.9 | MYH7 | 199 |
| Cardiovascular phenotype | 5742905 | APG05083, APG07433.1, APG07513.1, APG08290.1 | T > C | 15159 | NC_000021.8, NC_000021.9 | CBS | 200 |
| 3-Oxo-5 alpha-steroid delta 4-dehydrogenase deficiency | 9332964 | APG04583.1 | G > A | 18390 | NC_000002.11, NC_000002.12 | SRD5A2 | 201 |
| Acute myeloid leukemia | 11540652 | APG05083, APG07433.1, APG07513.1, APG08290.1 | G > A | 27395 | NC_000017.10, NC_000017.11 | TP53 | 202 |
| Acute myeloid leukemia | 11540652 | APG05459.1 | G > A | 27395 | NC_000017.10, NC_000017.11 | TP53 | 203 |
| Cutaneous malignant melanoma 3 | 11547328 | APG05459.1 | C > T | 31967 | NC_000012.11, NC_000012.12 | CDK4 | 204 |
| Alpha-1-antitrypsin deficiency | 28929474 | APG05459.1 | G > A | 33006 | NC_000014.8, NC_000014.9 | SERPINA1 | 205 |
| Charcot-Marie-Tooth disease, type 2 | 28933093 | APG05459.1 | G > A | 29543 | NC_000001.10, NC_000001.11 | LMNA | 206 |
| Hereditary cancer-predisposing syndrome | 28934578 | APG05083, APG07433.1, APG07513.1, APG08290.1 | G > A | 27413 | NC_000017.10, NC_000017.11 | TP53 | 207 |
| Hereditary cancer-predisposing syndrome | 28934578 | APG01688.1 | G > A | 27413 | NC_000017.10, NC_000017.11 | TP53 | 208 |
| Hereditary cancer-predisposing syndrome | 28934872 | APG05459.1 | G > A | 27436 | NC_000016.9, NC_000016.10 | TSC2 | 209 |
| Brugada syndrome | 28937316 | APG05083, APG07433.1, APG07513.1, APG08290.1 | G > A | 24408 | NC_000003.11, NC_000003.12 | SCN5A | 210 |
| Brugada syndrome | 28937318 | APG05459.1 | G > A | 24429 | NC_000003.11, NC_000003.12 | SCN5A | 211 |
| GRACILE syndrome | 28937590 | APG05459.1 | A > G | 21206 | NC_000002.11, NC_000002.12 | BCS1L | 212 |
| Enhanced s-cone syndrome | 28937873 | APG05459.1 | G > A | 20571 | NC_000015.9, NC_000015.10 | NR2E3 | 213 |
| Charcot-Marie-Tooth disease, type 2 | 28940293 | APG05083, APG07433.1, APG07513.1, APG08290.1 | T > C | 17309 | NC_000001.10,NC_000001.11 | MFN2 | 214 |
| Charcot-Marie-Tooth disease, type 2 | 28940293 | APG05459.1 | T > C | 17309 | NC_000001.10, NC_000001.11 | MFN2 | 215 |
| Arylsulfatase a, allele a | 28940893 | APG05459.1 | C > T | 18091 | NC_000022.10, NC_000022.11 | ARSA | 216 |
| Familial hypercholesterolemia | 28942078 | APG05459.1 | G > A | 18733 | NC_000019.9, NC_000019.10 | LDLR | 217 |
| Familial hypercholesterolemia | 28942079 | APG05459.1 | G > A | 18734 | NC_000019.9, NC_000019.10 | LDLR | 218 |
| HEMOGLOBIN ARLINGTON PARK | 33930165 | APG05083, APG07433.1, APG07513.1, APG08290.1 | G > A | 30165 | NC_000011.9, NC_000011.10 | HBB | 219 |
| Familial hypertrophic cardiomyopathy 1 | 36211715 | APG05459.1 | G > A | 29159 | NC_000014.8, NC_000014.9 | MYH7 | 220 |
| Cardiovascular phenotype | 36211723 | APG05459.1 | G > A | 45266 | NC_000011.9, NC_000011.10 | MYBPC3 | 221 |
| Cardiovascular phenotype | 36211723 | APG01688.1 | G > A | 45266 | NC_000011.9, NC_000011.10 | MYBPC3 | 222 |

TABLE 12-continued

Disease Targets for RGNs of the invention

| Disease | RS# (dbSNP) | RGN | Causal Mutation | Allele ID | Chromosome Accession | Gene Symbol | Target Seq (SEQ ID NO) |
|---|---|---|---|---|---|---|---|
| Brugada syndrome | 45546039 | APG05083, APG07433.1, APG07513.1, APG08290.1 | G > A | 48043 | NC_000003.11, NC_000003.12 | SCN5A | 223 |
| Brugada syndrome | 45546039 | APG01688.1 | G > A | 48043 | NC_000003.11, NC_000003.12 | SCN5A | 224 |
| Hereditary cancer-predisposing syndrome | 55863639 | APG05459.1 | G > A | 176641 | NC_000017.10, NC_000017.11 | TP53 | 225 |
| Deficiency of butyryl-CoA dehydrogenase | 57443665 | APG05459.1 | T > C | 18867 | NC_000012.11, NC_000012.12 | ACADS | 226 |
| Deficiency of butyryl-CoA dehydrogenase | 57443665 | APG01688.1 | T > C | 18867 | NC_000012.11, NC_000012.12 | ACADS | 227 |
| Benign scapuloperoneal muscular dystrophy with cardiomyopathy | 59332535 | APG05459.1 | G > A | 77828 | NC_000001.10, NC_000001.11 | LMNA | 228 |
| Benign scapuloperoneal muscular dystrophy with cardiomyopathy | 60458016 | APG05459.1 | G > A | 29564 | NC_000001.10, NC_000001.11 | LMNA | 229 |
| Cone-rod dystrophy 6 | 61750173 | APG05459.1 | G > A | 24396 | NC_000017.10, NC_000017.11 | GUCY2D | 230 |
| Cone-rod dystrophy 6 | 61750173 | APG01688.1 | G > A | 24396 | NC_000017.10, NC_000017.11 | GUCY2D | 231 |
| Stargardt disease 1 | 61750641 | APG05083, APG07433.1, APG07513.1, APG08290.1 | G > A | 105317 | NC_000001.10, NC_000001.11 | ABCA4 | 232 |
| Leber congenital amaurosis 2 | 61751276 | APG05459.1 | G > A | 104715 | NC_000001.10, NC_000001.11 | RPE65 | 233 |
| Cone-rod dystrophy 3 | 61751407 | APG05459.1 | G > A | 105292 | NC_000001.10, NC_000001.11 | ABCA4 | 234 |
| Nonsyndromic Oculocutaneous Albinism | 61754375 | APG05459.1 | G > A | 18835 | NC_000011.9, NC_000011.10 | TYR | 235 |
| Phenylketonuria | 62508646 | APG05459.1 | T > C | 15654 | NC_000012.11, NC_000012.12 | PAH | 236 |
| Phenylketonuria | 62516101 | APG05083, APG07433.1, APG07513.1, APG08290.1 | G > A | 15658 | NC_000012.11, NC_000012.12 | PAH | 237 |
| Breast-ovarian cancer, familial 1 | 62625303 | APG05459.1 | C > T | 68931 | NC_000017.10, NC_000017.11 | BRCA1 | 238 |
| Hyperphenylalaninemia, non-pku | 62644499 | APG05083, APG07433.1, APG07513.1, APG08290.1 | G > A | 15656 | NC_000012.11, NC_000012.12 | PAH | 239 |
| Hyperphenylalaninemia, non-pku | 62644499 | APG05459.1 | G > A | 15656 | NC_000012.11, NC_000012.12 | PAH | 240 |
| Hereditary cancer-predisposing syndrome | 63750217 | APG05459.1 | G > A | 32138 | NC_000003.11, NC_000003.12 | MLH1 | 241 |
| Hereditary cancer-predisposing syndrome | 63750741 | APG05083, APG07433.1, APG07513.1, APG08290.1 | T > C | 94663 | NC_000002.11, NC_000002.12 | MSH6 | 242 |
| Hereditary cancer-predisposing syndrome | 63750809 | APG05459.1 | T > C | 95480 | NC_000003.11, NC_000003.12 | MLH1 | 243 |
| Hereditary cancer-predisposing syndrome | 63751657 | APG05083, APG07433.1, APG07513.1, APG08290.1 | G > A | 95331 | NC_000003.11, NC_000003.12 | MLH1 | 244 |
| Hereditary cancer-predisposing syndrome | 63751711 | APG05083, APG07433.1, APG07513.1, APG08290.1 | G > A | 95792 | NC_000003.11, NC_000003.12 | MLH1 | 245 |
| Hereditary cancer-predisposing syndrome | 63751711 | APG01688.1 | G > A | 95792 | NC_000003.11, NC_000003.12 | MLH1 | 246 |
| Anterior segment dysgenesis 6 | 72549387 | APG05459.1 | G > A | 22776 | NC_000002.11, NC_000002.12 | CYP1B1 | 247 |
| Brugada syndrome | 72549410 | APG05083, APG07433.1, APG07513.1, APG08290.1 | G > A | 78547 | NC_000003.11, NC_000003.12 | SCN5A | 248 |
| Brugada syndrome | 72549410 | APG05459.1 | G > A | 78547 | NC_000003.11, NC_000003.12 | SCN5A | 249 |
| Ornithine carbamoyltransferase deficiency | 72554308 | APG01688.1 | G > A | 26053 | NC_000023.10, NC_000023.11 | OTC | 250 |
| Osteogenesis imperfecta type I | 72645321 | APG05083, APG07433.1, APG07513.1, APG08290.1 | G > A | 414022 | NC_000017.10, NC_000017.11 | COL1A1 | 251 |

TABLE 12-continued

Disease Targets for RGNs of the invention

| Disease | RS# (dbSNP) | RGN | Causal Mutation | Allele ID | ChromosomeAccession | Gene Symbol | Target Seq (SEQ ID NO) |
|---|---|---|---|---|---|---|---|
| Osteogenesis imperfecta type I | 72645321 | APG05083, APG07433.1, APG07513.1, APG08290.1 | G > A | 414022 | NC_000017.10, NC_000017.11 | COL1A1 | 252 |
| Constipation | 74799832 | APG05083, APG07433.1, APG07513.1, APG08290.1 | T > C | 28958 | NC_000010.10, NC_000010.11 | RET | 253 |
| Dopamine beta hydroxylase deficiency | 74853476 | APG05083, APG07433.1, APG07513.1, APG08290.1 | T > C | 16789 | NC_000009.11, NC_000009.12 | DBH | 254 |
| Cystic fibrosis | 75096551 | APG05083, APG07433.1, APG07513.1, APG08290.1 | G > A | 33858 | NC_000007.13, NC_000007.14 | CFTR | 255 |
| Phenylketonuria | 75193786 | APG01688.1 | T > C | 15675 | NC_000012.11, NC_000012.12 | PAH | 256 |
| Deficiency of UDPglucose-hexose-1-phosphate uridylyltransferase | 75391579 | APG05459.1 | A > G | 18653 | NC_000009.11, NC_000009.12 | GALT | 257 |
| Amyloid Cardiomyopathy, Transthyretin-related | 76992529 | APG05459.1 | G > A | 28465 | NC_000018.9, NC_000018.10 | TTR | 258 |
| Carbohydrate-deficient glycoprotein syndrome type I | 80338707 | APG01688.1 | G > A | 22758 | NC_000016.9, NC_000016.10 | PMM2 | 259 |
| Metachromatic leukodystrophy | 80338815 | APG01688.1 | G > A | 18090 | NC_000022.10, NC_000022.11 | ARSA | 260 |
| Smith-Lemli-Opitz syndrome | 80338857 | APG05083, APG07433.1, APG07513.1, APG08290.1 | G > A | 34128 | NC_000011.9, NC_000011.10 | DHCR7 | 261 |
| Deafness, autosomal recessive 1A | 80338940 | APG05459.1 | G > A | 32068 | NC_000013.10, NC_000013.11 | GJB2 | 262 |
| Congenital omphalocele | 80338945 | APG05083, APG07433.1, APG07513.1, APG08290.1 | T > C | 32055 | NC_000013.10, NC_000013.11 | GJB2 | 263 |
| Congenital omphalocele | 80338945 | APG05083, APG07433.1, APG07513.1, APG08290.1 | T > C | 32055 | NC_000013.10, NC_000013.11 | GJB2 | 264 |
| Congenital omphalocele | 80338945 | APG05459.1 | T > C | 32055 | NC_000013.10, NC_000013.11 | GJB2 | 265 |
| Congenital omphalocele | 80338945 | APG05459.1 | T > C | 32055 | NC_000013.10, NC_000013.11 | GJB2 | 266 |
| Congenital myotonia, autosomal dominant form | 80356701 | APG05083, APG07433.1, APG07513.1, APG08290.1 | T > C | 33902 | NC_000007.13, NC_000007.14 | CLCN1 | 267 |
| Breast-ovarian cancer, familial 1 | 80356914 | APG05459.1 | G > A | 70276 | NC_000017.10, NC_000017.11 | BRCA1 | 268 |
| Breast and/or ovarian cancer | 80356962 | APG05459.1 | G > A | 70247 | NC_000017.10, NC_000017.11 | BRCA1 | 269 |
| Breast-ovarian cancer, familial 1 | 80357212 | APG05459.1 | G > A | 70255 | NC_000017.10, NC_000017.11 | BRCA1 | 270 |
| Breast-ovarian cancer, familial 1 | 80357281 | APG05459.1 | T > C | 70177 | NC_000017.10, NC_000017.11 | BRCA1 | 271 |
| Breast-ovarian cancer, familial 1 | 80357307 | APG05459.1 | G > A | 70275 | NC_000017.10, NC_000017.11 | BRCA1 | 272 |
| Breast-ovarian cancer, familial 1 | 80357352 | APG05459.1 | C > T | 69958 | NC_000017.10, NC_000017.11 | BRCA1 | 273 |
| Breast-ovarian cancer, familial 1 | 80358145 | APG05459.1 | G > A | 46229 | NC_000017.10, NC_000017.11 | BRCA1 | 274 |
| Inborn genetic diseases | 80358259 | APG05083, APG07433.1, APG07513.1, APG08290.1 | T > C | 18006 | NC_000018.9, NC_000018.10 | NPC1 | 275 |
| Breast-ovarian cancer, familial 2 | 80358543 | APG05459.1 | G > A | 131539 | NC_000013.10, NC_000013.11 | BRCA2 | 276 |
| Breast-ovarian cancer, familial 2 | 80358544 | APG05459.1 | G > A | 46368 | NC_000013.10, NC_000013.11 | BRCA2 | 277 |
| Breast-ovarian cancer, familial 2 | 80358997 | APG05459.1 | G > A | 67062 | NC_000013.10, NC_000013.11 | BRCA2 | 278 |
| Breast and/or ovarian cancer | 80359003 | APG05083, APG07433.1, APG07513.1, APG08290.1 | G > A | 67069 | NC_000013.10, NC_000013.11 | BRCA2 | 279 |
| Breast-ovarian cancer, familial 2 | 80359004 | APG05083, APG07433.1, APG07513.1, APG08290.1 | G > A | 46672 | NC_000013.10, NC_000013.11 | BRCA2 | 280 |
| Breast-ovarian cancer, familial 2 | 80359071 | APG05459.1 | G > A | 67203 | NC_000013.10, NC_000013.11 | BRCA2 | 281 |
| Breast-ovarian cancer, familial 2 | 80359112 | APG05459.1 | C > T | 67292 | NC_000013.10, NC_000013.11 | BRCA2 | 282 |
| Breast-ovarian cancer, familial 2 | 80359115 | APG05459.1 | C > T | 67294 | NC_000013.10, NC_000013.11 | BRCA2 | 283 |
| Smith-Lemli-Opitz syndrome | 104886033 | APG05459.1 | A > G | 21833 | NC_000011.9, NC_000011.10 | DHCR7 | 284 |

TABLE 12-continued

Disease Targets for RGNs of the invention

| Disease | RS# (dbSNP) | RGN | Causal Mutation | Allele ID | ChromosomeAccession | Gene Symbol | Target Seq (SEQ ID NO) |
|---|---|---|---|---|---|---|---|
| Alport syndrome 1, X-linked recessive | 104886142 | APG05083, APG07433.1, APG07513.1, APG08290.1 | G > A | 35796 | NC_000023.10, NC_000023.11 | COL4A5 | 285 |
| Acute neuronopathic Gaucher's disease | 104886460 | APG05459.1 | G > A | 99352 | NC_000001.10, NC_000001.11 | GBA | 286 |
| Gonadotropin deficiency | 104893836 | APG05459.1 | A > G | 31062 | NC_000004.11, NC_000004.12 | GNRHR | 287 |
| Distal arthrogryposis type 1A | 104894129 | APG05459.1 | G > A | 27501 | NC_000009.11, NC_000009.12 | TPM2 | 288 |
| Distal arthrogryposis type 1A | 104894129 | APG05459.1 | G > A | 27501 | NC_000009.11, NC_000009.12 | TPM2 | 289 |
| Hereditary cancer-predisposing syndrome | 104894261 | APG05459.1 | C > T | 31727 | NC_000011.9, NC_000011.10 | MEN1 | 290 |
| Inborn genetic diseases | 104894313 | APG05459.1 | C > T | 18816 | NC_000011.9, NC_000011.10 | TYR | 291 |
| Death in early adulthood | 104894368 | APG05083, APG07433.1, APG07513.1, APG08290.1 | G > A | 29104 | NC_000012.11, NC_000012.12 | MYL2 | 292 |
| Death in early adulthood | 104894368 | APG05459.1 | G > A | 29104 | NC_000012.11, NC_000012.12 | MYL2 | 293 |
| Severe autosomal recessive muscular dystrophy of childhood - North African type | 104894423 | APG05459.1 | G > A | 17048 | NC_000013.10, NC_000013.11, NC_000013.9 | SGCG | 294 |
| Cardiovascular phenotype | 104894503 | APG05459.1 | G > A | 27495 | NC_000015.9, NC_000015.10 | TPM1 | 295 |
| Carbohydrate-deficient glycoprotein syndrome type I | 104894525 | APG01688.1 | G > A | 22747 | NC_000016.9, NC_000016.10 | PMM2 | 296 |
| Charcot-Marie-Tooth disease, type I | 104894621 | APG05459.1 | C > T | 23472 | NC_000017.10, NC_000017.11 | PMP22 | 297 |
| Inborn genetic diseases | 104894635 | APG05083, APG07433.1, APG07513.1, APG08290.1 | G > A | 20146 | NC_000017.10, NC_000017.11 | SGSH | 298 |
| Inborn genetic diseases | 104894635 | APG05459.1 | G > A | 20146 | NC_000017.10, NC_000017.11 | SGSH | 299 |
| Familial Mediterranean fever | 104895097 | APG05083, APG07433.1, APG07513.1, APG08290.1 | G > A | 17588 | NC_000016.9, NC_000016.10 | MEFV | 300 |
| Deafness, autosomal recessive 2 | 111033178 | APG05083, APG07433.1, APG07513.1, APG08290.1 | G > A | 52388 | NC_000011.9, NC_000011.10 | MYO7A | 301 |
| Deafness, autosomal recessive 2 | 111033178 | APG01688.1 | G > A | 52388 | NC_000011.9, NC_000011.10 | MYO7A | 302 |
| Deafness, X-linked 2 | 111033299 | APG05083, APG07433.1, APG07513.1, APG08290.1 | G > A | 53902 | NC_000013.10, NC_000013.11 | GJB2 | 303 |
| Enlarged vestibular aqueduct | 111033305 | APG05083, APG07433.1, APG07513.1, APG08290.1 | G > A | 52666 | NC_000007.13, NC_000007.14 | SLC26A4 | 304 |
| Congenital sensorineural hearing impairment | 111033364 | APG05459.1, APG01688.1 | G > A | 17396 | NC_000001.10, NC_000001.11 | USH2A | 305 |
| Deficiency of UDPglucose-hexose-1-phosphate uridylyltransferase | 111033728 | APG05459.1 | T > C | 36556 | NC_000009.11, NC_000009.12 | GALT | 306 |
| Very long chain acyl-CoA dehydrogenase deficiency | 112406105 | APG05459.1 | G > A | 200333 | NC_000017.10, NC_000017.11 | ACADVL | 307 |
| Cardiovascular phenotype | 112645512 | APG05459.1 | C > T | 178700 | NC_000015.10, NC_000015.9 | FBN1 | 308 |
| Pyruvate kinase deficiency of red cells | 113403872 | APG05459.1 | G > A | 16550 | NC_000001.10, NC_000001.11 | PKLR | 309 |
| Autosomal dominant progressive external ophthalmoplegia with mitochondrial DNA deletions 1 | 113994095 | APG05083, APG07433.1, APG07513.1, APG08290.1 | G > A | 28535 | NC_000015.9, NC_000015.10 | POLG | 310 |
| Very long chain acyl-CoA dehydrogenase deficiency | 113994167 | APG05459.1 | T > C | 33877 | NC_000017.10, NC_000017.11 | ACADVL | 311 |
| Cystinosis, ocular nonnephropathic | 113994205 | APG05459.1 | G > A | 19482 | NC_000017.10, NC_000017.11 | CTNS | 312 |
| Pyruvate kinase deficiency of red cells | 116100695 | APG05459.1 | C > T | 16552 | NC_000001.10, NC_000001.11 | PKLR | 313 |
| Distal myopathy, Tateyama type | 116840778 | APG01688.1 | G > A | 23322 | NC_000003.11, NC_000003.12 | CAV3; SSUH2 | 314 |
| Malignant hyperthermia, susceptibility to, 1 | 118192122 | APG05083, APG07433.1, | G > A | 76888 | NC_000019.9, NC_000019.10 | RYR1 | 315 |

TABLE 12-continued

Disease Targets for RGNs of the invention

| Disease | RS# (dbSNP) | RGN | Causal Mutation | Allele ID | ChromosomeAccession | Gene Symbol | Target Seq (SEQ ID NO) |
|---|---|---|---|---|---|---|---|
| Malignant hyperthermia, susceptibility to, 1 | 118192122 | APG07513.1, APG08290.1 APG05083, APG07433.1, APG07513.1, APG08290.1 | G > A | 76888 | NC_000019.9, NC_000019.10 | RYR1 | 316 |
| Myopathy, Central Core | 118192158 | APG05083, APG07433.1, APG07513.1, APG08290.1 | G > A | 76835 | NC_000019.9, NC_000019.10 | RYR1 | 317 |
| Myopathy, Central Core | 118192158 | APG05459.1 | G > A | 76835 | NC_000019.9, NC_000019.10 | RYR1 | 318 |
| Myopathy, Central Core | 118192158 | APG01688.1 | G > A | 76835 | NC_000019.9, NC_000019.10 | RYR1 | 319 |
| Malignant hyperthermia, susceptibility to, 1 | 118192170 | APG05083, APG07433.1, APG07513.1, APG08290.1 | T > C | 28014 | NC_000019.9, NC_000019.10 | RYR1 | 320 |
| Ceroid lipofuscinosis neuronal 2 | 119455954 | APG05083, APG01688.1 | G > A | 17681 | NC_000011.9, NC_000011.10 | TPP1 | 321 |
| Ceroid lipofuscinosis neuronal 2 | 119455954 | APG01688.1 | G > A | 17681 | NC_000011.9, NC_000011.10 | TPP1 | 322 |
| Niemann-Pick disease type C1 | 120074135 | APG05083, APG07433.1, APG07513.1, APG08290.1 | G > A | 18010 | NC_000018.9, NC_000018.10 | NPC1 | 323 |
| Glutaric aciduria, type 1 | 121434372 | APG05083, APG07433.1, APG07513.1, APG08290.1 | G > A | 17127 | NC_000019.9, NC_000019.10 | GCDH | 324 |
| CAPN3-Related Disorders | 121434548 | APG05083, APG07433.1, APG07513.1, APG08290.1 | G > A | 32661 | NC_000015.9, NC_000015.10 | CAPN3; POMT1 | 325 |
| CAPN3-Related Disorders | 121434548 | APG05459.1 | G > A | 32661 | NC_000015.9, NC_000015.10 | CAPN3; POMT1 | 326 |
| Glycogen storage disease, type II | 121907943 | APG05459.1 | C > T | 19073 | NC_000017.10, NC_000017.11 | GAA | 327 |
| Nonsyndromic Oculocutaneous Albinism | 121908011 | APG05083, APG07433.1, APG07513.1, APG08290.1 | G > A | 18814 | NC_000011.9, NC_000011.10 | TYR | 328 |
| Familial hypercholesterolemia | 121908033 | APG05459.1 | G > A | 18765 | NC_000019.9, NC_000019.10 | LDLR | 329 |
| Familial hypercholesterolemia | 121908039 | APG05459.1 | G > A | 18778 | NC_000019.9, NC_000019.10 | LDLR | 330 |
| Deafness, autosomal recessive 7 | 121908073 | APG05459.1 | C > T | 19142 | NC_000009.11, NC_000009.12 | TMC1 | 331 |
| Chronic infantile neurological, cutaneous and articular syndrome | 121908153 | APG05459.1 | G > A | 19416 | NC_000001.10, NC_000001.11 | NLRP3 | 332 |
| Eichsfeld type congenital muscular dystrophy | 121908185 | APG05459.1 | G > A | 19531 | NC_000001.10, NC_000001.11 | SELENON | 333 |
| Inborn genetic diseases | 121908192 | APG05459.1 | G > A | 23730 | NC_000016.9, NC_000016.10 | GFER | 334 |
| Hyperkalemic Periodic Paralysis Type 1 | 121908557 | APG05459.1 | G > A | 20958 | NC_000017.10, NC_000017.11 | SCN4A | 335 |
| Inclusion body myopathy 2 | 121908627 | APG05459.1 | G > A | 21067 | NC_000009.11, NC_000009.12 | GNE | 336 |
| Severe APG05083.1, APG07433.1, APG07513.1, APG08290.1 immunodeficiency due to ADA deficiency | 121908716 | APG05083, APG07433.1, APG07513.1, APG08290.1 | G > A | 16996 | NC_000020.10, NC_000020.11 | ADA | 337 |
| Severe APG05083.1, APG07433.1, APG07513.1, APG08290.1 immunodeficiency due to ADA deficiency | 121908739 | APG05083, APG07433.1, APG07513.1, APG08290.1 | T > C | 17004 | NC_000020.10, NC_000020.11 | ADA | 338 |
| Cardiovascular phenotype | 121908987 | APG05459.1 | G > A | 21885 | NC_000007.13, NC_000007.14 | PRKAG2 | 339 |
| Cystic fibrosis | 121909019 | APG05459.1 | G > A | 22197 | NC_000007.13, NC_000007.14 | CFTR | 340 |
| Cystic fibrosis | 121909036 | APG05459.1 | T > C | 22247 | NC_000007.13, NC_000007.14 | CFTR | 341 |
| Adrenocortical carcinoma, pediatric | 121912664 | APG01688.1 | G > A | 27418 | NC_000017.10, NC_000017.11 | TP53 | 342 |
| Fumarase deficiency | 121913123 | APG05459.1 | G > A | 31275 | NC_000001.10, NC_000001.11 | FH | 343 |
| Adenocarcinoma of prostate | 121913272 | APG05459.1 | T > C | 40610 | NC_000003.11, NC_000003.12 | PIK3CA | 344 |
| Familial hypertrophic cardiomyopathy 1 | 121913638 | APG05459.1 | G > A | 29144 | NC_000014.8, NC_000014.9 | MYH7 | 345 |
| Adult hypophosphatasia | 121918007 | APG05083, APG07433.1, APG07513.1, APG08290.1 | G > A | 28709 | NC_000001.10, NC_000001.11 | ALPL | 346 |

TABLE 12-continued

Disease Targets for RGNs of the invention

| Disease | RS# (dbSNP) | RGN | Causal Mutation | Allele ID | Chromosome Accession | Gene Symbol | Target Seq (SEQ ID NO) |
|---|---|---|---|---|---|---|---|
| Adult hypophosphatasia | 121918007 | APG01688.1 | G > A | 28709 | NC_000001.10, NC_000001.11 | ALPL | 347 |
| Adult hypophosphatasia | 121918007 | APG01688.1 | G > A | 28709 | NC_000001.10, NC_000001.11 | ALPL | 348 |
| Inborn genetic diseases | 121918166 | APG05083, APG07433.1, APG07513.1, APG08290.1 | G > A | 15994 | NC_000015.9, NC_000015.10 | OCA2 | 349 |
| Inborn genetic diseases | 121918243 | APG05083, APG07433.1, APG07513.1, APG08290.1 | G > A | 16464 | NC_000001.10, NC_000001.11 | MMACHC | 350 |
| Crouzon syndrome | 121918505 | APG05459.1 | T > C | 28329 | NC_000010.10, NC_000010.11 | FGFR2 | 351 |
| Propionyl-CoA carboxylase deficiency | 121964961 | APG05459.1 | A > G | 27057 | NC_000003.11, NC_000003.12 | PCCB | 352 |
| Cardiovascular phenotype | 121964962 | APG05083, APG07433.1, APG07513.1, APG08290.1 | G > A | 15156 | NC_000021.8, NC_000021.9 | CBS | 353 |
| Dysostosis multiplex | 121965019 | APG05083, APG07433.1, APG07513.1, APG08290.1 | G > A | 26947 | NC_000004.11, NC_000004.12 | IDUA | 354 |
| Multiple sulfatase deficiency | 137852850 | APG05459.1 | T > C | 17711 | NC_000003.11, NC_000003.12 | SUMF1 | 355 |
| Bifunctional peroxisomal enzyme deficiency | 137853096 | APG05459.1 | G > A | 22694 | NC_000005.9, NC_000005.10 | HSD17B4 | 356 |
| Bifunctional peroxisomal enzyme deficiency | 137853096 | APG01688.1 | G > A | 22694 | NC_000005.9, NC_000005.10 | HSD17B4 | 357 |
| Hereditary cancer-predisposing syndrome | 137853293 | APG05459.1 | C > T | 28112 | NC_000013.10, NC_000013.11 | RB1 | 358 |
| Cardiovascular phenotype | 137854478 | APG05083, APG07433.1, APG07513.1, APG08290.1 | G > A | 31496 | NC_000015.9, NC_000015.10 | FBN1 | 359 |
| Cardiovascular phenotype | 137854478 | APG05083, APG07433.1, APG07513.1, APG08290.1 | G > A | 31496 | NC_000015.9, NC_000015.10 | FBN1 | 360 |
| Limb-girdle muscular dystrophy, type 2L | 137854529 | APG05459.1 | C > T | 17205 | NC_000011.9, NC_000011.10 | ANO5 | 361 |
| Familial hypercholesterolemia | 137929307 | APG01688.1 | G > A | 171217 | NC_000019.9, NC_000019.10 | LDLR | 362 |
| Spastic Paraplegia, Recessive | 141659620 | APG05459.1 | G > A | 21858 | NC_000016.9, NC_000016.10 | SPG7 | 363 |
| Isovaleryl-CoA dehydrogenase deficiency | 142761835 | APG05459.1 | G > A | 177782 | NC_000015.9, NC_000015.10 | IVD | 364 |
| Familial hypercholesterolemia | 145787161 | APG05459.1 | G > A | 18783 | NC_000019.10, NC_000019.9 | LDLR | 365 |
| Biotinidase deficiency | 146015592 | APG05459.1 | G > A | 46845 | NC_000003.11, NC_000003.12 | BTD | 366 |
| Biotinidase deficiency | 146015592 | APG05459.1 | G > A | 46845 | NC_000003.11, NC_000003.12 | BTD | 367 |
| Leber congenital amaurosis | 150726175 | APG05459.1 | G > A | 45795 | NC_000001.10, NC_000001.11 | NMNAT1 | 368 |
| Familial hyperinsulinism | 151344623 | APG05083, APG07433.1, APG07513.1, APG08290.1 | G > A | 24127 | NC_000011.9, NC_000011.10 | ABCC8 | 369 |
| Familial cancer of breast | 180177122 | APG05083, APG07433.1, APG07513.1, APG08290.1 | G > A | 132185 | NC_000016.10, NC_000016.9 | PALB2 | 370 |
| Cohen syndrome | 180177366 | APG05459.1 | G > A | 71322 | NC_000008.10, NC_000008.11 | VPS13B | 371 |
| Cardiovascular phenotype | 187830361 | APG05083, APG07433.1, APG07513.1, APG08290.1 | T > C | 45267 | NC_000011.9, NC_000011.10 | MYBPC3 | 372 |
| Wilson disease | 193922103 | APG05459.1 | A > G | 44370 | NC_000013.10, NC_000013.11 | ATP7B | 373 |
| Wilson disease | 193922110 | APG05083, APG07433.1, APG07513.1, APG08290.1 | G > A | 44393 | NC_000013.10, NC_000013.11 | ATP7B | 374 |
| Wilson disease | 193922110 | APG05459.1 | G > A | 44393 | NC_000013.10, NC_000013.11 | ATP7B | 375 |
| Familial hypercholesterolemia | 193922566 | APG05459.1 | G > A | 45113 | NC_000019.9, NC_000019.10 | LDLR | 376 |
| Familial hypercholesterolemia | 193922566 | APG05459.1 | G > A | 45113 | NC_000019.9, NC_000019.10 | LDLR | 377 |
| Floating-Harbor syndrome | 199469464 | APG05459.1 | C > T | 39865 | NC_000016.9, NC_000016.10 | SRCAP | 378 |
| Congenital long QT syndrome | 199472712 | APG05083, APG07433.1, APG07513.1, APG08290.1 | G > A | 67758 | NC_000011.9, NC_000011.10 | KCNQ1 | 379 |

TABLE 12-continued

Disease Targets for RGNs of the invention

| Disease | RS# (dbSNP) | RGN | Causal Mutation | Allele ID | Chromosome Accession | Gene Symbol | Target Seq (SEQ ID NO) |
|---|---|---|---|---|---|---|---|
| Congenital long QT syndrome | 199472712 | APG05459.1 | G > A | 67758 | NC_000011.9, NC_000011.10 | KCNQ1 | 380 |
| Andersen Tawil syndrome | 199473384 | APG01688.1 | G > A | 78481 | NC_000017.10, NC_000017.11 | KCNJ2 | 381 |
| Cardiovascular phenotype | 199473460 | APG05083, APG07433.1, APG07513.1, APG08290.1 | T > C | 67776 | NC_000011.9, NC_000011.10 | KCNQ1 | 382 |
| Familial hypercholesterolemia | 200238879 | APG05459.1 | T > C | 18777 | NC_000019.9, NC_000019.10 | LDLR | 383 |
| Cardiovascular phenotype | 200411226 | APG05083, APG07433.1, APG07513.1, APG08290.1 | G > A | 174776 | NC_000011.9, NC_000011.10 | MYBPC3 | 384 |
| Gastrointestinal stroma tumor | 201286421 | APG05459.1 | C > T | 50215 | NC_000001.10, NC_000001.11 | SDHC | 385 |
| Dyskeratosis congenita | 201540674 | APG05459.1 | G > A | 51186 | NC_000020.10, NC_000020.11 | RTEL1 | 386 |
| Dyskeratosis congenita | 201540674 | APG01688.1 | G > A | 51186 | NC_000020.10, NC_000020.11 | RTEL1 | 387 |
| Glycogen storage disease IIIa | 267606640 | APG04583.1 | G > A | 16147 | NC_000001.10, NC_000001.11 | AGL | 388 |
| Dilated cardiomyopathy 1DD | 267607004 | APG05083, APG07433.1, APG07513.1, APG08290.1 | G > A | 15310 | NC_000010.10, NC_000010.11 | RBM20 | 389 |
| Renal carnitine transport defect | 267607054 | APG05459.1 | C > T | 21466 | NC_000005.9, NC_000005.10 | SLC22A5 | 390 |
| Baraitser-Winter syndrome 1 | 281875334 | APG05083, APG07433.1, APG07513.1, APG08290.1 | G > A | 38553 | NC_000007.13, NC_000007.14 | ACTB | 391 |
| Very long chain acyl-CoA dehydrogenase deficiency | 369560930 | APG05083, APG07433.1, APG07513.1, APG08290.1 | G > A | 98197 | NC_000017.10, NC_000017.11 | ACADVL | 392 |
| Familial hypercholesterolemia | 373822756 | APG05459.1 | A > G | 181233 | NC_000019.9, NC_000019.10 | LDLR | 393 |
| Limb-girdle muscular dystrophy, type 2A | 376107921 | APG05459.1 | G > A | 213634 | NC_000015.9, NC_000015.10 | CAPN3 | 394 |
| Familial hypercholesterolemia | 376459828 | APG05083, APG07433.1, APG07513.1, APG08290.1 | G > A | 198012 | NC_000019.10, NC_000019.9 | LDLR | 395 |
| Aortic aneurysm, familial thoracic 6 | 387906592 | APG05459.1 | G > A | 38552 | NC_000010.10, NC_000010.11 | ACTA2 | 396 |
| Acromicric dysplasia | 387906623 | APG05083, APG07433.1, APG07513.1, APG08290.1 | G > A | 38652 | NC_000015.9, NC_000015.10 | FBN1 | 397 |
| Charcot-Marie-Tooth disease type 2C | 387906905 | APG01688.1 | G > A | 39430 | NC_000012.11, NC_000012.12 | TRPV4 | 398 |
| Breast-ovarian cancer, familial 2 | 397507389 | APG01688.1 | G > A | 46666 | NC_000013.10, NC_000013.11 | BRCA2 | 399 |
| Breast-ovarian cancer, familial 1 | 397509284 | APG05459.1 | G > A | 70248 | NC_000017.10, NC_000017.11 | BRCA1 | 400 |
| Charcot-Marie-Tooth disease type 2C | 397514494 | APG05083, APG07433.1, APG07513.1, APG08290.1 | G > A | 48018 | NC_000012.11, NC_000012.12 | TRPV4 | 401 |
| Charcot-Marie-Tooth disease type 2C | 397514494 | APG01688.1 | G > A | 48018 | NC_000012.11, NC_000012.12 | TRPV4 | 402 |
| Hereditary cancer-predisposing syndrome | 397514495 | APG05459.1 | G > A | 152034 | NC_000017.10, NC_000017.11 | TP53 | 403 |
| Early infantile epileptic encephalopathy | 397514581 | APG05083, APG07433.1, APG07513.1, APG08290.1 | G > A | 48359 | NC_000020.10, NC_000020.11 | KCNQ2 | 404 |
| Early infantile epileptic encephalopathy | 397514581 | APG05459.1 | G > A | 48359 | NC_000020.10, NC_000020.11 | KCNQ2 | 405 |
| Early infantile epileptic encephalopathy | 397514581 | APG01688.1 | G > A | 48359 | NC_000020.10, NC_000020.11 | KCNQ2 | 406 |
| Acromicric dysplasia | 397515757 | APG05459.1 | G > A | 51454 | NC_000015.9, NC_000015.10 | FBN1 | 407 |
| Hypertrophic cardiomyopathy | 397515982 | APG05083, APG07433.1, APG07513.1, APG08290.1 | G > A | 51820 | NC_000011.9, NC_000011.10 | MYBPC3 | 408 |
| Cardiovascular phenotype | 397516031 | APG04583.1 | G > A | 51898 | NC_000011.9, NC_000011.10 | MYBPC3 | 409 |
| Cardiovascular phenotype | 397516074 | APG05083, APG07433.1, APG07513.1, APG08290.1 | G > A | 51962 | NC_000011.9, NC_000011.10 | MYBPC3 | 410 |

TABLE 12-continued

Disease Targets for RGNs of the invention

| Disease | RS# (dbSNP) | RGN | Causal Mutation | Allele ID | Chromosome Accession | Gene Symbol | Target Seq (SEQ ID NO) |
|---|---|---|---|---|---|---|---|
| Cardiovascular phenotype | 397516083 | APG01688.1 | G > A | 51977 | NC_000011.9, NC_000011.10 | MYBPC3 | 411 |
| Familial hypertrophic cardiomyopathy 1 | 397516269 | APG05083, APG07433.1, APG07513.1, APG08290.1 | T > C | 52276 | NC_000014.8, NC_000014.9 | MYH7 | 412 |
| Benign scapuloperoneal muscular dystrophy with cardiomyopathy | 397517889 | APG05459.1 | C > T | 57195 | NC_000001.10, NC_000001.11 | LMNA | 413 |
| Glycogen storage disease, type II | 398123172 | APG05083, APG07433.1, APG07513.1, APG08290.1 | G > A | 415590 | NC_000017.10, NC_000017.11 | GAA | 414 |
| Diffuse mesangial sclerosis | 587776576 | APG05083, APG07433.1, APG07513.1, APG08290.1 | G > A | 18532 | NC_000011.10, NC_000011.9 | WT1 | 415 |
| Colobomatous microphthalmia | 587776954 | APG05459.1 | A > G | 51108 | NC_000012.11, NC_000012.12 | C12orf57 | 416 |
| Ataxia-telangiectasia syndrome | 587779826 | APG05459.1 | T > C | 132814 | NC_000011.10, NC_000011.9 | ATM | 417 |
| Familial cancer of breast | 587780226 | APG05459.1 | C > T | 133611 | NC_000017.10, NC_000017.11 | BRIP1 | 418 |
| Limb-girdle muscular dystrophy, type 2A | 587780290 | APG01688.1 | G > A | 134019 | NC_000015.9, NC_000015.10 | CAPN3 | 419 |
| Hereditary cancer-predisposing syndrome | 587781462 | APG05459.1 | C > T | 150772 | NC_000002.11, NC_000002.12 | MSH6 | 420 |
| Asymmetric septal hypertrophy | 587782958 | APG01688.1 | G > A | 165560 | NC_000011.10, NC_000011.9 | MYBPC3 | 421 |
| Hereditary cancer-predisposing syndrome | 587783050 | APG05459.1 | G > A | 166264 | NC_000016.10, NC_000016.9 | CDH1 | 422 |
| Familial hypertrophic cardiomyopathy 2 | 727504247 | APG05083, APG07433.1, APG07513.1, APG08290.1 | G > A | 172354 | NC_000001.10, NC_000001.11 | TNNT2 | 423 |
| Familial hypertrophic cardiomyopathy 2 | 727504247 | APG01688.1 | G > A | 172354 | NC_000001.10, NC_000001.11 | TNNT2 | 424 |
| Familial hypertrophic cardiomyopathy 2 | 727504247 | APG01688.1 | G > A | 172354 | NC_000001.10, NC_000001.11 | TNNT2 | 425 |
| Erythrocytosis, familial, 2 | 730882035 | APG01688.1 | G > A | 180121 | NC_000003.12, NC_000003.11 | VHL | 426 |
| Death in infancy | 730882246 | APG05083, APG07433.1, APG07513.1, APG08290.1 | G > A | 181441 | NC_000014.9, NC_000014.8 | ISCA2 | 427 |
| Muscular Diseases | 751995154 | APG05459.1 | G > A | 200340 | NC_000017.10, NC_000017.11 | ACADVL | 428 |
| Familial hypercholesterolemia | 756039188 | APG04583.1 | G > A | 243266 | NC_000019.9, NC_000019.10 | LDLR | 429 |
| Familial cancer of breast | 761494650 | APG05459.1 | C > T | 185659 | NC_000022.10, NC_000022.11 | CHEK2 | 430 |
| Hereditary cancer-predisposing syndrome | 762307622 | APG01688.1 | G > A | 232266 | NC_000001.10, NC_000001.11 | MUTYH | 431 |
| Familial hypercholesterolemia | 769370816 | APG05083, APG07433.1, APG07513.1, APG08290.1 | G > A | 228176 | NC_000019.10, NC_000019.9 | LDLR | 432 |
| Familial hypercholesterolemia | 775092314 | APG05083, APG07433.1, APG07513.1, APG08290.1 | T > C | 228197 | NC_000019.9, NC_000019.10 | LDLR | 433 |
| Familial hypercholesterolemia | 775924858 | APG05083, APG07433.1, APG07513.1, APG08290.1 | G > A | 246116 | NC_000019.9, NC_000019.10 | LDLR | 434 |
| Inclusion body myopathy 2 | 779694939 | APG04583.1 | T > C | 214934 | NC_000009.12, NC_000009.11 | GNE | 435 |
| Ataxia-telangiectasia syndrome | 780619951 | APG05459.1 | C > T | 212851 | NC_000011.10, NC_000011.9 | ATM | 436 |
| Benign familial neonatal-infantile seizures | 794727152 | APG04583.1 | G > A | 191718 | NC_000002.11, NC_000002.12 | SCN2A | 437 |
| Marfan Syndrome/Loeys-Dietz Syndrome/Familial Thoracic Aortic Aneurysms and Dissections | 794728228 | APG05459.1 | C > T | 197690 | NC_000015.10, NC_000015.9 | FBN1 | 438 |
| Dilated cardiomyopathy 1G | 869320740 | APG01688.1 | T > C | 136355 | NC_000002.11, NC_000002.12 | TTN | 439 |
| Familial hypercholesterolemia | 875989911 | APG05459.1 | G > A | 228151 | NC_000019.9, NC_000019.10 | LDLR | 440 |
| Breast-ovarian cancer, familial 2 | 876657678 | APG05459.1 | C > T | 230443 | NC_000013.10, NC_000013.11 | BRCA2 | 441 |
| Familial hypercholesterolemia | 879254600 | APG05459.1 | G > A | 245669 | NC_000019.10, NC_000019.9 | LDLR | 442 |

TABLE 12-continued

Disease Targets for RGNs of the invention

| Disease | RS# (dbSNP) | RGN | Causal Mutation | Allele ID | Chromosome Accession | Gene Symbol | Target Seq (SEQ ID NO) |
|---|---|---|---|---|---|---|---|
| Familial hypercholesterolemia | 879254803 | APG05083, APG07433.1, APG07513.1, APG08290.1 | T > C | 246008 | NC_000019.10, NC_000019.9 | LDLR | 443 |
| Familial hypercholesterolemia | 879254803 | APG01688.1 | T > C | 246008 | NC_000019.10, NC_000019.9 | LDLR | 444 |
| Familial hypercholesterolemia | 879254849 | APG01688.1 | T > C | 246074 | NC_000019.10, NC_000019.9 | LDLR | 445 |
| Familial cancer of breast | 1057517585 | APG01688.1 | G > A | 358911 | NC_000016.10, NC_000016.9 | PALB2 | 446 |
| Hereditary hemorrhagic telangiectasia type 2 | 1057517944 | APG05459.1 | C > T | 360048 | NC_000012.11, NC_000012.12 | ACVRL1 | 447 |

Example 10: Targeting Mutations Responsible for Hurler Syndrome

The following describes a potential treatment for Hurler Syndrome, also referred to as MPS-1, is described, using an RNA directed base editing system that corrects a mutation responsible for Hurler syndrome in a large proportion of patients with the disease. This approach utilizes a base editing fusion protein that is RNA guided and that can be packaged into a single AAV vector for delivery to a wide range of tissue types. Depending on the exact regulatory elements and base editor domain used, it may also be possible to engineer a single vector that encodes for both the base editing fusion protein and a single guide RNA to target the diseased locus.

Example 10.1: Identifying RGN with Ideal PAM

The genetic disease MPS-1 is a lysosomal storage disease characterized at the molecular level by the accumulation of dermatan sulfate and heparan sulfate in lysosomes. This disease is generally an inherited genetic disorder caused by mutations in the IDUA gene (NCBI Reference sequence NG_008103.1), which encodes α-L-iduronidase. The disease is a result of a deficiency of α-L-iduronidase. The most common IDUA mutations found in studies of individuals of Northern European background are W402X and Q70X, both nonsense mutations resulting in premature termination of translation (Bunge et al. (1994), Hum. Mol. Genet, 3(6): 861-866, herein incorporated by reference). Reversion of a single nucleotide would restore the wild-type coding sequence and result in protein expression controlled by the endogenous regulatory mechanisms of the genetic locus.

The W402X mutation of the human Idua gene accounts for a high proportion of MPS-1H cases. Base editors can target a narrow sequence window relative to the binding site of the protospacer component of the guide RNA and thus the presence of a PAM sequence a specific distance from the target locus is essential for the success of the strategy. Given the constraints that the target mutation must be on the exposed non-target strand (NTS) during the interaction of the base editing protein and that the footprint of the RGN domain will block access to the region near the PAM, an accessible locus is thought to be 10-30 bp from the PAM. To avoid editing and mutagenesis of other nearby adenosine bases in this window, different linkers are screened. The ideal window is 12-16 bp from the PAM.

A PAM sequence compatible with APG07433.1 and APG08290.1 is readily apparent at the genetic locus and within the ideal base editing window as defined above. These nucleases have a PAM sequence of NNNNCC (SEQ ID NO: 6) and NNRNCC (SEQ ID NO: 32), respectively, and are compact in size—potentially allowing delivery via a single AAV vector. This delivery approach bestows multiple advantages relative to others, such as access to a wide range of tissues (liver, muscle, CNS) and well-established safety profile and manufacturing techniques.

Cas9 from *S. pyogenes* (SpyCas9) requires a PAM sequence of NGG (SEQ ID NO: 448), which is present near the W402X locus, but the size of SpyCas9 prevents packaging of a gene encoding a fusion protein of a base editing domain and the SpyCas9 nuclease into a single AAV vector, and thus forgoes the aforementioned advantages of this approach. Including a guide RNA encoding sequence on this vector would is even less feasible, even if there are to be significant technological improvements that reduce the size of gene regulatory elements or increase the packaging limits of AAV vectors. While a dual delivery strategy may be employed (for example, Ryu et al, (2018), Nat. Biotechnol., 36(6): 536-539, herein incorporated by reference), it would add significant manufacturing complexity and cost. Additionally, dual viral vector delivery significantly decreases the efficiency of gene correction, since a successful edit in a given cell requires infection with both vectors and assembly of the fusion protein in the cell.

A commonly used Cas9 ortholog from *S. aureus* (SauCas9) is considerably smaller in size relative to SpyCas9, but has a more complex PAM requirement—NGRRT (SEQ ID NO: 449). This sequence, however, is not within a range expected to be useful for base editing of the causative locus.

Example 10.2: RGN Fusion Constructs and sgRNA Sequences

A DNA sequence encoding a fusion protein with the following domains is produced using standard molecular biology techniques: 1) an RGN domain with mutations that inactivate the DNA cleavage activity ("dead" or "nickase"); 2) an adenosine deaminase useful for base editing. All constructs described in the table below comprise a fusion protein with the base editing active domain, in this example ADAT (SEQ ID NO: 450) operably fused to the N-terminal end of the RGN APG08290.1. It is known in the art that a fusion protein could also be made with the base-editing enzyme at the C-terminal end of the RGN. Additionally, the RGN and the base editor of the fusion protein are typically separated by a linker amino sequence. It is known in the art that lengths of standard linkers range from 15-30 amino acids. Further, it is known in the art that certain fusion proteins between an RGN and a base-editing enzyme, for example a cytidine deaminase, may also comprise at least one uracil glycosylase inhibitor (UGI) domain, which may increase base editing efficiency (U.S. Pat. No. 10,167,457, herein incorporated by reference). Therefore, a fusion protein may comprise APG08290.1, a base-modifying enzyme, and at least one UGI.

TABLE 13

Constructs for RNA-targeted base editing

| Seq ID No. | Construct | RGN | Dead (D) or Nickase (N) | Base editor | Linker |
|---|---|---|---|---|---|
| 451 | Nuc-ADAT-Linker-dAPG08290.1-Linker-SV40 | APG08290.1 | D | ADAT | XTEN1 |
| 452 | Nuc-ADAT-XTEN1-nAPG08290.1-Linker-SV40 | APG08290.1 | N | ADAT | XTEN1 |

The accessible editing sites of an RGN are determined by the PAM sequence. When combining an RGN with a base editing domain, the target residue for editing must reside on the non-target strand (NTS), since the NTS is single stranded while the RGN is associated with the locus. Evaluating a number of nucleases and corresponding guide RNAs enables the selection of the most appropriate gene editing tool for this particular locus. Several potential PAM sequences that can be targeted by the constructs described above in the human Idua gene are in the proximity of the mutant nucleotide responsible for the W402X mutation. A sequence encoding a guide RNA transcript containing 1) a "spacer" that is complementary to the non-coding DNA strand at the disease locus; and 2) RNA sequence required for association of the guide RNA with the RGN is also produced. Useful guide RNA sequences (sgRNA) are shown in Table 14 below. These guide RNA sequences can be evaluated for their efficiency in directing the base editors above to the locus of interest.

TABLE 14

Sequence of guide RNAs

| Sequence of target genomic sequence | SEQ ID NO. | Coding sequence of sgRNA (SEQ ID NO.) |
|---|---|---|
| 5'-GGAGCAGCTCTAGGCCGAAGTGTCG-3' | 453 | 456 |
| 5'-TAGGCCGAAGTGTCGCAGGCCGGGA-3' | 454 | 457 |
| 5'-GCTCTAGGCCGAAGTGTCGCAGGCC-3' | 455 | 458 |

Example 10.3: Assay for Activity in Cells from Hurler Disease Patients

To verify the genotype strategy and evaluate the constructs described above, fibroblasts from Hurler disease patients are used. A vector is designed containing appropriate promoters upstream of the fusion protein coding sequence and the sgRNA encoding sequence for expression of these in human cells, similar to those vectors described in Example 5. It is recognized that promoters and other DNA elements (for example enhancers, or terminators) which either are known for high levels of expression in human cells or may specifically express well in fibroblast cells may also be used. The vector is transfected into the fibroblasts using standard techniques, for example transfection similar to what is described in Example 6. Alternatively, electroporation may be used. The cells are cultured for 1-3 days. Genomic DNA (gDNA) is isolated using standard techniques. The editing efficiency is determined by performing a qPCR genotyping assay and/or next generation sequencing on the purified gDNA, as described further below.

Taqman™ qPCR analysis utilizes probes specific for the wild-type and mutant allele. These probes bear fluorophores which are resolved by their spectral excitation and/or emission properties using a qPCR instrument. A genotyping kit containing PCR primers and probes can be obtained commercially (i.e. Thermo Fisher Taqman™ SNP genotyping assayID C_27862753_10 for SNP ID rs121965019) or designed. An example of a designed primer and probe set is shown in Table 15.

TABLE 15

RT-PCR primers and probes

| Description | Sequence | SEQ ID NO. |
|---|---|---|
| Forward Amplification Primer | 5'-GACTCCTTCACCAAG-3' | 459 |
| Reverse Amplification Primer | 5'-GTAGATCAGCACCG-3' | 460 |
| Wild Type Probe | 5'-CTCTGGGCCGAAGT-3' | 461 |
| W402X Probe | 5'-CTCTAGGCCGAAGT-3' | 462 |

Following the editing experiment, the gDNA is subjected to qPCR analysis using standard methods and the primers and probes described above. Expected results are shown in Table 16. This in vitro system can be used to expediently evaluate constructs and choose one with high editing efficiency for further studies. The systems will be evaluated in comparison with cells with and without the W402X mutation, and preferably with some that are heterozygous for this mutation. The Ct values will be compared to either a reference gene or the total amplification of the locus using a dye such as Sybr green.

TABLE 16

Expected qPCR results

| Genotype | Transfected with base editor | Expected PCR result |
|---|---|---|
| $Idua^{WT/WT}$ | No | Homozygous WT |
| $Idua^{WT/W402X}$ | No | Heterozygous: 50% WT, 50% W402X |
| $Idua^{W402X/W402X}$ | No | Homozygous W402X |
| $Idua^{W402X/W402X}$ | Yes | Variable |

The tissues can also be analyzed by next generation sequencing. Primer binding sites such as the ones shown below (Table 17), or other suitable primer binding sites that can be identified by a person of skill in the art, can be used. Following PCR amplification, products containing Illumina Nextera XT overhang sequences undergo library preparation following the Illumina 16S Metagenomic Sequencing Library protocol. Deep sequencing is performed on an Illumina Mi-Seq platform. Typically, 200,000 of 250 bp paired-end reads (2×100,000 reads) are generated per amplicon. The reads are analyzed using CRISPResso (Pinello et al., 2016) to calculate the rates of editing. Output alignments are hand-curated to confirm insertion and deletion sites as well as identify microhomology sites at the recombination sites.

TABLE 17

NGS primer binding sites

| Direction | Sequence | SEQ ID NO. |
|---|---|---|
| Forward | 5'-ACTTCCTCCAGCC-3' | 463 |
| Reverse | 5'-GAACCCCGGCTTA-3' | 464 |

Western blotting of cell lysate of transfected cells and control cells using an anti-IDUA antibody is performed to verify expression of the full-length protein and an enzyme activity assay on the cell lysate using substrate 4-methylumbelliferyl α-L-iduronide verifies that the enzyme is catalytically active (Hopwood et al., Clin. Chim. ACta (1979), 92(2): 257-265, incorporated by reference herein). These experiments are performed in comparison with the original $Idua^{W402X/W402X}$ cell line (without transfection), the $Idua^{W402X/W402X}$ cell line transfected with the base editing construct and a random guide sequence, and a cell line expressing wild-type IDUA.

Example 10.4: Disease Treatment Validation in a Murine Model

To verify the efficacy of this therapeutic approach, a mouse model with a nonsense mutation in the analogous amino acid is used. The mouse strain bears a W392X mutation in its Idua gene (Gene ID: 15932) which corresponds to the homologous mutation in Hurler syndrome patients (Bunge et al., (1994), Hum. Mol. Genet. 3(6): 861-866, incorporated by reference herein). This locus comprises a distinct nucleotide sequence relative to that in humans, which lacks the PAM sequence necessary for correction with the base editors described in the previous examples, and thus necessitates design of a distinct fusion protein to perform the nucleotide correction. Amelioration of the disease in this animal can validate the therapeutic approach of correcting the mutation in tissues accessible by a gene delivery vector.

Mice homozygous for this mutation display a number of phenotypic characteristics similar to Hurler syndrome patients. A base editing-RGN fusion protein as described above (Table 13) along with an RNA guide sequence are incorporated into an expression vector that allows protein expression and RNA transcription in mice. A study design is shown below in Table 18. The study includes groups that are treated with a high dose of the expression vector comprising the base-editing fusion protein and RNA guide sequence, a low dose of same expression vector, control which is the model mouse treated with an expression vector that does not comprise the base editing fusion protein or the guide RNA, and a second control which is a wild type mouse treated with the same empty vector.

TABLE 18

Genome editing experiment in murine model

| Group | Mouse strain | N | Treatment |
|---|---|---|---|
| 1 | Idua-W392X[1] | ≥5 | Low dose of vector |
| 2 | Idua-W392X | ≥5 | High dose of vector |
| 3 | Idua-W392X | ≥5 | Vehicle |
| 4 | 129/Sv (WT) | 5 | Vehicle |

Endpoints to evaluate include body weight, urine GAG excretion, serum IDUA enzymatic activity, IDUA activity in tissues of interest, tissue pathology, genotyping of tissues of interest to verify correction of the SNP, and behavioral and neurological evaluation. Since some endpoints are terminal, additional groups may be added for evaluation of, for example, tissue pathology and tissue IDUA activities before the end of the study. Additional examples of endpoints can be found in published papers establishing Hurler syndrome animal models (Shull et al. (1994), Proc. Natl. Acad. Sci. U.S.A., 91(26): 12937-12941; Wang et al. (2010), Mol. Genet. Metab., 99(1): 62-71; Hartung et al. (2004), Mol. Ther., 9(6): 866-875; Liu et al. (2005), Mol. Ther., 11(1): 35-47; Clarke et al. (1997), Hum. Mol. Genet. 6(4): 503-511; all herein incorporated by reference).

One possible delivery vector utilizes the adeno associated virus (AAV). A vector is produced to include a base editor-dRGN fusion protein coding sequence (for example, SEQ ID NO: 452) preceded by a CMV enhancer (SEQ ID NO: 138) and promoter (SEQ ID NO: 137), or other suitable enhancer and promoter combination), optionally a Kozak sequence, and operably fused at the 3' end to a terminator sequence and a poly adenylation sequence such as the minimal sequence described in Levitt, N.; Briggs, D.; Gil, A.; Proudfoot, N. J. Definition of an Efficient Synthetic Poly(A) Site. Genes Dev. 1989, 3 (7), 1019-1025. The vector may further comprise an expression cassette encoding for a single guide RNA operably linked at its 5' end to a human U6 promoter (SEQ ID NO: 139), or another promoter suitable for production of small non-coding RNAs, and further comprising inverted terminal repeat (ITR) sequences necessary and well-known in the art for packaging into the AAV capsid. Production and viral packaging is performed by standard methods, such as those described in U.S. Pat. No. 9,587,250, herein incorporated by reference.

Other possible viral vectors include adenovirus and lentivirus vectors, which are commonly used and would contain similar elements, with different packaging capabilities and requirements. Non-viral delivery methods also be used, such as mRNA and sgRNA encapsulated by lipid nanoparticles (Cullis, P. R. and Allen, T. M. (2013), Adv. Drug Deliv. Rev. 65(1): 36-48; Finn et al. (2018), Cell Rep. 22(9): 2227-2235, both incorporated by reference) hydrodynamic injection of plasmid DNA (Suda T and Liu D, (2007) Mol. Ther. 15(12): 2063-2069, herein incorporated by reference), or ribonucleoprotein complexes of sgRNA and associated with gold nanoparticles (Lee, K.; Conboy, M.; Park, H. M.; Jiang, F.; Kim, H. J.; Dewitt, M. A.; Mackley, V. A.; Chang, K.; Rao, A.; Skinner, C.; et al. Nanoparticle Delivery of Cas9 Ribonucleoprotein and Donor DNA in Vivo Induces Homology-Directed DNA Repair. Nat. Biomed. Eng. 2017, 1 (11), 889-90).

Example 10.5: Disease Correction in a Murine Model with a Humanized Locus

To evaluate the efficacy of an identical base editor construct as would be used for human therapy, a mouse model in which the nucleotides near W392 are altered to match the sequence in humans around W402 is needed. This can be accomplished by a variety of techniques, including use of an RGN and an HDR template to cut and replace the locus in mouse embryos.

Due to the high degree of amino acid conservation, most nucleotides in the mouse locus can be altered to those of the human sequence with silent mutations as shown in Table 19. The only base changes resulting in altered coding sequence in the resulting engineered mouse genome occur after the introduced stop codon.

TABLE 19

Nucleotide mutations to generate a humanized mouse locus

| Feature | Human (W402X) Nucleotide (SEQ ID NO: 465) | Encoded AA | Mouse (W392X) Nucleotide (SEQ ID NO: 466) | Encoded AA | Humanized Mouse Nucleotide (SEQ ID NO: 467) | Encoded AA |
|---|---|---|---|---|---|---|
| Proto-spacer | G | E | A | G | G | G |
| | G | E | G | E | G | E |
| | A | | A | | A | |
| | G | | A | | G | |
| | C | Q | C | Q | C | Q |
| | A | | A | | A | |
| | G | | A | | G | |
| | C | L | C | L | C | L |
| | T | | T | | T | |
| | C | | C | | C | |
| | T | STOP | T | STOP | T | STOP |
| | A | | A | | A | |
| | G | | G | | G | |
| | G | A | G | A | G | A |
| | C | | C | | C | |
| | C | | A | | C | |
| | G | E | G | E | G | E |
| | A | | A | | A | |
| | A | | G | | A | |
| | G | V | G | V | G | V |
| | T | | T | | T | |
| | G | | C | | G | |
| | T | S | T | S | T | S |
| | C | | C | | C | |
| | G | | A | | G | |
| PAM, non-critical | C | Q | A | K | C | Q |
| | A | | A | | A | |
| | G | | G | | G | |
| | G | A | G | A | G | A |
| PAM, critical | C | | C | | C | |
| | C | | T | | C | |

Upon engineering of this mouse strain, similar experiments will be performed as described in Example 10.4.

Example 11: Targeting Mutations Responsible for Friedreich Ataxia

The expansion of the trinucleotide repeat sequence causing Friedreich's Ataxia (FRDA) occurs in a defined genetic locus within the FXN gene, referred to as the FRDA instability region. RNA guided nucleases (RGNs) may be used for excising the instability region in FRDA patient cells. This approach requires 1) an RGN and guide RNA sequence that can be programmed to target the allele in the human genome; and 2) a delivery approach for the RGN and guide sequence. Many nucleases used for genome editing, such as the commonly used Cas9 nuclease from S. pyogenes (SpCas9), are too large to be packaged into adeno-associated viral (AAV) vectors, especially when considering the length of the SpCas9 gene and the guide RNA in addition to other genetic elements required for functional expression cassettes. This makes a viable approach using SpCas9 unlikely.

The compact RNA guided nucleases of the invention, particularly APG07433.1 and APG08290.1, are uniquely well suited for the excision of the FRDA instability region. Each RGN has a PAM requirement that is in the vicinity of the FRDA instability region. Additionally, each of these RGNs can be packaged into an AAV vector along with a guide RNA. Packing two guide RNAs would likely require a second vector, but this approach still compares favorably to what would be required of a larger nuclease such as SpCas9, which would require splitting the protein sequence between two vectors.

Table 20 shows the location of genomic target sequences suitable for targeting APG07433.1 or APG08290.1 to the 5' and 3' flanks of the FRDA instability region. Once at the locus, the RGN would excise the FA instability region. Excision of the region can be verified with Illumina sequencing of the locus.

TABLE 20

Genomic target sequences for RGN systems

| Guide No. | Location relative to FRDA instability region | Genome target sequence | SEQ ID NO. |
|---|---|---|---|
| 1 | 5' | ATCACCTGAGGTCCGGAGTTCAAGA | 468 |
| 2 | 5' | GTCTTGAACTCCGGACCTCAGGTGA | 469 |
| 3 | 5' | TGAACTCCGGACCTCAGGTGATCCA | 470 |
| 4 | 3' | GAAAAGTTAGCCGGGCGTGGTGTCG | 471 |

Example 12: Targeting Mutations Responsible for Sickle Cell Diseases

Targeting sequences within the BCL11A enhancer region (SEQ ID NO: 472) may provide a mechanism for increasing fetal hemoglobulin (HbF) to either cure or alleviate the symptoms of sickle cell diseases. For example, genome wide association studies have identified a set of genetic variations at BCL11A that are associated with increased HbF levels. These variations are a collection of SNPs found in non-coding regions of BCL 11A that function as a stage-specific, lineage-restricted enhancer region. Further investigation revealed that this BCL11A enhancer is required in erythroid cells for BCL11A expression (Bauer et al, (2013) Science 343:253-257, incorporated by reference herein). The enhancer region was found within intron 2 of the BCL 11A gene, and three areas of DNAseI hypersensitivity (often indicative of a chromatin state that is associated with regulatory potential) in intron 2 were identified. These three areas were identified as "+62", "+58" and "+55" in accordance with the distance in kilobases from the transcription start site of BCL11A. These enhancer regions are roughly 350 (+55); 550 (+58); and 350 (+62) nucleotides in length (Bauer et al., 2013).

Example 12.1: Identifying Preferred RGN Systems

Here we describe a potential treatment for beta-hemoglobinopathies using an RGN system that disrupts BCL11A binding to its binding site within the HBB locus, which is the gene responsible for making beta-globin in adult hemoglobin. This approach uses NHEJ which is more efficient in mammalian cells. In addition, this approach uses a nuclease of sufficiently small size that can be packaged into a single AAV vector for in vivo delivery.

The GATA1 enhancer motif in the human BCL11A enhancer region (SEQ ID NO: 472) is an ideal target for disruption using RNA guided nucleases (RGNs) to reduce BCL11A expression with concurrent re-expression of HbF in adult human erythrocytes (Wu et al. (2019) Nat Med 387:2554). Several PAM sequences compatible with APG07433.1 and APG08290.1 are readily apparent at the genetic locus surrounding this GATA1 site. These nucleases have a PAM sequence of 5'-NNNNCC-3' (SEQ ID NO: 6) and are compact in size, potentially allowing their delivery along with an appropriate guide RNA in a single AAV or adenoviral vector. This delivery approach bestows multiple advantages relative to others, such as access to hematopoietic stem cells and a well-established safety profile and manufacturing techniques.

The commonly used Cas9 nuclease from S. pyogenes (SpyCas9) requires a PAM sequence of 5'-NGG-3', (SEQ ID NO: 448) several of which are present near the GATA1 motif. However, the size of SpyCas9 prevents packaging into a single AAV or adenoviral vector and thus forgoes the aforementioned advantages of this approach. While a dual delivery strategy may be employed, it would add significant manufacturing complexity and cost. Additionally, dual viral vector delivery significantly decreases the efficiency of gene correction, since a successful edit in a given cell requires infection with both vectors.

An expression cassette encoding a human codon optimized APG07433.1 (SEQ ID NO: 128) or APG08290.1 (SEQ ID NO: 130) is produced, similar to those described in Example 6. Expression cassettes which express guide RNAs for RGNs APG07433.1 and APG08290.1 are also produced. These guide RNAs comprise 1) a protospacer sequence that is complementary to either the non-coding or coding DNA strand within the BCL11A enhancer locus (the target sequence) and 2) an RNA sequence required for association of the guide RNA with the RGN (SEQ ID NO. 18 for APG07433.1 and SEQ ID NO: 35 for APG08290.1). Because several potential PAM sequences for targeting by APG07433.1 or APG08290.1 surround the BCL11A GATA1 enhancer motif, several potential guide RNA constructs are produced to determine the best protospacer sequence that produces robust cleavage and NHEJ mediated disruption of the BCL11A GATA1 enhancer sequence. The target genomic sequences in the table below (Table 21) are evaluated to direct the RGN to this locus.

TABLE 21

Target Sequences for BCL11A GATA1 enhancer locus

| Guide | Nuclease | Target genomic sequence | Target SEQ ID NO. |
|---|---|---|---|
| 1 | APG07433.1 | GCACTAGACTAGCTTCAAAGTTGTAG | 473 |
| 2 | APG07433.1 | CCTAATCAGAGGCCAAACCCTTCCTG | 474 |
| 3 | APG07433.1 | CAAGCTAACAGTTGCTTTTATCACAG | 475 |
| 4 | APG08290.1 | GCACTAGACTAGCTTCAAAGTTGTAG | 476 |
| 5 | APG08290.1 | CCTAATCAGAGGCCAAACCCTTCCTG | 477 |
| 6 | APG08290.1 | CAAGCTAACAGTTGCTTTTATCACAG | 478 |

To evaluate the efficiency with which APG07433.1 or APG08290.1 generates insertions or deletions that disrupt the BCL11A enhancer region, human cell lines such as human embryonic kidney cells (HEK cells) are used. A DNA vector comprising an RGN expression cassette (for example, as described in Example 6) is produced. A separate vector comprising an expression cassette comprising a coding sequence for a guide RNA sequence of Table 21 is also produced. Such an expression cassette may further comprise a human RNA polymerase III U6 promoter (SEQ ID NO: 139), as described in Example 6. Alternatively, a single vector comprising expression cassettes of both the RGN and guide RNA may be used. The vector is introduced into HEK cells using standard techniques such as those described in Example 6, and the cells are cultured for 1-3 days. Following this culture period, genomic DNA is isolated and the frequency of insertions or deletions is determined by using T7 Endonuclease I digestion and/or direct DNA sequencing, as described in Example 6.

A region of DNA encompassing the target BCL11A region is amplified by PCR with primers containing Illumina Nextera XT overhang sequences. These PCR amplicons are either examined for NHEJ formation using T7 Endonuclease I digestion, or undergo library preparation following the Illumina 16S Metagenomic Sequencing Library protocol or a similar Next Generation Sequencing (NGS) library preparation. Following deep sequencing, the reads generated are analyzed by CRISPResso to calculate rates of editing. Output alignments are hand-curated to confirm insertion and deletion sites. This analysis identifies the preferred RGN and the corresponding preferred guide RNA (sgRNA). The analysis may result in both APG07433.1 and APG08290.1 being equally preferred. Additionally, the analysis may determine there is more than one preferred guide RNA, or that all target genomic sequences in Table 21 are equally preferred.

Example 12.2: Assay for Expression of Fetal Hemoglobin

In this example, APG07433.1 or APG08290.1 generated insertions or deletions disrupting the BCL11A enhancer region are assayed for expression of fetal hemoglobin. Healthy human donor CD34$^+$ hematopoietic stem cells (HSCs) are used. These HSCs are cultured and vector(s) comprising expression cassettes comprising the coding regions of the preferred RGN and the preferred sgRNA are introduced using methods similar to those described in Example 11.1. Following electroporation, these cells are differentiated in vitro into erythrocytes using established protocols (for example, Giarratana et al. (2004) Nat Biotechnology 23:69-74, herein incorporated by reference). The expression of HbF is then measured using western blotting with an anti-human HbF antibody, or quantified via High Performance Liquid Chromatography (HPLC). It is expected that successful disruption of the BCL11A enhancer locus will lead to an increase in HbF production when compared to HSCs electroporated with only the RGN but no guide.

Example 12.3: Assay for Decreased Sickle Cell Formation

In this example, APG07433.1 or APG08290.1 generated insertions or deletions disrupting the BCL11A enhancer region are assayed for decreased sickle-cell formation. Donor CD34$^+$ hematopoietic stem cells (HSCs) from patients afflicted with sickle cell disease are used. These HSCs are cultured and vector(s) comprising expression cassettes comprising the coding regions of preferred RGN and the preferred sgRNA are introduced using methods similar to those described in Example 11.1. Following electroporation, these cells are differentiated in vitro into erythrocytes using established protocols (Giarratana et al. (2004) Nat Biotechnology 23:69-74). The expression of HbF is then measured using western blotting with an anti-human HbF antibody, or quantified via High Performance Liquid Chromatography (HPLC). It is expected that successful disruption of the BCL11A enhancer locus will lead to an increase in HbF production when compared to HSCs electroporated with only the RGN but no guide.

Sickle cell formation is induced in these differentiated erythrocytes by the addition of metabisulfite. The numbers of sickled vs normal erythrocytes are counted using a microscope. It is expected that the numbers of sickled cells are less in cells treated with APG07433.1 or APG08290.1 plus sgRNAs than with cells untreated, or treated with RGNs alone.

Example 12.4: Disease Treatment Validation in a Murine Model

To evaluate the efficacy of using APG07433.1 or APG08290.1 disruption of the BCL11A locus, suitable humanized mouse models of sickle cell anemia are used. Expression cassettes encoding for the preferred RGN and for the preferred sgRNA are packaged into AAV vectors or adenovirus vectors. In particular, adenovirus type Ad5/35 is effective at targeting HSCs. A suitable mouse model containing a humanized HBB locus with sickle cell alleles is chosen such as B6;FVB-Tg(LCR-HBA2, LCR-HBB*E26K)53Hhb/J or B6.Cg-HbatmlPaz HbbtmlTow Tg(HBA-HBBs)41Paz/HhbJ. These mice are treated with granulocyte colony-stimulating factor alone or in combination with plerixafor to mobilize HSCs into circulation. AAVs or adenoviruses carrying the RGN and guide plasmid are then injected intravenously, and the mice are allowed to recover for a week. Blood obtained from these mice is tested in an in vitro sickling assay using metabisulfite, and the mice are followed longitudinally to monitor mortality rates and hematopoietic function. It is expected that treatment with AAVs or adenoviruses carrying an RGN and guide RNA will reduce sickling, mortality, and improve hematopoietic function when compared to mice treated with viruses lacking both expression cassettes, or with viruses carrying the RGN expression cassette alone.

That which is claimed:

1. A nucleic acid molecule comprising a polynucleotide encoding an RNA-guided nuclease (RGN) polypeptide, wherein said polynucleotide comprises a nucleotide sequence encoding an RGN polypeptide comprising an amino acid sequence:
   (i) having at least 95% sequence identity to SEQ ID NOs: 11, 27, 45 or 54;
   (ii) having at least 98% sequence identity to SEQ ID NOs: 1 or 19; or
   (iii) set forth in SEQ ID NO: 36;
   wherein said RGN polypeptide binds a target DNA sequence in an RNA-guided sequence specific manner when bound to a guide RNA (gRNA) capable of hybridizing to said target DNA sequence, and
   wherein said polynucleotide encoding an RGN polypeptide is operably linked to a promoter heterologous to said polynucleotide.

2. The nucleic acid molecule of claim 1, wherein said RGN polypeptide is nuclease dead or functions as a nickase.

3. The nucleic acid molecule of claim 2, wherein the RGN polypeptide is operably fused to a base-editing polypeptide.

4. A vector comprising the nucleic acid molecule of claim 1.

5. The vector of claim 4, wherein said vector further comprises at least one nucleotide sequence encoding said guide RNA, and wherein the guide RNA comprises a CRISPR RNA comprising a CRISPR repeat sequence having at least 95% sequence identity to SEQ ID NOs: 2, 12, 20, 28, 37, 46, or 55.

6. The vector of claim 4, wherein the guide RNA comprises a tracrRNA having at least 95% sequence identity to SEQ ID NOs: 3, 13, 21, 29, 38, 47, or 56.

7. A cell comprising the nucleic acid molecule of claim 1.

8. A system for binding a target DNA sequence, said system comprising:
   a) one or more guide RNAs capable of hybridizing to said target DNA sequence or one or more nucleotide sequences encoding the one or more guide RNAs (gRNAs); and
   b) an RNA-guided nuclease (RGN) polypeptide comprising an amino acid sequence:
      (i) having at least 95% sequence identity to SEQ ID NOs: 11, 27, 45 or 54;
      (ii) having at least 98% sequence identity to SEQ ID NOs: 1 or 19;
      (iii) set forth in SEQ ID NO: 36; or
      a nucleotide sequence encoding the RGN polypeptide;
   wherein said nucleotide sequences encoding the one or more guide RNAs and encoding the RGN polypeptide are each operably linked to a promoter heterologous to each said nucleotide sequence;
   wherein the one or more guide RNAs hybridize to the target DNA sequence, and
   wherein the one or more guide RNAs form a complex with the RGN polypeptide, thereby directing said RGN polypeptide to bind to said target DNA sequence.

9. The system of claim 8, wherein the target DNA sequence is within a eukaryotic cell.

10. The system of claim 8, wherein said RGN polypeptide is nuclease dead or functions as a nickase, and wherein the RGN polypeptide is operably linked to a base-editing polypeptide.

11. The system of claim 8, wherein said system further comprises one or more donor polynucleotides or one or more nucleotide sequences encoding the one or more donor polynucleotides, wherein said nucleotide sequences encoding the one or more donor polynucleotides are each operably linked to a promoter heterologous to each said nucleotide sequence.

12. A method for binding a target DNA sequence comprising delivering the system according to claim 8, to said target DNA sequence or a cell comprising the target DNA sequence.

13. A method for cleaving and/or modifying a target DNA sequence, comprising contacting the target DNA sequence with:
   a) an RNA-guided nuclease (RGN) polypeptide comprising an amino acid sequence:
      (i) having at least 95% sequence identity to SEQ ID NOs: 11, 27, 45 or 54;
      (ii) having at least 98% sequence identity to SEQ ID NOs: 1 or 19; or
      (iii) set forth in SEQ ID NO: 36; and
   b) one or more guide RNAs capable of targeting the RGN of (a) to the target DNA sequence;
   wherein the one or more guide RNAs hybridize to the target DNA sequence, thereby directing said RGN polypeptide to bind to said target DNA sequence and cleavage and/or modification of said target DNA sequence occurs.

14. The method of claim 13, wherein said modified target DNA sequence comprises insertion of heterologous DNA into the target DNA sequence.

15. The method of claim 13, wherein said modified target DNA sequence comprises deletion of at least one nucleotide from the target DNA sequence.

16. The method of claim 13, wherein said modified target DNA sequence comprises mutation of at least one nucleotide in the target DNA sequence.

17. The method of claim 14, wherein the target DNA sequence is within a cell.

18. The method of claim 17, wherein the cell is a eukaryotic cell.

19. The method of claim 17, further comprising culturing the cell under conditions in which the RGN polypeptide is expressed and cleaves the target DNA sequence to produce a modified DNA sequence; and selecting a cell comprising said modified DNA sequence.

* * * * *

SEQUENCE LISTING

```
<160> NUMBER OF SEQ ID NOS: 651

<210> SEQ ID NO 1
<211> LENGTH: 1070
<212> TYPE: PRT
<213> ORGANISM: Bacillus sp.
<220> FEATURE:
<221> NAME/KEY: source
<223> OTHER INFORMATION: /note="APG05083.1"

<400> SEQUENCE: 1

Met Arg Glu Leu Asp Tyr Arg Ile Gly Leu Asp Ile Gly Thr Asn Ser
1               5                   10                  15

Ile Gly Trp Gly Ile Ile Glu Leu Ser Trp Asn Lys Asp Arg Glu Gln
            20                  25                  30

Tyr Glu Lys Ala Arg Ile Val Asp Lys Gly Val Arg Met Phe Asp Lys
        35                  40                  45

Ala Glu Ile Pro Lys Thr Gly Ala Ser Leu Ala Glu Pro Arg Arg Ile
    50                  55                  60

Ala Arg Ser Ser Arg Arg Arg Leu Asn Arg Lys Ser Gln Arg Lys Lys
65                  70                  75                  80

Asp Ile Arg Asn Leu Leu Val Gln His Glu Ile Ile Ser Gln Lys Glu
                85                  90                  95

Leu Ala Ser Leu Tyr Pro Leu Thr Lys Ser Ser Met Asp Ile Trp Asp
            100                 105                 110

Ile Arg Leu Asp Gly Leu Asp Arg Leu Leu Asp Arg Phe Glu Trp Thr
        115                 120                 125

Arg Leu Leu Ile His Leu Ala Gln Arg Arg Gly Phe Lys Ser Asn Arg
    130                 135                 140

Lys Ser Glu Leu Lys Asp Val Gly Thr Gly Lys Val Leu Ser Ser Ile
145                 150                 155                 160

Gln Ala Asn Glu Lys Arg Leu Ser Leu Tyr Arg Thr Val Gly Glu Met
                165                 170                 175

Trp Met Lys Asn Glu Asp Phe Ser Lys Tyr Asp Lys Arg Arg Asn Ser
            180                 185                 190
```

Ser Asn Glu Tyr Val Phe Ser Val Ser Arg Ala Asp Leu Glu Lys Glu
        195                 200                 205

Ile Val Thr Leu Phe Glu Ala Gln Arg Lys Phe Gln Ser Ser Tyr Ala
210                 215                 220

Ser Ala Asp Leu Gln Lys Thr Tyr Leu Gln Ile Trp Ala His Gln Leu
225                 230                 235                 240

Pro Phe Ala Ser Gly Asn Ala Ile Val Asn Lys Val Gly Tyr Cys Ser
                245                 250                 255

Leu Leu Lys Gly Lys Glu Lys Arg Val Pro Lys Ala Thr Tyr Thr Phe
                260                 265                 270

Gln Tyr Phe Ser Thr Leu Asp Gln Ile Asn Arg Thr Arg Leu Gly Pro
            275                 280                 285

Asn Phe Gln Pro Phe Thr Lys Glu Gln Arg Asp Val Ile Leu Asp Glu
290                 295                 300

Met Phe Asn Arg Thr Asp Tyr Tyr Lys Lys Thr Ile Pro Glu Val
305                 310                 315                 320

Thr Tyr Tyr Asp Ile Arg Lys Trp Leu Ala Leu Asp Glu Thr Ile Gln
                325                 330                 335

Phe Lys Gly Leu Thr Tyr Asp Pro Asn Glu Glu Leu Lys Lys Ile Glu
            340                 345                 350

Leu Lys Ser Phe Ile Asn Leu Lys Pro Phe Tyr Glu Ile Lys Lys Val
                355                 360                 365

Val Thr Asn Tyr Ala Lys Lys Thr Asn Glu Ala Phe Ser Thr Leu Asp
    370                 375                 380

Tyr Asp Thr Phe Ala Tyr Ala Leu Thr Val Tyr Lys Thr Asp Lys Asp
385                 390                 395                 400

Ile Arg Ser Tyr Leu Lys Lys Ser Asn Asn Leu Ser Lys Cys Cys Tyr
                405                 410                 415

Asp Asp Gln Leu Ile Glu Glu Leu Leu Thr Leu Ser Tyr Thr Lys Phe
            420                 425                 430

Gly His Leu Ser Phe Lys Ala Ile Asn His Val Leu Pro Ile Met Gln
            435                 440                 445

Glu Gly Arg Thr Tyr Gln Glu Ala Ile His Gln Leu Gly Tyr Asp Ala
    450                 455                 460

Thr Asn Leu Lys Lys Glu Asn Arg Ser Met Phe Leu Pro Leu Phe Pro
465                 470                 475                 480

Asp Glu Ile Thr Asn Pro Ile Val Lys Arg Ala Leu Thr Gln Ala Arg
            485                 490                 495

Lys Val Val Asn Ala Ile Ile Arg Arg Tyr Gly Ser Pro Asn Ser Val
            500                 505                 510

His Ile Glu Leu Ala Arg Glu Leu Ser Lys Ser His Asp Glu Arg Thr
    515                 520                 525

Lys Ile Met Lys Ala His Asp Glu Asn Tyr Lys Lys Asn Lys Gly Ala
    530                 535                 540

Ile Ser Ile Leu Ile Glu Asn Gly Ile Leu Asn Pro Thr Gly Tyr Asp
545                 550                 555                 560

Ile Val Arg Tyr Lys Leu Trp Lys Glu Gln Gly Glu Arg Cys Ala Tyr
                565                 570                 575

Ser Leu Lys Gln Ile Pro Ala Asn Thr Phe Phe Asn Glu Met Lys Lys
            580                 585                 590

Glu Arg Ser Gly Ser Pro Val Leu Glu Ile Asp His Ile Leu Pro Tyr
            595                 600                 605

```
Ser Gln Ser Phe Ile Asp Ser Tyr His Asn Lys Val Leu Val Tyr Gly
    610                 615                 620

Asp Glu Asn Gln Lys Lys Gly Asn Arg Ile Pro Tyr Thr Tyr Phe Leu
625                 630                 635                 640

Glu Gly Asn Lys Asp Trp Glu Ser Phe Glu Ser Tyr Val Arg Leu Asn
                645                 650                 655

Ser Phe Phe Ser Lys Lys Lys Arg Gly Tyr Leu Leu Lys Lys Ala Tyr
                660                 665                 670

Leu Pro Arg Glu Ser Asn Met Ile Lys Glu Arg His Leu Asn Asp Thr
                675                 680                 685

Arg Tyr Ala Ser Ser Tyr Leu Lys Asn Phe Ile Glu Lys Asn Leu Lys
690                 695                 700

Phe Lys Glu Val Glu Gly Ser Thr Arg Lys Lys His Val Gln Thr Val
705                 710                 715                 720

Asn Gly Ile Ile Thr Ala His Leu Arg Lys Arg Trp Gly Leu Glu Lys
                725                 730                 735

Asp Arg Gln Glu Thr Tyr Leu His His Ala Met Asp Ala Ile Ile Val
                740                 745                 750

Ala Cys Thr Asp His His Met Val Thr Lys Val Thr Glu Tyr Tyr Gln
            755                 760                 765

Ile Lys Glu Ser Asn Lys Ser Ile Arg Lys Pro Tyr Phe Pro Leu Pro
770                 775                 780

Trp Val Gly Phe Arg Glu Glu Ile Leu Ser His Leu Ala Arg Gln Pro
785                 790                 795                 800

Ile Ala Arg Lys Ile Ser Glu Glu Leu Lys Ile Gly Tyr Gln Ser Phe
                805                 810                 815

Asp Tyr Ile Leu Val Ser Arg Met Pro Lys Arg Ser Val Thr Gly Ala
                820                 825                 830

Ala His Glu Gln Thr Ile Met Lys Lys Gly Gly Ile Asp Lys Lys Gly
            835                 840                 845

Lys Thr Ile Ile Ile Lys Arg Val Tyr Leu Lys Asp Ile Lys Phe Asp
    850                 855                 860

Glu Asn Gly Asp Phe Lys Met Val Gly Lys Glu Gln Asp Leu Ala Thr
865                 870                 875                 880

Tyr Glu Ala Ile Lys Gln Arg Tyr Ile Glu Tyr Gly Lys Glu Ser Lys
                885                 890                 895

Lys Ala Phe Glu Thr Pro Leu Tyr Lys Pro Ser Lys Lys Gly Lys Gly
                900                 905                 910

Asn Leu Ile Lys Lys Ile Lys Val Glu Val Gln Thr Lys Ser Phe Val
            915                 920                 925

Arg Glu Val Asn Gly Gly Val Ala Gln Asn Gly Asp Leu Val Arg Val
930                 935                 940

Asp Leu Phe Glu Lys Asp Asn Arg Tyr Tyr Met Ile Pro Ile Tyr Val
945                 950                 955                 960

Met Asp Thr Val His Ser Glu Leu Pro Asn Lys Ala Val Thr Ser Ser
                965                 970                 975

Lys Gly Tyr Glu Gln Trp Leu Thr Ile Asp Asn Ser Phe Thr Phe Lys
            980                 985                 990

Phe Ser Leu Tyr Pro Tyr Asp Leu Val Arg Leu Val Lys Gly Asn Glu
            995                 1000                1005

Asp Arg Phe Leu Tyr Phe Ser Thr Leu Asp Ile Asn Ser Asp Arg
    1010                1015                1020

Leu Asn Phe Lys Asp Val Asn Lys Pro Ser Lys Gln Ala Glu Asn
```

```
                1025                1030                1035

Arg Tyr Ser Leu Lys Thr Ile Glu Asn Leu Glu Lys Tyr Glu Val
    1040                1045                1050

Gly Val Leu Gly Asp Leu Arg Phe Val Arg Gln Glu Ile Arg Lys
    1055                1060                1065

Asn Phe
    1070

<210> SEQ ID NO 2
<211> LENGTH: 19
<212> TYPE: RNA
<213> ORGANISM: Bacillus sp.
<220> FEATURE:
<221> NAME/KEY: source
<223> OTHER INFORMATION: /note="crRNA"

<400> SEQUENCE: 2
gucauaguuc cauuauugc                                                    19

<210> SEQ ID NO 3
<211> LENGTH: 84
<212> TYPE: RNA
<213> ORGANISM: Bacillus sp.
<220> FEATURE:
<221> NAME/KEY: source
<223> OTHER INFORMATION: /note="tracrRNA"

<400> SEQUENCE: 3
gcuuugaugu uucuaugaua agggcuuagg cccguggcgu uggggaucgc cugcccauuu       60
uaaugggcuu cuccccaucu auuu                                              84

<210> SEQ ID NO 4
<211> LENGTH: 137
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L1"

<400> SEQUENCE: 4
gagcggacag cagcuuccua uaucucguac gucauaguuc cauuauugca aaggcuuuga       60
uguuucuaug auaagggcuu aggcccgugg cguuggggau cgccugccca uuuuaauggg      120
cuucucccca ucuauuu                                                     137

<210> SEQ ID NO 5
<211> LENGTH: 137
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L2"

<400> SEQUENCE: 5
ccaugauaua gacguugugg cuguguagu gucauaguuc cauuauugca aaggcuuuga        60
uguuucuaug auaagggcuu aggcccgugg cguuggggau cgccugccca uuuuaauggg      120
```
cuucucccca ucuauuu                                                              137

<210> SEQ ID NO 6
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="PAM"
<220> FEATURE:
<221> NAME/KEY: modified_base
<222> LOCATION: (1)..(4)
<223> OTHER INFORMATION: a, c, t, g, unknown or other

<400> SEQUENCE: 6 nnnncc                                                                          6

<210> SEQ ID NO 7
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="PAM examplary"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 7 nnrncc                                                                          6

<210> SEQ ID NO 8
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 1"
<220> FEATURE:
<221> NAME/KEY: modified_base
<222> LOCATION: (31)..(38)
<223> OTHER INFORMATION: a, c, t, g, unknown or other

<400> SEQUENCE: 8
gagcggacag cagcttccta tatctcgtac nnnnnnnn                                        38

<210> SEQ ID NO 9
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<220> FEATURE:
<221> NAME/KEY: source
<223> OTHER INFORMATION: /note="Target seq and PAM region of plasmid
      library 2"
<220> FEATURE:
<221> NAME/KEY: modified_base
<222> LOCATION: (31)..(38)
<223> OTHER INFORMATION: a, c, t, g, unknown or other

<400> SEQUENCE: 9
ccatgatata gacgttgtgg ctgttgtagt nnnnnnnn                            38

<210> SEQ ID NO 10
<211> LENGTH: 132
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA with N's"
<220> FEATURE:
<221> NAME/KEY: modified_base
<222> LOCATION: (1)..(25)
<223> OTHER INFORMATION: a, c, u, g, unknown or other

<400> SEQUENCE: 10
nnnnnnnnnn nnnnnnnnnn nnnnngucau aguuccauua uugcaaaggc uuugauguuu    60
cuaugauaag ggcuuaggcc cguggcguug gggaucgccu gcccauuuua augggcuucu   120
ccccaucuau uu                                                       132

<210> SEQ ID NO 11
<211> LENGTH: 1071
<212> TYPE: PRT
<213> ORGANISM: Bacillus sp.
<220> FEATURE:
<221> NAME/KEY: source
<223> OTHER INFORMATION: /note="APG07433.1"

<400> SEQUENCE: 11

Met Arg Glu Leu Asp Tyr Arg Ile Gly Leu Asp Ile Gly Thr Asn Ser
1               5                   10                  15

Ile Gly Trp Gly Val Ile Glu Leu Ser Trp Asn Lys Asp Arg Glu Arg
            20                  25                  30

Tyr Glu Lys Val Arg Ile Val Asp Gln Gly Val Arg Met Phe Asp Arg
        35                  40                  45

Ala Glu Met Pro Lys Thr Gly Ala Ser Leu Ala Glu Pro Arg Arg Ile
    50                  55                  60

Ala Arg Ser Ser Arg Arg Arg Leu Asn Arg Lys Ser Gln Arg Lys Lys
65                  70                  75                  80

Asn Ile Arg Asn Leu Leu Val Gln His Gly Val Ile Thr Gln Glu Glu
                85                  90                  95

Leu Asp Ser Leu Tyr Pro Leu Ser Lys Lys Ser Met Asp Ile Trp Gly
            100                 105                 110

Ile Arg Leu Asp Gly Leu Asp Arg Leu Leu Asn His Phe Glu Trp Ala
        115                 120                 125

Arg Leu Leu Ile His Leu Ala Gln Arg Arg Gly Phe Lys Ser Asn Arg
    130                 135                 140

Lys Ser Glu Leu Lys Asp Thr Glu Thr Gly Lys Val Leu Ser Ser Ile
145                 150                 155                 160
```

```
Gln Leu Asn Glu Lys Arg Leu Ser Leu Tyr Arg Thr Val Gly Glu Met
                165                 170                 175
Trp Met Lys Asp Pro Asp Phe Ser Lys Tyr Asp Arg Lys Arg Asn Ser
            180                 185                 190
Pro Asn Glu Tyr Val Phe Ser Val Ser Arg Ala Glu Leu Glu Lys Glu
        195                 200                 205
Ile Val Thr Leu Phe Ala Ala Gln Arg Arg Phe Gln Ser Pro Tyr Ala
    210                 215                 220
Ser Lys Asp Leu Gln Glu Thr Tyr Leu Gln Ile Trp Thr His Gln Leu
225                 230                 235                 240
Pro Phe Ala Ser Gly Asn Ala Ile Leu Asn Lys Val Gly Tyr Cys Ser
                245                 250                 255
Leu Leu Lys Gly Lys Glu Arg Arg Ile Pro Lys Ala Thr Tyr Thr Phe
            260                 265                 270
Gln Tyr Phe Ser Ala Leu Asp Gln Val Asn Arg Thr Arg Leu Gly Pro
        275                 280                 285
Asp Phe Gln Pro Phe Thr Lys Glu Gln Arg Glu Ile Ile Leu Asn Asn
    290                 295                 300
Met Phe Gln Arg Thr Asp Tyr Tyr Lys Lys Thr Ile Pro Glu Val
305                 310                 315                 320
Thr Tyr Tyr Asp Ile Arg Lys Trp Leu Glu Leu Asp Glu Thr Ile Gln
                325                 330                 335
Phe Lys Gly Leu Asn Tyr Asp Pro Asn Glu Leu Lys Lys Ile Glu
            340                 345                 350
Lys Lys Pro Phe Ile Asn Leu Lys Ala Phe Tyr Glu Ile Asn Lys Val
        355                 360                 365
Val Ala Asn Tyr Ser Glu Arg Thr Asn Glu Thr Phe Ser Thr Leu Asp
    370                 375                 380
Tyr Asp Gly Ile Gly Tyr Ala Leu Thr Val Tyr Lys Thr Asp Lys Asp
385                 390                 395                 400
Ile Arg Ser Tyr Leu Lys Ser Ser His Asn Leu Pro Lys Arg Cys Tyr
                405                 410                 415
Asp Asp Gln Leu Ile Glu Glu Leu Leu Ser Leu Ser Tyr Thr Lys Phe
            420                 425                 430
Gly His Leu Ser Leu Lys Ala Ile Asn His Val Leu Ser Ile Met Gln
        435                 440                 445
Lys Gly Asn Thr Tyr Lys Glu Ala Val Asp Gln Leu Gly Tyr Asp Thr
    450                 455                 460
Ser Gly Leu Lys Lys Glu Lys Arg Ser Lys Phe Leu Pro Pro Ile Ser
465                 470                 475                 480
Asp Glu Ile Thr Asn Pro Ile Val Lys Arg Ala Leu Thr Gln Ala Arg
                485                 490                 495
Lys Val Val Asn Ala Ile Ile Arg Arg His Gly Ser Pro His Ser Val
            500                 505                 510
His Ile Glu Leu Ala Arg Glu Leu Ser Lys Asn His Asp Glu Arg Thr
        515                 520                 525
Lys Ile Val Ser Ala Gln Asp Glu Asn Tyr Lys Lys Asn Lys Gly Ala
    530                 535                 540
Ile Ser Ile Leu Ser Glu His Gly Ile Leu Asn Pro Thr Gly Tyr Asp
545                 550                 555                 560
Ile Val Arg Tyr Lys Leu Trp Lys Glu Gln Gly Glu Arg Cys Ala Tyr
                565                 570                 575
Ser Leu Lys Glu Ile Pro Ala Asp Thr Phe Phe Asn Glu Leu Lys Lys
```

```
                580                 585                 590
Glu Arg Asn Gly Ala Pro Ile Leu Glu Val Asp His Ile Leu Pro Tyr
            595                 600                 605

Ser Gln Ser Phe Ile Asp Ser Tyr His Asn Lys Val Leu Val Tyr Ser
    610                 615                 620

Asp Glu Asn Arg Lys Lys Gly Asn Arg Ile Pro Tyr Thr Tyr Phe Leu
625                 630                 635                 640

Glu Thr Asn Lys Asp Trp Glu Ala Phe Glu Arg Tyr Val Arg Ser Asn
                645                 650                 655

Lys Phe Phe Ser Lys Lys Arg Glu Tyr Leu Leu Lys Arg Ala Tyr
            660                 665                 670

Leu Pro Arg Glu Ser Glu Leu Ile Lys Glu Arg His Leu Asn Asp Thr
        675                 680                 685

Arg Tyr Ala Ser Thr Phe Leu Lys Asn Phe Ile Glu Gln Asn Leu Gln
    690                 695                 700

Phe Lys Glu Ala Glu Asp Asn Pro Arg Lys Arg Val Gln Thr Val
705                 710                 715                 720

Asn Gly Val Ile Thr Ala His Phe Arg Lys Arg Trp Gly Leu Glu Lys
                725                 730                 735

Asp Arg Gln Glu Thr Tyr Leu His His Ala Met Asp Ala Ile Ile Val
            740                 745                 750

Ala Cys Thr Asp His His Met Val Thr Arg Val Thr Gly Tyr Tyr Gln
        755                 760                 765

Ile Lys Glu Ser Asn Lys Ser Val Lys Lys Pro Tyr Phe Pro Met Pro
    770                 775                 780

Trp Glu Gly Phe Arg Asp Glu Leu Leu Ser His Leu Ala Ser Gln Pro
785                 790                 795                 800

Ile Ala Lys Lys Ile Ser Glu Glu Leu Lys Ala Gly Tyr Gln Ser Leu
                805                 810                 815

Asp Tyr Ile Phe Val Ser Arg Met Pro Lys Arg Ser Ile Thr Gly Ala
            820                 825                 830

Ala His Lys Gln Thr Ile Met Arg Lys Gly Gly Ile Asp Lys Lys Gly
        835                 840                 845

Lys Thr Ile Ile Ile Glu Arg Leu His Leu Lys Asp Ile Lys Phe Asp
    850                 855                 860

Glu Asn Gly Asp Phe Lys Met Val Gly Lys Glu Gln Asp Met Ala Thr
865                 870                 875                 880

Tyr Glu Ala Ile Lys Gln Arg Tyr Leu Glu His Gly Lys Asn Ser Lys
                885                 890                 895

Lys Ala Phe Glu Thr Pro Leu Tyr Lys Pro Ser Lys Lys Gly Thr Gly
            900                 905                 910

Asn Leu Ile Lys Arg Val Lys Val Glu Gly Gln Ala Lys Ser Phe Val
        915                 920                 925

Arg Glu Val Asn Gly Gly Val Ala Gln Asn Gly Asp Leu Val Arg Val
    930                 935                 940

Asp Leu Phe Glu Lys Asp Asp Lys Tyr Tyr Met Val Pro Ile Tyr Val
945                 950                 955                 960

Pro Asp Thr Val Cys Ser Glu Leu Pro Lys Val Val Ala Ser Ser
                965                 970                 975

Lys Gly Tyr Glu Gln Trp Leu Thr Leu Asp Asn Ser Phe Thr Phe Lys
            980                 985                 990

Phe Ser Leu Tyr Pro Tyr Asp Leu  Val Arg Leu Val Lys  Gly Asp Glu
        995                 1000                1005
```

```
Asp Arg Phe Leu Tyr Phe Gly Thr Leu Asp Ile Asp Ser Asp Arg
    1010                1015                1020

Leu Asn Phe Lys Asp Val Asn Lys Pro Ser Lys Asn Glu Tyr
    1025                1030                1035

Arg Tyr Ser Leu Lys Thr Ile Glu Asp Leu Glu Lys Tyr Glu Val
    1040                1045                1050

Gly Val Leu Gly Asp Leu Arg Leu Val Arg Lys Glu Thr Arg Arg
    1055                1060                1065

Asn Phe His
    1070

<210> SEQ ID NO 12
<211> LENGTH: 21
<212> TYPE: RNA
<213> ORGANISM: Bacillus sp.
<220> FEATURE:
<221> NAME/KEY: source
<223> OTHER INFORMATION: /note="crRNA"

<400> SEQUENCE: 12
gucauaguuc cauuaaagcc a                                         21

<210> SEQ ID NO 13
<211> LENGTH: 85
<212> TYPE: RNA
<213> ORGANISM: Bacillus sp.
<220> FEATURE:
<221> NAME/KEY: source
<223> OTHER INFORMATION: /note="tracrRNA"

<400> SEQUENCE: 13
uggcuuugau guuucuauga uaaggguuuc gacccguggc gucggggauc gccugcccau   60 ugaaugggc uucuccccau uuauu                                         85

<210> SEQ ID NO 14
<211> LENGTH: 140
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L1"

<400> SEQUENCE: 14
gagcggacag cagcuuccua uaucucguac gucauaguuc cauuaaagcc agaaauggcu   60
uugauguuuc uaugauaagg guuucgaccc guggcgucgg ggaucgccug cccauugaaa  120
ugggcuucuc cccauuuauu                                              140

<210> SEQ ID NO 15
<211> LENGTH: 140
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L2"

<400> SEQUENCE: 15
```

```
ccaugauaua gacguugugg cuguuguagu gucauaguuc cauuaaagcc agaaauggcu      60
uugauguuuc uaugauaagg guuucgaccc guggcgucgg ggaucgccug cccaugaaa      120 ugggcuucuc cccauuuauu                                                 140
```

<210> SEQ ID NO 16
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 1"
<220> FEATURE:
<221> NAME/KEY: modified_base
<222> LOCATION: (31)..(38)
<223> OTHER INFORMATION: a, c, t, g, unknown or other

<400> SEQUENCE: 16

```
gagcggacag cagcttccta tatctcgtac nnnnnnnn                             38
```

<210> SEQ ID NO 17
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 2"
<220> FEATURE:
<221> NAME/KEY: modified_base
<222> LOCATION: (31)..(38)
<223> OTHER INFORMATION: a, c, t, g, unknown or other

<400> SEQUENCE: 17

```
ccatgatata gacgttgtgg ctgttgtagt nnnnnnnn                             38
```

<210> SEQ ID NO 18
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA with N's"
<220> FEATURE:
<221> NAME/KEY: modified_base
<222> LOCATION: (1)..(25)
<223> OTHER INFORMATION: a, c, u, g, unknown or other

<400> SEQUENCE: 18

```
nnnnnnnnnn nnnnnnnnnn nnnnngucau aguuccauua aagccaaaag uggcuuugau      60
guuucuauga uaaggguuuc gacccguggc gucgggggauc gccugcccau ugaaaugggc    120
uucuccccau uuauu                                                      135
```

<210> SEQ ID NO 19
<211> LENGTH: 1071

```
<212> TYPE: PRT
<213> ORGANISM: Bacillus sp.
<220> FEATURE:
<221> NAME/KEY: source
<223> OTHER INFORMATION: /note="APG07513.1"

<400> SEQUENCE: 19
```

| | | | | | | | | | | | | | | |
|---|---|---|---|---|---|---|---|---|---|---|---|---|---|---|
| Met | Arg | Glu | Leu | Asp | Tyr | Arg | Ile | Gly | Leu | Asp | Ile | Gly | Thr | Asn | Ser |
| 1 | | | | 5 | | | | | 10 | | | | | 15 | |

| Ile | Gly | Trp | Gly | Val | Ile | Glu | Leu | Ser | Trp | Asn | Lys | Asp | Arg | Glu | Gln |
|---|---|---|---|---|---|---|---|---|---|---|---|---|---|---|---|
| | | | 20 | | | | | 25 | | | | | 30 | | |

| Tyr | Glu | Lys | Thr | Arg | Ile | Val | Asp | Lys | Gly | Val | Arg | Met | Phe | Asp | Lys |
|---|---|---|---|---|---|---|---|---|---|---|---|---|---|---|---|
| | | | 35 | | | | | 40 | | | | | 45 | | |

| Ala | Glu | Ile | Pro | Lys | Thr | Gly | Ala | Ser | Leu | Ala | Glu | Pro | Arg | Arg | Ile |
|---|---|---|---|---|---|---|---|---|---|---|---|---|---|---|---|
| | 50 | | | | | 55 | | | | | 60 | | | | |

| Ala | Arg | Ser | Ser | Arg | Arg | Arg | Leu | Asn | Arg | Lys | Ser | Gln | Arg | Lys | Lys |
|---|---|---|---|---|---|---|---|---|---|---|---|---|---|---|---|
| 65 | | | | | 70 | | | | | 75 | | | | | 80 |

| Asp | Ile | Arg | Asn | Leu | Leu | Val | Gln | His | Glu | Ile | Ile | Ser | Gln | Lys | Glu |
|---|---|---|---|---|---|---|---|---|---|---|---|---|---|---|---|
| | | | | 85 | | | | | 90 | | | | | 95 | |

| Leu | Thr | Ser | Leu | Tyr | Pro | Leu | Ser | Lys | Ser | Ser | Met | Asp | Ile | Trp | Asp |
|---|---|---|---|---|---|---|---|---|---|---|---|---|---|---|---|
| | | | 100 | | | | | 105 | | | | | 110 | | |

| Ile | Arg | Leu | Asp | Gly | Leu | Asp | Arg | Leu | Leu | Asp | Arg | Phe | Glu | Trp | Ala |
|---|---|---|---|---|---|---|---|---|---|---|---|---|---|---|---|
| | | | 115 | | | | | 120 | | | | | 125 | | |

| Arg | Leu | Leu | Ile | His | Leu | Ala | Gln | Arg | Arg | Gly | Phe | Lys | Ser | Asn | Arg |
|---|---|---|---|---|---|---|---|---|---|---|---|---|---|---|---|
| | 130 | | | | | 135 | | | | | 140 | | | | |

| Lys | Ser | Glu | Leu | Lys | Asp | Val | Glu | Thr | Gly | Lys | Val | Leu | Ser | Ser | Ile |
|---|---|---|---|---|---|---|---|---|---|---|---|---|---|---|---|
| 145 | | | | | 150 | | | | | 155 | | | | | 160 |

| Gln | Val | Asn | Glu | Lys | Arg | Leu | Ser | Leu | Tyr | Arg | Thr | Val | Gly | Glu | Met |
|---|---|---|---|---|---|---|---|---|---|---|---|---|---|---|---|
| | | | | 165 | | | | | 170 | | | | | 175 | |

| Trp | Met | Lys | Asn | Ala | Asp | Cys | Ser | Lys | Tyr | Gly | Lys | Arg | Arg | Asn | Ser |
|---|---|---|---|---|---|---|---|---|---|---|---|---|---|---|---|
| | | | 180 | | | | | 185 | | | | | 190 | | |

| Pro | Asn | Glu | Tyr | Val | Phe | Ser | Val | Ser | Arg | Ala | Asp | Leu | Glu | Lys | Glu |
|---|---|---|---|---|---|---|---|---|---|---|---|---|---|---|---|
| | | | 195 | | | | | 200 | | | | | 205 | | |

| Ile | Val | Thr | Leu | Phe | Glu | Ala | Gln | Arg | Lys | Phe | His | Ser | Ser | Tyr | Ala |
|---|---|---|---|---|---|---|---|---|---|---|---|---|---|---|---|
| | 210 | | | | | 215 | | | | | 220 | | | | |

| Ser | Val | Asp | Leu | Gln | Lys | Thr | Tyr | Ile | Gln | Ile | Trp | Ala | His | Gln | Leu |
|---|---|---|---|---|---|---|---|---|---|---|---|---|---|---|---|
| 225 | | | | | 230 | | | | | 235 | | | | | 240 |

| Pro | Phe | Ala | Ser | Gly | Asn | Ala | Ile | Val | Asn | Lys | Val | Gly | Tyr | Cys | Ser |
|---|---|---|---|---|---|---|---|---|---|---|---|---|---|---|---|
| | | | | 245 | | | | | 250 | | | | | 255 | |

| Leu | Leu | Lys | Gly | Lys | Glu | Lys | Arg | Val | Pro | Lys | Ala | Thr | Tyr | Thr | Phe |
|---|---|---|---|---|---|---|---|---|---|---|---|---|---|---|---|
| | | | 260 | | | | | 265 | | | | | 270 | | |

| Gln | Tyr | Phe | Asn | Thr | Leu | Asp | Gln | Ile | Asn | Arg | Thr | Arg | Leu | Gly | Pro |
|---|---|---|---|---|---|---|---|---|---|---|---|---|---|---|---|
| | | | 275 | | | | | 280 | | | | | 285 | | |

| Asn | Phe | Gln | Pro | Phe | Thr | Lys | Glu | Gln | Arg | Asp | Ile | Ile | Leu | Asp | Lys |
|---|---|---|---|---|---|---|---|---|---|---|---|---|---|---|---|
| | 290 | | | | | 295 | | | | | 300 | | | | |

| Met | Phe | Gln | Arg | Thr | Asp | Tyr | Tyr | Lys | Lys | Lys | Thr | Ile | Pro | Glu | Val |
|---|---|---|---|---|---|---|---|---|---|---|---|---|---|---|---|
| 305 | | | | | 310 | | | | | 315 | | | | | 320 |

| Thr | Tyr | Tyr | Asp | Ile | Arg | Lys | Trp | Leu | Ala | Leu | Asp | Glu | Thr | Ile | Gln |
|---|---|---|---|---|---|---|---|---|---|---|---|---|---|---|---|
| | | | | 325 | | | | | 330 | | | | | 335 | |

| Phe | Lys | Gly | Leu | Thr | Tyr | Asp | Pro | Asn | Glu | Glu | Leu | Lys | Lys | Ile | Glu |
|---|---|---|---|---|---|---|---|---|---|---|---|---|---|---|---|
| | | | 340 | | | | | 345 | | | | | 350 | | |

| Met | Lys | Pro | Phe | Ile | Asn | Leu | Lys | Pro | Phe | Tyr | Glu | Ile | Lys | Lys | Val |
|---|---|---|---|---|---|---|---|---|---|---|---|---|---|---|---|
| | | | 355 | | | | | 360 | | | | | 365 | | |

| Val | Thr | Asn | Tyr | Ala | Lys | Lys | Thr | Asn | Glu | Val | Phe | Ser | Ala | Leu | Asp |
|---|---|---|---|---|---|---|---|---|---|---|---|---|---|---|---|
| | 370 | | | | | 375 | | | | | 380 | | | | |

```
Tyr Asp Thr Val Ala Tyr Ala Leu Thr Val Tyr Lys Thr Asp Lys Asp
385                 390                 395                 400

Ile Arg Ser Tyr Leu Lys Arg Ser Asn Asn Leu Ser Lys Arg Cys Tyr
            405                 410                 415

Asp Asp Gln Leu Ile Glu Glu Leu Leu Thr Leu Ser Tyr Thr Lys Phe
            420                 425                 430

Gly His Leu Ser Phe Lys Ala Ile Asn His Val Leu Pro Ile Met Gln
            435                 440                 445

Glu Gly Arg Thr Tyr Gln Glu Ala Ile His Gln Leu Gly Tyr Asp Thr
            450                 455                 460

Thr Asn Leu Lys Lys Glu Asn Arg Ser Met Phe Leu Pro Ile Ile Pro
465                 470                 475                 480

Asp Glu Ile Thr Asn Pro Ile Val Lys Arg Ala Leu Thr Gln Ala Arg
            485                 490                 495

Lys Val Val Asn Ala Ile Ile Arg Arg Tyr Gly Ser Pro Asn Ser Val
            500                 505                 510

His Ile Glu Leu Ala Arg Glu Leu Ser Lys Ser His Asp Glu Arg Lys
            515                 520                 525

Lys Ile Met Thr Ala His Asp Glu Asn Tyr Lys Asn Lys Gly Ala
            530                 535                 540

Val Ser Ile Leu Ile Asp Asn Gly Ile Leu Asn Pro Thr Gly Tyr Asp
545                 550                 555                 560

Ile Val Arg Tyr Lys Leu Trp Lys Glu Gln Gly Glu Arg Cys Ala Tyr
            565                 570                 575

Ser Leu Lys Lys Ile Pro Ala Asn Thr Phe Phe Asn Glu Leu Lys Lys
            580                 585                 590

Glu Arg Ser Gly Pro Pro Val Leu Glu Val Asp His Ile Leu Pro Tyr
            595                 600                 605

Ser Gln Ser Phe Ile Asp Ser Tyr His Asn Lys Val Leu Val Tyr Gly
            610                 615                 620

Asp Glu Asn Gln Lys Lys Gly Asn Arg Ile Pro Tyr Thr Phe Phe Ser
625                 630                 635                 640

Glu Glu Asp Lys Glu Trp Glu Ser Phe Glu Ser Tyr Val Arg Ser Asn
            645                 650                 655

Ser Phe Phe Ser Lys Lys Lys Arg Gly Tyr Leu Leu Lys Lys Ala Tyr
            660                 665                 670

Leu Pro Arg Glu Ser Asn Leu Ile Lys Glu Arg His Leu Asn Asp Thr
            675                 680                 685

Arg Tyr Ala Ser Ser Tyr Leu Lys Asn Phe Ile Glu Lys Asn Leu Lys
            690                 695                 700

Phe Lys Glu Ala Val Gly Ile Thr Arg Lys Lys Tyr Val Gln Thr Val
705                 710                 715                 720

Asn Gly Val Ile Thr Ala His Leu Arg Lys Arg Trp Gly Leu Glu Lys
            725                 730                 735

Asp Arg Gln Glu Thr Tyr Leu His His Ala Met Asp Ala Ile Ile Val
            740                 745                 750

Ala Cys Thr Asp His His Met Val Thr Lys Val Thr Glu Tyr Tyr Gln
            755                 760                 765

Ile Lys Glu Gly Asn Lys Ser Ile Lys Lys Pro Tyr Phe Pro Leu Pro
            770                 775                 780

Trp Met Gly Phe Arg Glu Glu Ile Leu Ser His Leu Glu Ser Gln Pro
785                 790                 795                 800
```

```
Ile Ala Arg Lys Ile Ser Glu Glu Leu Lys Ile Gly Tyr Gln Ser Pro
                805                 810                 815

Asp Tyr Ile Leu Val Ser Arg Met Pro Lys Arg Ser Val Thr Gly Ser
            820                 825                 830

Ala His Asp Gln Thr Val Met Lys Gly Asp Ile Asp Lys Lys Gly
        835                 840                 845

Lys Thr Ile Ile Ile Lys Arg Val His Leu Asp Ile Lys Phe Asp
    850                 855                 860

Glu Asn Gly Asp Phe Lys Met Val Gly Lys Glu Gln Asp Leu Ala Thr
865                 870                 875                 880

Tyr Glu Ala Ile Lys Gln Arg Tyr Leu Glu Tyr Arg Lys Glu Ser Lys
                885                 890                 895

Lys Ala Phe Glu Thr Pro Leu Tyr Lys Pro Ser Lys Lys Gly Lys Gly
            900                 905                 910

Asn Leu Ile Lys Lys Ile Lys Val Glu Val Gln Thr Lys Ser Phe Val
        915                 920                 925

Arg Glu Ile Asn Gly Gly Val Ala Gln Asn Gly Asp Leu Val Arg Val
    930                 935                 940

Asp Leu Phe Glu Lys Asp Asn Arg Tyr Tyr Met Val Pro Ile Tyr Val
945                 950                 955                 960

Val Asp Thr Val Arg Ser Glu Leu Pro Asn Lys Ala Val Thr Ser Ser
                965                 970                 975

Lys Gly Tyr Glu Gln Trp Leu Ser Ile Asp Asn Ser Phe Thr Phe Lys
            980                 985                 990

Phe Ser Leu Tyr Pro Tyr Asp Leu Val Arg Leu Val Lys Gly Asp Glu
        995                 1000                1005

Asp Arg Phe Leu Tyr Phe Ser Thr Leu Asp Ile Asn Ser Asp Arg
    1010                1015                1020

Leu Asn Phe Lys Asp Val Asn Lys Pro Ser Lys Gln Ala Glu Tyr
    1025                1030                1035

Arg Tyr Ser Leu Lys Thr Ile Glu Asn Leu Glu Lys Tyr Glu Ile
    1040                1045                1050

Gly Val Leu Gly Asp Leu Arg Leu Val Arg Gln Glu Thr Arg Lys
    1055                1060                1065

Ile Phe Lys
    1070

<210> SEQ ID NO 20
<211> LENGTH: 27
<212> TYPE: RNA
<213> ORGANISM: Bacillus sp.
<220> FEATURE:
<221> NAME/KEY: source
<223> OTHER INFORMATION: /note="crRNA"

<400> SEQUENCE: 20
gucauaguuc cauuaaagcc auugcug                                    27

<210> SEQ ID NO 21
<211> LENGTH: 93
<212> TYPE: RNA
<213> ORGANISM: Bacillus sp.
<220> FEATURE:
<221> NAME/KEY: source
<223> OTHER INFORMATION: /note="tracrRNA"

<400> SEQUENCE: 21
acagcaaugg cuuugauguu ucaugauaa gggcuucggc ccguggcguu ggggaucgcc  60
```

```
ugcccauuuu aaugggcuuc uccccaucua uuu                                 93
```

<210> SEQ ID NO 22
<211> LENGTH: 154
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L1"

<400> SEQUENCE: 22

```
gagcggacag cagcuuccua uaucucguac gucauaguuc cauuaaagcc auugcugaaa    60
gacagcaaug gcuuugaugu uucuaugaua agggcuucgg cccguggcgu uggggaucgc   120
cugcccauuu uaaugggcuu cuccccaucu auuu                               154
```

<210> SEQ ID NO 23
<211> LENGTH: 154
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L2"

<400> SEQUENCE: 23

```
ccaugauaua gacguugugg cuguuguagu gucauaguuc cauuaaagcc auugcugaaa    60
gacagcaaug gcuuugaugu uucuaugaua agggcuucgg cccguggcgu uggggaucgc   120
cugcccauuu uaaugggcuu cuccccaucu auuu                               154
```

<210> SEQ ID NO 24
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 1"
<220> FEATURE:
<221> NAME/KEY: modified_base
<222> LOCATION: (31)..(38)
<223> OTHER INFORMATION: a, c, t, g, unknown or other

<400> SEQUENCE: 24

```
gagcggacag cagcttccta tatctcgtac nnnnnnnn                            38
```

<210> SEQ ID NO 25
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid

```
           library 2"
<220> FEATURE:
<221> NAME/KEY: modified_base
<222> LOCATION: (31)..(38)
<223> OTHER INFORMATION: a, c, t, g, unknown or other

<400> SEQUENCE: 25
ccatgatata gacgttgtgg ctgttgtagt nnnnnnnn                              38

<210> SEQ ID NO 26
<211> LENGTH: 149
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA with N's"
<220> FEATURE:
<221> NAME/KEY: modified_base
<222> LOCATION: (1)..(25)
<223> OTHER INFORMATION: a, c, u, g, unknown or other

<400> SEQUENCE: 26
nnnnnnnnnn nnnnnnnnnn nnnnngucau aguuccauua aagccauugc ugaaagacag      60
caauggcuuu gauguuucua ugauaagggc uucggcccgu ggcguugggg aucgccugcc     120
cauuuuaaug ggcuucuccc caucuauuu                                      149

<210> SEQ ID NO 27
<211> LENGTH: 1072
<212> TYPE: PRT
<213> ORGANISM: Bacillus sp.
<220> FEATURE:
<221> NAME/KEY: source
<223> OTHER INFORMATION: /note="APG08290.1"

<400> SEQUENCE: 27

Met Ser Glu Leu Asp Tyr Arg Ile Gly Leu Asp Ile Gly Thr Asn Ser
1               5                   10                  15

Ile Gly Trp Gly Val Ile Glu Leu Phe Trp Asn Lys Asp Arg Glu Arg
            20                  25                  30

Tyr Glu Lys Val Arg Ile Val Asp Lys Gly Val Arg Met Phe Asp Lys
        35                  40                  45

Ala Glu Ile Pro Asn Lys Gly Ala Ser Leu Ala Glu Pro Arg Arg Ile
    50                  55                  60

Ala Arg Ser Ser Arg Arg Arg Leu Asn Arg Lys Ser Gln Arg Lys Lys
65                  70                  75                  80

Glu Ile Arg Asn Leu Leu Val Gln His Gly Met Ile Thr Gln Glu Glu
                85                  90                  95

Leu Asp Leu Leu Tyr Pro Leu Ser Lys Lys Ser Ile Asp Ile Trp Asp
            100                 105                 110

Ile Arg Leu Asp Gly Leu Asp Arg Leu Leu Asn His Leu Glu Trp Ala
        115                 120                 125

Arg Leu Leu Ile His Leu Ala Gln Arg Arg Gly Phe Lys Ser Asn Arg
    130                 135                 140

Lys Ser Glu Leu Lys Asp Ala Glu Thr Gly Lys Val Leu Ser Ser Ile
145                 150                 155                 160

Gln Val Asn Glu Lys Arg Leu Phe Leu Tyr Arg Thr Val Gly Glu Met
                165                 170                 175
```

Trp Ile Lys Asp Ala Glu Phe Ser Lys Tyr Asp Arg Arg Asn Ser
            180                 185                 190

Pro Asn Glu Tyr Val Phe Ser Val Ser Arg Ala Asp Leu Glu Lys Glu
        195                 200                 205

Ile Val Thr Leu Phe Glu Ala Gln Arg Lys Phe Gln Ser Ser Tyr Ala
        210                 215                 220

Ser Lys Asn Leu Gln Glu Thr Tyr Leu Gln Ile Trp Ala His Gln Leu
225                 230                 235                 240

Pro Phe Ala Ser Gly Asn Ala Ile Leu Asn Lys Val Gly Tyr Cys Ser
            245                 250                 255

Leu Leu Lys Gly Lys Glu Arg Arg Ile Pro Lys Ala Thr Tyr Thr Phe
            260                 265                 270

Gln Tyr Phe Ser Ala Leu Asp Gln Val Asn Arg Thr Arg Leu Gly Pro
        275                 280                 285

Asp Phe Gln Pro Phe Thr Gln Glu Gln Lys Glu Ile Ile Leu Asp Lys
        290                 295                 300

Met Phe Gln Arg Thr Asp Tyr Tyr Lys Lys Thr Ile Pro Glu Val
305                 310                 315                 320

Ser Tyr Tyr Asp Ile Arg Lys Trp Leu Glu Leu Asp Glu Thr Ile Gln
            325                 330                 335

Phe Lys Gly Leu Asn Tyr Asp Pro Asn Glu Glu Leu Lys Lys Ile Glu
            340                 345                 350

Lys Lys Pro Phe Ile Asn Leu Lys Ala Phe Tyr Glu Ile Lys Lys Val
        355                 360                 365

Val Ala Asn Tyr Ala Glu Arg Thr Asn Glu Ala Phe Ser Thr Leu Asp
370                 375                 380

Tyr Asp Ala Ile Ala Tyr Ala Leu Thr Val Tyr Lys Thr Asp Lys Asp
385                 390                 395                 400

Ile Arg Ser Tyr Leu Lys Lys Ser Asn Asn Leu Ser Lys Arg Cys Tyr
            405                 410                 415

Asp Asp Gln Leu Ile Glu Glu Leu Phe Thr Leu Ser Tyr Thr Lys Phe
        420                 425                 430

Gly His Leu Ser Phe Lys Ala Ile Asn His Val Leu Pro Ile Met Gln
        435                 440                 445

Glu Gly Arg Thr Tyr Gln Glu Ala Ile His Gln Leu Gly Tyr Asp Thr
        450                 455                 460

Thr Asn Leu Lys Lys Glu Asn Arg Ser Met Phe Leu Pro Leu Ile Pro
465                 470                 475                 480

Asp Glu Ile Thr Asn Pro Ile Val Lys Arg Ala Ile Thr Gln Ala Arg
            485                 490                 495

Lys Val Val Asn Ala Ile Ile Arg Arg Tyr Gly Ser Pro Asn Ser Val
        500                 505                 510

His Ile Glu Leu Ala Arg Glu Leu Ser Lys Ser His Asp Glu Arg Lys
        515                 520                 525

Lys Ile Met Thr Ala His Asp Glu Asn Tyr Lys Asn Lys Gly Ala
530                 535                 540

Ile Ser Ile Leu Ile Glu Asn Gly Ile Leu Asn Pro Thr Gly Tyr Asp
545                 550                 555                 560

Ile Val Arg Tyr Lys Leu Trp Lys Glu Gln Gly Glu Arg Cys Ala Tyr
            565                 570                 575

Ser Leu Lys Glu Ile Pro Pro Asp Thr Phe Phe Asn Glu Leu Lys Lys
        580                 585                 590

Glu Arg Asn Gly Ser Pro Ile Leu Glu Val Asp His Ile Leu Pro Tyr

```
                     595                 600                 605
Ser Gln Ser Phe Ile Asp Ser Tyr His Asn Lys Val Leu Val Tyr Ser
    610                 615                 620

Asp Glu Asn Arg Asn Lys Gly Asn Arg Ile Pro Tyr Thr Tyr Phe Leu
625                 630                 635                 640

Glu Thr Asn Lys Asp Trp Glu Ala Phe Glu Arg Tyr Val Arg Ser Asn
                645                 650                 655

Lys Leu Phe Ser Lys Lys Arg Glu Tyr Leu Leu Lys Lys Thr Tyr
                660                 665                 670

Leu Pro Arg Glu Ser Glu Leu Ile Lys Glu Arg His Leu Asn Asp Thr
                675                 680                 685

Arg Tyr Ala Ser Thr Phe Leu Lys Asn Phe Ile Glu Gln Asn Leu Gln
            690                 695                 700

Phe Lys Glu Val Glu Val Asn Leu Arg Lys Lys Arg Val Gln Thr Val
705                 710                 715                 720

Asn Gly Val Ile Thr Ala His Leu Arg Lys Arg Trp Gly Leu Glu Lys
                    725                 730                 735

Asn Arg Gln Glu Thr Tyr Leu His His Ala Met Asp Ala Ile Ile Val
                740                 745                 750

Ala Cys Thr Asp His His Met Val Thr Arg Ile Thr Glu Tyr Tyr Gln
                755                 760                 765

Ile Lys Glu Ser Asn Lys Ser Val Lys Lys Pro Tyr Phe Pro Met Pro
770                 775                 780

Trp Glu Gly Phe Arg Asp Glu Leu Leu Ser His Leu Ala Ser Gln Pro
785                 790                 795                 800

Ile Ala Lys Lys Ile Ser Glu Glu Leu Lys Ala Gly Tyr Gln Ser Ser
                805                 810                 815

Asp Tyr Ile Phe Val Ser Arg Met Pro Lys Arg Ser Val Thr Gly Ala
                820                 825                 830

Ala His Asp Gln Thr Ile Arg Arg Lys Gly Gly Ile Asp Lys Lys Gly
            835                 840                 845

Lys Thr Ile Ile Ile Lys Arg Val Arg Leu Lys Asp Ile Lys Phe Asp
850                 855                 860

Glu Asn Gly Asp Phe Lys Met Val Gly Lys Glu Gln Asp Leu Ala Thr
865                 870                 875                 880

Tyr Glu Ala Ile Lys Gln Arg Tyr Leu Glu His Arg Lys Asn Ser Lys
                885                 890                 895

Lys Ala Phe Glu Thr Pro Leu Tyr Lys Pro Ser Lys Lys Gly Thr Gly
                900                 905                 910

Asn Leu Ile Lys Arg Val Lys Ile Glu Gly Gln Thr Lys Ala Phe Val
            915                 920                 925

Arg Glu Val Asn Gly Gly Val Ala Gln Asn Ser Asp Leu Val Arg Val
            930                 935                 940

Asp Leu Phe Glu Lys Asp Asp Lys Tyr Tyr Met Val Pro Ile Tyr Val
945                 950                 955                 960

Pro Asp Thr Val Cys Ser Glu Leu Pro Lys Lys Val Val Lys Ser Gly
                965                 970                 975

Lys Gly Tyr Glu Gln Trp Leu Thr Leu Asp Asn Ser Phe Thr Phe Lys
            980                 985                 990

Ser Ser Leu Tyr Pro Tyr Asp Leu Val Arg Leu Val Lys Gly Asn Glu
            995                1000                1005

Asp Arg Phe Leu Tyr Phe Gly Thr Leu Asp Ile Asp Ser Asp Arg
            1010                1015                1020
```

```
Leu Asn  Phe Lys Asp Val  Asn  Lys Pro Ser  Lys Gln  Asn Glu Tyr
    1025             1030              1035

Arg Tyr  Ser Leu Lys Thr  Ile  Glu Asn Leu  Glu Lys  Tyr Glu Val
    1040             1045              1050

Gly Val  Leu Gly Asp Leu  Arg  Leu Val Lys  Gln Glu  Thr Arg Arg
    1055             1060              1065

Ile Phe  Asn Arg
    1070

<210> SEQ ID NO 28
<211> LENGTH: 21
<212> TYPE: RNA
<213> ORGANISM: Bacillus sp.
<220> FEATURE:
<221> NAME/KEY: source
<223> OTHER INFORMATION: /note="crRNA"

<400> SEQUENCE: 28
gucauaguuc caugaaagcc a                                            21

<210> SEQ ID NO 29
<211> LENGTH: 85
<212> TYPE: RNA
<213> ORGANISM: Bacillus sp.
<220> FEATURE:
<221> NAME/KEY: source
<223> OTHER INFORMATION: /note="tracrRNA"

<400> SEQUENCE: 29
uggcuuugau guuucuauga uaaggguuuc ggcccguggc gucggggauc gccugcccau    60
uccgaugggc uucuccccau uuauu                                         85

<210> SEQ ID NO 30
<211> LENGTH: 140
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L1"

<400> SEQUENCE: 30
gagcggacag cagcuuccua uaucucguac gucauaguuc caugaaagcc aaaaguggcu    60
uugauguuuc uaugauaagg guuucggccc guggcgucgg ggaucgccug cccauuccga   120
ugggcuucuc cccauuuauu                                              140

<210> SEQ ID NO 31
<211> LENGTH: 140
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L2"

<400> SEQUENCE: 31
ccaugauaua gacguugugg cuguuguagu gucauaguuc caugaaagcc aaaaguggcu    60
```
uugauguuuc uaugauaagg guuucggccc guggcgucgg ggaucgccug cccauuccga    120
ugggcuucuc cccauuuauu                                                140

<210> SEQ ID NO 32
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="PAM"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 32 nnrncc                                                               6

<210> SEQ ID NO 33
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 1"
<220> FEATURE:
<221> NAME/KEY: modified_base
<222> LOCATION: (31)..(38)
<223> OTHER INFORMATION: a, c, t, g, unknown or other

<400> SEQUENCE: 33
gagcggacag cagcttccta tatctcgtac nnnnnnnn                            38

<210> SEQ ID NO 34
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 2"
<220> FEATURE:
<221> NAME/KEY: modified_base
<222> LOCATION: (31)..(38)
<223> OTHER INFORMATION: a, c, t, g, unknown or other

<400> SEQUENCE: 34
ccatgatata gacgttgtgg ctgttgtagt nnnnnnnn                            38

<210> SEQ ID NO 35
<211> LENGTH: 135
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA with N's"
<220> FEATURE:
<221> NAME/KEY: modified_base
<222> LOCATION: (1)..(25)
<223> OTHER INFORMATION: a, c, u, g, unknown or other

<400> SEQUENCE: 35
nnnnnnnnnn nnnnnnnnnn nnnnngucau aguuccauga aagccaaaag uggcuuugau      60
guuucuauga uaaggguuuc ggcccguggc gucgggauc gccugcccau uccgaugggc      120 uucucccau uuauu                                                       135

<210> SEQ ID NO 36
<211> LENGTH: 1337
<212> TYPE: PRT
<213> ORGANISM: Enterococcus sp.
<220> FEATURE:
<221> NAME/KEY: source
<223> OTHER INFORMATION: /note="APG05459.1"

<400> SEQUENCE: 36
```

Met Lys Lys Asp Tyr Val Ile Gly Leu Asp Ile Gly Thr Asn Ser Val
1               5                   10                  15

Gly Trp Ala Val Met Thr Glu Asp Tyr Gln Leu Val Lys Lys Lys Met
            20                  25                  30

Pro Ile Tyr Gly Asn Thr Glu Lys Lys Ile Lys Lys Asn Phe Trp
        35                  40                  45

Gly Val Arg Leu Phe Glu Glu Gly His Thr Ala Glu Asp Arg Arg Leu
    50                  55                  60

Lys Arg Thr Ala Arg Arg Ile Ser Arg Arg Asn Arg Leu Arg
65                  70                  75                  80

Tyr Leu Gln Ala Phe Phe Glu Glu Ala Met Thr Ala Leu Asp Glu Asn
                85                  90                  95

Phe Phe Ala Arg Leu Gln Glu Ser Phe Leu Val Pro Glu Asp Lys Lys
            100                 105                 110

Trp His Arg His Pro Ile Phe Ala Lys Leu Glu Asp Glu Val Ala Tyr
        115                 120                 125

His Glu Thr Tyr Pro Thr Ile Tyr His Leu Arg Lys Lys Leu Ala Asp
    130                 135                 140

Ser Ser Glu Gln Ala Asp Leu Arg Leu Ile Tyr Leu Ala Leu Ala His
145                 150                 155                 160

Ile Val Lys Tyr Arg Gly His Phe Leu Ile Glu Gly Lys Leu Ser Thr
                165                 170                 175

Glu Asn Ile Ser Val Lys Glu Gln Phe Gln Gln Phe Met Ile Ile Tyr
            180                 185                 190

Asn Gln Thr Phe Val Asn Gly Glu Ser Arg Leu Val Ser Ala Pro Leu
        195                 200                 205

Pro Glu Ser Val Leu Ile Glu Glu Leu Thr Glu Lys Ala Ser Arg
    210                 215                 220

Thr Lys Lys Ser Glu Lys Val Leu Gln Gln Phe Pro Gln Glu Lys Ala
225                 230                 235                 240

Asn Gly Leu Phe Gly Gln Phe Leu Lys Leu Met Val Gly Asn Lys Ala
                245                 250                 255

Asp Phe Lys Lys Val Phe Gly Leu Glu Glu Glu Ala Lys Ile Thr Tyr

```
                260                 265                 270
Ala Ser Glu Ser Tyr Glu Glu Asp Leu Glu Gly Ile Leu Ala Lys Val
            275                 280                 285

Gly Asp Glu Tyr Ser Asp Val Phe Leu Ala Ala Lys Asn Val Tyr Asp
290                 295                 300

Ala Val Glu Leu Ser Thr Ile Leu Ala Asp Ser Asp Lys Lys Ser His
305                 310                 315                 320

Ala Lys Leu Ser Ser Ser Met Ile Val Arg Phe Thr Glu His Gln Glu
            325                 330                 335

Asp Leu Lys Lys Phe Lys Arg Phe Ile Arg Glu Asn Cys Pro Asp Glu
            340                 345                 350

Tyr Asp Asn Leu Phe Lys Asn Glu Gln Lys Asp Gly Tyr Ala Gly Tyr
            355                 360                 365

Ile Ala His Ala Gly Lys Val Ser Gln Leu Lys Phe Tyr Gln Tyr Val
            370                 375                 380

Lys Lys Ile Ile Gln Asp Ile Ala Gly Ala Glu Tyr Phe Leu Glu Lys
385                 390                 395                 400

Ile Ala Gln Glu Asn Phe Leu Arg Lys Gln Arg Thr Phe Asp Asn Gly
                405                 410                 415

Val Ile Pro His Gln Ile His Leu Ala Glu Leu Gln Ala Ile Ile His
            420                 425                 430

Arg Gln Ala Ala Tyr Tyr Pro Phe Leu Lys Glu Asn Gln Glu Lys Ile
            435                 440                 445

Glu Gln Leu Val Thr Phe Arg Ile Pro Tyr Tyr Val Gly Pro Leu Ser
450                 455                 460

Lys Gly Asp Ala Ser Thr Phe Ala Trp Leu Lys Arg Gln Ser Glu Glu
465                 470                 475                 480

Pro Ile Arg Pro Trp Asn Leu Gln Glu Thr Val Asp Leu Asp Gln Ser
                485                 490                 495

Ala Thr Ala Phe Ile Glu Arg Met Thr Asn Phe Asp Thr Tyr Leu Pro
            500                 505                 510

Ser Glu Lys Val Leu Pro Lys His Ser Leu Leu Tyr Glu Lys Phe Met
            515                 520                 525

Val Phe Asn Glu Leu Thr Lys Ile Ser Tyr Thr Asp Arg Gly Ile
530                 535                 540

Lys Ala Asn Phe Ser Gly Lys Glu Lys Ile Phe Asp Tyr Leu
545                 550                 555                 560

Phe Lys Thr Arg Arg Lys Val Lys Lys Asp Ile Ile Gln Phe Tyr
                565                 570                 575

Arg Asn Glu Tyr Asn Thr Glu Ile Val Thr Leu Ser Gly Leu Glu Glu
            580                 585                 590

Asp Gln Phe Asn Ala Ser Phe Ser Thr Tyr Gln Asp Leu Leu Lys Cys
            595                 600                 605

Gly Leu Thr Arg Ala Glu Leu Asp His Pro Asp Asn Ala Glu Lys Leu
610                 615                 620

Glu Asp Ile Ile Lys Ile Leu Thr Ile Phe Glu Asp Arg Gln Arg Ile
625                 630                 635                 640

Arg Thr Gln Leu Ser Thr Phe Lys Gly Gln Phe Ser Ala Glu Val Leu
                645                 650                 655

Lys Lys Leu Glu Arg Lys His Tyr Thr Gly Trp Gly Arg Leu Ser Lys
            660                 665                 670

Lys Leu Ile Asn Gly Ile Tyr Asp Lys Glu Ser Gly Lys Thr Ile Leu
            675                 680                 685
```

-continued

Asp Tyr Leu Ile Lys Asp Asp Gly Val Ser Lys His Tyr Asn Arg Asn
690                 695                 700

Phe Met Gln Leu Ile Asn Asp Ser Gln Leu Ser Phe Lys Asn Ala Ile
705                 710                 715                 720

Gln Lys Ala Gln Ser Ser Glu His Glu Glu Thr Leu Ser Glu Thr Val
            725                 730                 735

Asn Glu Leu Ala Gly Ser Pro Ala Ile Lys Lys Gly Ile Tyr Gln Ser
                740                 745                 750

Leu Lys Ile Val Asp Glu Leu Val Ala Ile Met Gly Tyr Ala Pro Lys
            755                 760                 765

Arg Ile Val Val Glu Met Ala Arg Glu Asn Gln Thr Thr Ser Thr Gly
770                 775                 780

Lys Arg Arg Ser Ile Gln Arg Leu Lys Ile Val Glu Lys Ala Met Ala
785                 790                 795                 800

Glu Ile Gly Ser Asn Leu Leu Lys Glu Gln Pro Thr Thr Asn Glu Gln
            805                 810                 815

Leu Arg Asp Thr Arg Leu Phe Leu Tyr Tyr Met Gln Asn Gly Lys Asp
            820                 825                 830

Met Tyr Thr Gly Asp Glu Leu Ser Leu His Arg Leu Ser His Tyr Asp
            835                 840                 845

Ile Asp His Ile Ile Pro Gln Ser Phe Met Lys Asp Asp Ser Leu Asp
850                 855                 860

Asn Leu Val Leu Val Gly Ser Thr Glu Asn Arg Gly Lys Ser Asp Asp
865                 870                 875                 880

Val Pro Ser Lys Glu Val Val Lys Asp Met Lys Ala Tyr Trp Glu Lys
                885                 890                 895

Leu Tyr Ala Ala Gly Leu Ile Ser Gln Arg Lys Phe Gln Arg Leu Thr
            900                 905                 910

Lys Gly Glu Gln Gly Gly Leu Thr Leu Glu Asp Lys Ala His Phe Ile
            915                 920                 925

Gln Arg Gln Leu Val Glu Thr Arg Gln Ile Thr Lys Asn Val Ala Gly
            930                 935                 940

Ile Leu Asp Gln Arg Tyr Asn Ala Asn Ser Lys Glu Lys Lys Val Gln
945                 950                 955                 960

Ile Ile Thr Leu Lys Ala Ser Leu Thr Ser Gln Phe Arg Ser Ile Phe
            965                 970                 975

Gly Leu Tyr Lys Val Arg Glu Val Asn Asp Tyr His His Gly Gln Asp
            980                 985                 990

Ala Tyr Leu Asn Cys Val Val Ala Thr Thr Leu Leu Lys Val Tyr Pro
            995                 1000                1005

Asn Leu Ala Pro Glu Phe Val Tyr Gly Glu Tyr Pro Lys Phe Gln
    1010                1015                1020

Ala Phe Lys Glu Asn Lys Ala Thr Ala Lys Thr Ile Ile Tyr Thr
    1025                1030                1035

Asn Leu Met Arg Phe Phe Thr Glu Asp Glu Pro Arg Phe Met Lys
    1040                1045                1050

Asp Gly Glu Ile Leu Trp Ser Asn Ser Tyr Leu Lys Asn Ile Lys
    1055                1060                1065

Lys Glu Leu Asn Tyr His Gln Met Asn Ile Val Lys Lys Val Glu
    1070                1075                1080

Val Gln Lys Gly Gly Phe Ser Lys Glu Ser Ile Lys Pro Lys Gly
    1085                1090                1095

| | | | | | | | | | | |
|---|---|---|---|---|---|---|---|---|---|---|
| Pro | Ser | Asn | Lys | Leu | Ile | Pro | Val | Lys | Asn | Gly | Leu | Asp | Pro | Gln |
| | 1100 | | | | 1105 | | | | 1110 | |
| Lys | Tyr | Gly | Gly | Phe | Asp | Ser | Pro | Val | Val | Ala | Tyr | Thr | Val | Leu |
| | 1115 | | | | 1120 | | | | 1125 | |
| Phe | Thr | His | Glu | Lys | Gly | Lys | Lys | Pro | Leu | Ile | Lys | Gln | Glu | Ile |
| | 1130 | | | | 1135 | | | | 1140 | |
| Leu | Gly | Ile | Thr | Ile | Met | Glu | Lys | Thr | Arg | Phe | Glu | Gln | Asn | Pro |
| | 1145 | | | | 1150 | | | | 1155 | |
| Ile | Leu | Phe | Leu | Glu | Glu | Lys | Gly | Phe | Leu | Arg | Pro | Arg | Val | Leu |
| | 1160 | | | | 1165 | | | | 1170 | |
| Met | Lys | Leu | Pro | Lys | Tyr | Thr | Leu | Tyr | Glu | Phe | Pro | Glu | Gly | Arg |
| | 1175 | | | | 1180 | | | | 1185 | |
| Arg | Arg | Leu | Leu | Ala | Ser | Ala | Lys | Glu | Ala | Gln | Lys | Gly | Asn | Gln |
| | 1190 | | | | 1195 | | | | 1200 | |
| Met | Val | Leu | Pro | Glu | His | Leu | Leu | Thr | Leu | Leu | Tyr | His | Ala | Lys |
| | 1205 | | | | 1210 | | | | 1215 | |
| Gln | Cys | Leu | Leu | Pro | Asn | Gln | Ser | Glu | Ser | Leu | Ala | Tyr | Val | Glu |
| | 1220 | | | | 1225 | | | | 1230 | |
| Gln | His | Gln | Pro | Glu | Phe | Gln | Glu | Ile | Leu | Glu | Arg | Val | Val | Asp |
| | 1235 | | | | 1240 | | | | 1245 | |
| Phe | Ala | Glu | Val | His | Thr | Leu | Ala | Lys | Ser | Lys | Val | Gln | Gln | Ile |
| | 1250 | | | | 1255 | | | | 1260 | |
| Val | Lys | Leu | Phe | Glu | Ala | Asn | Gln | Thr | Ala | Asp | Val | Lys | Glu | Ile |
| | 1265 | | | | 1270 | | | | 1275 | |
| Ala | Ala | Ser | Phe | Ile | Gln | Leu | Met | Gln | Phe | Asn | Ala | Met | Gly | Ala |
| | 1280 | | | | 1285 | | | | 1290 | |
| Pro | Ser | Thr | Phe | Lys | Phe | Phe | Gln | Lys | Asp | Ile | Glu | Arg | Ala | Arg |
| | 1295 | | | | 1300 | | | | 1305 | |
| Tyr | Thr | Ser | Ile | Lys | Glu | Ile | Phe | Asp | Ala | Thr | Ile | Ile | Tyr | Gln |
| | 1310 | | | | 1315 | | | | 1320 | |
| Ser | Thr | Thr | Gly | Leu | Tyr | Glu | Thr | Arg | Arg | Lys | Val | Val | Asp |
| | 1325 | | | | 1330 | | | | 1335 | |

```
<210> SEQ ID NO 37
<211> LENGTH: 16
<212> TYPE: RNA
<213> ORGANISM: Enterococcus sp.
<220> FEATURE:
<221> NAME/KEY: source
<223> OTHER INFORMATION: /note="crRNA"

<400> SEQUENCE: 37
guuuuagagu cauguu                                                       16

<210> SEQ ID NO 38
<211> LENGTH: 74
<212> TYPE: RNA
<213> ORGANISM: Enterococcus sp.
<220> FEATURE:
<221> NAME/KEY: source
<223> OTHER INFORMATION: /note="tracrRNA"

<400> SEQUENCE: 38
aacauagcaa guuaaaauaa gguuuuaacc guaaucaacu guaaaguggc gcuguuucgg       60
cgcuuuuuuu guuu                                                         74

<210> SEQ ID NO 39
<211> LENGTH: 124
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L1"

<400> SEQUENCE: 39
gagcggacag cagcuuccua uaucucguac guuuuagagu cauguuaaag aacauagcaa      60
guuaaaauaa gguuuuaacc guaaucaacu guaaaguggc gcuguuucgg cgcuuuuuuu    120
guuu                                                                 124

<210> SEQ ID NO 40
<211> LENGTH: 124
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L2"

<400> SEQUENCE: 40
ccaugauaua gacguugugg cuguuguagu guuuuagagu cauguuaaag aacauagcaa      60
guuaaaauaa gguuuuaacc guaaucaacu guaaaguggc gcuguuucgg cgcuuuuuuu    120
guuu                                                                 124

<210> SEQ ID NO 41
<211> LENGTH: 3
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="PAM"
<220> FEATURE:
<221> NAME/KEY: modified_base
<222> LOCATION: (1)..(1)
<223> OTHER INFORMATION: a, c, t, g, unknown or other

<400> SEQUENCE: 41 ngg                                                                    3

<210> SEQ ID NO 42
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 1"
<220> FEATURE:
<221> NAME/KEY: modified_base
<222> LOCATION: (31)..(38)
<223> OTHER INFORMATION: a, c, t, g, unknown or other

<400> SEQUENCE: 42
```
gagcggacag cagcttccta tatctcgtac nnnnnnnn                                        38

<210> SEQ ID NO 43
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 2"
<220> FEATURE:
<221> NAME/KEY: modified_base
<222> LOCATION: (31)..(38)
<223> OTHER INFORMATION: a, c, t, g, unknown or other

<400> SEQUENCE: 43
ccatgatata gacgttgtgg ctgttgtagt nnnnnnnn                                        38

<210> SEQ ID NO 44
<211> LENGTH: 119
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA with N's"
<220> FEATURE:
<221> NAME/KEY: modified_base
<222> LOCATION: (1)..(25)
<223> OTHER INFORMATION: a, c, u, g, unknown or other

<400> SEQUENCE: 44
nnnnnnnnnn nnnnnnnnnn nnnnnguuuu agagucaugu uaaagaacau agcaaguuaa              60
aauaagguuu uaaccguaau caacuguaaa guggcgcugu uucggcgcuu uuuuguuu               119

<210> SEQ ID NO 45
<211> LENGTH: 1436
<212> TYPE: PRT
<213> ORGANISM: Enterococcus sp.
<220> FEATURE:
<221> NAME/KEY: source
<223> OTHER INFORMATION: /note="APG04583.1"

<400> SEQUENCE: 45

Met Ala Lys Asn Ile Leu Gly Leu Asp Leu Gly Thr Asn Ser Ile Gly
1               5                   10                  15

Trp Ala Leu Val Gln Gln Asp Phe Glu Asn Lys Glu Gly Asn Ile Leu
            20                  25                  30

Gly Met Gly Ser Arg Ile Ile Pro Met Ser Gln Asp Ile Leu Gly Glu
        35                  40                  45

Phe Gly Lys Gly Asn Ser Ile Ser Gln Thr Ala Glu Arg Thr Gly Tyr
    50                  55                  60

Arg Gly Val Arg Arg Leu Arg Glu Arg His Leu Leu Arg Arg Glu Arg
65                  70                  75                  80

Leu His Arg Val Leu His Leu Leu Gly Phe Leu Pro Lys His Tyr Asp
                85                  90                  95

Glu Lys Ile Asp Phe Thr Gln Arg Phe Gly Lys Phe Ile Asn Gln Ala
            100                 105                 110

```
Glu Pro Lys Leu Ala Phe Asp Ser Glu Phe Leu Phe Lys Asp Ser Phe
        115                 120                 125

His Glu Met Leu Ala Asp Phe Lys Gln Asn Gln Pro Glu Phe Leu Lys
    130                 135                 140

Asp Lys Asn Gly Glu Asp Cys Leu Val Pro Tyr Asp Trp Thr Ile Tyr
145                 150                 155                 160

Tyr Leu Arg Lys Lys Ala Leu Thr Gln Lys Ile Glu Lys Tyr Glu Leu
            165                 170                 175

Ala Trp Leu Ile Leu Asn Phe Asn Gln Lys Arg Gly Tyr Tyr Gln Leu
        180                 185                 190

Arg Gly Glu Glu Glu Lys Glu Asn Pro Asn Lys Leu Val Gly Phe His
        195                 200                 205

Ser Leu Lys Ile Val Asp Val Ile Pro Asp Ala Glu Thr Asn Lys Lys
    210                 215                 220

Gly Glu Thr Trp Tyr Ser Leu His Leu Glu Asn Gly Trp Val Tyr Arg
225                 230                 235                 240

Arg Ser Ser Lys Ile Ser Leu Ala Asp Trp Lys Asp Lys Val Arg Asp
            245                 250                 255

Phe Ile Val Thr Thr Asp Leu Asn Asp Asp Gly Ser Glu Lys Leu Asp
        260                 265                 270

Lys Asp Gly Ile Val Lys Arg Ser Phe Arg Ala Pro Ser Ala Asp Asp
    275                 280                 285

Trp Thr Leu Leu Lys Lys Lys Thr Glu Lys Asp Ile Asp Asn Ser Asn
290                 295                 300

Lys Thr Val Gly Thr Tyr Ile Tyr Asp Asn Leu Leu Asn Pro Lys
305                 310                 315                 320

Gln Lys Ile Lys Gly Lys Met Val Arg Thr Ile Glu Arg Lys Phe Tyr
            325                 330                 335

Lys Gln Glu Leu Glu Gln Ile Leu Lys Thr Gln Lys Glu Phe His Ser
        340                 345                 350

Glu Leu Gln Ser Glu Asn Leu Leu Gln Asp Cys Val Arg Glu Leu Tyr
    355                 360                 365

Arg Asn Asn Glu Gln His Gln Gln Met Leu Glu Ala Lys Asp Phe Val
370                 375                 380

His Leu Phe Leu Asn Asp Ile Ile Phe Tyr Gln Arg Pro Leu Arg Ser
385                 390                 395                 400

Gln Lys Ser Ser Ile Ser Asn Cys Thr Leu Glu Phe Arg Lys Ser Lys
            405                 410                 415

Asn Glu Asn Gly Glu Glu Val Ile His Arg Leu Lys Val Ile Ala Lys
        420                 425                 430

Ser Asn Pro Tyr Tyr Gln Glu Phe Arg Leu Leu Gln Trp Val Gln Asn
    435                 440                 445

Leu Ala Ile Tyr Thr Lys Asp Asp Lys Asn Val Thr Asn Glu Phe
450                 455                 460

Leu Lys Ser Thr Gln Asp Trp Glu Asp Leu Leu Arg Trp Leu His Ser
465                 470                 475                 480

Lys Lys Glu Ile Lys Gln Asp Ala Leu Ile Lys Phe Leu Ile Glu Lys
            485                 490                 495

Lys Gly Leu Lys Gly Lys Ala Leu Thr Ile Glu Val Ala Lys Tyr Arg
        500                 505                 510

Trp Asn Tyr Val Gln Asp Lys Asp Tyr Pro Gly Asn Glu Thr Arg Tyr
    515                 520                 525
```

-continued

```
Leu Ile Gln Ser Arg Leu Asp Lys Val Glu Tyr Ala Pro Lys Asp Phe
        530                 535                 540

Leu Thr Tyr Glu Asn Glu Met Ala Leu Trp His Ile Ile Tyr Ser Ile
545                 550                 555                 560

Asn Asp Lys Ile Glu Tyr Glu Lys Ala Leu Lys Ser Phe Ala Asn Lys
                565                 570                 575

Lys Gly Leu Asp Glu Val Thr Phe Val Glu Ala Phe Lys Lys Phe Pro
                580                 585                 590

Pro Phe Lys Ser Asp Tyr Gly Ser Phe Ser Glu Lys Ala Ile Lys Lys
            595                 600                 605

Leu Leu Pro Leu Met Arg Phe Gly Thr Gln Trp Asn Trp Asp Asn Ile
610                 615                 620

Asp Gln Asn Ser Lys Glu Arg Ile Gly Lys Ile Leu Thr Gly Glu Tyr
625                 630                 635                 640

Asp Glu Asn Ile Lys Gly Arg Val Arg Glu Lys Ala Arg His Leu Asn
                645                 650                 655

Ser Glu Thr Asp Phe Gln Ala Leu Pro Leu Trp Leu Ala Gln Tyr Val
                660                 665                 670

Val Tyr Gly Arg His Ser Glu Ala Asp Ile Ala Gly Lys Trp Asn Ser
            675                 680                 685

Val Asp Asp Leu Lys Gln Phe Leu Asp Phe Lys Gln His Ser Leu
690                 695                 700

Arg Asn Pro Ile Val Glu Gln Val Ile Thr Glu Thr Leu Arg Ala Val
705                 710                 715                 720

Lys Asp Ile Trp Asn Phe Tyr Gly Lys Gly Ala Lys Asp Phe Phe Ser
                725                 730                 735

Glu Ile His Ile Glu Leu Gly Arg Glu Met Lys Asn Thr Ala Asp Glu
                740                 745                 750

Arg Lys Arg Ile Thr Thr Met Val Thr Asp Asn Glu Asn Thr Asn Leu
            755                 760                 765

Arg Ile Lys Ala Leu Leu Ala Glu Met Ala Leu Asp Gln Asn Val Asp
770                 775                 780

Asn Val Arg Pro Tyr Ser Pro Met Gln Gln Glu Ile Leu Lys Ile Tyr
785                 790                 795                 800

Glu Glu Gly Val Leu Asn Ala Glu Glu Asn Ile Asp Asp Ile Leu
                805                 810                 815

Lys Ile Ser Lys Thr Ala Gln Pro Ser Ala Thr Asp Leu Lys Arg Tyr
                820                 825                 830

Lys Leu Trp Leu Glu Gln Lys Tyr Arg Ser Pro Tyr Thr Gly Gln Met
            835                 840                 845

Ile Pro Leu Asn Lys Leu Phe Thr Pro Glu Tyr Glu Ile Glu His Ile
850                 855                 860

Ile Pro Gln Ser Arg Tyr Phe Asp Asp Ser Met Ser Asn Lys Val Ile
865                 870                 875                 880

Cys Glu Ala Ala Val Asn Lys Leu Lys Asp Asn Gln Ile Gly Leu Val
                885                 890                 895

Phe Ile Lys Asn His His Gly Glu Val Val Asp Phe Gly Met Gly Lys
                900                 905                 910

Gln Val Lys Ile Leu Glu Val Ser Asp Tyr Glu Asp Phe Val Lys Gln
            915                 920                 925

Asn Tyr Asn Lys Asn Arg Gly Lys Arg Asn Lys Leu Leu Leu Glu Asp
930                 935                 940

Ile Pro Glu Lys Met Ile Glu Arg Gln Leu Asn Asp Thr Arg Tyr Ile
```

-continued

```
945                 950                 955                 960
Ser Lys Tyr Ile Thr Gln Val Leu Ser Asn Ile Val Arg Asp Asp Lys
                965                 970                 975
Glu Gly Ser Lys Asp Asp Gly Val Asn Ser Lys Asn Ile Val Pro Gly
                980                 985                 990
Asn Gly Lys Ile Thr Thr Arg Leu Lys Gln Asp Trp Gly Leu Asn Asp
        995                 1000                1005
Val Trp Asn Asp Leu Val Leu Pro Arg Phe Glu Arg Met Asn Thr
    1010                1015                1020
Leu Thr Asn Ser Asn Asp Phe Thr Ser Lys Asn Thr His Gly Lys
    1025                1030                1035
Thr Ile Pro Thr Val Pro Ile Glu Leu Ser Lys Gly Phe Ser Lys
    1040                1045                1050
Lys Arg Ile Asp His Arg His Ala Met Asp Ala Leu Val Ile
    1055                1060                1065
Ala Cys Ala Thr Arg Asp His Val Asn Leu Leu Asn Asn Glu Ser
    1070                1075                1080
Ser Lys Ser Asp Thr Lys Arg Tyr Asp Leu Asn Arg Lys Leu Arg
    1085                1090                1095
Lys Tyr Glu Lys Val Ala Tyr Asn Asp Pro Lys Thr Gly Glu Arg
    1100                1105                1110
Ile Glu Lys Glu Val Pro Lys Asp Phe Ile Lys Pro Trp Glu Thr
    1115                1120                1125
Phe Thr Glu Asp Thr Arg Thr Leu Leu Glu Asn Ile Val Ile Ser
    1130                1135                1140
Phe Lys Gln Asn Leu Arg Val Ile Asn Lys Ala Thr Asn Tyr Tyr
    1145                1150                1155
Glu Lys Ile Glu Asn Gly Lys Lys Val Lys Val Glu Gln Lys Gly
    1160                1165                1170
Ile Asn Trp Ala Val Arg Lys Ala Leu His Lys Glu Thr Val Ser
    1175                1180                1185
Gly Gln Val His Leu Asp Arg Ile Lys Val Ala Lys Gly Lys Ile
    1190                1195                1200
Leu Thr Ala Thr Arg Lys Thr Leu Asp Ala Ser Phe Asn Glu Lys
    1205                1210                1215
Thr Ile Glu Ser Ile Thr Asp Thr Gly Ile Gln Lys Ile Leu Leu
    1220                1225                1230
Asn Tyr Leu Lys Ser Lys Asp Asn Asn Pro Glu Val Ala Phe Ser
    1235                1240                1245
Pro Glu Gly Ile Glu Glu Leu Asn Lys Asn Ile Arg Leu Tyr Asn
    1250                1255                1260
Asp Gly Lys Ala His Gln Pro Ile Leu Lys Val Arg Val Phe Glu
    1265                1270                1275
Gln Gly Ser Lys Phe Thr Leu Gly Glu Thr Gly Asn Lys Thr Thr
    1280                1285                1290
Lys Phe Val Glu Ala Ala Lys Gly Thr Asn Leu Phe Phe Gly Ile
    1295                1300                1305
Tyr Glu Asp Lys Ser Gly Lys Arg Ser Tyr Glu Thr Ile Pro Leu
    1310                1315                1320
Asn Ile Val Ile Glu Arg Gln Lys Gln Gly Leu Gln Ala Val Pro
    1325                1330                1335
Glu Thr Asn Glu Lys Gly Lys Gln Leu Leu Phe Thr Leu Ser Pro
    1340                1345                1350
```

```
Asn Asp Leu Val Tyr Val Pro Glu Glu Gly Val Phe Asp Glu Asn
    1355            1360                1365

Asn Ile Lys Val Asp Arg Ile Tyr Lys Val Val Ser Phe Ser Thr
    1370            1375                1380

Tyr Gln Cys Phe Phe Val Arg Asn Asp Val Ser Thr Ser Val Val
    1385            1390                1395

Asn Lys Val Glu Tyr Ser Ala Leu Asn Lys Met Glu Lys Ser Ile
    1400            1405                1410

Asp Asn Ile Met Ile Lys Glu Asn Cys Val Lys Leu Asn Val Asp
    1415            1420                1425

Arg Leu Gly Lys Ile Ser Lys Ala
    1430            1435

<210> SEQ ID NO 46
<211> LENGTH: 16
<212> TYPE: RNA
<213> ORGANISM: Enterococcus sp.
<220> FEATURE:
<221> NAME/KEY: source
<223> OTHER INFORMATION: /note="crRNA"

<400> SEQUENCE: 46
guugugaguu ccuuuc                                                      16

<210> SEQ ID NO 47
<211> LENGTH: 78
<212> TYPE: RNA
<213> ORGANISM: Enterococcus sp.
<220> FEATURE:
<221> NAME/KEY: source
<223> OTHER INFORMATION: /note="tracrRNA"

<400> SEQUENCE: 47
gaaaggaacu cacaauaagg auuauuccgu ugugaaaaca uuuagcgccu cgacuaucuu      60
cggggcuuuu uuauuuuu                                                    78

<210> SEQ ID NO 48
<211> LENGTH: 128
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L1"

<400> SEQUENCE: 48
gagcggacag cagcuuccua uaucucguac guugugaguu ccuuucacuu gaaaggaacu      60
cacaauaagg auuauuccgu ugugaaaaca uuuagcgccu cgacuaucuu cggggcuuuu    120
uuauuuuu                                                             128

<210> SEQ ID NO 49
<211> LENGTH: 128
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
```

<223> OTHER INFORMATION: /note="sgRNA L2"

<400> SEQUENCE: 49
ccaugauaua dacguugugg cuguuguagu guugugaguu ccuuucacuu gaaaggaacu    60
cacaauaagg auuauuccgu ugugaaaaca uuuagcgccu cgacuaucuu cggggcuuuu   120
uuauuuuu                                                           128

<210> SEQ ID NO 50
<211> LENGTH: 7
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="PAM"
<220> FEATURE:
<221> NAME/KEY: modified_base
<222> LOCATION: (1)..(2)
<223> OTHER INFORMATION: a, c, t, g, unknown or other

<400> SEQUENCE: 50 nnraaty                                                              7

<210> SEQ ID NO 51
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 1"
<220> FEATURE:
<221> NAME/KEY: modified_base
<222> LOCATION: (31)..(38)
<223> OTHER INFORMATION: a, c, t, g, unknown or other

<400> SEQUENCE: 51
gagcggacag cagcttccta tatctcgtac nnnnnnnn                            38

<210> SEQ ID NO 52
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 2"
<220> FEATURE:
<221> NAME/KEY: modified_base
<222> LOCATION: (31)..(38)
<223> OTHER INFORMATION: a, c, t, g, unknown or other

<400> SEQUENCE: 52
ccatgatata gacgttgtgg ctgttgtagt nnnnnnnn                            38

<210> SEQ ID NO 53
<211> LENGTH: 123
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA with N's"
<220> FEATURE:
<221> NAME/KEY: modified_base
<222> LOCATION: (1)..(25)
<223> OTHER INFORMATION: a, c, u, g, unknown or other

<400> SEQUENCE: 53
nnnnnnnnnn nnnnnnnnnn nnnnnguugu gaguuccuuu caaaggaaag gaacucacaa      60
uaaggauuau uccguuguga aaacauuuag cgccucgacu aucuucgggg cuuuuuauu     120 uuu                                                                   123

<210> SEQ ID NO 54
<211> LENGTH: 1456
<212> TYPE: PRT
<213> ORGANISM: Empedobacter sp.
<220> FEATURE:
<221> NAME/KEY: source
<223> OTHER INFORMATION: /note="APG01688.1"

<400> SEQUENCE: 54
```

Met Met Ile Lys Asn Ile Leu Gly Leu Asp Leu Gly Thr Asn Ser Ile
1               5                   10                  15

Gly Trp Ala Leu Ile Lys Gln Asp Phe Glu Asn Lys His Gly Glu Ile
            20                  25                  30

Leu Gly Met Gly Ser Arg Ile Ile Pro Met Ser Gln Asp Ile Leu Gly
        35                  40                  45

Asp Phe Gly Lys Gly Asn Ser Ile Ser Gln Thr Ala Asp Arg Thr Lys
    50                  55                  60

Tyr Arg Ser Val Arg Arg Leu Arg Glu Arg Phe Leu Leu Arg Arg Glu
65                  70                  75                  80

Arg Leu His Arg Val Leu His Leu Leu Asn Phe Leu Pro Gln His Tyr
                85                  90                  95

Ala Ser Gln Ile Asp Phe Glu Lys Lys Phe Gly Lys Phe Lys Ser Glu
            100                 105                 110

Thr Glu Pro Lys Leu Ala Trp Glu Asn Trp Gly Gly Lys Phe Ser Phe
        115                 120                 125

Leu Phe Gln Asn Ser Phe Asn Glu Met Leu Gly Asp Phe Lys Ala Ala
    130                 135                 140

Gly Gln Gly Leu Lys Ile Pro Tyr Asp Trp Thr Ile Tyr Tyr Leu Arg
145                 150                 155                 160

Lys Lys Ala Leu Ser Gln Lys Ile Glu Lys Glu Leu Ala Trp Ile
                165                 170                 175

Leu Leu Asn Phe Asn Gln Lys Arg Gly Tyr Tyr Gln Leu Arg Gly Glu
            180                 185                 190

Glu Glu Glu Glu Asn Pro Asn Lys Leu Val Glu Phe Tyr Ser Leu Lys
        195                 200                 205

Ile Val Asp Val Val Ala Asp Glu Pro Gln Lys Gly Lys Ser Asp Ile
    210                 215                 220

Trp Tyr Ser Leu Ile Leu Glu Asn Gly Trp Val Tyr Arg Arg Ala Ser
225                 230                 235                 240

Lys Ile Pro Leu Phe Asp Trp Lys Asp Lys Thr Arg Asp Phe Ile Val
                245                 250                 255

```
Thr Thr Asp Leu Asn Asp Asp Arg Ser Val Lys Thr Asp Lys Glu Gly
        260                 265                 270

Asn Glu Lys Arg Ser Phe Arg Ala Pro Ser Glu Asn Asp Trp Thr Leu
        275                 280                 285

Val Lys Lys Lys Thr Glu Gln Glu Ile Asp Gln Ser His Lys Thr Val
290                 295                 300

Gly Thr Tyr Ile Tyr Glu Thr Leu Leu Leu Asn Pro Lys Gln Lys Ile
305                 310                 315                 320

Lys Gly Lys Leu Val Arg Thr Ile Glu Arg Lys Phe Tyr Lys Asp Glu
                325                 330                 335

Leu Lys Gln Ile Leu Glu Lys Gln Lys Glu Phe His Gln Glu Leu Lys
                340                 345                 350

Asn Asp Asp Leu Tyr Asn Asp Cys Ile Arg Glu Leu Tyr Arg Asn Asn
                355                 360                 365

Glu Ala His Gln Leu Thr Leu Ser Lys Lys Asp Phe Val His Leu Leu
        370                 375                 380

Met Asp Asp Leu Ile Phe Tyr Gln Arg Pro Leu Arg Ser Gln Lys Ser
385                 390                 395                 400

Ser Ile Ser Asn Cys Thr Leu Glu Phe Arg Lys Tyr Lys Asp Glu Asn
                405                 410                 415

Gly Ile Glu His Thr Gln Tyr Leu Lys Ala Ile Pro Lys Ser Asn Pro
            420                 425                 430

Tyr Tyr Gln Glu Phe Arg Leu Trp Gln Trp Met Tyr Asn Leu Asn Ile
            435                 440                 445

Tyr Arg Lys Asp Asp Glu Ala Asn Val Thr Lys Glu Phe Leu Asn Thr
        450                 455                 460

Asn Lys Asp Phe Glu Ser Leu Phe Glu Phe Leu Asn Asn Arg Lys Glu
465                 470                 475                 480

Ile Glu Gln Lys Pro Leu Ile Lys Phe Leu Glu Gln Lys Asp Ile
                485                 490                 495

Asn Lys Lys Leu Leu Asn Ala Glu Ala Glu Lys Tyr Arg Trp Asn Tyr
                500                 505                 510

Val Glu Asp Lys Lys Tyr Pro Cys Asn Glu Thr Lys Thr Met Ile Ser
        515                 520                 525

Ser Arg Leu Asp Lys Val Glu Asn Ile Ser Asp Asp Phe Leu Thr Arg
        530                 535                 540

Asp Ile Glu Gln Lys Ile Trp His Ile Ile Tyr Ser Val Asn Asp Lys
545                 550                 555                 560

Ile Glu Tyr Glu Lys Ala Leu Lys Ser Phe Ala Thr Arg Asn Asp Leu
                565                 570                 575

Asp Glu Asn Ser Phe Ile Glu Ala Phe Lys Lys Phe Ser Pro Phe Lys
            580                 585                 590

Ser Glu Tyr Gly Ser Phe Ser Glu Lys Ala Ile Lys Lys Leu Leu Pro
            595                 600                 605

Leu Met Arg Leu Gly Lys Tyr Trp Tyr Glu Asp Glu Ile Val Lys His
        610                 615                 620

Ser Asp Ile Tyr Phe Lys Asn Ile Glu Asn Leu Leu Gly Asp Phe Ser
625                 630                 635                 640

Asn Arg Asp Lys Lys Ile Ser Glu Glu Asp Lys Glu Lys Trp Asn Lys
                645                 650                 655

Ser Ile Asn Leu Lys Leu Gln Glu Glu Leu Lys Asp Phe Gln Thr Ala
            660                 665                 670
```

```
Glu Ile Asp Leu Phe Gln Gly Leu Arg Leu His Ile Ala Gln Tyr Leu
        675                 680                 685

Val Tyr Gly Arg His Ser Glu Ala Ser Met Ile Gly Lys Trp Asn Ser
    690                 695                 700

Ala Glu Asp Leu Glu Glu Phe Leu Lys Asp Phe Lys Gln His Ser Leu
705                 710                 715                 720

Arg Asn Pro Ile Val Glu Gln Val Ile Thr Glu Thr Leu Arg Val Val
                725                 730                 735

Lys Asp Ile Trp Leu Lys Tyr Gly Asn Gly Ala Lys Asp Phe Phe Asn
            740                 745                 750

Glu Ile His Ile Glu Leu Gly Arg Glu Met Lys Leu Pro Ala Asp Asp
        755                 760                 765

Arg Lys Lys Leu Thr Asn Gln Ile Ser Glu Asn Glu Asn Thr Asn Phe
    770                 775                 780

Arg Ile Lys Ala Leu Leu Ala Glu Met Met Asn Asp Ser Ser Val Glu
785                 790                 795                 800

Asn Val Arg Pro Phe Ser Pro Met Gln Gln Glu Ile Leu Lys Ile Tyr
                805                 810                 815

Glu Asp Asp Val Leu Lys Ser Asp Ile Glu Ile Glu Asp Asp Ile Leu
            820                 825                 830

Lys Ile Ser Lys Thr Ala Gln Pro Ser Pro Ser Asp Leu Lys Arg Tyr
        835                 840                 845

Lys Leu Trp Leu Glu Gln Lys Tyr Lys Ser Pro Tyr Thr Gly Gln Ile
    850                 855                 860

Ile Pro Leu Asn Lys Leu Phe Thr Pro Glu Tyr Glu Ile Glu His Ile
865                 870                 875                 880

Ile Pro Gln Ser Arg Tyr Phe Asp Asp Ser Phe Ser Asn Lys Val Ile
                885                 890                 895

Cys Glu Ser Ala Val Asn Lys Leu Lys Asp Asn Tyr Ile Gly Leu Glu
            900                 905                 910

Phe Ile Lys Gln Phe Gly Gly Thr Ile Ile Glu Leu Gly Phe Gly Lys
        915                 920                 925

Ser Ile Lys Val Phe Glu Thr Lys Glu Tyr Glu Asp Phe Val Lys Lys
    930                 935                 940

His Tyr Ala Asn Asn Gln Gly Lys Arg Asn Lys Leu Leu Met Glu Asp
945                 950                 955                 960

Ile Pro Glu Lys Met Ile Glu Arg Gln Met Asn Asp Thr Arg Tyr Ile
                965                 970                 975

Ser Lys Tyr Ile Ser Gly Val Leu Ser Asn Ile Val Arg Val Glu Asp
            980                 985                 990

Gly Ser Asp Glu Gly Val Asn Ser Lys Asn Ile Val Pro Gly Asn Gly
        995                 1000                1005

Lys Ile Thr Thr Gln Leu Lys Gln Asp Trp Gly Leu Asn Asp Val
        1010                1015                1020

Trp Asn Asp Leu Ile Leu Pro Arg Phe Glu Arg Met Asn Gln Leu
        1025                1030                1035

Thr Asn Ser Lys Val Phe Thr Ala Trp Asn Glu Asn Tyr Gln Lys
        1040                1045                1050

Phe Leu Pro Thr Val Pro Ile Glu Tyr Ser Lys Gly Phe Ser Lys
        1055                1060                1065

Lys Arg Ile Asp His Arg His Ala Leu Asp Ala Leu Val Ile
        1070                1075                1080

Ala Cys Ala Thr Lys Asp His Val Asn Leu Leu Asn Asn Gln Ser
```

|   |   |   | 1085 |   |   |   | 1090 |   |   |   | 1095 |   |   |

Ala Lys Ser Asp Thr Lys Arg Tyr Asp Leu Lys Lys Lys Ser Met
1100                1105                1110

Lys Phe Glu Lys Val Val Tyr Asn Asp Ala Lys Thr Gly Glu Lys
1115                1120                1125

Ile Glu Arg Glu Val Pro Lys Gln Phe Leu Lys Pro Trp Glu Asn
1130                1135                1140

Phe Thr Leu Asp Val Lys His Asn Leu Glu Thr Ile Ile Val Ser
1145                1150                1155

Phe Lys Gln Asn Leu Arg Val Ile Asn Lys Ala Thr Asn Tyr Tyr
1160                1165                1170

Glu Lys Tyr Val Glu Lys Asp Gly Thr Lys Asn Lys Glu Arg Val
1175                1180                1185

Glu Gln Thr Gly Thr Asn Trp Ala Ile Arg Lys Pro Met His Lys
1190                1195                1200

Asp Thr Val Ser Gly Lys Val Asp Leu Pro Trp Val Lys Val Pro
1205                1210                1215

Lys Gly Lys Ile Leu Thr Ala Thr Arg Lys Ser Leu Asp Ser Ser
1220                1225                1230

Phe Asp Leu Lys Ser Ile Gly Ser Ile Thr Asp Thr Gly Ile Gln
1235                1240                1245

Lys Ile Leu Lys Asn Tyr Leu Ala Phe Lys Asp Gly Asn Pro Glu
1250                1255                1260

Leu Ala Phe Ser Pro Glu Gly Ile Asp Asp Leu Asn Lys Asn Ile
1265                1270                1275

Glu Lys Tyr Asn Asp Gly Lys Pro His Gln Pro Ile Asn Lys Val
1280                1285                1290

Arg Val Phe Glu Leu Gly Ser Lys Phe Gln Val Gly Gln Ser Gly
1295                1300                1305

Asn Lys Lys Asp Lys Tyr Val Glu Ala Ala Lys Gly Thr Asn Leu
1310                1315                1320

Phe Phe Ala Val Tyr Glu Asp Glu Lys Gly Lys Arg Asn Tyr Glu
1325                1330                1335

Thr Ile Pro Leu Asn Glu Val Ile Glu Arg Gln Lys Gln Gly Leu
1340                1345                1350

Ser Val Val Asp Leu Lys Gly Thr Asn Asp Phe Tyr Leu Cys Pro
1355                1360                1365

Asn Asp Phe Val Tyr Ile Pro Ser Gly Asp Glu Leu Glu Asn Ile
1370                1375                1380

Asn Asn Val Asp Phe Lys Asp Ile Lys Lys Glu Ile Asn Glu Arg
1385                1390                1395

Ile Tyr Lys Val Val Ser Phe Thr Gly Asn Arg Leu Ser Cys Ile
1400                1405                1410

Pro Tyr Met Val Ala Thr Thr Ile Val Asn Lys Leu Glu Phe Thr
1415                1420                1425

Gln Leu Asn Lys Ile Glu Phe Thr Lys Glu Lys Glu Ile Cys Ile
1430                1435                1440

Lys Leu Asn Val Asp Arg Leu Gly Asn Ile Ser Lys Ala
1445                1450                1455

<210> SEQ ID NO 55
<211> LENGTH: 18
<212> TYPE: RNA
<213> ORGANISM: Empedobacter sp.

```
<220> FEATURE:
<221> NAME/KEY: source
<223> OTHER INFORMATION: /note="crRNA"

<400> SEQUENCE: 55
guugugaauu gcuuucaa                                                          18

<210> SEQ ID NO 56
<211> LENGTH: 75
<212> TYPE: RNA
<213> ORGANISM: Empedobacter sp.
<220> FEATURE:
<221> NAME/KEY: source
<223> OTHER INFORMATION: /note="tracrRNA"

<400> SEQUENCE: 56
uugaaaagca auucacaaua aggauuauuc cguugugaaa acauucaagg cggggcaacu            60
cgucuuuuuu cuuuu                                                            75

<210> SEQ ID NO 57
<211> LENGTH: 127
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L1"

<400> SEQUENCE: 57
gagcggacag cagcuuccua uaucucguac guugugaauu gcuuucaaaa aguugaaaag            60
caauucacaa uaaggauuau uccguuguga aacauucaa ggcggggcaa cucgucuuuu            120
uucuuuu                                                                    127

<210> SEQ ID NO 58
<211> LENGTH: 127
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L2"

<400> SEQUENCE: 58
ccaugauaua gacguugugg cuguuguagu guugugaauu gcuuucaaaa aguugaaaag            60
caauucacaa uaaggauuau uccguuguga aacauucaa ggcggggcaa cucgucuuuu            120
uucuuuu                                                                    127

<210> SEQ ID NO 59
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="PAM"
<220> FEATURE:
<221> NAME/KEY: modified_base
```

```
<222> LOCATION: (1)..(2)
<223> OTHER INFORMATION: a, c, t, g, unknown or other
<220> FEATURE:
<221> NAME/KEY: modified_base
<222> LOCATION: (4)..(5)
<223> OTHER INFORMATION: a, c, t, g, unknown or other

<400> SEQUENCE: 59 nnrnnc                                                                  6

<210> SEQ ID NO 60
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 1"
<220> FEATURE:
<221> NAME/KEY: modified_base
<222> LOCATION: (31)..(38)
<223> OTHER INFORMATION: a, c, t, g, unknown or other

<400> SEQUENCE: 60
gagcggacag cagcttccta tatctcgtac nnnnnnnn                               38

<210> SEQ ID NO 61
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 2"
<220> FEATURE:
<221> NAME/KEY: modified_base
<222> LOCATION: (31)..(38)
<223> OTHER INFORMATION: a, c, t, g, unknown or other

<400> SEQUENCE: 61
ccatgatata gacgttgtgg ctgttgtagt nnnnnnnn                               38

<210> SEQ ID NO 62
<211> LENGTH: 122
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA with N's"
<220> FEATURE:
<221> NAME/KEY: modified_base
<222> LOCATION: (1)..(25)
<223> OTHER INFORMATION: a, c, u, g, unknown or other

<400> SEQUENCE: 62
nnnnnnnnnn nnnnnnnnnn nnnnnguugu gaauugcuuu caaaaaguug aaaagcaauu       60
cacaauaagg auuauuccgu ugugaaaaca uucaaggcgg ggcaacucgu cuuuuucuu       120 uu                                                                    122
```

```
<210> SEQ ID NO 63
<211> LENGTH: 4
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="4bp linker"

<400> SEQUENCE: 63 aaag                                                                      4

<210> SEQ ID NO 64
<211> LENGTH: 4
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="4bp linker"

<400> SEQUENCE: 64 gaaa                                                                      4

<210> SEQ ID NO 65
<211> LENGTH: 4
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="4bp linker"

<400> SEQUENCE: 65 acuu                                                                      4

<210> SEQ ID NO 66
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="6bp linker"

<400> SEQUENCE: 66 caaagg                                                                    6

<210> SEQ ID NO 67
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: source
<223> OTHER INFORMATION: /note="NLS"

<400> SEQUENCE: 67

Pro Lys Lys Lys Arg Lys Val
1               5

<210> SEQ ID NO 68
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="conserved sequence in base of hairpin
      stem of tracrRNA"
<220> FEATURE:
<221> NAME/KEY: modified_base
<222> LOCATION: (2)..(2)
<223> OTHER INFORMATION: a, c, u, g, unknown or other
<220> FEATURE:
<221> NAME/KEY: modified_base
<222> LOCATION: (4)..(5)
<223> OTHER INFORMATION: a, c, u, g, unknown or other

<400> SEQUENCE: 68 unanng                                                              6

<210> SEQ ID NO 69
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="APG05083.1/exemplary PAM"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 69 nnrncc                                                              6

<210> SEQ ID NO 70
<211> LENGTH: 7
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="APG07433.1/exemplary PAM"
<220> FEATURE:
<221> NAME/KEY: modified_base
<222> LOCATION: (1)..(4)
<223> OTHER INFORMATION: a, c, t, g, unknown or other

<400> SEQUENCE: 70 nnnnccr                                                             7
```

```
<210> SEQ ID NO 71
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="APG07513.1/exemplary PAM"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 71 nnrncc                                                                  6

<210> SEQ ID NO 72
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="APG01688.1/exemplary PAM"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other

<400> SEQUENCE: 72 nnranc                                                                  6

<210> SEQ ID NO 73
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 73
gagcggacag cagcttccta tatctcgtac                                       30

<210> SEQ ID NO 74
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="mismatch repair Table 4"

<400> SEQUENCE: 74
gagcggacag cagcttccta tatctcgtag                                              30

<210> SEQ ID NO 75
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 75
gagcggacag cagcttccta tatctcgttc                                              30

<210> SEQ ID NO 76
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 76
gagcggacag cagcttccta tatctcgaac                                              30

<210> SEQ ID NO 77
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 77
gagcggacag cagcttccta tatctcctac                                              30

<210> SEQ ID NO 78
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 78
gagcggacag cagcttccta tatctggtac                                              30

<210> SEQ ID NO 79
<211> LENGTH: 30
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 79
gagcggacag cagcttccta tatcacgtac                                         30

<210> SEQ ID NO 80
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 80
gagcggacag cagcttccta tatgtcgtac                                         30

<210> SEQ ID NO 81
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 81
gagcggacag cagcttccta taactcgtac                                         30

<210> SEQ ID NO 82
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 82
gagcggacag cagcttccta tttctcgtac                                         30

<210> SEQ ID NO 83
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 83
gagcggacag cagcttccta aatctcgtac                                         30
```

<210> SEQ ID NO 84
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="mismatch repair Table 4"

<400> SEQUENCE: 84
gagcggacag cagcttcctt tatctcgtac                                    30

<210> SEQ ID NO 85
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="mismatch repair Table 4"

<400> SEQUENCE: 85
gagcggacag cagcttccaa tatctcgtac                                    30

<210> SEQ ID NO 86
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="mismatch repair Table 4"

<400> SEQUENCE: 86
gagcggacag cagcttcgta tatctcgtac                                    30

<210> SEQ ID NO 87
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="mismatch repair Table 4"

<400> SEQUENCE: 87
gagcggacag cagcttgcta tatctcgtac                                    30

<210> SEQ ID NO 88
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:

```
<221> NAME/KEY: source
<223> OTHER INFORMATION: /note="mismatch repair Table 4"

<400> SEQUENCE: 88
gagcggacag cagctaccta tatctcgtac                               30

<210> SEQ ID NO 89
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 89
gagcggacag cagcatccta tatctcgtac                               30

<210> SEQ ID NO 90
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 90
gagcggacag caggttccta tatctcgtac                               30

<210> SEQ ID NO 91
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 91
gagcggacag caccttccta tatctcgtac                               30

<210> SEQ ID NO 92
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 92
gagcggacag ctgcttccta tatctcgtac                               30

<210> SEQ ID NO 93
<211> LENGTH: 30
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 93
gagcggacag gagcttccta tatctcgtac                                   30

<210> SEQ ID NO 94
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 94
gagcggacac cagcttccta tatctcgtac                                   30

<210> SEQ ID NO 95
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 95
gagcggactg cagcttccta tatctcgtac                                   30

<210> SEQ ID NO 96
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 96
gagcggagag cagcttccta tatctcgtac                                   30

<210> SEQ ID NO 97
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 97
```
gagcggtcag cagcttccta tatctcgtac                                           30

<210> SEQ ID NO 98
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 98
gagcgcacag cagcttccta tatctcgtac                                           30

<210> SEQ ID NO 99
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 99
gagccgacag cagcttccta tatctcgtac                                           30

<210> SEQ ID NO 100
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 100
gaggggacag cagcttccta tatctcgtac                                           30

<210> SEQ ID NO 101
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 101
gaccggacag cagcttccta tatctcgtac                                           30

<210> SEQ ID NO 102
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<220> FEATURE:
<221> NAME/KEY: source
<223> OTHER INFORMATION: /note="mismatch repair Table 4"

<400> SEQUENCE: 102
gtgcggacag cagcttccta tatctcgtac                                    30

<210> SEQ ID NO 103
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 4"

<400> SEQUENCE: 103
cagcggacag cagcttccta tatctcgtac                                    30

<210> SEQ ID NO 104
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 104
gagcggacag cagcttccta tatctcgtat                                    30

<210> SEQ ID NO 105
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 105
gagcggacag cagcttccta tatctcgtgc                                    30

<210> SEQ ID NO 106
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 106
gagcggacag cagcttccta tatctcgcac                                    30

<210> SEQ ID NO 107
<211> LENGTH: 30
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 107
gagcggacag cagcttccta tatctcatac                                          30

<210> SEQ ID NO 108
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 108
gagcggacag cagcttccta tatcttgtac                                          30

<210> SEQ ID NO 109
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 109
gagcggacag cagcttccta tatcccgtac                                          30

<210> SEQ ID NO 110
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 110
gagcggacag cagcttccta tatttcgtac                                          30

<210> SEQ ID NO 111
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 111
```
gagcggacag cagcttccta tacctcgtac                                              30

<210> SEQ ID NO 112
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 112
gagcggacag cagcttccta tgtctcgtac                                              30

<210> SEQ ID NO 113
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 113
gagcggacag cagcttccta catctcgtac                                              30

<210> SEQ ID NO 114
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 114
gagcggacag cagcttcctg tatctcgtac                                              30

<210> SEQ ID NO 115
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 115
gagcggacag cagcttccca tatctcgtac                                              30

<210> SEQ ID NO 116
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

```
<210> SEQ ID NO 117
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 116
gagcggacag cagcttctta tatctcgtac                                      30

<210> SEQ ID NO 117
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 117
gagcggacag cagctttcta tatctcgtac                                      30

<210> SEQ ID NO 118
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 118
gagcggacag cagctcccta tatctcgtac                                      30

<210> SEQ ID NO 119
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 119
gagcggacag cagcctccta tatctcgtac                                      30

<210> SEQ ID NO 120
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 120
gagcggacag cagtttccta tatctcgtac                                      30

<210> SEQ ID NO 121
```

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 121
gagcggacag caacttccta tatctcgtac                                      30

<210> SEQ ID NO 122
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 122
gagcggacag cggcttccta tatctcgtac                                      30

<210> SEQ ID NO 123
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 123
gagcggacag tagcttccta tatctcgtac                                      30

<210> SEQ ID NO 124
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 124
gagcggacaa cagcttccta tatctcgtac                                      30

<210> SEQ ID NO 125
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"
```

<400> SEQUENCE: 125

```
gagcggacgg cagcttccta tatctcgtac                                30
```

<210> SEQ ID NO 126
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 126

```
gagcggatag cagcttccta tatctcgtac                                30
```

<210> SEQ ID NO 127
<211> LENGTH: 3210
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG05083.1 mammalian codon optimized
      sequence"

<400> SEQUENCE: 127

```
atgagagagc tggattaccg gatcggcctg gatatcggga ccaactccat ggatggggc    60 atcatcgagc tgtcttggaa caaagacaga gaacagtacg agaaggcaag aatcgtggac   120
aagggcgtga aatgttcga caaggccgaa atacccaaga ccggagccag cctggccgag    180
cctagaagaa ttgccagatc aagcagaaga cggctcaaca gaaagtctca gagaaaaaaa   240
gatattcgga acctgctggt ccagcacgag atcatcagcc aaaaggaact cgctagcctg   300
tatcctctga ccaagagcag catggacatt tgggacatca gactggacgg cctggacaga   360
ctgctggata gattcgagtg gaccagattg ctgatccacc tggctcagcg agagggcttc   420
aaaagcaacc ggaagagcga gctgaaggac gtggaaaccg gcaaggtgct ctccagcatc   480
caggctaatg agagcggct gtccctgtac agaactgtgg cgagatgtg gatgaagaat     540 gaagatttta gcaagtacga caaaagaaga aatagtagca cgaatacgt gttctctgtg    600 tcccgggccg acctggaaaa ggaaatcgtg acactgtttg aagctcagcg gaagttccag    660
agcagctatg ccagcgccga tcttcaaaaa acctacctcc agatctgggc ccatcaactg    720
cctttcgcct ctggcaacgc catcgttaac aaggtgggct actgcagcct actgaaaggc    780
aaggagaaga gagttcctaa ggccacctac accttccaat acttcagcac cctggatcag    840
atcaacagaa ccagactggg cccaaacttc agcccttca ccaaggaaca gagagatgtg      900
atcctggacg agatgtttaa ccggaccgat tattacaaga agaagaccat ccctgaggtg    960
acgtactacg atatcagaaa atggctggcc ctggacgaga caatccagtt caagggcctg   1020
acctacgacc taatgaaga actgaagaaa attgagctaa agtcttttat caatctgaag    1080
cctttctacg agataaagaa ggtggtgaca aactacgcca agaagacaaa tgaggccttt   1140
agcacactgg actatgacac ctttgcctac gccctgacag tgtacaagac cgacaaggac   1200
atccgctcct acctgaaaaa gagtaacaac ctgtccaaat gctgctacga cgaccaactg   1260
```

```
atcgaggaat tgctgacact gagctacacc aaattcggcc acctgagctt caaggctatc   1320
aaccacgttc tgcctatcat gcaggagggc agaacctacc aggaggccat tcaccagctc   1380
ggctacgatg ccacaaacct caaaaagag aaccggtcta tgttcctgcc tctgttccct   1440
gacgagatca ccaaccccat cgtgaagagg gccctgaccc aggccaggaa ggtggtcaac   1500
gccatcatca gacgatacgg gtctccaaac agcgtgcaca tcgagctggc cagagagctg   1560
agcaagagcc acgacgagag aacaaagatc atgaaagctc atgatgaaaa ctacaaaaag   1620
aacaagggcg ctatcagcat cctgatcgag aacggtattc tgaatcctac aggttatgac   1680
atcgtccggt acaagctgtg gaaggaacag ggcgagagat cgcctattc tctgaaacag   1740 atccccgcca acaccttctt caacgaaatg aagaaggagc ggtccggcag ccctgtgctg   1800
gaaatcgatc acatcctgcc ctacagccag agcttcatcg acagctacca acaaaagtg   1860 ctggtgtacg gggatgagaa ccagaaaaag ggcaatagaa tcccgtacac ctacttcctg   1920
gaaggcaaca aggactggga gtctttcgag agctatgtgc gcctgaactc cttttttcagc   1980 aagaaaaagc gaggatatct gctgaagaag gcttacctgc aagagagag taacatgatc   2040 aaggaacggc acctcaacga cacccggtac gccagctcct acctgaagaa cttcatcgag   2100
aagaatctga gttcaagga ggtggaaggc tctacccgga gaagcacgt gcaaaccgtg   2160 aacggcataa tcacagccca cctgagaaag agatggggcc tggaaaagga ccgccaggag   2220
acatatcttc atcacgctat ggacgccatc atcgtggcat gcaccgacca ccacatggtg   2280
acaaaggtga ccgagtacta ccagatcaaa gaaagcaata aatctattag aaagccttac   2340
ttccccctgc cttgggtggg ctttagagag gaaattctgt cccacctggc tcggcagcct   2400
atcgccagaa agatctctga agagctgaag atcggatacc agagcttcga ttacatcctc   2460
gtgtctagaa tgcctaaaag atcagtgacc ggcgccgccc acgagcagac cattatgaaa   2520
aagggaggca tcgacaaaaa aggaaaaacc atcatcatta gcgggtcta cctgaaggat   2580 atcaagttcg acgagaatgg cgatttcaag atggttggaa aggaacagga cctggctacc   2640
tacgaggcca tcaagcagag atacatcgag tacggcaagg aatccaagaa ggccttcgag   2700
acccctctgt ataagcccag caagaaaggc aaaggcaacc tgatcaagaa gatcaaagtg   2760
gaagtgcaaa ccaagagctt tgtgagagaa gtcaacggcg gagtggccca gaacggcgat   2820
ctggtgcggg ttgacctgtt cgagaaggat aatagatact acatgatccc catctacgtg   2880
atggataccg tgcacagcga acttcctaac aaggccgtga ccagcagcaa aggctatgag   2940
caatggctga ccatcgacaa cagcttcacc ttcaagttca gcctataccc ctacgacctg   3000
gtgcggctgg tcaagggtaa cgaggacaga ttcctgtact tttccaccct ggatattaac   3060
agtgatagac tcaacttcaa agacgtcaac aagcccagca gcaggccga aacagatat   3120 agcctgaaga caatcgaaaa cctggaaaaa tacgaggtgg gcgtcctggg cgacctcaga   3180
tttgtgagac aggagatcag aaagaacttc                                    3210
```

<210> SEQ ID NO 128
<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG07433.1 mammalian codon optimized sequence"

<400> SEQUENCE: 128

```
atgagagagc tggactacag aattggcctg gacatcggca ccaacagcat cggatggggc    60
gtgatcgagc tgtcctggaa caaagaccgg gagagatacg agaaggtcag aatcgtggat   120
caaggcgtga gaatgttcga cagagccgag atgcccaaga caggcgccag cttagctgaa   180
cccagaagaa tcgccagatc cagcagacgg agactgaatc gcaagtccca gagaaagaaa   240
aacatccgga acctgctggt gcaacacggc gtgatcacac aggaggaact ggatagcctg   300
taccccctga gcaaaaagag catggacatc tggggcattc ggctcgacgg cctggacaga   360
ctcctcaatc atttcgagtg ggccagactg ctgatccacc tggctcagag acggggcttt   420
aagtccaaca gaaagagtga actgaaagat acagagacag gcaaggtgct gagcagcatc   480
caactgaacg agaaacggct gagcttgtat agaaccgtgg gcgagatgtg gatgaaggac   540
cccgacttct ctaaatacga taggaagaga aatagcccca cgaatacgt gttcagcgtg   600
tctagagccg agctggaaaa ggaaatcgtg accctgttcg ccgccagcg gagattccag   660
agcccttacg ccagcaaaga tctgcaggag acatatctgc agatctggac ccaccaactg   720
cctttcgcca gcggcaatgc catcctgaac aaggtcggat actgctccct gttgaaaggc   780
aaagaaagaa ggattcccaa ggctacatac accttccaat acttctctgc tctggaccag   840
gtgaatcgga ccagactggg acctgatttc cagcccttca ccaaggagca acggaaatt   900
atcttgaaca acatgttcca gaggacagat tactacaaga gaaaaccat ccccgaggtg   960
acctactatg acatacggaa gtggctggaa ttggacgaga caattcagtt caagggcctg  1020
aactacgacc ctaacgagga actgaagaag atcgagaaga agcctttat caatctgaag  1080
gccttctacg agatcaacaa ggtggtggcc aactacagcg aaagaaccaa cgagaccttc  1140
tccaccctgg actacgacgg catcggctac gccctgaccg tgtacaaaac cgacaaggat  1200
atccgcagct acctgaagag cagtcacaac ctacctaaga gatgctacga cgaccaactg  1260
atcgaggaac tgctgagcct gagctacaca aagttcggcc acctgtccct gaaagccatc  1320
aaccacgtgc tgtctatcat gcagaagggc aatacctaca aggaagccgt ggaccaactg  1380
ggctacgaca ccagcggcct taagaaggag aagaggtcca agttcctgcc acctatttct  1440
gatgaaatca cgaatccaat cgtgaaaagg ccctgaccc aggccagaaa agtggtgaac  1500
gccataatta aagacacgg atctcctcac tccgtgcaca tcgagctggc cagagagctg  1560
agcaagaacc acgacgagcg gacaaagatc gtcagcgccc aggatgaaaa ctacaagaaa  1620
aacaagggcg ctatcagcat cctgtctgag cacggcatcc tgaaccctac aggctacgac  1680
atcgtgagat acaaactgtg gaaggagcag ggcgaacggt gcgcctacag cctgaaggaa  1740
atccctgccg atacattttt caacgagctg aagaaggaac gcaacggcgc ccctatcctt  1800
gaagtggacc acatcctgcc ctacagccag tccttcatcg actcctacca caacaaggtc  1860
ctggtgtaca gcgacgaaaa ccggaaaaag gcaacagaa tcccttatac ctacttcctg  1920
gaaaccaaca aggattggga ggcctttgag cggtacgtgc ggagcaacaa attcttctcc  1980
aagaaaaagc gagagtacct tctgaagcgg gcttatctgc ctagagaatc tgagctgatc  2040
aaagaacgcc acctgaacga caccagatac gcctctacct tcctgaagaa cttcatcgag  2100
cagaacctgc agttcaagga agccgaggac aaccccagaa aaagacgggt gcaaaccgtg  2160
aacggcgtta tcaccgccca cttcagaaag cggtggggcc tggagaagga ccggcaggag  2220
acatacctcc atcacgctat ggacgccatc atcgtggctt gtacagacca ccacatggtc  2280
```

| | |
|---|---|
| accagagtga ccgagtacta tcagatcaag gaaagcaaca agagcgtgaa gaagccctat | 2340 |
| tttcctatgc cttgggaagg cttccggac gagctgctga gccacttggc ttctcagcct | 2400 |
| atcgccaaga aaatcagcga ggaactgaag gccggctacc agagcctgga ctacatcttc | 2460 |
| gtgtccagaa tgcctaagag aagcattaca ggcgctgctc ataagcagac catcatgcgg | 2520 |
| aagggaggaa ttgacaagaa gggcaaaaca atcatcatcg aacggctgca cctgaaggat | 2580 |
| atcaagttcg acgagaacgg agatttcaag atggtgggca aggaacagga catggccaca | 2640 |
| tacgaagcta ttaaacagag atacctggag cacggcaaga atagcaagaa ggccttcgag | 2700 |
| acccctctgt acaagcccag caaaaagggc acaggtaacc tgatcaagcg ggtgaaggtg | 2760 |
| gaaggacagg ccaagagctt tgtgagggaa gtgaacggcg gagtggccca aaatggcgat | 2820 |
| ctggttagag ttgatttgtt tgagaaggat gataagtact acatggtccc catctacgtg | 2880 |
| ccagacaccg tgtgtagcga gctgcccaaa aaggtggtcg ccagctctaa gggctatgag | 2940 |
| cagtggctga cactggataa cagcttcacc tttaagttca gcctgtaccc ttatgatctg | 3000 |
| gtgcggctgg tcaagggaga tgaggatcgg ttcctgtact ttggcaccct ggacatcgac | 3060 |
| agcgacagac ttaacttcaa ggacgtgaac aagccaagca agaagaacga gtaccggtac | 3120 |
| agcttgaaaa ccatcgagga cttggagaag tacgaggtgg gcgtgctggg cgatctaaga | 3180 |
| ctggtccgga aggaaactcg aagaaacttc cac | 3213 |

<210> SEQ ID NO 129
<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: source
<223> OTHER INFORMATION: /note="APG07513.1 mammalian codon optimized
    sequence"

<400> SEQUENCE: 129

| | |
|---|---|
| atgcgggaac tggattacag aattggactg gacatcggga ccaactcaat tggctgggga | 60 |
| gtgatcgagc tgagctggaa caaggacaga gagcagtacg agaagaccag aatcgtggac | 120 |
| aagggcgtta ggatgttcga caaggccgag atccccaaga ccggagccag cctgccgag | 180 |
| cctagacgta tcgccagatc ctccagacgt agactgaaca gaaagtccca gaggaagaag | 240 |
| gacattcgga acctgctggt gcaacacgag atcattagcc aaaaagaact gaccagcctg | 300 |
| taccctctgt ctaaatccag catggacatc tgggacatcc ggctggacgg cctggacaga | 360 |
| ctgcttgata gattcgagtg ggcccggctc ctgatccacc tggctcagcg gcggggcttt | 420 |
| aaaagcaacc ggaagtctga gcttaaagac gtggaaacag aaaagttcct gtccagcatc | 480 |
| caggtgaatg aaaagcggct gagcctgtac agaaccgtgg cgagatgtg atgaagaac | 540 |
| gccgattgca gcaagtacgg caaacgtaga atagcccca cgagtacgt gttcagcgtg | 600 |
| tctagagccg acttggagaa agaaattgtg acactttcg aggcccagcg aaaattccac | 660 |
| agcagctacg ccagtgtgga cctgcagaag acatacatcc aaatctgggc tcatcaactg | 720 |
| ccatttgcct ctggcaatgc cattgtgaac aaggtgggat actgctctct gctgaagggc | 780 |
| aaagaaaaga gagtgcctaa ggccacatac acctttcgt attttaacac cctggaccag | 840 |
| atcaaccgga caagactggg ccctaacttc caacctttca ccaaggagca gagagatatc | 900 |
| atcctagaca aaatgttcca gagaaccgac tactacaaga aaaaaacaat ccctgaggtg | 960 |

```
acatactacg atatcagaaa gtggctggcc ctggacgaaa ccatccagtt caagggcctg    1020
acctacgatc ctaatgaaga actgaagaag atcgagatga agccattcat caacctgaaa    1080
cctttctacg agatcaagaa ggtggtgacc aactacgcca agaagacaaa cgaggtgttc    1140
tctgccctgg actatgacac cgtggcttat gccctcaccg tgtacaaaac agacaaggat    1200
atcagaagct accttaagcg gtccaacaac ctgagcaaga gatgttacga cgaccaactg    1260
atcgaggaac tgctgacact gagctacacc aagttcggcc acctgtcctt caaggccatc    1320
aatcacgtgc tgcccatcat gcaggagggc agaacctacc aagaggctat tcaccaactg    1380
ggctatgaca cgaccaacct gaagaaggaa aatagaagca tgttcctgcc catcatccct    1440
gacgagatca ccaaccctat cgtgaagcgg gccctgacgc aggcccggaa agtggtgaat    1500
gccatcatcc gcagatacgg ctctcctaat tctgtccaca tcgagctggc cagagagctg    1560
agcaaaagcc acgacgagcg gaagaagatc atgaccgccc acgacgagaa ctacaagaaa    1620
aacaagggcg ccgtgtccat cctgatcgat aacggcatcc tgaatcctac aggatacgat    1680
atcgtgcggt acaagctgtg gaaggaacag ggcgaaagat cgcctatag cctgaaaaaa    1740 atccccgcca acaccttctt caacgagcta aaaaaggaac ggagcggccc acctgtgctg    1800
gaagtggacc acatcctgcc ctacagccag agcttcatcg acagctacca caacaaggtg    1860
ctggtgtacg cgacgagaa ccagaagaag ggcaatagaa tcccttacac atttttcagc    1920
gaagaagata aggaatggga gagcttcgag agctacgttc ggagcaacag cttcttcagc    1980
aagaaaaagc gcggctacct gctgaagaag gcctacctgc ccagagaaag caacctgatc    2040
aaggaacggc acctcaacga cacacggtac gccagcagtt acctgaagaa tttcatcgag    2100
aagaacctga gttcaagga agccgtgggg atcacccgga agaagtacgt gcaaaccgtg    2160
aacggcgtga tcaccgccca cctgcggaag cggtggggcc ttgagaagga ccggcaggag    2220
acctacctgc accacgctat ggacgccatc atcgtggcct gcaccgatca ccacatggtg    2280
acgaaggtga ccgagtacta ccagatcaaa gaaggcaata agagcatcaa gaagccttat    2340
tttcctctgc cctggatggg cttcagaaa gaaatcctgt ctcacctgga gtctcaacct    2400
atcgccagaa aaatttctga agagctgaaa attggatacc agtcccccga ttacatcctg    2460
gtcagccgga tgcctaagag aagcgtgacc ggcagcgccc acgatcagac cgtgatgaag    2520
aagggcgata tcgataagaa gggcaagaca atcatcatca gcgggtgca cctgaaggat    2580 atcaagttcg acgaaaatgg cgacttcaaa atggtgggca aggagcagga cctggctaca    2640
tacgaagcta tcaaacagag ataccgtggag taccggaagg aaagcaagaa ggccttcgag    2700 accctctgt acaagccatc taaaaaagga aaggtaacc tgatcaaaaa gatcaaggtg    2760
gaagtgcaaa ccaaatcttt cgtgagagag attaacggcg gagtggccca gaacggcgac    2820
ctggttagag tggatctgtt cgagaaggac aacagatatt acatggtccc catctacgtg    2880
gtggacaccg tgcggtctga actccccaac aaagcagtga caagctccaa aggctatgaa    2940
cagtggctga gcatcgacaa tagtttcacc ttcaagttta gtctgtaccc ctacgacctc    3000
gtgcggctgg tcaagggcga cgaggatcgc ttcctgtact tctccaccct ggatatcaac    3060
agcgacagac tgaacttcaa ggacgtgaac aagcctagca gcaggctga ataccggtac    3120 agcctgaaga cgatcgagaa cctggaaaaa tacgagatcg tgttctgggg agatctgaga    3180
ctcgttagac aggagacaag aaaaattttc aag                                3213
```

<210> SEQ ID NO 130

```
<211> LENGTH: 3216
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG08290.1 mammalian codon optimized
      sequence"

<400> SEQUENCE: 130
atgagcgagc tggattatag aatcggcctg gatatcggca ccaattctat cggatgggga     60
gtgatcgagc tgttctggaa caaggatcgg aacggtacg agaaggtccg catcgtggac    120 aaagggtca gaatgtttga caaggccgag atccccaaca agggcgccag cctggccgag    180
cctcggagaa tcgcccggag cagcagaaga cgcctgaaca ggaagtccca aggaagaag    240 gagatccgga acctgctggt gcaacacggc atgatcaccc agaggaact ggacctcctg    300 taccctctga gcaaaaagtc catcgatatc tgggacatca gactagacgg cctggacaga    360
ctgctgaacc acttagagtg ggctagactg ctgattcacc tggcccagcg gcggggcttc    420
aagagcaacc gcaaaagcga gctgaaggac gctgaaacag gcaaggtgtt gtctagcatc    480
caggtgaacg agaagcggct gttcctgtac agaaccgtgg gggaaatgtg gatcaaggac    540
gcagagttca gcagtacga caggcgtaga aactccccaa cgaatacgt gttcagcgtg    600 tcaagagccg acctggaaaa ggaaatcgtg acactgtttg aggctcagag aaagttccag    660
agcagctatg cctctaaaaa tctgcaggag acctacctgc agatctgggc ccaccaactg    720
cctttcgcca gcggcaatgc catcctgaac aaagtgggct actgcagcct gctgaaaggg    780
aaggaaaggc ggattcccaa ggccacatac accttccagt acttctccgc cctggatcag    840
gttaaccgga cccggctcgg ccctgacttc caaccttcca cccaggaaca aaaggagatc    900
atcctggata gatgttcca gagaacagac tactacaaga agaagaccat ccccgaggtt    960
tcttattatg atatcagaaa gtggctggaa ctcgacgaga caatccagtt aagggactg   1020 aattacgacc caacgaaga gctgaagaag atcgaaaaaa aaccttcat caacctgaag   1080 gccttctacg agatcaagaa ggtggttgct aactacgccg aaagaacaaa tgaagccttt   1140 tctacccctgg actacgacgc tatcgcctat gccctgacag tctacaagac cgacaaggac   1200
atccggtcct acctgaagaa atccaacaac ctgtccaagc ggtgctacga tgatcaactg   1260
atcgaggaac tgtttaccct gagctacacc aaattcggcc acctgtcttt caaggccatt   1320
aaccacgtgc tgcctatcat gcaggagggc agaacctacc aggaggccat acaccaactg   1380
ggctacgaca ccaccaacct gaagaaagag aatagaagca tgttcctgcc tctgatccct   1440
gacgagatca caaaccccat tgtgaagcgg gccatcaccc aggccagaaa ggtggtgaac   1500
gccatcatca agatacgg ctctcctaac agtgtgcaca tcgaactggc cagagagctg   1560
agcaagagcc acgatgagcg gaaaaagatc atgaccgccc acgacgagaa ctacaagaaa   1620
aataagggcg ctatttctat cctgatcgag aacggcattc tgaaccctac cggctacgac   1680
atcgtgagat acaagctgtg gaaggaacaa ggcgagagat cgcctacag cctgaaagaa   1740 attccacctg atactttttt caacgagctg aagaagaaa gaaacggcag ccccattctg   1800
gaagtggacc acatcctgcc ttacagccag tccttcatcg acagctacca acaaaagtg   1860 ctggtgtact ctgacgagaa cagaaacaag gcaacagaa tccctacac ctacttcctg   1920 gaaacaaaca aggactggga ggcctttgaa agatacgtgc ggagtaacaa actgttttct   1980
```

| | |
|---|---|
| aagaaaaaga gagaatatct gctgaagaag acttacctgc ctagagagtc tgaactaatc | 2040 |
| aaggaacggc acctgaacga cactcggtat gcttctacat tcctgaagaa tttcatcgag | 2100 |
| cagaatctgc agttcaaaga ggtcgaggtc aatctgagaa aaagagagt gcaaaccgtg | 2160 |
| aatggcgtga tcaccgccca cctcagaaag cgttggggcc tggagaagaa ccggcaggag | 2220 |
| acgtacctgc accacgctat ggacgccatc atcgtggctt gtacagacca ccacatggtg | 2280 |
| acccggataa cagagtacta ccagatcaag gaatccaaca agagcgtgaa gaaaccttac | 2340 |
| ttccccatgc cttgggaggg ctttagagat gagctgttgt ctcacctcgc tagccagcct | 2400 |
| atcgcaaaga agatcagcga ggaactgaag gccggctacc agagcagcga ctacatcttc | 2460 |
| gtgtccagaa tgcccaagag aagcgtgacc ggcgccgccc atgatcagac catcagaaga | 2520 |
| aagggcggca tcgacaagaa gggcaagaca atcatcatta agcgggtgcg gctgaaagat | 2580 |
| atcaagttcg acgaaaacgg cgatttcaag atggtgggca agagcagga cctggcaacc | 2640 |
| tacgaggcca tcaagcagag atacctggag cacagaaaga acgtaagaa ggccttcgag | 2700 |
| accccctctgt acaaacctag caagaaggga acaggaaacc tgattaagcg ggtgaaaatc | 2760 |
| gagggacaga ctaaggcctt cgtgcggaa gtgaacggag cgtggccca aaatagcgac | 2820 |
| ctggtcagag tggacctgtt cgagaaggac gacaagtact atatggtgcc tatctacgtg | 2880 |
| ccagacaccg tgtgtagcga gctgcctaag aaggtggtta agagcggaaa aggctatgag | 2940 |
| cagtggctga ccctggacaa cagcttcacc ttcaagtcta gcctgtaccc ctacgatctg | 3000 |
| gtgcggctcg tgaagggcaa cgaggacaga ttcctgtact cggcacact ggacattgac | 3060 |
| tccgatagac tgaatttcaa ggatgtgaac aagcccagca gcagaacga gtaccggtac | 3120 |
| agcctgaaaa caatcgagaa cctggaaaaa tacgaggttg gagtgctggg agatctgcgg | 3180 |
| ctggtgaaac aggagaccag gaggatcttt aacaga | 3216 |

<210> SEQ ID NO 131
<211> LENGTH: 4011
<212> TYPE: DNA
<213> ORGANISM: Artificial Sequence
<220> FEATURE:
<221> NAME/KEY: source
<223> OTHER INFORMATION: /note="Description of Artificial Sequence:
  Synthetic polynucleotide"
<220> FEATURE:
<221> NAME/KEY: source
<223> OTHER INFORMATION: /note="APG05459.1 mammalian codon optimized
  sequence"

<400> SEQUENCE: 131

| | |
|---|---|
| atgaaaaaag attacgtgat cggcctggac attggcacca acagcgtcgg ctgggccgtg | 60 |
| atgacagagg actaccaact ggtgaagaag aagatgccaa tctatggcaa tactgagaag | 120 |
| aaaaagataa aaagaattt ctggggcgtg cggctgtttg aggagggcca caccgccgag | 180 |
| gatcggcggc tgaaacggac cgctagaaga cggatctctc gccgcagaaa tagactgaga | 240 |
| tatctgcagg ccttcttcga ggaagccatg accgccctgg acgagaactt cttcgccaga | 300 |
| ctgcaggaga gcttcctggt gcctgaggac aagaaatggc accggcaccc tatcttcgcc | 360 |
| aagctggagg atgaggtggc ctatcacgaa acctacccta caatctacca cctgagaaag | 420 |
| aaactggctg attcctctga acaggctgac ctgagactga tctatctggc cctggcccat | 480 |
| atcgtgaagt acgaggcca cttcctgatc gaaggaaagc tgagtaccga gaacatcagc | 540 |
| gtcaaggagc agttccagca gttcatgatt atctataacc agacatttgt gaacggcgaa | 600 |

| | | |
|---|---|---|
| agccggctgg tgtctgcccc tctgcctgag agcgtgctga tcgaagaaga gctgaccgaa | 660 | |
| aaggccagcc ggacaaagaa atctgagaag gtgctgcaac agtttcctca ggagaaagcc | 720 | |
| aatggactgt tcggccagtt cctgaaactt atggtaggca acaaagccga tttcaagaaa | 780 | |
| gtctttggcc tggaagaaga ggccaaaata acatacgcca gcgagtccta cgaggaggat | 840 | |
| ctggaaggca ttctggccaa ggtgggcgac gagtacagcg atgttttcct ggccgctaag | 900 | |
| aacgtctacg acgccgtgga actgtctacc atcctggccg actccgacaa gaagagccac | 960 | |
| gccaagttgt ctagtagcat gatcgttaga ttcaccgagc accaggagga cctgaagaag | 1020 | |
| ttcaagcggt ttatcagaga gaattgcccc gacgagtacg ataacctgtt caagaacgag | 1080 | |
| caaaaagacg gctacgccgg ctacatcgcc cacgccggca aggtgtccca actgaagttc | 1140 | |
| taccagtacg tgaagaagat aatccaggac atcgccggcg ccgaatactt cctggagaaa | 1200 | |
| atcgcccagg agaacttcct gcgaaaacag aggaccttcg acaacggcgt gatcccccac | 1260 | |
| cagatccacc tggccgagct gcaggccatc atccacagac aggctgctta ctacccttc | 1320 | |
| ctgaaggaaa tcaggaaaaa gattgagcaa ctggtgacat tcagaatccc ctactacgtc | 1380 | |
| ggccctctga gcaaaggaga tgccagcacc ttcgcctggc tgaaaagaca aagcgaggaa | 1440 | |
| cctatccggc cttggaacct gcaagagaca gtggacctgg accgtctgc taccgcattc | 1500 | |
| atcgagagaa tgaccaactt cgatacctac ctgccttctg agaaggtgct gcccaagcac | 1560 | |
| agcctgctct acgaaaaatt tatggtgttc aacgagctga ccaagatttc ttacactgat | 1620 | |
| gacagaggca tcaaggccaa cttcagcggc aaggagaagg agaagatatt cgactacctg | 1680 | |
| tttaagaccc gccggaaggt gaagaaaaag gatatcatcc agttctaccg gaacgagtac | 1740 | |
| aacaccgaga tcgtcacccc tgtctggcctg gaagaggacc agttcaatgc cagcttcagc | 1800 | |
| acctaccaag atctgctgaa gtgcggccta actagagccg aactggacca ccctgataat | 1860 | |
| gccgagaaac tggaggacat cattaagatc ctaaccatct tcgaggatag acagcggatc | 1920 | |
| agaacacagc tcagcacctt caagggacag ttcagcgccg aggtgctgaa gaagctggaa | 1980 | |
| cggaagcact acaccggctg gggcagactg tccaagaaac tcatcaacgg catctacgac | 2040 | |
| aaggaatccg aaagacaat cctggactac ctgatcaaag atgacggcgt ttctaagcac | 2100 | |
| tacaacagaa acttcatgca gctaatcaac gacagccaac tgagcttcaa gaacgccatc | 2160 | |
| cagaaggccc agagcagcga gcatgaggaa cccgtctg agaccgtgaa cgagctggcc | 2220 | |
| ggcagccctg ccatcaagaa aggcatctac cagagcttaa aaatcgttga tgagctggtt | 2280 | |
| gccatcatgg gctacgcccc taagagaatc gtggtggaga tggctagaga gaaccagaca | 2340 | |
| acaagcaccg gaaagagaag aagcatccag aggctgaaga tcgtggaaaa agctatggcc | 2400 | |
| gagattggaa gcaacctgct caaggaacag cctaccacaa acgagcaact gagagataca | 2460 | |
| agactcttcc tgtattatat gcagaacggt aaggacatgt acaccggcga cgagctgagc | 2520 | |
| ctgcacagac tgtctcacta cgacatcgac cacatcattc ctcagtcctt catgaaggac | 2580 | |
| gattccctgg ataacctggt gctggtgggc agcaccgaga ccgggcaa gtctgacgac | 2640 | |
| gtgcccagca aggaagtggt gaaggacatg aaagcctact gggagaagct ctacgctgct | 2700 | |
| ggcttgatca gccagcggaa attccagaga ctgacgaagg gcgagcaggg cggcctgacc | 2760 | |
| ctggaggaca agctcattt catccagaga caactggtgg agacaagaca gatcaccaag | 2820 | |
| aacgtggctg gaattctgga tcagagatac aacgccaaca gcaaagaaaa aaaggtgcaa | 2880 | |
| atcataacac tgaaagcctc tctgaccagc cagttccgga gcatcttcgg cctgtataag | 2940 | |
| gtcagagaag tgaacgacta tcaccacggc caggatgcgt acctgaactg cgtggtggcc | 3000 | |

-continued

```
actacactcc tgaaagtgta ccccaacctg gctcctgagt tcgtgtacgg cgagtacccc    3060
aagtttcagg cctttaagga aaacaaggct acagccaaga ccatcatcta caccaatctg    3120
atgcggtttt tcaccgagga tgaacccaga ttcatgaagg acggcgagat cctgtggagc    3180
aacagctacc tgaagaacat taagaaagaa ctcaactacc atcagatgaa catagtgaaa    3240
aaggtggaag tgcaaaaggg tggcttctcc aaggaaagca tcaagcctaa gggccccagc    3300
aacaagctga tccctgtgaa gaacgggttg accccccaga aatacggcgg atttgactct    3360
ccagtggtcg cttacacagt gctgtttacc cacgagaagg gcaaaaaacc actgatcaag    3420
caggagatcc tgggaatcac catcatggaa aagaccagat cgagcagaa tcctatcctg    3480 ttcctggaag aaaaaggctt cctgaggcct agagtgctga tgaagctgcc taaatacacc    3540
ctgtacgagt tccctgaggg aagacggcgg ctgctggcca cgccaaaga agcccagaaa    3600 gggaatcaga tggtgctccc cgaacacctg ctgaccctgc tgtaccacgc caaacagtgt    3660
ctgctgccta accagagcga atctctcgct tacgtggaac aacaccaacc ggagttccaa    3720
gagatcctgg agagtggt ggacttcgct gaggtgcaca cactggccaa gagcaaggtg    3780
caacagatcg tgaaactgtt tgaggcaaac cagaccgcag atgtgaagga atcgccgcc    3840 tccttcatcc aactgatgca gttcaacgca atgggagccc catctaccttt aaattcttc    3900 cagaaggaca tcgagcgggc ccggtacact agcatcaagg aaatcttcga cgccaccatc    3960
atctaccaga gcacaaccgg cctctacgag acacggagaa aggtggtgga c             4011
```

<210> SEQ ID NO 132
<211> LENGTH: 4308
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG04583.1 mammalian codon optimized sequence"

<400> SEQUENCE: 132

```
atggccaaga atatcctggg cctggatctg ggtacaaaca gcatcggctg ggctctggtc      60
cagcaggact tcgagaacaa ggagggaaac atcctgggca tgggatctag aatcatccct     120
atgagccagg acatcctggg cgaattcggt aagggcaaca gcatcagcca gaccgccgag     180
agaacaggat accggggcgt gcgtagactg agagagagac acctcctgag aagagagaga     240
ctgcatagag tgctgcacct gctcggcttt ctgcctaagc actacgatga aaaaatcgac     300
tttacacaaa gattcggcaa gttcatcaac caggctgagc taagctggc ttttgatagc     360 gagttcctgt tcaaggacag cttccacgag atgctggccg acttcaagca gaatcaacct     420
gaattcctga agacaagaa cggagaggac tgcctggttc cttacgactg gaccatctac     480
tacctgagaa agaaggctct gacccagaag atcgagaaat cgaactagc ttggctgatc     540 ctgaacttca accaaaagcg gggctactac cagcttagag gcgaagaaga gaaggaaaac     600
cctaacaaac tggtgggctt ccactctctg aagattgttg atgtgatccc tgatgccgag     660
accaacaaaa agggcgagac atggtacagc ctgcacctgg aaaacggctg ggtgtacagg     720
cggagcagca agatcagcct ggccgactgg aaggacaagg ttcgggactt catcgtcact     780
acagatctga cgacgatgg cagcgagaag ctggacaagg acggcatcgt gaagaggtcc     840
```

```
ttcagagccc cttctgccga cgattggaca ctcctgaaaa aaaagactga aaggacatc      900
gacaactcca acaagactgt gggcacctac atctacgaca acttgctgct gaaccctaaa     960
cagaagatca aggggaaaat ggtcagaacc atcgaacgaa agttctacaa gcaggagctg    1020
gagcaaatcc tgaaaaccca gaaagaattt cactccgagc tgcagtctga aaacctgctg    1080
caggactgcg tgagggagct gtaccggaac aacgagcagc accagcagat gctggaagcc    1140
aaggattttg tgcacctgtt cctgaacgat atcatcttct accagagacc cctgcgcagc    1200
cagaaaagct ctattagcaa ctgcaccctg gaattccgga gagcaagaa cgagaatgga     1260
gaagaagtga tccaccggct gaaggtgatc gccaagtcca cccctacta tcaagagttt     1320
cggctgctgc agtgggtgca aaacctggct atctacacta aggacgacga caaaaacgtc    1380
acaaacgaat tcctgaagag cacccaggac tgggaggatc tgctgagatg gctgcacagc    1440
aagaaagaaa tcaagcagga tgccctgatc aaattcctga tcgaaaagaa aggcctgaag    1500
ggtaaggccc tgaccattga agtggctaag tacagatgga attacgtgca agacaaggat    1560
tatcctggca acgagacaag atacctgatt cagagccggc tggacaaggt ggaatacgcc    1620
cctaaggact cctcacgta cgaaaatgag atggccctgt ggcacatcat ctactctatc     1680
aacgataaga tcgaatacga aaaggcccta agagcttcg ccaacaagaa aggtctcgac     1740
gaggtgacct tcgtggaagc ctttaagaaa ttcccacctt tcaagagcga ttacggcagc    1800
ttcagcgaga aggccatcaa gaagctgctg cctctcatgc ggttcggcac acaatggaac    1860
tgggacaaca tcgaccagaa ctcgaaggaa aggattggaa aaatcctgac cggcgagtac    1920
gacgagaata tcaagggtag agtgcgggaa aaagctagac acctgaacag cgagacggac    1980
tttcaggcgc tccctctgtg gctggcccag tacgtggtgt acggcagaca tagcgaagct    2040
gacatcgccg gcaagtggaa tagtgtggac gacctgaagc agttcttgga cgacttcaag    2100
caacacagcc tgagaaatcc cattgtagaa caggtgatta ctgagacact gcgggccgtg    2160
aaggatatct ggaacttcta cggcaagggc gccaaggact tttctctga gatccacatc     2220
gagctgggaa gagagatgaa aaacaccgcc gacgagagaa aaaggattac cacaatggtg    2280
acagataatg agaataccaa tctgagaatc aaagctctgc tggctgagat ggcccctggat   2340
cagaacgtgg acaatgtgcg gccttacagc cccatgcagc aagaaatcct gaaaatctat    2400
gaggaaggcg tgctgaacgc cgaagagaac atcgacgatg acatcctgaa gatctctaaa    2460
actgctcagc ctagcgctac cgatctgaag agatacaagc tgtggctgga acagaagtac    2520
agaagcccct ataccggaca gatgatccct ctgaacaagc tgttcacccc tgagtatgaa    2580
atcgagcaca ttatccccca gagcagatac ttcgacgatt ctatgagcaa caaggtgatc    2640
tgcgaggccg ccgtgaacaa gctgaaggat aaccagatcg gcctggtgtt catcaagaac    2700
caccacggcg aagtggtgga ctttggcatg ggcaagcagg tgaaaatcct ggaggtgtct    2760
gattacgaag atttcgtgaa gcagaactac aacaaaaaca gaggcaaacg gaacaagctg    2820
ctcctcgaag atatccccga gaaatgatt gaacggcaac tgaacgatac cagatatatc    2880
agcaagtaca tcactcaggt gctgtctaat atcgtcagag acgacaagga aggctctaag    2940
gatgacgagc tgaacagcaa gaacattgtg cccggcaacg gcaagattac aaccagactc    3000
aagcaggatt ggggcctgaa cgatgtgtgg aacgacctgg tgctgcctag attcgagaga    3060
atgaacaccc tcacaaactc caatgatttt acaagcaaga acacacacgg caagaccatt    3120
cctaccgtgc ctatcgagct gagcaagggg ttcagcaaaa agcggatcga tcacagacac    3180
cacgctatgg acgccctggt gatcgcctgc gccacccggg accacgtgaa cctgctgaat    3240
```

| | | | |
|---|---|---|---|
| aacgaatcca | gcaagtctga | cacaaagcgg | tacgacctga | atagaaaact gagaaaatac | 3300 |
| gagaaggtgg | cctacaacga | ccccaaaacc | ggcgagagga | ttgaaaaaga agtgccaaaa | 3360 |
| gacttcatca | agccttggga | aacttttacc | gaagatacca | gaacactgct ggagaatatc | 3420 |
| gtgatctcat | tcaaacagaa | cctgagagtg | atcaacaagg | ccaccaacta ctacgagaag | 3480 |
| atcgagaacg | gcaaaaggt | gaaggtggaa | caaaagggaa | tcaactgggc cgtgagaaag | 3540 |
| gctctccata | aggagaccgt | gtccggccag | gtccaccttg | acagaatcaa ggtggccaag | 3600 |
| ggcaagatcc | tgaccgccac | aagaaagacc | ctggacgctt | cttttaacga gaaaaccata | 3660 |
| gagagcatca | ccgataccgg | catccagaag | atcctgctga | actacctgaa gtcaaaggac | 3720 |
| aacaaccctg | aggtggcctt | ctccccagaa | ggaattgagg | aactaaacaa gaatatcaga | 3780 |
| ctgtacaatg | acggcaaggc | ccaccagcca | atcctaaaag | tgcgggtgtt cgagcagggc | 3840 |
| agcaagttca | cactgggcga | gacaggcaac | aagacaacca | agttcgtgga agctgccaag | 3900 |
| ggcaccaatc | ttttcttcgg | aatctacgag | gacaagagcg | gaaaacgtag ctacgagacc | 3960 |
| atcccctga | atatcgttat | tgaaagacag | aaacagggcc | tccaggccgt gcccgagacc | 4020 |
| aacgagaagg | gcaagcaact | gctgttcacc | ctgagcccca | cgacctggt ctacgtgcca | 4080 |
| gaggaaggcg | tattcgacga | gaacaacatc | aaggtggata | gaatctacaa ggtcgtgtct | 4140 |
| ttcagcacat | accaatgttt | tttcgtgcgg | aacgacgtat | ctaccagcgt ggtcaacaag | 4200 |
| gtggagtaca | gcgccctgaa | caagatggaa | aaatccatcg | acaatatcat gatcaaggaa | 4260 |
| aactgtgtga | agctgaatgt | ggaccggctg | ggtaagatca | gcaaggcc | 4308 |

<210> SEQ ID NO 133
<211> LENGTH: 4368
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG01688.1 mammalian codon optimized sequence"

<400> SEQUENCE: 133

| | | | |
|---|---|---|---|
| atgatgatca | gaacattct | gggactggat | ttgggcacaa | acagcattgg atgggctctg | 60 |
| atcaagcagg | acttcgagaa | caaacacggc | gagatcctgg | gcatgggcag cagaatcatc | 120 |
| cctatgagcc | aggatatcct | gggcgatttc | ggcaaaggga | actcgataag ccagactgct | 180 |
| gacagaacca | agtacagaag | cgtgcggaga | ctgagagaaa | gattcttgct gcggcgggaa | 240 |
| cgcctgcacc | gggtgctcca | cctgctgaac | ttcctccctc | aacactacgc ctctcagatc | 300 |
| gacttcgaga | agaagttcgg | caagtttaag | tctgagaccg | aacctaagct ggcctgggaa | 360 |
| aactggggag | gtaaattctc | tttcctcttc | cagaacagct | tcaacgagat gctggaagac | 420 |
| ttcaaggccg | ccggccaggg | actcaagatt | ccctatgact | ggaccatcta ctacctacgg | 480 |
| aagaaagctc | tgtcccagaa | gatcgagaaa | gaggagcttg | cctggattct gctgaacttc | 540 |
| aaccagaagc | gaggctacta | ccagctcaga | ggcgaggaag | aagaagagaa cccgaacaag | 600 |
| ctggtggagt | ctactccct | gaagatcgtg | gatgtggtcg | ccgacgagcc tcagaagggg | 660 |
| aagagcgaca | tctggtattc | tctgatcctg | gaaacggct | gggtctaccg cagagccagt | 720 |
| aagatcccac | tgtttgattg | gaaggataag | accagagatt | tcatcgtcac cacagacctt | 780 |

| | |
|---|---:|
| aatgacgaca gaagcgtgaa gaccgacaaa gagggcaacg agaagcggtc ctttcgggcc | 840 |
| cctagcgaaa atgattggac cctggtcaag aagaagacag agcaggagat tgaccagagc | 900 |
| cacaagaccg tgggcaccta catctacgag acactgctgc tcaatccaaa gcagaaaatc | 960 |
| aagggcaagc tggtgcgaac aatcgagaga aaattttata aggacgagct gaagcaaatc | 1020 |
| ctggaaaagc agaaggaatt tcaccaggag ctgaaaaacg acgatctgta caacgactgc | 1080 |
| atcagagagc tgtaccggaa caacgaggcc caccaactga ccctgagcaa gaaagatttc | 1140 |
| gtgcacctgc tgatggacga tctgatcttc taccaaagac ccctgcgaag ccagaagtcc | 1200 |
| agcatctcta actgcaccct ggaattcaga aaatacaagg acgaaaacgg catcgaacac | 1260 |
| acccagtacc tgaaggccat cccaaagagt aatccgtact accaagagtt tagactgtgg | 1320 |
| cagtggatgt acaacctgaa catctacaga aggacgacg aggctaatgt gaccaaggaa | 1380 |
| ttcctgaaca ccaataagga cttcgagagc ctgtttgagt tcctgaataa tagaaaggaa | 1440 |
| atcgaacaga agcctctgat caagttcctc ctggaacaga agatattaa caagaagctg | 1500 |
| ctgaacgccg aggccgaaaa gtatcggtgg aattacgtgg aagataagaa gtatccttgc | 1560 |
| aacgaaacga agaccatgat ctccagcaga ctggacaaag tggagaatat ctctgacgac | 1620 |
| ttcctgacca gagacattga gcagaagatc tggcacatca tctacagcgt caacgacaag | 1680 |
| atagaatacg agaaggccct gaagtccttc gccaccagaa acgatctcga cgagaacagc | 1740 |
| tttatcgaag cctttaagaa gttcagccca ttcaagagcg agtacggatc ttttctgag | 1800 |
| aaagccatca gaaactgct gccctgatg agactgggaa agtactggta cgaggacgag | 1860 |
| attgtgaagc actctgatat ttactttaag aacatcgaaa atcttctggg cgacttctcc | 1920 |
| aacagagata aaaaaatatc tgaggaagac aaagagaaat ggaacaagtc tatcaacctg | 1980 |
| aaactgcagg aggaactgaa ggactttcag accgccgaga tcgacctgtt ccagggcctt | 2040 |
| agactccata tcgcccagta cctggtgtac ggccggcaca gcgaagccag catgatcgga | 2100 |
| aagtggaaca gcgccgagga tctggaagaa ttcctgaagg acttcaagca gcacagcctg | 2160 |
| agaaacccca tcgtcgagca agtgatcacc gagaccctga gggtggttaa ggatatatgg | 2220 |
| ctgaaatacg gcaacggcgc caaggacttc ttcaacgaga ttcacatcga gctgggcaga | 2280 |
| gaaatgaagc tgcctgccga cgaccggaaa aagctgacca ccagatcag cgagaacgaa | 2340 |
| aacacaaatt tcagaatcaa ggccctgctg gctgaaatga tgaacgacag cagtgtggaa | 2400 |
| aatgtgcggc ctttcagccc tatgcagcag gagatcctga gatctatga agatgacgtc | 2460 |
| ctgaagtctg acattgaaat cgaggatgac atccttaaga tctctaaaac cgcccagcct | 2520 |
| tctcctagcg atctcaagcg atacaagctc tggctggagc agaagtacaa gtctccatac | 2580 |
| accggccaga tcatacctct gaacaagctg tttacccctg aatacgagat cgagcacatt | 2640 |
| atccctcagt ctagatattt cgacgacagc ttcagcaaca agtgatctg cgagagcgcc | 2700 |
| gtgaacaagc tgaaagacaa ctacattggc ctggaattca tcaagcaatt tggaggcacc | 2760 |
| atcatcgaac tgggctttgg caagtccatc aaagtgttcg agaccaaaga gtacgaggac | 2820 |
| ttcgtgaaga acactacgc caacaatcag ggcaagagaa acaagctgct catggaagac | 2880 |
| atccccgaga aaatgatcga gagacagatg aacgacacca gatacatctc taagtacatc | 2940 |
| agcggagtgc tgagcaacat cgtcagagtg aagatggat ctgatgaggg cgtgaacagc | 3000 |
| aagaacatcg tgcccggcaa cggcaagatt acaacacaac tgaagcagga ctggggcctg | 3060 |
| aatgacgtgt ggaacgacct tatcctgccg cggttcgaga gaatgaatca actgaccaac | 3120 |
| agcaaggtgt tcacagcctg gaacgaaaac taccagaagt tcctgcctac agtgccaatc | 3180 |

```
gaatacagca aaggcttcag caagaagcgt atcgatcaca gacaccacgc cctggatgct    3240
ctggttatcg cctgcgccac caaggaccac gtgaacctgc tgaacaacca gtctgccaag    3300
agcgacacca agagatacga cttaaagaaa aaagtatga aattcgagaa agtggtgtac     3360
aatgatgcca agaccggcga aaagatcgag cgggaagtgc ccaagcagtt cctgaagcct    3420
tgggagaact tcaccctgga tgtgaagcac aacctggaaa cgatcatcgt ctcttttaaa    3480
caaaatctgc gggtgatcaa taaagccacg aactactacg agaagtacgt cgagaaggac    3540
ggcaccaaaa acaaagagcg cgtggagcag acagggacaa actgggccat tagaaagccc    3600
atgcacaagg atacagtgtc cggcaaagtg gaccttcctt gggtgaaggt gcctaaggga    3660
aagatcctga ccgccacacg gaagagcttg gatagcagct tcgacctcaa gagcatcggc    3720
tctataacag atacaggcat tcagaagatc ctaaagaatt acctggcatt caaggacggg    3780
aaccctgagc tggctttcag ccctgagggc atcgacgatc tgaacaagaa catagagaag    3840
tacaacgatg gcaaacctca ccagcctatc aacaaggtgc gagtgtttga gctgggcagc    3900
aagttccagg tgggacaatc tggtaacaag aaggacaagt atgtggaagc tgctaagggc    3960
accaatctct tcttcgccgt gtacgaggat gaaaaaggaa agcggaacta cgagaccatc    4020
cctctcaacg aggtgatcga gagacagaag cagggcctga gcgtggtgga cctgaagggt    4080
acaaacgact tctacctgtg ccctaacgac tttgtgtaca tcccaagcgg cgacgagctg    4140
gaaaacatca acaacgtgga cttcaaggac atcaagaagg agattaacga gcgcatctac    4200
aaagtggtgt cttttacagg caatagactt tcttgtatcc cttacatggt ggccacaacg    4260
atcgtcaaca aactcgaatt cactcaactg aacaaaatcg agtttaccaa ggaaaaagaa    4320
atttgtatca agctcaacgt ggacagactg ggcaatatct ccaaggcc                 4368
```

<210> SEQ ID NO 134
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="SV40 large T-antigen nuclear
      localization sequence"

<400> SEQUENCE: 134
cctaagaaga aagaaaggt g                                               21

<210> SEQ ID NO 135
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Triple FLAG epitope tag"

<400> SEQUENCE: 135
gactacaagg accacgacgg cgactacaaa gatcacgata tcgactacaa ggacgacgat    60
gataag                                                               66

<210> SEQ ID NO 136
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Nucleoplasmin nuclear localization
sequence"

<400> SEQUENCE: 136
aaaagacctg ccgctacaaa gaaggccggc caggccaaga aaaagaag                    48

<210> SEQ ID NO 137
<211> LENGTH: 203
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="Cytomegalovirus mammalian transcription
promoter"

<400> SEQUENCE: 137
tgatgcggtt ttggcagtac atcaatgggc gtggatagcg gtttgactca cggggatttc      60
caagtctcca ccccattgac gtcaatggga gtttgttttg gcaccaaaat caacgggact     120
ttccaaaatg tcgtaacaac tccgccccat tgacgcaaat gggcggtagg cgtgtacggt     180
gggaggtcta tataagcaga gct                                              203

<210> SEQ ID NO 138
<211> LENGTH: 304
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="Cytomegalovirus transcription enhancer"

<400> SEQUENCE: 138
cgttacataa cttacggtaa atggcccgcc tggctgaccg cccaacgacc cccgcccatt      60
gacgtcaata atgacgtatg ttcccatagt aacgccaata gggactttcc attgacgtca    120
atgggtggag tatttacggt aaactgccca cttggcagta catcaagtgt atcatatgcc    180
aagtacgccc cctattgacg tcaatgacgg taaatggccc gcctggcatt atgcccagta    240
catgacctta tgggactttc ctacttggca gtacatctac gtattagtca tcgctattac    300
catg                                                                   304

<210> SEQ ID NO 139
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="Human U6 RNA promoter"

<400> SEQUENCE: 139

```
tgtacaaaaa agcaggcttt aaaggaacca attcagtcga ctggatccgg taccaaggtc    60
gggcaggaag agggcctatt tcccatgatt ccttcatatt tgcatatacg atacaaggct   120
gttagagaga taattagaat taatttgact gtaaacacaa agatattagt acaaaatacg   180
tgacgtagaa agtaataatt tcttgggtag tttgcagttt taaaattatg ttttaaaatg   240
gactatcata tgcttaccgt aacttgaaag tatttcgatt tcttggcttt atatatcttg   300
tggaaaggac gaaacacc                                                 318
```

<210> SEQ ID NO 140
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 189"

<400> SEQUENCE: 140

```
cctgaatgct gtgcggctct                                                20
```

<210> SEQ ID NO 141
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 185"

<400> SEQUENCE: 141

```
ggacagtgcg catctccctg                                                20
```

<210> SEQ ID NO 142
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 168"

<400> SEQUENCE: 142

```
cacatctcga gcaagacgtt                                                20
```

<210> SEQ ID NO 143
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 135"

<400> SEQUENCE: 143
gggccattaa aacctctcca                                    20

<210> SEQ ID NO 144
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 139"

<400> SEQUENCE: 144
aggttttaat ggcccagcct                                    20

<210> SEQ ID NO 145
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 143"

<400> SEQUENCE: 145
catggcagta cattagagca                                    20

<210> SEQ ID NO 146
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 190"

<400> SEQUENCE: 146
cctgaatgct gtgcggctct                                    20

<210> SEQ ID NO 147
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 194"

<400> SEQUENCE: 147
gccgcacagc attcaggtcg                                    20

<210> SEQ ID NO 148
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 165"

<400> SEQUENCE: 148
atggggaatg tagcaagacc                                                     20

<210> SEQ ID NO 149
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 169"

<400> SEQUENCE: 149
cacatctcga gcaagacgtt                                                     20

<210> SEQ ID NO 150
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 173"

<400> SEQUENCE: 150
cttctatagc ctccttcccc                                                     20

<210> SEQ ID NO 151
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 144"

<400> SEQUENCE: 151
catggcagta cattagagca                                                     20

<210> SEQ ID NO 152
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 136"

<400> SEQUENCE: 152
gggccattaa aacctctcca                                                     20
```

```
<210> SEQ ID NO 153
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 145"

<400> SEQUENCE: 153
catggcagta cattagagca                                               20

<210> SEQ ID NO 154
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 188"

<400> SEQUENCE: 154
ggacagtgcg catctccctg                                               20

<210> SEQ ID NO 155
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 192"

<400> SEQUENCE: 155
cctgaatgct gtgcggctct                                               20

<210> SEQ ID NO 156
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 196"

<400> SEQUENCE: 156
gccgcacagc attcaggtcg                                               20

<210> SEQ ID NO 157
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="target for Guide 167"

<400> SEQUENCE: 157
atggggaatg tagcaagacc                                              20

<210> SEQ ID NO 158
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 171"

<400> SEQUENCE: 158
cacatctcga gcaagacgtt                                              20

<210> SEQ ID NO 159
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 175"

<400> SEQUENCE: 159
cttctatagc ctccttcccc                                              20

<210> SEQ ID NO 160
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 197"

<400> SEQUENCE: 160
cctcaccccc acgagcttgt aggaa                                        25

<210> SEQ ID NO 161
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 199"

<400> SEQUENCE: 161
acagtgcgca tctccctggt cacca                                        25

<210> SEQ ID NO 162
<211> LENGTH: 25
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 146"

<400> SEQUENCE: 162
ggctgggcca ttaaaacctc tccag                                      25

<210> SEQ ID NO 163
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 148"

<400> SEQUENCE: 163
gaggctgggc cattaaaacc tctcc                                      25

<210> SEQ ID NO 164
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 176"

<400> SEQUENCE: 164
gaggctgaga caggagagtt gcttg                                      25

<210> SEQ ID NO 165
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 177"

<400> SEQUENCE: 165
cccacaaacc gatgtagctc aagag                                      25

<210> SEQ ID NO 166
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 209"

<400> SEQUENCE: 166
tagggtctta ctctgttgtc cacgc                                      25
```

```
<210> SEQ ID NO 167
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 151"

<400> SEQUENCE: 167
ttctcccgag ccaagtacac gtttc                                          25

<210> SEQ ID NO 168
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 152"

<400> SEQUENCE: 168
gaaaatctgc tcttagggct caagg                                          25

<210> SEQ ID NO 169
<211> LENGTH: 3210
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG05083.1 Soy optimized"

<400> SEQUENCE: 169
atgagagagc tagattacag gatcggactc gatatcggaa ctaattcaat cgggtgggga      60
ataattgagc tgtcctggaa taaagatcgc gagcaatatg aaaaggctag gattgtggat     120
aagggagtga ggatgttcga taaggctgaa attcctaaga ctggagcttc tcttgctgaa     180
ccaagaagaa ttgctagatc tagcaggagg agattaaaca ggaagtctca gcgcaagaag     240
gatataagga accttctcgt tcagcatgaa atcatttctc agaaggagct tgcttctctc     300
taccctctaa ccaaatcaag catggacatc tgggatataa ggcttgatgg actcgatagg     360
cttcttgata gatttgagtg gaccaggctt ctaatacacc ttgctcaaag aagggcttc     420 aaatcaaacc gcaagtccga attaaaggat gttgagactg gaaaggtgct ttcaagcatc     480
caagctaatg aaaagaggct ttctttgtac aggactgttg gggagatgtg gatgaaaaac     540
gaggacttct caaaatacga taaaaggagg aactcctcca acgagtacgt gttctctgtt     600
tctagggctg atcttgagaa ggagattgtg actcttttg aggctcaacg caagttccaa     660
tcaagctacg cttctgctga tcttcaaaag acctaccttc aaatttgggc tcatcagctt     720
ccttttgctt ctggaaacgc cattgtgaat aaagtgggat actgctccct attaaaggga     780
aaggagaaga gagtgcctaa ggctacctat acattccagt acttctctac cctcgatcaa     840
atcaatagaa ctaggcttgg acctaacttc agcccttta ctaaggagca gagggatgtg     900
```

```
atcctcgatg aaatgttcaa caggaccgac tactataaaa agaagaccat tcccgaggtg    960
acctactacg atataagaaa gtggcttgct ctcgatgaaa ccattcagtt caagggacta   1020
acttatgacc ccaacgagga gctgaagaaa atagaactca agtccttcat aaacctcaag   1080
cccttctacg aaatcaagaa ggtggtaacc aactacgcca agaagaccaa cgaagcattc   1140
tctaccctcg attacgatac attcgcttac gctcttaccg tgtataaaac cgacaaggat   1200
ataaggtcct acctcaagaa atcaaacaac ctctccaagt gctgctacga cgatcaatta   1260
attgaggagc ttctcaccct ctcctatact aagttcggac acctctcttt caaggcaatc   1320
aaccatgtgc ttccaataat gcaagaggga agaacttacc aagaggcaat acaccaactt   1380
ggatacgatg ctaccaacct taagaaggag aacaggtcta tgttccttcc tctcttccct   1440
gatgagatta ctaaccctat tgtgaagaga gcttttgactc aagctaggaa ggtggtgaat   1500
gctattatta ggaggtacgg atcacctaac tctgtgcata ttgagcttgc tagggagctt   1560
tctaagtctc atgatgagag gaccaagatt atgaaggctc acgatgagaa ctacaagaag   1620
aacaagggg ctatttccat tctcattgag aacggaattc ttaaccctac cggatacgat   1680
attgtgaggt acaagttgtg gaaggagcaa ggagagagat gcgcttactc tcttaagcaa   1740
attcctgcta acaccttctt caacgagatg aagaaggaaa gatcaggatc tcctgtgctt   1800
gagattgatc acattctccc ttactcccag tccttcattg attcttacca caacaaggtg   1860
cttgtttacg gagatgagaa ccaaaagaag gggaacagga ttccttacac ttacttcctt   1920
gagggaaaca aggattggga gtctttcgag tcttacgtga ggcttaactc cttcttctct   1980
aagaagaaga ggggatacct tcttaagaag gcttatcttc ctagggagtc caatatgatt   2040
aaggagaggc acctaaacga taccaggtac gcttcttctt acctcaagaa cttcatcgag   2100
aagaacctta agttcaagga ggttgaggga tctactagga agaagcatgt tcagaccgtg   2160
aacggaatta ttactgctca tcttagaaag aggtggggac ttgagaagga taggcaagag   2220
acttaccttc atcacgctat ggatgctatt attgtggctt gcactgatca ccatatggtg   2280
actaaggtta ccgagtacta ccagattaag gagtcaaaca agtccatcag gaagccttat   2340
tttcctcttc cttgggttgg attcagggag gagattcttt ctcatcttgc tagacaacct   2400
atcgctagaa agatttccga ggagcttaag attggatacc agtccttcga ttacattctt   2460
gtgtctagga tgcctaagag gtctgttact ggagctgctc atgagcagac tattatgaag   2520
aagggaggaa ttgataagaa ggggaagacc atcatcatta agagggtgta cctaaaggac   2580
atcaagttcg atgagaacgg ggatttcaag atggttggaa aggagcagga tcttgctact   2640
tacgaggcta ttaagcagag gtacattgag tatggaaagg agtctaagaa ggctttcgag   2700
actcctcttt acaagccttc taagaaggga aaggggaacc tcatcaagaa gattaaggtt   2760
gaggttcaga ctaagtcttt cgttagggag gttaatggag gagttgctca gaatggagat   2820
cttgtgaggg ttgatctatt cgagaaggac aacaggtact acatgatccc tatctacgtg   2880
atggatactg ttcattccga gcttcctaac aaggctgtta cttcttctaa gggatacgag   2940
cagtggctta ccattgataa ctcttttcacc ttcaagttct ctctctaccc ttacgatctt   3000
gttaggcttg ttaagggaaa cgaggatagg ttcctctact tctccaccct cgatattaac   3060
tctgataggc tcaacttcaa ggatgtgaac aagccttcaa agcaagctga gaacaggtac   3120
tctcttaaga ccattgagaa ccttgagaag tacgaagtgg gagttcttgg agatcttagg   3180
ttcgttaggc aagagattag gaagaacttc                                    3210
```

<210> SEQ ID NO 170
<211> LENGTH: 3210
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG05083.1 Corn optimized"

<400> SEQUENCE: 170

| | | | | | |
|---|---|---|---|---|---|
| atgcgcgagc | tagattacag | gatcggcctg | gatatcggca | ctaactcaat | aggctggggc | 60 |
| atcatcgagc | tgagctggaa | taaagaccgc | gagcagtatg | aaaaggccag | gatcgtggac | 120 |
| aagggcgtga | ggatgttcga | taaggccgag | atcccaaaga | caggcgcctc | tctggccgaa | 180 |
| ccaaggagga | tcgccaggtc | ttctaggagg | agattaaaca | ggaagtctca | gcgcaagaag | 240 |
| gatataagga | acctgctggt | ccagcatgaa | atcatctctc | agaaggagct | ggccagcctg | 300 |
| tacccgctga | ccaagtcaag | catggacatc | tgggatataa | ggctggatgg | cctggatagg | 360 |
| ctgctggata | ggttcgagtg | gacaaggctg | ctgatacatc | tggcccagag | gaggggcttc | 420 |
| aaatcaaata | ggaagagcga | attaaaggac | gtggagacag | gcaaggtgct | gtcaagcatt | 480 |
| caggccaatg | aaaagcgcct | gagcctgtac | aggacagtgg | cgagatgtg | gatgaaaaac | 540 |
| gaggacttct | caaaatacga | caagcgccgc | aacagcagca | acgagtacgt | gttcagcgtg | 600 |
| agcagggccg | acctggagaa | ggagatcgtg | acactgttcg | aggcccagag | gaagttccaa | 660 |
| tcaagctacg | cctctgccga | tctgcagaag | acatacctgc | agatctgggc | ccaccagctg | 720 |
| ccattcgcta | gcggcaatgc | catcgtgaat | aaagtgggct | actgctctct | attaaagggc | 780 |
| aaggagaaga | gggtgccaaa | ggccacctat | acattccagt | acttcagcac | cctggaccaa | 840 |
| atcaatagga | cacgcctggg | cccaaacttc | cagccattca | caaggagca | gcgcgacgtg | 900 |
| atcctggatg | aaatgttcaa | ccgcaccgac | tactataaaa | agaagaccat | cccggaggtg | 960 |
| acatactacg | atataaggaa | gtggctggcc | ctggatgaaa | ccatccagtt | caagggccta | 1020 |
| acctacgacc | cgaacgagga | gctgaagaaa | atagaactga | gagcttcat | aaacctgaag | 1080 |
| ccgttctacg | aaatcaagaa | ggtggtaacc | aactacgcca | agaaaaccaa | cgaagcattc | 1140 |
| agcaccctgg | actacgatac | attcgcctac | gccctgaccg | tgtataaaac | cgacaaggat | 1200 |
| ataaggagct | acctgaagaa | atcaaacaac | ctgagcaagt | gctgctacga | cgaccaatta | 1260 |
| atcgaggagc | tgctgaccct | gagctatact | aagttcggcc | acctgagctt | caaggcaatc | 1320 |
| aaccacgtgc | tgccaataat | gcaggagggc | cgcacctacc | aggaggcaat | acaccagctg | 1380 |
| ggctacgacg | caaccaacct | gaagaaggag | aaccgaagca | tgttcctgcc | gctgttcccg | 1440 |
| gacgagatca | ccaacccgat | cgtgaagcgc | gccctgaccc | aggcccgcaa | ggtggtgaac | 1500 |
| gccatcatcc | gccgctacgg | ctcaccgaac | agcgtgcaca | ttgagctggc | ccgcgagctg | 1560 |
| agcaagagcc | acgacgagcg | cacaaagatc | atgaaggccc | acgacgagaa | ctacaagaag | 1620 |
| aacaagggcg | ccatcagcat | cctgatcgag | aacggcatcc | tgaacccaac | aggctacgac | 1680 |
| atcgtgaggt | acaagctgtg | gaaggagcag | ggcgagaggt | cgcctactc | tctgaagcag | 1740 |
| atcccagcca | atacattctt | caacgagatg | aagaaggaga | ggtcaggctc | tccagtgctg | 1800 |
| gagattgatc | acatcctgcc | atacagccag | agcttcatcg | acagctacca | caacaaggtg | 1860 |
| ctggtgtacg | gcgatgagaa | ccagaagaag | ggcaatcgca | tcccatacac | atacttcctg | 1920 |

| | |
|---|---|
| gagggcaaca aggattggga gagcttcgag agctacgtga ggctgaacag cttcttcagc | 1980 |
| aagaagaaga ggggctacct gctgaagaag gcctacctgc aagggagag caacatgatc | 2040 |
| aaggagaggc acctaaacga tacaaggtac gccagcagct acctgaagaa cttcatcgag | 2100 |
| aagaacctga agttcaagga ggtggagggc agcacccgta agaagcacgt ccagaccgtg | 2160 |
| aacggcatca tcacagccca cctgaggaag aggtggggcc tggagaagga taggcaggag | 2220 |
| acatacctgc atcacgccat ggatgccatc atcgtggctt gcacagatca ccacatggtg | 2280 |
| acaaaggtga cagagtacta ccagatcaag gagagcaaca agtcaatccg caagccatac | 2340 |
| ttcccactgc catgggtggg cttcaggag gagatcctgt ctcacctggc caggcagcca | 2400 |
| atcgccagga agatctctga ggagctgaag atcggctacc agtctttcga ttacatcctg | 2460 |
| gtgtctagga tgccaaagag gtctgtgaca ggcgccgccc acgagcagac aatcatgaag | 2520 |
| aagggcggca tcgataagaa gggcaagaca atcatcatca gagggtgta cctgaaggat | 2580 |
| atcaagttcg atgagaacgg cgatttcaag atggtgggca aggagcagga tctagccaca | 2640 |
| tacgaggcca tcaagcagag gtacatcgag tacggcaagg agtctaagaa ggccttcgag | 2700 |
| acaccactgt acaagccatc taagaagggc aagggcaacc tgatcaagaa gatcaaggtg | 2760 |
| gaggttcaga ccaagagctt cgtgagggag gtgaatggcg cgtggcccca gaatggcgat | 2820 |
| ctggtgaggg tggatctgtt cgagaaggat aacaggtact acatgatccc gatctacgtg | 2880 |
| atggatacag tgcacagcga gctgccaaac aaggccgtga catcttctaa gggctacgag | 2940 |
| cagtggctaa ccatcgacaa cagcttcacc ttcaagttca gcctgtaccc atacgacctg | 3000 |
| gtgaggctgg tgaagggcaa tgaggacagg ttcctgtact tcagcaccct ggacatcaac | 3060 |
| agcgacaggc tgaacttcaa ggacgtgaac aagccatcta gcaggccga gaacaggtac | 3120 |
| agcctgaaga ccatcgagaa cctggagaag tacgaggtgg gcgtgctggg cgatctgagg | 3180 |
| ttcgtgaggc aggagatcag gaagaatttc | 3210 |

<210> SEQ ID NO 171
<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG07433.1 Soy optimized"

<400> SEQUENCE: 171

| | |
|---|---|
| atgagagagc tagattacag gatcggactc gatatcggaa ctaattcaat ggatggggc | 60 |
| gtgattgagc tttcctggaa taaagatagg gagcgttatg aaaaggttag gattgtggat | 120 |
| cagggagtta ggatgtttga tagagctgag atgcctaaga ctggagcttc attagctgaa | 180 |
| ccaagaagga ttgctagatc tagcaggagg agattaaaca ggaagtctca gcgcaagaag | 240 |
| aatataagga accttcttgt tcagcacgga gttattactc aggaggagct tgattctctc | 300 |
| taccctctct ccaagaaatc aatggatatc tggggaatta ggcttgatgg actcgatcgc | 360 |
| ctattaaacc attttgagtg ggctaggctt ctaatacacc ttgctcaaag aaggggcttc | 420 |
| aaatcaaacc gcaagtccga attaaaggat actgagactg gaaaggtgct ttcaagcatc | 480 |
| cagctcaatg aaaagaggct ttctttgtat aggactgttg gggagatgtg gatgaaagat | 540 |
| cccgacttct caaaatacga taggaagagg aactctccta cgagtacgt gttttctgtt | 600 |

```
tctagagctg agcttgagaa ggagattgtg actttgtttg ctgctcaaag gaggttccaa    660
tctccttacg cttctaagga tcttcaagag acctaccttc agatttggac tcatcagctt    720 cctttttgctt ccgggaacgc tattctcaat aaagtgggat actgctcctt attaaaggga   780
aaggagagaa ggattcctaa ggccacctat acattccagt acttctctgc tcttgatcaa    840
gtgaatagaa ctaggcttgg acctgatttc cagccttttta ctaaggagca gcgcgagatc   900
atcctcaata atatgttcca gaggaccgac tactataaaa agaagaccat tcccgaggtg    960
acctactacg atataagaaa gtggcttgag cttgatgaaa ccattcagtt caagggatta   1020
aactacgacc ccaacgagga gctgaagaaa atagagaaga agcccttcat aaacctcaag   1080
gccttctacg aaatcaacaa ggtggtggct aactactctg agcgaaccaa tgaaaccttc   1140
tctaccctcg attacgatgg aattggatac gctcttaccg tgtataaaac cgacaaggat   1200
ataaggtcct acctcaaatc aagccataat ctccctaaga ggtgctacga cgatcaatta   1260
attgaggagc ttctctccct ctcctatact aagttcgggc acctctctct taaggcaatc   1320
aaccatgttc taagcattat gcagaagggg aacacatata aggaggctgt tgatcagctt   1380
ggatacgata cttctggact taagaaggag aagaggtcta agttcctccc tcctatttct   1440
gatgagatta ccaaccctat tgtgaagaga gctttgactc aagctaggaa ggtggtgaat   1500
gctattatta ggaggcatgg atcctcctcat tctgtgcata ttgagcttgc tagggagctt   1560
tcaaagaatc acgatgagag gactaagatt gtttctgctc aggacgagaa ctacaagaag   1620 aacaagggg ctatttctat tctctctgag cacggaattc ttaaccctac cggatacgat   1680
attgtgaggt ataagttgtg gaaggagcaa ggagagagat gcgcttactc tcttaaggaa   1740
attcctgctg ataccttctt caacgagctt aagaaggaaa ggaacggtgc tcctattcta   1800
gaggtggatc acattcttcc ttactcccag tccttcattg attcttacca taacaaggtg   1860
cttgtgtatt ccgatgagaa caggaagaag ggaaacagga ttccttacac ctacttcctt   1920
gagactaata aggattggga ggcttttgag aggtacgtga ggtctaacaa gttcttctct   1980
aagaagaaga gggagtacct tcttaagagg gcttatcttc ctagggagtc agagcttatt   2040
aaggagaggc atcttaacga taccaggtac gcttctacct tcctcaagaa cttcattgag   2100
cagaaccttc aattcaagga agctgaggat aatcctagaa agaggagggt tcagactgtg   2160
aacggagtta ttactgctca ttttagaaag aggtggggac ttgagaagga taggcaagag   2220
acttaccttc atcacgctat ggatgctatt attgtggctt gcactgatca tcatatggtg   2280
actagggtta ccgagtacta ccagatcaag gagtcaaaca agtctgtgaa gaagccttat   2340
tttcctatgc cttgggaagg attcagggat gagcttcttt ctcatcttgc ttctcagcct   2400
atcgctaaga agatttctga agagcttaag gctggatacc agtcccttga ttacatttttc   2460 gtgtctagaa tgcctaagag gtctattact ggagctgctc acaagcagac tattatgagg   2520 aaggaggaa ttgataagaa ggggaagacc atcattattg agaggctcca cctcaaggat   2580
atcaagttcg atgagaacgg agatttcaag atggttggaa aggagcagga tatggctact   2640
tacgaggcta ttaagcagag atatctagag cacggaaaga actctaagaa ggctttcgag   2700
actcctcttt acaagccttc taagaaggga accggaaacc ttattaagag agttaaggtt   2760
gagggacagg ctaagtcttt cgttagagag gttaatggag gagttgctca gaatggagat   2820
cttgtgaggg ttgatctttt cgagaaggac gataagtact acatggtgcc tatctacgtt   2880
cctgatactg tttgttccga gcttcctaag aaggttgttg cttcttctaa gggatacgag   2940
caatggctta cccttgataa ctctttcacc ttcaagttct ctctctaccc ttacgatctt   3000
```

| | |
|---|---|
| gttaggctag ttaagggaga tgaggatagg ttcctttact tcgggaccct cgatattgat | 3060 |
| tctgataggc tcaacttcaa ggatgtgaac aagccttcta agaagaacga gtacaggtac | 3120 |
| tctctcaaga ccattgagga tcttgagaag tacgaagtgg gagttcttgg agatcttaga | 3180 |
| cttgttagaa aggagactag gaggaacttc cac | 3213 |

```
<210> SEQ ID NO 172
<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG07433.1 Corn optimized"

<400> SEQUENCE: 172
```

| | |
|---|---|
| atgcgcgagc tagattacag gatcggcctg gatatcggca ctaactcaat cggctggggc | 60 |
| gtgatcgagc tgagctggaa taaagatcgc gagcgctatg aaaaggtgcg catcgtggat | 120 |
| cagggcgtta ggatgttcga tagggccgag atgccaaaga caggcgcctc actggccgaa | 180 |
| ccaaggagga tagccaggtc ttctaggagg agattaaaca ggaagtctca gcgcaagaaa | 240 |
| aatatcagga acctgctggt tcagcacgga gtgatcacac aggaggagct ggattctctg | 300 |
| tacccactga gcaagaaaag catggacatc tggggcatta ggctagatgg cctggaccgc | 360 |
| ctattaaacc acttcgagtg ggcccgccta ttaattcacc tggcccagag gaggggcttc | 420 |
| aaatcaaata ggaagagcga attaaaggac accgagacag gcaaggtgct gtcaagcatc | 480 |
| cagctgaatg aaaagcgcct gagcctgtac aggacagtgg cgagatgtg gatgaaagac | 540 |
| ccggacttct caaaatacga ccgcaagcgc aacagcccga acgagtacgt gttctctgtg | 600 |
| tctagggccg agctggagaa ggagatcgtg acactgttcg ccgctcagag gaggttccag | 660 |
| tctccatacg cctctaagga tctgcaagag acatacctgc agatctggac acaccagctg | 720 |
| ccattcgcct ctggcaatgc catcctgaat aaagtgggct actgctctct attaaagggc | 780 |
| aaggagagga ggattccaaa ggccacctat acattccagt acttcagcgc cctggaccag | 840 |
| gtgaatagga caaggctggg cccagatttc cagccattca caaggagca gcgcgagatc | 900 |
| atcctgaata atatgttcca gcgcaccgac tactataaaa agaagaccat cccggaggtg | 960 |
| acatactacg atataaggaa gtggctggag ctggatgaaa ccatccagtt caagggatta | 1020 |
| aactacgacc cgaacgagga gctgaagaaa atagagaaga agccgttcat aaacctgaag | 1080 |
| gccttctacg aaatcaacaa ggtggtggcc aactacagcg agcgaaccaa cgagaccttc | 1140 |
| agcaccctgg actacgacgg catcggctac gccctgaccg tgtataaaac cgacaaggat | 1200 |
| ataaggagct acctgaaatc aagccacaac ctgccgaagc gctgctacga cgaccaatta | 1260 |
| atcgaggagc tgctgagcct gagctatact aagttcggcc acctgagcct gaaggcaatc | 1320 |
| aaccacgtgc taagcatcat gcagaagggc aatacataca aggaggccgt ggaccagctg | 1380 |
| ggctacgaca ccagcggcct gaagaaggag aagcgcagca gttcctgcc gccgatcagc | 1440 |
| gacgagatca ccaacccgat cgtgaagcgc gccctgaccc aggccaggaa ggtggtgaac | 1500 |
| gccatcatca ggaggcacgg ctctccacat agcgtgcaca tcgagctggc cagggagctg | 1560 |
| tctaagaatc acgatgagag gacaaagatc gtgtcagccc aggacgagaa ctacaagaag | 1620 |
| aataagggcg ccatctctat cctgtctgag cacggcatcc tgaacccaac aggctacgac | 1680 |

| | | | | |
|---|---|---|---|---|
| atcgtgaggt | acaagctgtg | gaaggagcag | ggcgagaggt | gcgcctactc tctgaaggag | 1740 |
| atcccagccg | atacattctt | caatgagctg | aagaaggaga | ggaatggcgc cccaatcctg | 1800 |
| gaggtggatc | acatcctgcc | atactctcag | agcttcatcg | attcatacca caacaaggtg | 1860 |
| ctggtgtaca | gcgacgagaa | caggaagaag | ggcaatcgca | tcccatacac atacttcctg | 1920 |
| gagaccaaca | aggattggga | ggccttcgag | aggtacgtgc | gcagcaacaa gttcttcagc | 1980 |
| aagaagaagc | gcgagtacct | gctgaagagg | gcctacctgc | ctagggagtc tgagctgatc | 2040 |
| aaggagaggc | acctgaatga | tacaaggtac | gccagcacct | tcctgaagaa cttcatcgag | 2100 |
| cagaacctac | agttcaagga | ggccgaggat | aacccaagga | agaggagggt tcagacagtg | 2160 |
| aatggcgtga | tcacagccca | cttcaggaag | aggtggggcc | tggagaagga taggcaggag | 2220 |
| acatacctgc | atcacgccat | ggatgccatc | atcgtggctt | gcacagatca ccacatggtg | 2280 |
| acaagggtga | cagagtacta | ccagatcaag | gagagcaaca | gagcgtgaa gaagccatac | 2340 |
| ttcccaatgc | catgggaggg | cttcaggat | gagctactgt | ctcacctggc ctctcagcca | 2400 |
| atcgccaaga | agatctctga | ggagctgaag | gccggctacc | agtctctgga ttacatcttc | 2460 |
| gtgtctagga | tgccaaagag | gtctatcaca | ggcgccgccc | acaagcagac aatcatgagg | 2520 |
| aagggcggca | tcgataagaa | gggcaagaca | atcatcatcg | agaggctgca tctgaaggac | 2580 |
| atcaagttcg | atgagaacgg | cgatttcaag | atggtgggca | aggagcagga tatggccaca | 2640 |
| tacgaggcca | tcaagcagcg | ctacctagag | cacggcaaga | actctaagaa ggccttcgag | 2700 |
| acaccactgt | acaagccatc | taagaagggc | accggcaatc | tgatcaagag ggtgaaggtg | 2760 |
| gagggccagg | ccaagtcttt | cgtgagggag | gtgaatggcg | gcgtggccca gaatggcgat | 2820 |
| ctggtgaggg | tggatctgtt | cgagaaggat | gataagtact | acatggtgcc aatctacgtg | 2880 |
| ccagatacag | tgtgctctga | gctgccaaag | aaggtggtgg | cctcttctaa gggctacgag | 2940 |
| cagtggctaa | cactggataa | cagcttcaca | ttcaagttca | gcctgtaccc atacgatctg | 3000 |
| gtgaggctgg | tgaagggcga | tgaggatagg | ttcctgtact | tcggcacact ggatatcgat | 3060 |
| agcgacaggc | tgaacttcaa | ggacgtgaac | aagccgagca | agaagaacga gtaccgctac | 3120 |
| agcctgaaga | caatcgagga | cctggagaag | tacgaggtgg | gcgtgctggg cgatctgagg | 3180 |
| ctggtgagga | aggagacaag | gaggaatttc | cac | | 3213 |

<210> SEQ ID NO 173
<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence:
   Synthetic polynucleotide"
<220> FEATURE:
<221> NAME/KEY: source
<223> OTHER INFORMATION: /note="APG07513.1 Soy optimized"

<400> SEQUENCE: 173

| | | | | |
|---|---|---|---|---|
| atgagagagc | tagattacag | gatcggactc | gatatcggaa | ctaattcaat tggatggggc | 60 |
| gtgattgagc | tttcctggaa | taaagatcgc | gagcaatatg | aaaagaccag gattgtggat | 120 |
| aagggagtga | ggatgttcga | taaggctgaa | attcctaaga | ctggagcttc tcttgctgaa | 180 |
| ccaagaagaa | ttgctagatc | tagcaggagg | agattaaaca | ggaagtctca gcgcaagaag | 240 |
| gatataagga | acctcctcgt | tcagcatgaa | atcattttccc | agaaggaatt aacctctctc | 300 |
| taccctctct | ccaaatcaag | catggacatc | tgggatataa | ggcttgatgg actcgatagg | 360 |

```
cttcttgata gatttgagtg ggctaggctt ctaatacacc ttgctcaaag aagggcttc      420 aaatcaaacc gcaagtccga attaaaggat gttgagactg gaaaggtgct ttcaagcatc    480
caggtgaatg aaaagaggct ttctttgtat aggactgttg gggagatgtg gatgaaaaac    540
gccgattgct caaaatatgg aaagaggagg aactctccta acgagtacgt gttttctgtt    600
tctagggctg atcttgagaa ggagattgtg actcttttg aggctcagag gaagttccac     660
tcttcttacg cttctgtgga tctccaaaag acatacattc agatttgggc tcatcagctt    720 cctttgctt ctggaaacgc cattgtgaat aaagtgggat actgctccct attaaaggga     780
aaggagaaga gagtgcctaa ggctacctat acattccagt acttcaatac cctcgatcaa    840
atcaacagaa ctaggcttgg acctaacttc cagccttta ctaaggagca gagggatata     900
atcctcgata aaatgttcca gcgcaccgac tactataaaa agaagaccat ccccgaggtg    960
acctactacg atataagaaa gtggcttgct ctcgatgaaa ccattcagtt caagggacta   1020
acttatgacc ccaacgagga gctgaagaaa atagagatga aacccttcat aaacctcaag   1080
cccttctacg aaatcaagaa ggtggtaacc aactacgcca agaaaaccaa cgaggtgttc   1140
tctgctcttg attacgatac tgtggcttac gctcttaccg tgtataaaac cgacaaggat   1200
ataaggtctt acctcaagcg ctccaataat ctctctaaga ggtgctacga cgatcaatta   1260
attgaggagc ttctcaccct ctcctatact aagttcggac acctctcttt caaggcaatc   1320
aaccatgtgc ttccaataat gcaagaggga agaacttacc aagaggcaat acaccagctt   1380
ggatacgata caaccaacct caagaaggag aatagaagca tgttcctccc aatcatccct   1440
gatgaaataa ccaaccctat tgtgaagaga gctttgactc aagctaggaa ggtggtgaat   1500
gcaataatta ggaggtacgg atcacctaac tctgtgcata ttgagcttgc cagggaatta   1560
agcaagtctc atgatgagag gaagaagatt atgactgctc acgacgagaa ctacaagaag   1620
aacaagggag ctgtgtccat tctcattgat aacggaattc ttaaccctac cggatacgat   1680
attgtgaggt acaagttgtg gaaggagcaa ggagagagat gcgcttactc tcttaagaag   1740
attcctgcta acaccttctt caacgagctt aagaaggaaa gatctggacc tcctgttctt   1800
gaggtggatc acattctacc ttactcccag tccttcattg attcttacca taacaaggtg   1860
cttgtttacg gagatgagaa ccaaaagaag gggaacagga ttccttacac tttcttctct   1920
gaagaagata aggagtggga gtcttttcgag tcttacgtga ggtccaactc cttcttctct   1980
aagaagaaga ggggataccct tcttaagaag gcttatcttc ctagggagtc taaccttatt   2040
aaggagaggc accttaacga taccaggtac gcttcatctt acctcaagaa cttcatcgag   2100
aagaacctta agttcaagga ggctgtggga attactagga agaagtacgt tcagactgtg   2160
aacggagtga ttactgctca tcttagaaag agatggggac ttgagaagga taggcaagag   2220
acttaccttc atcacgctat ggatgctatt attgtggctt gcactgatca ccatatggtg   2280
actaaggtta ccgagtacta ccaaattaag gaggggaaca agtccatcaa gaagccttat   2340
tttcctctac cttggatggg attcagggag gagattcttt ctcatcttga gtctcaacct   2400
atcgctagaa agatttccga ggagcttaag attggatacc agtcccctga ttacattctt   2460
gtgtctagaa tgcctaagag gtctgttact ggatctgctc atgatcagac tgtgatgaag   2520
aagggggata ttgataagaa ggggaagacc atcattatta agagggtgca cctcaaggac   2580
atcaagttcg atgagaacgg agatttcaag atggttggaa aggagcagga tctagctact   2640
tacgaggcta ttaagcagag gtatcttgag tataggaagg agtctaagaa ggctttcgag   2700
```

-continued

| | |
|---|---|
| actcctctttt acaagccttc taagaaggga aaggggaacc tcatcaagaa gattaaggtt | 2760 |
| gaggttcaga ctaagtcttt cgtgaggag attaatggag gagttgctca gaatggagat | 2820 |
| cttgtgaggg ttgatctttt cgagaaggac aacaggtact acatggtgcc tatctacgtt | 2880 |
| gttgatactg ttaggtctga gctacctaac aaggctgtta cttcttctaa gggatacgag | 2940 |
| cagtggctct ctattgataa ctctttcacc ttcaagttct ctctctaccc ttacgatctt | 3000 |
| gttaggcttg ttaagggaga tgaggatagg ttcctctact tctccaccct cgatattaac | 3060 |
| tctgataggc tcaacttcaa ggatgtgaac aagccttcta agcaagctga gtacaggtac | 3120 |
| tctcttaaga ccattgagaa ccttgagaag tacgagattg gagttcttgg agatctaagg | 3180 |
| cttgttaggc aggagaccag gaagattttc aag | 3213 |

<210> SEQ ID NO 174
<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: source
<223> OTHER INFORMATION: /note="APG07513.1 Corn optimized"

<400> SEQUENCE: 174

| | |
|---|---|
| atgcgcgagc tagattacag gatcggcctg gatatcggca ctaactcaat cggctggggc | 60 |
| gtgatcgagc tgagctggaa taaagatcgc gagcagtatg aaaagaccag gatcgtggac | 120 |
| aagggcgtga ggatgttcga taaggccgag atcccaaaga caggcgcctc tctggccgaa | 180 |
| ccaaggagga tcgccaggtc ttctaggagg agattaaaca ggaagtctca gcgcaagaag | 240 |
| gatataagga acctgctggt ccagcatgaa atcatcagcc agaaggagct gacaagcctg | 300 |
| tacccgctga gcaagtcaag catggacatc tgggatataa ggctggatgg cctggatagg | 360 |
| ctgctggata ggttcgagtg gccaggctg ctgatacatc tggcccagag gaggggcttc | 420 |
| aaatcaaatc gcaagagcga attaaaggac gtggagacag gcaaggtgct gtcaagcatt | 480 |
| caggtgaatg aaaagaggct gagcctgtac aggacagtgg gcgagatgtg gatgaaaaac | 540 |
| gccgactgct caaaatacgg caagcgccgc aacagcccaa acgagtacgt gttctctgtg | 600 |
| tctagggccg atctggagaa ggagatcgtg acactgttcg aggcccagag gaagttccac | 660 |
| tcttcttacg cctctgtgga cctgcagaag acatacatcc agatctgggc ccaccagctg | 720 |
| ccattcgcct ctggcaatgc catcgtgaat aaagtgggct actgctctct attaaagggc | 780 |
| aaggagaaga gggtgccaaa ggccaccctat acattccagt acttcaatac cctggaccaa | 840 |
| atcaacagga cccgcctggg cccaaacttc cagccattca caaggagca gcgcgatata | 900 |
| atcctggata aaatgttcca gcgcaccgac tactataaaa agaagaccat cccggaggtg | 960 |
| acatactacg atataaggaa gtggctgcc ctggatgaaa ccatccagtt caagggccta | 1020 |
| acctacgacc cgaacgagga gctgaagaag atcgagatga accgttcat aaacctgaag | 1080 |
| ccgttctacg aaatcaagaa ggtggtaacc aactacgcca gaaaaccaa cgaggtgttc | 1140 |
| agcgccctgg actacgacac cgtggcctac gccctgaccg tgtataaaac cgacaaggat | 1200 |
| ataaggagct acctgaagcg cagcaataat ctgagcaagc gctgctacga cgaccaatta | 1260 |
| atcgaggagc tgctgaccct gagctatact aagttcggcc acctgagctt caaggcaatc | 1320 |
| aaccacgtgc tgccaataat gcaggagggc cgcacctacc aggaggcaat acaccagctg | 1380 |

```
ggctacgaca caaccaacct gaagaaggag aaccgaagca tgttcctgcc aataatcccg    1440
gacgagataa ccaacccgat cgtgaagcgc gccctgaccc aggcccgcaa ggtggtgaac    1500
gcaataatcc gccgctacgg ctcaccgaac agcgtgcaca ttgagctggc ccgcgaatta    1560
agcaagagcc acgacgagcg caagaagatc atgaccgccc acgatgaaaa ctacaagaaa    1620
aataagggcg ccgtgagcat cctgatcgac aacggcatcc tgaacccgac cggctacgac    1680
atcgtgcgct acaagctgtg gaaggagcag ggcgagaggt gcgcctactc tctgaagaag    1740
atcccagcca acaccttctt caacgagctg aagaaggaga ggtctggccc accagtgctg    1800
gaggtggatc acatcctgcc atactcacag agcttcatcg atagctacca caacaaggtg    1860
ctggtgtacg gcgatgagaa ccagaagaag ggcaatcgca tcccatacac attcttcagc    1920
gaggaggata aggagtggga gagcttcgag agctacgtga ggagcaacag cttcttcagc    1980
aagaagaaga ggggctacct gctgaagaag gcctacctgc aagggagtc taacctgatc    2040 aaggagaggc acctgaacga tacaaggtac gccagcagct acctaaagaa cttcatcgag    2100
aagaacctga agttcaagga ggccgtgggc atcacccgca agaagtacgt ccagacagtg    2160
aacggcgtga tcacagccca cctgaggaag aggtggggcc tggagaagga taggcaggag    2220
acatacctgc atcacgccat ggatgccatc atcgtggctt gcacagatca ccacatggtg    2280
acaaaggtga cagagtacta ccagatcaag gagggcaaca agagcatcaa gaagccatac    2340
ttcccactac catggatggg cttcagggag agatcctgt ctcacctgga gtctcagcca    2400
atcgccagga agatctctga ggagctgaag atcggctacc agtctccaga ttacatcctg    2460
gtgtctagga tgccaaagag gtctgtgaca ggctctgccc acgatcagac agtgatgaag    2520
aagggcgata tcgacaagaa gggcaagacc atcatcatca gagggtgca cctgaaggac    2580 atcaagttcg acgagaacgg cgacttcaag atggtgggca aggagcagga tctagccaca    2640
tacgaggcca tcaagcagcg ctacctggag tacaggaagg agtctaagaa ggccttcgag    2700
acaccactgt acaagccatc taagaaggc aagggcaacc tgatcaagaa gatcaaggtg    2760
gaggtccaga ccaagagctt cgtgagggag atcaatggcg gcgtggccca gaatggcgat    2820
ctggtgaggg tggatctgtt cgagaaggat aacaggtact acatggtgcc aatctacgtg    2880
gtggatacag tgaggagcga gctaccaaac aaggccgtga catcttctaa gggctacgag    2940
cagtggctga gcatcgacaa cagcttcacc ttcaagttca gcctgtaccc atacgatctg    3000
gtgaggctgg tgaagggcga tgaggacagg ttcctgtact tcagcacact ggacatcaac    3060
agcgacaggc tgaacttcaa ggacgtgaac aagccatcta gcaggccgga gtacaggtac    3120
agcctgaaga ccatcgagaa cctggagaag tacgagatcg gcgtgctggg cgatctaagg    3180
ctggtgaggc aggagacaag gaagatcttc aag                                3213
```

<210> SEQ ID NO 175
<211> LENGTH: 3216
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG08290.1 Soy optimized"

<400> SEQUENCE: 175

```
atgtctgagc tagattacag gatcggactc gatatcggaa ctaattcaat tggatgggga    60
```

```
gtgattgagc ttttctggaa taaagatcgc gagcgctatg aaaaggttag gattgtggat    120
aagggagtga ggatgttcga taaggccgag attcctaata aaggagcttc acttgctgaa    180
ccaagaagga ttgctagatc tagcaggagg agattaaaca ggaagtctca gaggaagaag    240
gagattagga accttcttgt tcagcacgga atgattactc aggaggagct tgatcttctc    300
taccctctct ccaagaaatc aatcgatatc tgggatataa ggcttgatgg actcgatagg    360
ctattaaacc atcttgagtg ggctaggctt ctaatacacc ttgctcaaag aaggggcttc    420
aaatcaaacc gcaagtccga attaaaggat gctgagactg gaaaggttct ttcaagcatc    480
caggtgaatg aaaagaggct tttcttgtat aggactgtgg gcgagatgtg gataaaagat    540
gccgagttct caaaatatga taggaggagg aactctccta acgagtacgt gttttctgtt    600
tctagggctg atcttgagaa ggagattgtg actttgtttg aggctcaacg caagttccaa    660
tcaagctacg cttctaagaa ccttcaagag acctaccttc aaatttgggc tcatcagctt    720
ccttttgctt ccgggaacgc tattctcaat aaagtgggat actgctcctt attaaaggga    780
aaggagagaa ggattcctaa ggccacctat acattccagt acttctctgc tcttgatcaa    840
gtgaatagaa ctaggcttgg acctgatttc caacctttca ctcaggagca gaaggaaata    900
atcctcgata aaatgttcca gcgcaccgac tactataaaa agaagaccat ccccgaggtg    960
tcctactacg atataagaaa gtggcttgag cttgatgaaa ccattcagtt caagggatta   1020
aactacgacc ccaacgagga gctgaagaaa atagagaaga agcccttcat aaacctcaag   1080
gccttctacg aaatcaagaa ggtggttgct aactacgctg aacgaaccaa cgaagcattc   1140
tctaccctcg attacgatgc tattgcttac gctcttaccg tgtataaaac cgacaaggat   1200
ataaggtcct acctcaagaa atcaaacaac ctctccaaga ggtgctacga cgatcaatta   1260
atcgaggagc ttttcacccct ctcctatact aagttcggac acctctcttt caaggcaatc   1320
aaccatgtgc ttcctattat gcaagaggga agaacttacc aagaggctat tcatcagctt   1380
ggatacgata ccaccaacct taagaaggag aacaggtcta tgttcctccc tctcattcct   1440
gatgagatta ctaaccctat tgtgaagagg gctattactc aagctaggaa ggtggtgaat   1500
gctattatta ggaggtacgg atcacctaac tctgtgcata ttgagcttgc tagggagctt   1560
tctaagtctc atgatgagag gaagaagatt atgactgctc acgacgagaa ctacaagaag   1620 aacaagggggg ctatttccat tctcattgag aacggaattc ttaacccctac cggatacgat   1680 attgtgaggt acaagttgtg gaaggagcaa ggagagagat gcgcttactc tcttaaggaa   1740
attcctcctg ataccttctt caacgagctt aagaaggaga ggaacggatc acctattctt   1800
gaggtggatc acattcttcc ttactcccag tccttcattg attcttacca taacaaggtg   1860
cttgtgtatt ccgatgagaa caggaacaag ggaaacagga ttccttacac ctacttcctt   1920
gagactaata aggattggga ggcttttgag aggtatgtga ggtctaacaa gctcttctct   1980
aagaagaaga gggagtacct ccttaagaag acttaccttc ctagggagtc tgagcttatt   2040
aaggagaggc atctaaacga taccaggtac gcttctacct tcctcaagaa cttcattgag   2100
cagaaccttc aattcaagga ggttgaggtt aaccttagga agaagagggt tcagactgtg   2160
aacggagtta ttactgctca tcttagaaag agatggggac ttgagaagaa caggcaagag   2220
acttaccttc atcacgctat ggatgctatt attgtggctt gcactgatca tcacatggtg   2280
actaggatta ccgagtacta ccagattaag gagtcaaaca agtctgtgaa gaagccttat   2340
tttcctatgc cttgggaggg attcaggat gagcttcttt ctcatcttgc ttctcagcct   2400
atcgctaaga agatttctga agagcttaag gctggatacc agtcctctga ttacatttc   2460
```

```
gtgtctagaa tgcctaagag gtctgttact ggagctgctc atgatcaaac tattaggagg    2520
aagggaggaa ttgataagaa ggggaagacc atcattatta agagggtgag gctaaaggac    2580
atcaagttcg atgagaacgg ggatttcaag atggttggaa aggagcagga tcttgctact    2640
tacgaggcta ttaagcagag atatcttgag cacaggaaga actctaagaa ggctttcgag    2700
actcctcttt acaagccttc taagaaggga accggaaacc ttatcaagag agttaagatt    2760
gagggacaga ctaaggcttt cgttagagag gttaatggag gagttgctca gaactctgat    2820
cttgtgaggg ttgatctatt cgagaaggac gataagtact acatggtgcc tatctacgtt    2880
cctgatactg tttgttccga gcttcctaag aaggttgtta agtctggaaa gggatacgag    2940
caatggctta cccttgataa ctctttcacc ttcaagtctt ctctctaccc ttacgatctt    3000
gttaggcttg ttaagggaaa cgaggatagg ttccttact tcgggaccct cgatattgat    3060
tctgataggc tcaacttcaa ggatgtgaac aagccttcaa agcaaaacga gtacaggtac    3120
tctctcaaga ccattgagaa ccttgagaag tacgaagtgg gagttcttgg agatcttagg    3180
cttgttaagc aagagaccag gaggattttc aatagg                              3216

<210> SEQ ID NO 176
<211> LENGTH: 3216
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG08290.1 Corn optimized"

<400> SEQUENCE: 176
atgtcagagc tggactacag gatcggcctg gacataggca ctaattcaat cggctggggc      60
gtgatcgagc tgttctggaa taaagaccgc gagcgctatg aaaaggtgcg catcgtggac     120
aagggcgtta ggatgttcga taaggccgag atcccgaata aaggcgcctc actagccgaa     180
ccaaggagga tcgccaggtc ttctaggagg agattaaaca ggaagtctca gaggaagaag     240
gagatcagga acctgctggt ccagcacggc atgatcacac aggaggagct ggatctgctg     300
tacccactga gcaagaaaag cattgacatc tgggacatca ggctagatgg cctggacagg     360
ctgctgaatc acctggagtg ggccaggctg ctgatacatc tggcccagag gaggggcttc     420
aaatcaaatc gcaagtctga attaaaggat gccgagacag gcaaggtgct gtcaagcatc     480
caggtgaatg aaaagaggct gttcctctac cgcacagtgg gcgagatgtg gataaaagac     540
gccgagttca gcaagtacga caggaggagg aacagcccaa cgagtacgt gttctctgtg     600 tcaagggccg atctggagaa ggagatcgtg acactgttg aggctcagcg caagttccaa     660
tcaagctacg ccagcaagaa cctgcaagag acctacctgc agatctgggc ccaccagctg     720
ccattcgcta gcggcaatgc catcctgaat aaagtgggct actgctctct attaaagggc     780
aaggagagga ggattccaaa ggccaccat acattccagt acttcagcgc cctggaccag     840
gtgaatagga caaggctggg cccagatttc cagccattca cacaggagca gaaggaaata     900
atcctggata aaatgttcca gcgcaccgac tactataaaa agaagaccat cccggaggtg     960
tcatactacg atataaggaa gtggctggag ctggatgaaa ccatccagtt caagggatta    1020
aactacgacc gaaacgagga gctgaagaaa atagagaaga agccgttcat aaaacctgaag    1080 gccttctacg aaatcaagaa ggtggtggcc aactacgccg agcgaaccaa cgaagcattc    1140
```

```
agcaccctgg actacgacgc catcgcctac gccctgaccg tgtataaaac cgacaaggat    1200
ataaggtcat acctgaagaa atcaaacaac ctgagcaagc gctgctacga cgaccaatta    1260
atcgaggagc tgttcaccct gagctatact aagttcggcc acctgagctt caaggcaatc    1320
aaccacgtgc tgccaataat gcaggagggc cgcacctacc aggaggcaat acaccagctg    1380
ggctacgaca ccaccaacct gaagaaggag aaccgcagca tgttcctgcc gctaatcccg    1440
gacgagatca ccaacccgat cgtgaagcgc gccatcaccc aggctaggaa ggtggtgaac    1500
gccatcatcc gccgctacgg cagcccgaac agcgtgcaca tcgagctggc ccgcgagctg    1560
agcaagagcc acgacgagcg caagaagatc atgacagccc acgacgagaa ctacaagaag    1620
aacaagggcg ccatctcaat cctgatcgag aacggcatcc tgaacccaac cggctatgac    1680
atcgtgcgct acaagctgtg gaaggagcag ggcgagaggt gcgcctactc tctgaaggag    1740
atcccaccag atacattctt caacgagctg aagaaggaga ggaatggctc tccaatcctg    1800
gaggtggatc acatcctgcc atacagccag tcattcatcg acagctacca caacaaggtg    1860
ctggtgtaca gcgatgagaa caggaacaag ggcaaccgca tcccgtacac atacttcctg    1920
gagaccaaca aggattggga ggccttcgag aggtacgtga ggagcaacaa gctgttcagc    1980
aagaagaagc gcgagtacct gctgaagaag acctacctgc aagggagtc agagctgatc    2040 aaggagaggc acctgaacga tacaaggtac gctagcacct tcctgaagaa cttcatcgag    2100
cagaacctgc agttcaagga ggtggaggtg aacctgagga gaagcgcgt tcagacagtg    2160 aacggcgtga tcacagccca cctgaggaag aggtggggcc tggagaagaa taggcaggag    2220
acatacctac accacgccat ggatgccatc atcgtggctt gcacagatca ccacatggtg    2280
acaaggatca cagagtacta ccagatcaag gagagcaaca gagcgtgaa gaagccatac    2340 ttcccaatgc catgggaggg cttcagggat gagctgctgt ctcacctggc ctctcagcca    2400
atcgccaaga gatctcaga ggagctgaag gccggctacc agtcttctga ttacatcttc    2460
gtgtctagga tgccaaagag gtctgtgaca ggcgccgccc acgatcagac aatcaggagg    2520
aagggcggca tcgataagaa gggcaagaca atcatcatca gagggtgag gctgaaggat    2580 atcaagttcg atgagaacgg cgatttcaag atggtgggca aggagcagga tctagccaca    2640
tacgaggcca tcaagcagcg ctacctggag cacaggaaga actctaagaa ggccttcgag    2700
acaccactgt acaagccatc taagaagggc accggcaatc tgatcaagag ggtgaagatc    2760
gagggccaga caaaggcctt cgtgagggag gtgaatggcg gcgtggccca gaattctgat    2820
ctggtgaggg tggatctatt cgagaaggac gataagtact acatggtgcc aatctacgtg    2880
ccagatacag tgtgctccga gctgccaaag aaggtggtga gtctggcaa gggctacgag    2940 cagtggctca cactggataa cagcttcaca ttcaagagca gcctgtaccc atacgatctg    3000
gtgaggctgg tgaagggcaa tgaggacagg ttcctgtact cggcacact agacatcgat    3060 agcgacaggg tgaacttcaa ggacgtgaac aagccaagca gcagaacga gtaccgctac    3120 agcctgaaga ccatcgagaa cctggagaag tacgaggtgg gcgtgctggg cgatctgagg    3180
ctggtgaagc aggagacaag gaggatcttc aatagg                              3216
```

<210> SEQ ID NO 177
<211> LENGTH: 4011
<212> TYPE: DNA
<213> ORGANISM: Artificial Sequence
<220> FEATURE:
<221> NAME/KEY: source
<223> OTHER INFORMATION: /note="Description of Artificial Sequence:

```
        Synthetic polynucleotide"
<220> FEATURE:
<221> NAME/KEY: source
<223> OTHER INFORMATION: /note="APG05459.1 Soy optimized"

<400> SEQUENCE: 177
atgaagaagg actacgtgat cggactagat attggaacta actctgtggg atgggctgtt      60
atgactgagg attaccagct agttaagaag aagatgccca tctacgggaa tacagagaag     120
aagaagatca agaagaactt ctggggagtg agactatttg aagagggtca tactgctgag     180
gataggagat aaagagaac tgctaggaga aggatttcta ggaggaggaa caggcttcgt      240
taccttcaag cattctttga agaggctatg accgctctag atgaaaattt cttcgctagg     300
cttcaggagt cttttcttgt gcctgaggat aaaaagtggc acaggcatcc tattttgct     360 aagttagagg atgaggtggc ttaccatgaa acctacccta ctatctacca ccttaggaag     420
aagttggctg attcttcaga gcaagccgac ttgagattaa tctaccttgc tcttgcccac     480
attgtaaaat atagggggaca cttccttatc gagggaaaac tctccaccga aaatatttca     540
gtgaaggagc agtttcagca gttcatgatc atctataacc aaaccttcgt gaacggagaa     600
tcaaggcttg tgtctgctcc tcttcctgag tccgtattaa ttgaggagga acttactgag     660
aaagcatcca gaaccaagaa gtctgagaag gttcttcaac agtttcctca agagaaggct     720
aacggacttt tcggacagtt cctcaaatta atggtgggga ataaagccga cttcaagaag     780 gttttttggac ttgaggagga ggccaaaata acttacgctt ctgagtctta tgaggaggat     840
cttgagggaa tactagctaa ggtgggagat gaatacagcg atgttttcct tgctgctaag     900
aacgtttacg acgctgtgga attaagcacc atactagctg actccgataa aaagtctcac     960
gccaaactct cttcaagcat gattgttagg ttcactgagc atcaggagga tcttaagaag    1020
ttcaagaggt tcattaggga gaactgccct gatgagtacg ataacctttt caagaacgag    1080
caaaaggatg gtacgctgg atacattgct catgctggaa aggtgtcaca attaaagttc     1140
taccagtacg tgaagaaaat aatccaggat atcgctggag ccgagtactt ccttgagaaa    1200
atagctcagg agaacttcct taggaagcag aggactttcg ataacggagt gattcctcac    1260
caaatacacc ttgctgagct acaggcaata attcataggc aagctgcata ctatcctttc    1320
ctcaaggaga atcaagagaa aatagagcag ctcgtgacct tcagaattcc atactacgtg    1380
ggacctcttt ctaagggaga tgcttctact tttgcttggc ttaagagaca gtcagaggaa    1440
ccaattaggc cttggaatct tcaagagact gtggatcttg atcaatctgc tactgctttc    1500
atagagagga tgaccaactt cgatacatac cttccttctg agaaggtgct ccctaagcat    1560
tctctcctct atgaaaagtt catggtgttc aacgagctaa ccaaaatatc ctacaccgac    1620 gatagggaa tcaaggctaa tttctctgga aggagaagg agaaaatatt cgactacctc     1680
ttcaagacca ggaggaaggt gaagaagaag gacataatac agttctaccg caacgaatac    1740
aacaccgaga ttgtgacctt gtcaggactt gaggaggatc aattcaacgc ttcttctct     1800 acctaccagg atctattaaa gtgcggactt actagggctg agcttgatca tcctgataat    1860
gctgagaagc tggaggacat aatcaagata ctaaccatct tcgaggatag gcaaaggatt    1920
aggacccagc tttctacttt caagggacaa ttctctgctg aggttcttaa gagttggag    1980 aggaagcatt atactggatg gggaaggctc tctaagaagc tcattaacgg aatctacgat    2040
aaggagtcag ggaagaccat cctagattac ctcattaagg atgatggagt gtctaagcac    2100
tacaacagga acttcatgca gctcattaac gattcccagc tctccttcaa gaacgctatt    2160
```

| | |
|---|---|
| caaaaggctc aatcttctga gcatgaagag actctttctg agactgttaa cgaattagct | 2220 |
| gggtcccctg ctattaagaa gggaatctac cagtctctca agattgtgga tgagcttgtg | 2280 |
| gctattatgg gatatgctcc taagaggatt gttgttgaga tggctaggga gaaccaaact | 2340 |
| acttctactg gaaagaggag gtctattcag aggctaaaga ttgttgaaaa ggctatggct | 2400 |
| gagattggat ctaaccttct taaggagcag cctactacta acgagcaact tagggatacc | 2460 |
| aggctcttcc tttactacat gcagaacgga aaggatatgt acactggaga tgagcttttct | 2520 |
| cttcataggc tctcacacta cgacatagat cacattatcc ctcagtcctt catgaaggat | 2580 |
| gattctctcg ataaccttgt gcttgtggga tctactgaga ataggggaaa gtctgatgat | 2640 |
| gttccttcta aggaggtggt taaggatatg aaggcttact gggagaaact atacgctgct | 2700 |
| ggacttattt ctcaaaggaa gttccagaga cttactaagg gagagcaagg aggacttact | 2760 |
| cttgaggata aggctcattt cattcaaagg cagcttgttg agaccaggca gattactaag | 2820 |
| aacgtggctg gaattctaga tcaaaggtac aacgctaact ctaaggagaa gaaggttcag | 2880 |
| atcattaccc tcaaggcttc tcttacctcc cagttcaggt ctattttcgg actttacaag | 2940 |
| gttagggagg tgaacgatta ccatcatgga caagatgctt accttaactg cgtggttgct | 3000 |
| actactctac ttaaggttta tcctaacctt gctcctgagt tcgtttacgg agagtatcct | 3060 |
| aagttccagg ctttcaagga gaataaggct accgctaaga ccattatcta caccaacctt | 3120 |
| atgaggttct ttactgagga tgagcctagg tttatgaagg atggagagat tctctggtca | 3180 |
| aactcctacc tcaagaacat caagaaggag cttaactacc accagatgaa cattgtgaag | 3240 |
| aaggtggagg ttcaaaaggg aggattctcc aaggagtcta ttaagcctaa gggaccttct | 3300 |
| aacaagctca ttcctgtgaa gaacggactt gatcctcaaa agtacggagg attcgattca | 3360 |
| cctgttgttg cttacactgt tcttttcact cacgaaaagg ggaagaagcc tctcattaag | 3420 |
| caggagattc tcggaattac cattatggag aagactaggt tcgagcagaa ccctattctt | 3480 |
| tttctagagg agaagggatt tcttaggcct agggttctta tgaagctccc taagtacact | 3540 |
| ctttatgagt ttcctgaggg aagaaggaga cttcttgctt ctgctaagga ggctcaaaag | 3600 |
| ggaaaccaaa tggttcttcc tgagcacctt cttactcttc tttaccatgc taagcaatgc | 3660 |
| ctacttccta accaatctga gtctcttgct tacgtagaac aacatcaacc tgagttccaa | 3720 |
| gagattcttg agagggttgt ggatttcgct gaggttcata cccttgctaa gtctaaggtt | 3780 |
| cagcagattg ttaagttgtt cgaggctaac cagactgctg atgttaagga gatcgctgct | 3840 |
| tcattcattc agcttatgca attcaatgct atgggtgctc cttctacctt caagttcttc | 3900 |
| cagaaggata tagagagggc taggtacacc tccatcaagg agattttcga tgctaccatt | 3960 |
| atctaccagt ctactactgg actttatgag actaggagga aggtggttga t | 4011 |

<210> SEQ ID NO 178
<211> LENGTH: 4011
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: source
<223> OTHER INFORMATION: /note="APG05459.1 Corn optimized"

<400> SEQUENCE: 178

| | |
|---|---|
| atgaaaaagg actacgtgat cggcctggac atcggcacta attcagtggg ctgggccgtg | 60 |

| | |
|---|---|
| atgacagagg actaccagct ggtgaagaag aagatgccta tctacggcaa cactgagaag | 120 |
| aagaagatca agaagaactt ctggggcgtg cgcctattcg aggagggcca cacagccgag | 180 |
| gaccgcagat taaagaggac agccaggagg aggatctcta ggaggaggaa taggctgcgc | 240 |
| tacctgcaag cattcttcga ggaggccatg acagccctgg atgaaaattt cttcgccagg | 300 |
| ctgcaggagt ctttcctagt gccggaggat aaaaagtggc acaggcaccc tatcttcgcc | 360 |
| aagctggagt atgaggtggc ctaccatgaa acatacccaa caatctacca cctgaggaag | 420 |
| aagctggccg attcttctga gcaggccgac ctgagattaa tctacctggc cctggcccac | 480 |
| atcgtcaaat acaggggcca cttcctgatc gagggcaaac tgagcacaga aaatatcagc | 540 |
| gtgaaggagc agttccagca gttcatgatc atctataacc aaaccttcgt gaacggcgaa | 600 |
| tcaaggctgg tgagcgcccc actgccggag agcgtattaa tcgaggagga actgaccgag | 660 |
| aaagcatccc gaaccaagaa gagcgagaag gtgctgcagc agttcccgca agagaaggct | 720 |
| aatggcctgt tcggtcagtt cctgaaactg atggtgggca ataaagccga cttcaagaag | 780 |
| gtgttcggcc tagaggagga ggccaaaata acctacgcca gcgagagcta cgaggaggac | 840 |
| ctggagggca tactagccaa ggtgggcgat gaatacagcg atgtgttcct ggccgccaag | 900 |
| aatgtgtacg atgccgtgga gctgtctaca atactagccg acagcgataa aaagagccac | 960 |
| gccaagctct cttcaagcat gatcgtgagg ttcacagagc atcaggagga cctgaagaag | 1020 |
| ttcaagcgct tcatcaggga gaactgcccg gacgagtacg acaacctgtt caagaacgag | 1080 |
| cagaaggatg gctacgccgg atacatcgcc cacgccggta aggtgtccca attaaagttc | 1140 |
| taccagtacg tgaagaaaat aatccaggac atcgccggcg ccgagtactt cctggagaaa | 1200 |
| atagcccagg agaacttcct gcgcaagcag aggacattcg acaacggcgt catcccgcac | 1260 |
| cagatacatc tggccgagct gcaggccatc atacataggc aggccgcata ctacccattc | 1320 |
| ctaaaggaga accaagagaa aatagagcag ctggtgacct ccgcatccc atactacgtg | 1380 |
| ggcccactgt ctaagggcga tgcctctaca ttcgcctggc tgaagaggca gtctgaggaa | 1440 |
| ccaatcaggc catggaatct gcaagagaca gtggatctgg atcagtctgc cacagccttc | 1500 |
| atcgagagga tgaccaactt cgatacatac ctaccaagcg agaaggtgct gccaaagcat | 1560 |
| agcctgctgt atgaaaagtt catggtgttc aacgagctaa ccaagatcag ctacaccgac | 1620 |
| gaccgcggaa tcaaggccaa cttcagcggc aaggagaagg agaaaatatt cgactacctg | 1680 |
| ttcaagaccc gccgcaaggt gaagaagaag gacataatac agttctaccg caacgaatac | 1740 |
| aacaccgaga tcgtgaccct gagcggcctt gaggaggacc agttcaacgc cagcttctca | 1800 |
| acctaccagg acctattaaa gtgcggcctg accgcgccg agctggacca cccggataac | 1860 |
| gccgagaagc tggaggacat aatcaagata ctaaccatct tcgaggaccg ccagcgcatc | 1920 |
| cgcacccaat taagcacctt caagggccag ttcagcgccg aggtattaaa gaagctggag | 1980 |
| cgcaagcatt acacaggctg gggcaggctg agcaagaagc taatcaacgg catctacgac | 2040 |
| aaggagagcg gcaagaccat ccttgactac ctgatcaagg acgatggcgt gagcaagcac | 2100 |
| tacaaccgca acttcatgca gctgatcaac gacagccagc tgagcttcaa gaacgccatc | 2160 |
| cagaaggccc agtcttctga gcacgaggag acactgtctg agacagtgaa tgagctggcc | 2220 |
| ggctcaccag ccatcaagaa gggcatctac cagtctctga gatcgtgga tgagctggtg | 2280 |
| gccatcatgg gctacgcccc aaagaggatc gtggtggaga tggccaggga gaatcagaca | 2340 |
| acatcaacag gcaagaggag gtctatccag aggctgaaga tcgtggagaa ggccatggcc | 2400 |
| gagatcggct ctaatctgct gaaggagcag ccaacaacaa atgagcagct gagggataca | 2460 |

| | |
|---|---|
| aggctgttcc tgtactacat gcagaatggc aaggatatgt acacaggcga tgagctgtct | 2520 |
| ctgcataggc tgagccacta cgacatcgat cacatcatcc cgcagtcatt catgaaggac | 2580 |
| gactctctgg ataatctggt gctggtgggc tctacagaga acaggggcaa gagcgatgat | 2640 |
| gtgccatcta aggaggtggt gaaggatatg aaggcctact gggagaagct gtacgccgcc | 2700 |
| ggcctgatct ctcagaggaa gttccagagg ctgacaaagg gcgagcaggg cggcctgaca | 2760 |
| ctggaggata aggcccactt catccagagg cagctagtgg agacaaggca gatcacaaag | 2820 |
| aatgtggccg gcatcctgga tcagaggtac aatgccaatt ctaaggagaa gaaggttcag | 2880 |
| atcatcacac tgaaggcctc tctgacatct cagttcaggt ctatcttcgg cctgtacaag | 2940 |
| gtgcgcgagg tgaatgatta ccaccacggc caggatgcct acctgaattg cgtggtggcc | 3000 |
| acaacactac tgaaggtgta cccaaatctg gccccagagt tcgtgtacgg cgagtaccca | 3060 |
| aagttccagg ccttcaagga gaataaggcc acagccaaga caatcatcta cacaaacctg | 3120 |
| atgaggttct tcacagagga cgagccaagg ttcatgaagg atggcgagat cctgtggagc | 3180 |
| aacagctacc tgaagaacat caagaaggag ctgaactacc accagatgaa catcgtgaag | 3240 |
| aaggtggagg tccagaaggg cggcttctca aggagagca tcaagccgaa gggcccgagc | 3300 |
| aacaagctga tcccagtgaa gaatggcctg gacccacaga agtacggcgg ctttgattct | 3360 |
| ccagtggtgg cctacacagt gctgttcaca cacgagaagg caagaagcc actgatcaag | 3420 |
| caggagatcc tgggcatcac aatcatggag aagacaaggt tcgagcagaa cccaatcctg | 3480 |
| ttcctggagg agaagggctt cctgaggcca agggtgctga tgaagctacc aaagtacaca | 3540 |
| ctgtacgagt tcccagaggg caggaggagg ctgctggcct ctgccaagga ggcccagaag | 3600 |
| ggcaatcaga tggtgctgcc tgagcacctg ctgacactgc tgtaccacgc caagcagtgc | 3660 |
| ctgctgccaa atcagtctga gtctctggcc tacgtggagc agcaccagcc agagttccag | 3720 |
| gagatcctgg agagggtggt ggatttcgcc gaggtgcaca cactggctaa gtctaaggtt | 3780 |
| cagcagatcg tgaagctgtt cgaggccaat cagacagccg atgtgaagga gatcgccgcc | 3840 |
| tcattcatcc agctgatgca gttcaatgcc atgggcgccc catctacatt caagttcttc | 3900 |
| cagaaggata tcgagagggc caggtacaca tctatcaagg agatcttcga tgccacaatc | 3960 |
| atctaccagt ctacaacagg cctgtacgag acaaggagga aggtggtgga t | 4011 |

<210> SEQ ID NO 179
<211> LENGTH: 4308
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: source
<223> OTHER INFORMATION: /note="APG04583.1 Soy optimized"

<400> SEQUENCE: 179

| | |
|---|---|
| atggccaaaa atattctagg actcgatctc ggaaccaact ctattggatg ggctcttgtt | 60 |
| cagcaggact ttgaaaataa ggaggggaac atactaggaa tggggtccag aataattcct | 120 |
| atgtctcagg atatactagg agagttcggg aagggtaact ctatttctca aactgctgag | 180 |
| agaactggat ataggggagt tagaaggtta agggagagac atcttcttag aagggagagg | 240 |
| cttcataggg tgcttcatct tcttggattc ctacctaagc attacgacga gaaaatagac | 300 |
| ttcactcaga ggttcgggaa gttcatcaat caagctgaac caaagttggc tttcgattca | 360 |

```
gagttcctct tcaaggactc cttccatgaa atgctagctg acttcaagca gaatcaacct    420
gagttcctca aggataaaaa cggagaggat tgccttgttc cttacgactg gactatatac    480
tacctaagga agaaagcatt gacccagaag atcgaaaaat atgagctggc ctggctcatc    540
ctcaacttca atcaaaagag gggatactat caattagggg gagaggagga aaggagaac     600 cctaataaac tcgtggggtt ccactctctc aaaatagtgg atgttattcc tgacgctgaa    660
accaataaaa agggagagac ctggtactca cttcatcttg agaacggatg ggtttatagg    720
aggtcctcca aaatatctct cgctgattgg aaggacaaag tgagggattt cattgtgacc    780
accgatctta atgatgatgg atcagagaag ctcgataagg atggaattgt gaagaggtct    840
tttagggctc cttctgctga tgactggacc ctattaaaga agaagaccga aaggatatc     900 gacaactcta ataaaaccgt ggggacctac atctacgaca acctcctatt aaaccccaag    960
cagaaaatca agggaaagat ggttaggacc attgagagga agttctacaa gcaagagctg   1020
gagcagatat aaagactca gaaggagttc cattctgagc ttcagtctga aacttgctt    1080 caagattgcg ttagggagct gtacaggaat aatgagcaac atcaacagat gcttgaggct   1140
aaggatttcg tgcacctctt cctcaacgat ataattttct accagaggcc tcttaggtcc   1200
cagaaatcaa gcatttctaa ttgcacccct gagttccgca agtccaagaa tgaaaacgga   1260
gaggaggtaa tacacagatt aaaggtgatc gccaaatcaa acccatacta ccaggagttc   1320
aggcttcttc aatgggttca gaacctcgct atctatacta aggacgacga taagaacgta   1380
accaacgagt tcctcaaatc aactcaggat tgggaggatc ttcttaggtg gcttcactct   1440
aagaaggaaa tcaagcagga tgctctaatc aagttcctca ttgagaagaa gggactcaag   1500
gggaaagcat tgactattga ggtggcaaaa tataggtgga actacgttca ggataaggat   1560
taccctggaa atgaaaccccg ctacctcatt caatcaaggc ttgataaggt tgagtacgct   1620
cctaaggatt tcctcaccta tgaaaatgaa atggccctct ggcatatcat ctactcaatc   1680
aacgacaaga tcgagtatga aaaggcatta agtccttcg ccaataaaaa ggggctcgat   1740
gaggtgacct tcgtggaagc attcaagaag ttccctcctt tcaagtccga ttacggatct   1800
ttctctgaga aggcaatcaa gaagctcctt ccattaatga ggttcggaac tcaatggaac   1860
tgggataaca tcgaccaaaa tagcaaggag aggattggaa aaatactaac cggggagtac   1920
gatgaaaata ttaaagggag ggttagggag aaggctaggc accttaactc tgagaccgat   1980
tttcaagcat tacctctttg gcttgctcag tacgttgttt atggaaggca ctctgaagct   2040
gatattgctg gaaagtggaa ctctgtggat gatctcaagc agttccttga tgatttcaag   2100
cagcattcct tgaggaaccc tattgtggag caggttatta ctgagactct tagggctgtt   2160
aaggatattt ggaacttcta cggaaagggg gctaaggatt tcttctcaga aatacacatt   2220
gagcttggga gggagatgaa aaataccgct gatgaaagga gaggattac caccatggtg    2280 accgacaatg aaaataccaa cctcagaatc aaagcattgc ttgctgagat ggctcttgat   2340
cagaacgttg ataacgttag gccttactct cctatgcagc aggagattct taagatctat   2400
gaggagggag ttctaaacgc tgaggagaac atcgatgatg atatcctcaa gatttctaag   2460
actgctcagc cttctgctac cgatcttaag aggtataagt tgtggcttga gcaaaagtac   2520
aggtctcctt acactggaca gatgattcct cttaacaagt tgttcacccc tgagtacgag   2580
atcgagcaca ttattcctca gtctaggtac ttcgacgatt caatgtccaa caaggttatt   2640
tgcgaggctg ctgtgaacaa gttgaaggat aaccagattg gactcgtgtt cattaagaac   2700
```

| | |
|---|---|
| catcatggag aggtggttga tttcggaatg ggaaagcagg tgaagattct tgaggtttct | 2760 |
| gattacgagg atttcgtgaa gcagaactat aacaagaaca ggggaaagag gaacaagctc | 2820 |
| ctcttagagg atatccctga agatgatt gagaggcagc ttaacgatac caggtacatc | 2880 |
| tctaagtaca ttacccaggt gctttccaac attgttaggg atgataagga gggatctaag | 2940 |
| gatgatggag tgaactccaa gaacattgtt cctggaaacg gaaagattac caccaggctt | 3000 |
| aaacaggatt ggggacttaa cgatgtgtgg aacgatcttg ttcttcctag gttcgagagg | 3060 |
| atgaacactc ttaccaactc taacgatttc acctctaaga cactcacgg aaagactatt | 3120 |
| cctactgtgc ctattgagct ttcaaaggga ttctccaaga gaggattga tcacaggcat | 3180 |
| catgctatgg atgctcttgt tattgcttgc gctactaggg atcatgtgaa ccttctcaac | 3240 |
| aacgagtctt ctaagtctga taccaagagg tacgatctta caggaagtt gaggaagtac | 3300 |
| gagaaggttg cttacaacga tcctaagact ggagagagaa ttgagaagga ggtgcctaag | 3360 |
| gattttatta agccttggga gacctttact gaggatacta ggacccttct tgagaacatc | 3420 |
| gtgatttctt tcaagcagaa cctcaggtg attaacaagg ctaccaacta ctacgagaag | 3480 |
| attgagaacg gaaagaaggt gaaggttgag cagaagggaa ttaattgggc tgttaggaag | 3540 |
| gctctacata aggagactgt ttctggacag gtgcaccttg ataggattaa agtggctaag | 3600 |
| ggaaagattc ttaccgctac taggaagact cttgatgctt ctttcaacga gaagaccatt | 3660 |
| gagtctatta ccgataccgg gattcagaag attctcctca actacctcaa gtccaaggat | 3720 |
| aacaatcctg aggttgcttt ctctcctgaa ggaattgagg agcttaacaa gaacatcagg | 3780 |
| ctctataacg atgaaaaggc tcaccagcct attcttaagg ttagggtttt cgagcaggga | 3840 |
| tctaagttta ctcttggaga gactggaaac aagactacta gtttgttga ggctgctaag | 3900 |
| ggaaccaacc ttttcttcgg aatctacgag gataagtctg gaaagaggtc ttacgagacc | 3960 |
| atcccttga acattgttat tgagaggcaa aagcaaggac tacaagctgt tcctgagact | 4020 |
| aacgagaagg gaaagcagct tcttttcacc ctttctccta cgatcttgt ttatgttcct | 4080 |
| gaggagggag ttttcgatga gaacaacatc aaggtggata ggatctacaa ggtggtgtct | 4140 |
| ttctctactt accaatgctt cttcgtgagg aacgatgtgt ctacttctgt ggttaacaag | 4200 |
| gttgagtact ctgctctcaa caagatggag aagtccatcg acaacatcat gattaaggag | 4260 |
| aactgcgtga agttgaacgt tgataggctc ggaaagattt ccaaggct | 4308 |

<210> SEQ ID NO 180
<211> LENGTH: 4308
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: source
<223> OTHER INFORMATION: /note="APG04583.1 Corn optimized"

<400> SEQUENCE: 180

| | |
|---|---|
| atggccaaga acatactagg cctggaccctc ggaaccaatt ctatcggctg ggccctggtt | 60 |
| cagcaggact ttgagaacaa ggagggcaac atactaggca tgggcagccg aataatccct | 120 |
| atgtctcagg acatactggg cgagttcggt aagggcaaca gcatctcaca gacagccgag | 180 |
| aggacaggct accgcggcgt gaggaggctc agggagaggc acctgcttag gagggagagg | 240 |
| ctacacaggg tgctgcatct gctgggcttc ctgccaaagc attacgatga aaagatagat | 300 |

```
ttcacacaga ggttcggcaa gttcatcaat caagccgaac caaagctagc cttcgattct    360
gagttcctgt tcaaggacag cttccatgaa atgctggccg acttcaagca gaatcaaccg    420
gagttcctga aggataaaaa cggcgaggac tgcctagtgc cgtacgactg gaccatatac    480
tacctgcgca agaaggccct cacccagaag atcgaaaaat acgagctggc ctggctgatc    540
cttaacttca accaaaagcg cggatactac cagctacgcg gcgaggagga aaggagaac     600 ccgaataaac tggtgggctt ccacagcctg aaaatagtgg acgtgatccc ggacgccgag    660
actaataaaa agggcgagac ctggtactca cttcacctgg agaacggctg ggtgtaccgc    720
aggagcagca aaatatctct ggccgactgg aaggataaag tgagggactt catcgtgacc    780
acagacctga cgacgatgg ctcagagaag ctggacaagg atggcatcgt gaagaggtca     840
ttcagggccc catctgccga tgactggacc ctattaaaga agaagaccga aaggacatc     900 gacaacagca ataaaaccgt gggcacctac atctacgaca acctgctatt aaacccgaag    960
cagaaaatca agggcaagat ggtgcgcacc atcgagcgca agttctacaa gcaggagctg   1020
gagcagatac taaagaccca agaggagttc cacagcgagc tgcagagcga aacctgctg    1080 caggactgcg tgcgcgagct gtaccgcaat aatgagcagc accagcagat gctggaggcc   1140
aaggacttcg tgcacctgtt cctgaacgat ataatcttct accagaggcc gctcaggagc   1200
cagaagtcaa gcatcagcaa ttgcacccctg gagttccgca agagcaagaa tgaaaacggc  1260
gaggaggtga tacatcgatt aaaggtgatc gccaagagca acccctacta ccaggagttc   1320
cgcctgctgc agtgggtcca gaacctggcc atctatacta aggacgacga caagaacgta   1380
accaacgagt tcctgaaatc aaccccaggac tgggaggacc tgctgcgctg gctccacagc   1440
aagaaggaaa tcaagcagga cgccctaatc aagttcctga tcgagaagaa gggattaaag   1500
ggcaaagcat tgaccatcga ggtggcaaaa tacaggtgga actacgtcca ggacaaggac   1560
tacccgggca atgaaacccg ctacctaata cagagccgcc tggacaaggt ggagtacgcc   1620
ccgaaggact tcctgaccta cgagaatgaa atggccctgt ggcatatcat ctactcaatc   1680
aacgacaaga tcgagtatga aaaggcatta aagagcttcg ccaataaaaa gggcctggac   1740
gaggtgacct tcgtggaagc attcaagaag ttccccgccgt tcaagagcga ctacggcagc   1800
ttcagcgaga aggcaatcaa gaagctgctg ccattaatgc gcttcggcac ccagtggaac   1860
tgggacaaca tcgaccaaaa tagcaaggag cgcatcggca aaatactaac cggcgagtac   1920
gacgagaaca taaagggccg cgtgcgcgag aaggcccgcc acctgaacag cgagaccgac   1980
ttccaagcat tgccgctgtg gctggcccag tacgtggtct acggcaggca cagcgaggcc   2040
gatatcgccg gcaagtggaa cagcgtggat gatctcaagc agttcctgga cgatttcaag   2100
cagcacagcc tgaggaatcc aatcgtggag caggtgatca cagagacact aagggccgtg   2160
aaggacatct ggaatttcta cggcaagggc gccaaggact tcttcagcga gatacatatc   2220 gagctggggcc gcgagatgaa aaacaccgcc gatgaaagga gaggatcac aaccatggtg    2280 accgacaatg aaaacaccaa cctgcgaatc aaggccctgc tggccgagat ggcctggat    2340 cagaacgtgg ataacgtgag gccatactct ccaatgcagc aggagatcct gaaaatatac   2400
gaggagggcc tattaaacgc cgaggaaaat atcgacgacg acatcctgaa aataagcaag   2460
accgcccaac caagcgccac cgacctgaag cgatataagc tgtggctgga gcaaaaatac   2520
aggagcccgt acaccggcca gatgatcccg ctgaataaac tgttcacccc ggagtatgaa   2580
atcgagcata taatccctca gagccgctac ttcgacgaca gcatgagcaa caggtgatc    2640 tgcgaggccg ccgtgaacaa gctaaaggac aaccagatcg gcctggtgtt catcaagaac   2700
```

```
caccacggcg aggtggtgga cttcggcatg ggcaagcagg tgaagatcct ggaggtgagc    2760
gactacgagg acttcgtgaa gcagaactac aacaagaacc gcggcaagag gaacaagctg    2820
ctgctggagg acatccctga gaagatgatc gagaggcagc tgaacgacac ccgctacatc    2880
agcaagtaca tcacacaggt gctgagcaac atcgtgaggg acgataagga gggctcaaag    2940
gatgatggcg tgaacagcaa gaacatcgtg ccaggcaacg gcaagatcac aacaaggctg    3000
aagcaggatt ggggcctgaa cgatgtgtgg aatgatctgg tgctgccaag gttcgagagg    3060
atgaacaccc tgaccaacag caacgacttc acctctaaga cacccacgg caagacaatc    3120 ccaacagtgc cgatcgagct gagcaagggc ttcagcaaga gaggatcga tcacaggcac    3180 cacgccatgg atgccctggt gatcgcctgc gccacaaggg atcacgtgaa tctactgaat    3240
aacgagtcta gcaagagcga tacaaagagg tacgatctga acaggaagct gcgcaagtac    3300
gagaaggtgg cctacaacga tccaaagaca ggcgagagga tcgagaagga ggtgccgaag    3360
gatttcatca agccatggga gacattcaca gaggacacaa ggaccctgct ggagaacatc    3420
gtgatcagct tcaagcagaa cctgcgcgtg atcaacaagg ccaccaacta ctacgagaag    3480
atcgagaacg gcaagaaggt gaaggtggag cagaagggca tcaattgggc cgtgaggaag    3540
gccctacata aggagacagt gtctggccag gtgcacctgg ataggatcaa ggtggccaag    3600
ggcaagatcc tgacagccac aaggaagaca ctggatgcct ctttcaacga gaagacaatc    3660
gagagcatca cagacaccgg catccagaag atcctgctga actacctgaa gagcaaggac    3720
aacaacccag aggtggcctt ctctccagag ggcatcgagg agctgaacaa gaacatcagg    3780
ctgtacaatg atggcaaggc ccaccagcca atcctgaagg tgcgcgtgtt cgagcagggc    3840
tcaaagttca cactgggcga gacaggcaat aagacaacaa agttcgtgga ggccgccaag    3900
ggcacaaatc tgttcttcgg catctacgag gataagtctg gcaagaggtc ttacgagaca    3960
atcccgctga atatcgtgat cgagaggcag aagcagggac tgcaggccgt gccagagaca    4020
aatgagaagg gcaagcagct gctgttcaca ctgtctccaa atgatctggt gtacgtgcca    4080
gaggagggcg tgttcgatga gaacaatatc aaggtggaca ggatctacaa ggtggtgagc    4140
ttctcaacct accagtgctt cttcgtgagg aacgacgtga gcacaagcgt ggtgaacaag    4200
gtggagtaca gcgccctgaa caagatggag aagagcatcg acaacatcat gatcaaggag    4260
aactgcgtga gctgaacgt ggaccgcctg ggcaagatct ctaaggcc                 4308
```

<210> SEQ ID NO 181
<211> LENGTH: 4368
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG01688.1 Soy optimized"

<400> SEQUENCE: 181

```
atgatgatca gaacatact aggactcgat ctcggaacca actctatcgg atgggctcta      60
atcaagcagg atttcgagaa caagcatgga gaaatactag ggatgggctc cagaataatt    120
cctatgtccc aggatatact aggagatttc ggaaagggta actctatttc tcagaccgct    180
gatagaacca agtataggtc tgttagaagg cttagggaga gatttcttct taggagagag    240
aggcttcata gggtgctcca cctattaaac ttccttcctc aacactacgc ttctcagatc    300
```

-continued

```
gatttcgaga agaagttcgg aaagtttaag tctgagaccg aaccaaagtt agcttgggaa      360
aattggggag gaaagttctc tttcctcttc caaaatagct tcaatgaaat gctggaggat      420
ttcaaggctg ctggacaggg gctcaaaata ccttacgact ggaccatata ctatctcagg      480
aagaaagcat tgtcccagaa aatagagaag gaggagctag cttggatact cctcaacttc      540
aatcaaaaga ggggatacta tcaattaaga ggtgaggagg aggaggagaa ccctaataaa      600
ctcgtggagt tctactccct caaaatagtg gatgttgttg ctgatgagcc tcagaaggga      660
aagtccgata tctggtactc attaattctt gagaacggat gggtttatcg cagggcttcc      720 aaaataccctc tcttcgactg gaaggataaa accaggatt tcattgtgac caccgatctt      780
aacgatgata ggtctgtgaa gactgataag gagggaaatg aaaagaggtc ttttagggct      840
ccttcagaga acgattggac tcttgtgaag aagaagactg agcaggagat tgatcagtct      900
cataaaaccg tgggaaccta catctatgaa accctcctat taaaccccaa gcagaaaatc      960
aagggaaagt tggtgaggac cattgagagg aagttctaca aggacgagct taagcagata     1020
ctagagaagc aaaaggagtt ccaccaggaa ttaaagaacg acgacctata taacgactgc     1080
attagggagc tgtacaggaa taatgaggct caccaattaa ccctctccaa gaaggatttc     1140
gtgcacctat taatggacga tctcattttc taccagaggc ctcttaggtc ccagaaatca     1200
agcatttcta attgcaccct ggagttcaga aaatacaagg atgaaaacgg gattgagcac     1260
acccagtacc tcaaggctat cccaaaatca aacccatact accaagagtt taggctttgg     1320
cagtggatgt acaacttgaa catctacaga aaggatgatg aggctaacgt aaccaaggag     1380
ttcctcaaca ccaataaaga cttcgagtct ctcttcgagt tcctcaataa tcgcaaggag     1440
attgagcaga agccccctaat caagttcctt cttgagcaga aggacataaa caagaagcta     1500
ttaaacgccg aggctgagaa atacaggtgg aactacgtgg aggataaaaa gtaccctgc      1560 aatgaaacca agaccatgat ttcctctagg cttgacaagg tggaaaatat ctccgatgat     1620
ttcctcacca gggacatcga gcagaaaata tggcatataa tctactccgt gaacgacaag     1680
atcgagtatg aaaaggcatt aaagtccttc gctaccagga acgacctcga tgaaaatagc     1740
ttcatcgaag cattcaagaa gttctcccct ttcaagtccg agtacggatc tttctctgag     1800
aaggcaatca agaagctcct tccattaatg aggctcggaa aatactggta cgaggatgaa     1860
atcgtgaagc attccgacat ctacttcaaa aatattgaga acctcctcgg ggatttctcc     1920
aaccgcgaca agaaaatatc tgaggaagac aaggagaagt ggaacaagtc aatcaacctt     1980
aagctccagg aggaattaaa ggatttccag accgctgaga ttgatttgtt ccagggactt     2040
aggcttcaca ttgctcagta ccttgtttat ggaaggcact ccgaagcatc tatgattgga     2100
aagtggaatt ctgctgagga tcttgaggag ttccttaagg atttcaagca gcattccctt     2160
aggaacccta ttgtggagca ggttattact gagactctta gggtggttaa ggatatttgg     2220
ctaaagtacg gaaacggggc taaggatttc ttcaacgaga ttcatattga gcttggaagg     2280
gaaatgaagt tgcctgctga tgataggaag aagctcacca accaaatttc tgagaacgag     2340
aacaccaact tcaggattaa ggctctcctt gctgagatga tgaacgattc ttctgttgag     2400
aacgttaggc ctttctctcc tatgcagcag gagattctaa agatctacga ggatgatgtg     2460
ctcaagtccg atatcgagat cgaggatgat atcctcaaga tttctaagac tgctcaacct     2520
tctccttctg atcttaagag gtacaagttg tggcttgagc agaagtacaa gtctccttac     2580
accggacaga ttattcctct taacaagttg ttcacccctg agtacgagat cgagcacatt     2640
```

| | |
|---|---|
| attcctcagt caaggtactt cgatgattcc ttctccaata aggtgatttg cgagtctgct | 2700 |
| gtgaacaagc tcaaggataa ctacatcggg cttgagttca ttaagcagtt cggaggaact | 2760 |
| attattgagc ttggattcgg gaagtctatt aaggtgttcg agactaagga gtacgaggat | 2820 |
| ttcgtgaaga agcattacgc taacaaccag ggaaagagga acaagctcct tatgaagat | 2880 |
| atccctgaga agatgattga gaggcagatg aacgatacca ggtacatctc aaagtacatt | 2940 |
| tctggggtgc tttctaacat tgttagggtg gaagatggat ctgatgaggg agtgaactct | 3000 |
| aagaacattg ttcctggaaa cggaaagatt accacccaac ttaagcagga ttgggacttt | 3060 |
| aacgatgtgt ggaacgatct cattcttcct aggttcgaga ggatgaatca gcttactaac | 3120 |
| tctaaggttt tcactgcttg gaacgagaac taccagaagt tccttcctac tgtgcctatt | 3180 |
| gagtactcca agggattctc aaagaagagg attgatcaca ggcatcatgc tcttgatgct | 3240 |
| cttgttattg cttgcgctac taaggatcac gtgaaccttc ttaacaacca gtctgctaag | 3300 |
| tctgatacca agaggtacga tctcaagaag aagtccatga agttcgagaa ggtggtttac | 3360 |
| aacgatgcta agactggaga aaagattgag agggaggttc taagcaatt tcttaagcct | 3420 |
| tgggagaact tcactcttga tgtgaagcac aaccttgaga ccatcattgt gtcattcaag | 3480 |
| cagaacctca gggtgattaa caaggctacc aactactacg agaagtacgt tgagaaggat | 3540 |
| ggaactaaga ataaggagag ggttgagcaa actggaacta actgggctat taggaagcct | 3600 |
| atgcacaagg atactgtgtc tggaaaagtt gatcttcctt gggttaaggt gcctaaggga | 3660 |
| aagattctta ctgctaccag gaagtctctc gattcttctt tcgatctcaa gtccattgga | 3720 |
| tctattaccg ataccgggat tcagaagatc ctaaagaact acctcgcttt caaggatgga | 3780 |
| aatcctgagc ttgctttctc tcctgaggga attgatgacc tcaacaagaa catcgagaag | 3840 |
| tataacgatg gaaagcctca ccagcctatt aacaaggtta gggttttcga gcttggatct | 3900 |
| aagttccaag ttggacagtc tggaaacaag aaggataagt atgttgaggc tgctaaggga | 3960 |
| accaaccttt tcttcgctgt ttatgaggat gagaagggaa agaggaacta cgagactatt | 4020 |
| cctctaaacg aggttattga gaggcaaaag cagggacttt ctgtggttga tcttaagggg | 4080 |
| accaacgatt tctatctttg ccctaacgat ttcgtgtaca ttccttctgg agatgagctg | 4140 |
| gagaacatca acaacgtgga cttcaaggat atcaagaagg agattaacga gaggatctac | 4200 |
| aaggtggtgt ctttcactgg aaacaggctt tcttgcattc cttacatggt ggctaccact | 4260 |
| attgtgaaca agttggagtt cacccagcta aacaagattg agttcaccaa ggagaaggag | 4320 |
| atctgcatta agttgaacgt ggataggctc ggaaacattt ctaaggct | 4368 |

<210> SEQ ID NO 182
<211> LENGTH: 4368
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG01688.1 Corn optimized"

<400> SEQUENCE: 182

| | |
|---|---|
| atgatgatca agaacatcct aggcctggac ctcggaacca attctatcgg ctgggccctg | 60 |
| atcaagcagg acttcgagaa caagcatggc gagatactag gcatgggcag ccgaataatc | 120 |
| ccgatgagcc aggacatact aggcgatttc ggcaagggca atagcatctc tcagaccgcc | 180 |

```
gacagaacca agtacaggtc tgttaggagg ctgagggaga ggttccttct taggagggag     240
aggctgcata gggtgctcca cctattaaac ttcctgccac agcactacgc cagccagatc     300
gacttcgaga agaagttcgg caagttcaag agcgagacag aaccaaagct ggcttgggaa     360
aactggggcg gcaagttcag cttcctgttc caaaatagct tcaatgaaat gctggaggac     420
ttcaaggccg ccggccaggg attaaagatc ccctacgact ggaccatata ctacctgcgc     480
aagaaagcat tgagccagaa aatagagaag gaggagctgg cctggatact gctgaacttc     540
aaccaaaagc gcggatacta ccagctgcgc ggtgaggagg aggaggagaa cccgaataaa     600
ctggtggagt tctactcact gaaaatagtg gacgtggtgg ccgacgagcc gcagaagggc     660
aagagcgaca tctggtacag cctgatacta gagaacggct gggtgtaccg ccgcgctagc     720
aaaataccgc tgttcgactg gaaggataaa acccgcgact tcatcgtgac caccgacctg     780
aacgacgaca ggagcgtgaa gacagataag gagggcaatg aaaagaggag cttcagggcc     840
ccaagcgaga acgattggac cctggtgaag aagaagacag agcaggagat cgatcagagc     900
cataaaaccg tgggcacata catctatgaa accctgctat aaacccgaa gcagaaaatc      960 aagggcaagc tggtgcgcac catcgagcgc aagttctaca aggacgagct gaagcagata    1020
ctagagaagc agaaggagtt ccaccaggaa ttaaagaacg acgacctata taacgactgc    1080
atccgcgagc tgtaccgcaa taatgaggcc caccaattaa ccctgagcaa gaaggacttc    1140
gtgcacctat taatgacga cctgatcttc taccagcgcc cgctgcgcag ccagaagtca    1200
agcatcagca attgcaccct ggagttccgc aaatacaagg atgaaaacgg catcgagcac    1260
acccagtacc tgaaggccat cccgaagagc aacccatact accaggagtt ccgcctgtgg    1320
cagtggatgt acaacctgaa catctaccgc aaggacgacg aggccaacgt aaccaaggag    1380
ttcctgaata caaataaaga cttcgagagc ctgttcgagt tcctgaataa tcgcaaggag    1440
atcgagcaga agccgctaat caagttcctg ctggagcaga aggacataaa caagaagcta    1500
ttaaacgccg aggccgagaa atacaggtgg aactacgtgg aggataaaaa gtacccgtgc    1560
aacgaaacca agaccatgat cagcagccgc ctggacaagg tggaaaatat cagcgacgac    1620
ttcctgaccc gcgacatcga gcagaaaata tggcatataa tctacagcgt gaacgacaag    1680
atcgagtatg aaaaggcatt aaagagcttc gccacccgca acgacctgga tgaaaacagc    1740
ttcatcgaag cattcaagaa gttcagcccg ttcaagagcg agtacggcag cttcagcgag    1800
aaggcaatca agaagctgct gccattaatg cgcctgggaa atactggta cgaggacgag    1860 atcgtgaagc atagcgacat ctacttcaaa aatatcgaga acctgctggg cgacttcagc    1920
aaccgcgaca agaaaataag cgaggaggac aaggagaagt ggaacaaaag catcaacctg    1980
aagctgcagg aggaattaaa ggacttccag accgccgaga tcgacctgtt ccagggcctg    2040
cgcctccaca tcgcccagta cctggtgtac ggccgccaca gcgaggcaag catgatcggc    2100
aagtggaaca gcgccgagga cctggaggag ttcctgaagg acttcaagca gcatagcctg    2160
cgcaacccga tcgtggagca ggtgatcacc gagaccctgc gcgtggtgaa ggacatctgg    2220
ctaaaatacg gcaacggcgc caaggacttc ttcaatgaaa ttcacatcga gctgggccgc    2280
gagatgaaac tgccggccga cgaccgcaag aagctgacca ccaaatcag cgagaatgaa    2340 aacaccaact tccgaatcaa ggccctgctg gccgagatga tgaacgacag cagcgtggag    2400
aacgtgcgcc cgttcagccc gatgcagcag gagatcctga aaatatcga ggacgacgtg    2460 ctgaagagcg acatcgagat cgaggacgac atccctgaaga tcagcaagac cgcccagccg    2520
agcccgagcg acctgaagcg ctacaagctg tggctggagc agaagtacaa gagcccgtac    2580
```

| | | |
|---|---|---|
| accggccaga tcatcccgct aaacaagctg ttcaccccgg agtacgagat cgagcacatc | 2640 |
| atcccgcaga gccgctactt cgacgacagc ttcagcaaca aggtgatctg cgagagcgcc | 2700 |
| gtgaacaagc tgaaggataa ctacatcggc ctggagttca tcaagcagtt cggcggcacc | 2760 |
| atcatcgagc tgggcttcgg caagagcatc aaggtgttcg agaccaagga gtacgaggac | 2820 |
| ttcgtgaaga agcactacgc caacaaccag ggcaagcgca acaagctgct gatggaggac | 2880 |
| atcccggaga gatgatcga gcgccagatg aacgacaccc gctacatcag caagtacatc | 2940 |
| agcggcgtgc tgagcaacat cgtgcgcgtg gaggatggct cagatgaggg cgtgaacagc | 3000 |
| aagaacattg tgccgggcaa cggcaagatc acaacacagc ttaagcagga ctggggcctg | 3060 |
| aacgatgtgt ggaacgatct gattctgcca aggttcgaga ggatgaacca gctgaccaac | 3120 |
| agcaaggtgt tcaccgcctg gaacgagaac taccagaagt tcctgccaac cgtgccaatc | 3180 |
| gagtacagca agggcttcag caagaagagg atcgatcaca ggcatcatgc tctggatgct | 3240 |
| ctggtgatcg cctgcgctac aaaggatcac gtgaacctgc tgaacaacca gagcgccaag | 3300 |
| agcgacacaa agaggtacga cctgaagaag aagagcatga gttcgagaa ggtggtgtac | 3360 |
| aacgacgcca agaccggcga gaagattgag agggaggtgc cgaagcagtt cctaaagcca | 3420 |
| tgggagaact tcacactgga cgtgaagcac aacctggaga ccatcatcgt gagcttcaag | 3480 |
| cagaacctga gggtgatcaa caaggccacc aactactacg agaagtacgt ggagaaggac | 3540 |
| ggcaccaaga caaggagag ggtggagcag acaggcacaa attgggccat ccgcaagcca | 3600 |
| atgcacaagg atacagtgtc tggcaaggtg gatctgccat gggttaaggt gccaaagggc | 3660 |
| aagatcctga cagccacaag gaagagcctg gatagcagct tcgatctgaa gagcatcggc | 3720 |
| tctatcacag acaccggcat ccagaagatc ctgaagaact acctggcctt caaggatggc | 3780 |
| aatccagagc tggctttctc tccagagggc atcgacgacc tgaacaagaa catcgagaag | 3840 |
| tacaacgacg gcaagccaca ccagccaatc aataaggtgc gcgtgttcga gctaggctct | 3900 |
| aagttccagg ttggccagag cggcaacaag aaggataagt acgttgaggc cgccaagggc | 3960 |
| acaaatctgt tcttcgctgt gtacgaggat gagaagggca agcgcaacta cgagacaatc | 4020 |
| ccactgaacg aggtgatcga aaggcagaag cagggcctgt ctgttgtgga tctgaagggc | 4080 |
| accaacgatt tctacctgtg cccgaacgac ttcgtgtaca ttccatctgg cgacgagctg | 4140 |
| gagaacatca caacgtgga cttcaaggac atcaagaagg atcaacga gcgcatctac | 4200 |
| aaggtggtga gcttcaccgg caacaggctg agctgcatcc catacatggt ggccaccacc | 4260 |
| atcgtgaaca gctggagtt cacccagctg aacaagatcg agttcaccaa ggagaaggag | 4320 |
| atctgcatca agctgaacgt ggacaggctg ggcaacatca gcaaggcc | 4368 |

<210> SEQ ID NO 183
<211> LENGTH: 3210
<212> TYPE: DNA
<213> ORGANISM: Bacillus sp.
<220> FEATURE:
<221> NAME/KEY: source
<223> OTHER INFORMATION: /note="APG05083.1 Native Seq"

<400> SEQUENCE: 183

| | | |
|---|---|---|
| atgagagagt tggattatcg cataggatta gatattggaa cgaattctat tggctggggg | 60 |
| atcattgaat tatcttggaa caaagataga gaacaatatg agaaagcaag aattgtcgac | 120 |
| aagggtgttc gtatgtttga taaggctgaa atacctaaga ctggtgcttc tcttgctgaa | 180 |
| ccgaggcgta tagcacgctc atcacgtaga agattaaatc gcaaaagcca gagaaaaaaa | 240 |

```
gatatacgta atttactcgt tcaacatgaa attattagtc aaaaggaatt ggcttcgtta    300 tatccoctga caaaaagttc aatggatatt tgggatattc gcttggatgg attagatcgc    360
ttgttagacc gttttgaatg gactcgatta ttaattcatt tagcgcaaag acgcggtttt    420
aaatcaaatc gaaagtctga actgaaagat gtggagacag gaaaagtatt atcaagtatt    480
caagcaaatg aaaaacgatt atcactgtac cgtacagtgg gagagatgtg gatgaagaat    540
gaagatttta gtaaatatga caaaaggcgt aattcttcta atgagtatgt attttcggtt    600
agccgtgcag atttagaaaa agaaattgtg acactatttg aagcgcaaag aaaatttcag    660
tcatcatatg catcggctga tttacaaaaa acatacttac aaatttgggc acaccaactt    720
ccttttgctt ctgggaatgc aattgtaaat aaagtaggat attgttcatt attaaaaggg    780
aaagaaaaga gagttccgaa agcaacatat acttttcaat atttcagtac actagatcaa    840
ataaatcgaa cacgattagg tcctaatttc caaccattta cgaaggaaca gagagacgtt    900
attttagatg aaatgtttaa tcgaacagat tattataaaa aaaagacaat acccgaagtc    960
acttactatg atattcggaa atggttagca ttagatgaaa caattcaatt taaaggactt    1020
acctatgacc caaatgaaga gctgaaaaaa atagaattga atcctttat taatttaaag    1080 ccattctatg aaattaaaaa ggtagttact aattacgcca aaaaaacaaa tgaggcattc    1140
tcaacattag actatgatac atttgcatat gctttaacag tttataaaac ggacaaagat    1200
attagatctt atttaaagaa atctaataat ttatcaaaat gttgctacga tgatcaatta    1260
atagaagagc tattaactct ctcctataca aagtttggtc atttatcatt taaagcaatt    1320
aatcatgtac tgccaattat gcaagaggga aggacttatc aggaagcaat acaccaatta    1380
ggatatgatg ccactaatct aaaaaaagaa aacagaagta tgttcttgcc ccttttccc    1440 gatgagataa caaatccaat tgttaaaaga gcactaactc aagcacgtaa agttgtaaat    1500
gctattatta aagatatgg ttcccccaat tctgttcata ttgaactagc tcgtgagctt    1560
tctaaaagtc atgatgagag aacgaaaata atgaaagctc atgatgaaaa ttataagaaa    1620
aataaaggag ccatatcaat tttgattgag aatggaattt taaatccgac aggatatgat    1680
attgtacgtt ataagttatg gaaagagcaa ggagaacgat gtgcttattc gctaaaacag    1740
attcctgcta atacgttttt taatgaaatg aaaaaagagc gaagtggctc cccagttcta    1800
gagatagatc acattttacc gtatagtcag agttttattg atagttatca taataaagta    1860
ctagtttatg gagatgagaa tcaaaaaaag ggaaatcgaa ttccatatac ttatttttta    1920
gaaggaaata aggactggga aagctttgaa agctacgtac gattgaatag ttttttttct    1980
aaaaagaagc gcggatattt attgaaaaaa gcttacttgc caagagagag taacatgatt    2040
aaggagcgtc atttaaatga tactcgatat gctagtagct atttgaaaaa cttcattgag    2100
aaaaatttga aatttaaaga agttgaaggt agtacacgaa aaaaacatgt acagacggtt    2160
aacggtataa ttacagccca tcttcgaaaa agatggggat tagaaaaaga taggcaggaa    2220
acatatttgc atcatgcaat ggacgctatt attgttgctt gtacagacca tcatatggtc    2280
actaaagtaa cggagtacta tcaaataaaa gaaagtaata agtcaataag gaaaccatac    2340
tttcctttgc catgggtggg ctttagagag gaaattttat cacatttagc aaggcagcca    2400
attgctagaa aaattagtga ggaacttaaa attggatatc aatcatttga ttatatactt    2460
gtatcgcgaa tgccaaaaag atctgtcact ggagcagctc atgaacagac aatcatgaaa    2520
aaaggtggta tcgacaaaaa aggaaaaact attatcataa agcgtgtgta cttaaaggat    2580
```

-continued

| | |
|---|---|
| attaagtttg tgagaatgg cgattttaaa atggttggaa agaacagga tttagcaact | 2640 |
| tatgaagcga taaagcaaag atatatagag tatggaaaag aatcgaaaaa agcatttgaa | 2700 |
| acacctttat acaagcctag taaaaaagga aaaggaaacc tcattaaaaa gatcaaagta | 2760 |
| gaagtgcaaa ccaaatcttt tgttcgagaa gttaatgggg gcgtagctca aaatggtgat | 2820 |
| ttagtaagag tagatttgtt tgaaaaggat aatagatatt atatgatacc tatttatgta | 2880 |
| atggatactg ttcattccga actaccaaat aaagctgtaa caagcagtaa aggctatgag | 2940 |
| caatggttaa caatagataa cagctttacg ttcaaattca gtttatatcc ttatgattta | 3000 |
| gtacgacttg taaaaggtaa tgaagatcgt ttcctatatt ttagtaccct tgatattaat | 3060 |
| tcggatcgtc ttaatttcaa agatgtaaac aagccatcaa agcaggctga aaatcgttat | 3120 |
| agccttaaaa caattgagaa tttagaaaaa tatgaggttg gtgttttagg tgatttaagg | 3180 |
| tttgtgagac aagaaatacg taaaaatttt | 3210 |

<210> SEQ ID NO 184
<211> LENGTH: 3210
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG05083.1 E. coli optimized"

<400> SEQUENCE: 184

| | |
|---|---|
| atgcgcgagc tagattatcg catcggcctg gatattggca ctaactcaat aggctggggc | 60 |
| atcatcgaac tgagctggaa taaagaccgc gagcagtatg aaaaggcgcg catcgtggat | 120 |
| aaaggcgtgc gcatgttcga caaagcggaa attccgaaaa ccggtgcaag tctggcggaa | 180 |
| ccaagacgta ttgcacgtag tagtcgccgc cgattaaacc gcaaaagtca gcgcaagaag | 240 |
| gatataagga acctgctggt ccagcatgaa atcatcagcc agaaggaact ggcgagcctg | 300 |
| tacccgctga ccaaatcaag tatgacatc tgggatataa ggctggacgg cctggatcgt | 360 |
| ctgctggatc gctttgaatg gacccgccta ttaatccatc tggcacagcg ccgtggcttc | 420 |
| aaatcaaacc gcaagagcga attaaaggac gtggagaccg gtaaagtgct gtcaagcatt | 480 |
| caggcgaatg aaaagcgcct gagcctgtat cgtaccgtgg gcgagatgtg gatgaaaaac | 540 |
| gaggacttct caaaatacga taaaaggcgc aacagcagca acgagtacgt gttcagcgtg | 600 |
| agccgcgcgg acctggagaa agaaatcgtg accctgtttg aggcgcagcg caaattccaa | 660 |
| tcaagctatg cgagcgcgga tctgcagaaa acctacctgc agatttgggc acatcagctg | 720 |
| ccgtttgcaa gcgtaacgc gatcgtgaat aaagtgggct attgcagcct attaaaaggc | 780 |
| aaagaaaaac gcgtgccgaa agcgacctat acattccagt acttcagcac cctggaccaa | 840 |
| atcaaccgca cccgcctggg cccgaacttc agccgttca ccaaagaaca gcgcgacgtg | 900 |
| atcctggatg aaatgttcaa ccgcaccgac tactataaaa agaaaccat cccggaggtg | 960 |
| acatactacg atataaggaa atggctggcg ctggatgaaa ccatccagtt caaaggctta | 1020 |
| acctacgatc cgaacgagga attaagaag atcgaattaa aatcgttcat taatctgaaa | 1080 |
| ccgttctatg aaattaaaaa ggtggtaacc aactacgcga agaaaaccaa cgaagcattc | 1140 |
| agcacccctgg actacgatac attcgcgtac gcgctgaccg tgtataaaac cgacaaggat | 1200 |
| ataaggagct acctgaagaa atcaaacaac ctgagcaaat gctgctacga cgaccaatta | 1260 |

```
atcgaagaac tgctgaccct gagctacacc aaattcggcc acctgagctt caaagcgatc    1320
aaccacgtgc tgccgatcat gcaggaaggc cgcacctacc aggaagcgat ccaccagctg    1380
ggctacgatg cgaccaacct gaaaaaggaa accgcagca tgttcctgcc gctgttccct     1440
gatgaaatca ccaacccgat cgtgaaacgc gcgctgaccc aggcgcgcaa ggtggtgaac    1500
gcgatcatcc gccgctacgg ctcaccgaac agcgtgcaca tcgaactggc gcgcgaactg    1560
agcaaaagcc acgatgaacg caccaaaatc atgaaagcgc acgatgaaaa ctacaaaaag    1620
aacaaaggcg cgatcagcat cctgatcgaa aacggcatcc tgaacccgac cggctacgat    1680
atcgtgcgct acaaactgtg gaagaacag ggcgaacgct cgcgtacag cctgaaacag      1740
atcccggcga acaccttctt caacgaaatg aaaaaggaac gctcaggcag cccggtgctg    1800
gaaatcgatc acatcctgcc gtacagccag agcttcatcg atagctacca acaaaagtg     1860
ctggtgtacg cgatgaaaa ccagaaaaag ggcaaccgca tcccgtacac ctacttcctg     1920
gaaggcaaca aagattggga gagcttcgaa agctacgtgc gcctgaacag cttcttcagc    1980
aaaaagaaac gcggctacct gctgaaaaag gcgtacctgc cgcgcgaaag caacatgatc    2040
aaagaacgcc acttaaacga taccccgctac gcgagcagct acctgaaaaa cttcatcgag   2100
aaaaacctga aattcaaaga agtggaaggc agcacccgta aaaagcatgt ccagaccgtg    2160
aacggcatca tcaccgcgca tctgcgcaaa cgctggggcc tggaaaaaga tcgccaggaa    2220
acctatctgc atcatgcgat ggatgcgatc atcgtggcgt gcaccgatca tcatatggtg    2280
accaaagtga ccgaatatta tcagatcaaa gaaagcaaca atcaatccg caaaccgtat     2340
tttccgctgc cgtgggtggg ctttcgcgaa gaaatcctga ccatctggc gcgtcagccg     2400
atcgcgcgta aaatcagcga agaactgaaa atcggctatc agagctttga ttatatcctg   2460
gtgagccgca tgccgaaacg cagcgtgacc ggcgcgcgc atgaacagac catcatgaaa    2520
aagggcggca tcgataaaaa gggcaaaacc atcatcatca acgcgtgta tctgaaagat    2580
atcaaatttg atgaaaacgg cgattttaaa atggtgggca aggaacagga cttagcgacc    2640
tacgaagcga tcaaacagcg ctacatcgag tacggcaaag agagcaaaaa ggcgtttgaa    2700
accccgctgt acaaaccgag caaaagggc aagggcaacc tgatcaaaaa gatcaaagtg     2760
gaagtccaga ccaaatcgtt tgtgcgcgaa gtgaacggcg gcgtggcgca aacggcgat    2820
ctggtgcgcg tggatctgtt tgaaaaagat aaccgctact atatgatccc gatctacgtg    2880
atggataccg tgcatagcga gctgccgaac aaagcggtga ccagcagcaa aggctatgaa    2940
cagtggttaa ccatcgataa cagctttacc ttcaaattca gcctgtatcc gtacgacctg    3000
gtgcgcctgg tgaaaggcaa cgaagatcgc ttcctgtatt tcagcaccct ggacatcaac    3060
agcgatcgcc tgaacttcaa ggacgtgaac aaaccgagca acaggcgga aaaccgctat     3120
agcctgaaga ccatcgagaa cctggagaaa tatgaagtgg gcgtgctggg cgatctgcgc    3180
tttgtgcgcc aggaaattcg caaaaacttc                                    3210
```

<210> SEQ ID NO 185
<211> LENGTH: 3213
<212> TYPE: DNA
<213> ORGANISM: Bacillus sp.
<220> FEATURE:
<221> NAME/KEY: source
<223> OTHER INFORMATION: /note="APG07433.1 Native Seq"

<400> SEQUENCE: 185

```
atgagggagt tggactatcg cataggtta gatattggga cgaattctat tggatgggt     60
```

```
gttattgaat tatcctggaa caaggacaga gaacgatatg aaaaagtaag gattgtcgac      120
cagggtgttc gtatgtttga tagggctgaa atgccaaaaa caggtgcttc tcttgctgaa      180
ccgaggcgta tagcacgttc atcacgtaga aggttaaatc gtaaaagtca gaggaagaaa      240
aatatacgta atttacttgt tcaacatggg gtgattactc aagaagagct ggattcgtta      300
tatcctcttt caaaaaaatc aatggatatt tggggtattc gattggatgg attagatcgt      360
ctgctaaatc attttgaatg ggctcgatta ttaattcatt tagctcaaag acgtggtttt      420
aaatcgaatc gtaagtctga actgaaagat acggagacgg ggaaggtatt atcgagtatt      480
caattaaatg aaaaacgatt atcactgtac cgtacagtgg gagaaatgtg gatgaaagat      540
cctgatttta gtaagtatga tagaaaacgg aattctccta atgagtatgt attttcggtt      600
agtcgtgcgg aactagaaaa ggaaatagtt actttatttg cagcacaaag aaggtttcag      660
tcaccatacg catcgaagga tttacaagaa acatatttac aaatttggac acaccaactt      720 cccttttgctt ctgggaatgc aattttaaat aaagtgggat attgttcatt attgaaaggg      780
aaagaaagaa gaattccgaa agcaacatat acttttcagt attttagtgc actagatcaa      840
gtgaatcgaa cacgattagg acctgatttt cagccatttta cgaaggaaca aagagaaatt      900
attttaaata acatgtttca acgtacagat tattataaaa aaaagactat acctgaagtt      960
acatactatg atatccggaa atggctagaa ctagatgaaa ctattcaatt taaaggactt     1020
aattatgatc caaacgaaga attgaaaaaa atagaaaaga aaccatttat taatttaaag     1080
gcattctatg aaattaataa ggtagtcgca aattattctg agagaacaaa tgagacattt     1140
tcaacgttag actatgatgg gattggatat gctttaacag tttataaaac ggacaaagat     1200
attaggtctt atttgaagag ctctcataat ttacctaaac gttgttacga tgatcaatta     1260
atagaggaac tattaagtct ttcttataca aagtttggtc acttatcact gaaagcaatc     1320
aatcacgtac tatcgattat gcaaaaaggc aatacttata agaagcagt agaccagtta     1380 gggtatgata caagcggttt aaagaaagaa aaaagaagta agttcttgcc tcctatttca     1440
gatgagataa cgaatccaat tgttaaaaga gcgttaacac aagcgcgtaa agttgtgaat     1500
gctataatta aagacatgg ttctccacat tcagttcata ttgaactggc tcgtgaactt     1560
tctaaaaatc atgacgagag aacaaaaata gtgtcagctc aagatgaaaa ttataagaag     1620
aataaagggg ctatatcaat tttaagtgag catggaattt tgaatccaac aggctatgat     1680
attgttcgtt ataagttatg gaaagaacaa ggagaacgat gtgcttattc gttaaaggag     1740
attcctgcgg atacgttttt taatgaatta aaaaaagaac gaaatggtgc tccaattcta     1800
gaggtagatc acatttttacc gtacagtcaa agttttattg atagttatca taataaagta     1860
ttagtttaca gtgatgaaaa tcgaaaaaag gggaatcgaa ttccatatac ctattttttta     1920 gagacaaata aggattggga agcttttgaa agatatgtaa gatcaaataa attttttttct     1980 aaaaagaagc gtgagtattt attgaaaaga gcatatttgc caagagaaag tgaactgata     2040
aaggagcgac atttaaatga tacgcgatat gctagtacct ttttgaaaaa cttcattgag     2100
cagaatttgc aatttaaaga agctgaagat aatccgcgta aagacgtgt acaaacagtt     2160 aacggtgtaa ttacagcaca ttttcgaaaa agatggggat tagaaaaaga tagcaagaa     2220 acatacttac atcatgcaat ggacgctatc attgttgctt gtacagacca tcatatggtt     2280
actagagtaa cagagtatta tcaaataaaa gaaagtaata aatcagtaaa gaaaccgtat     2340
tttcctatgc catgggaggg ctttagagat gaactcttat cacatttagc gagtcagcca     2400
atagctaaaa aaattagtga ggagcttaaa gctggatatc aatcattaga ttatatatttt     2460
```

```
gtgtctcgaa tgccaaaaag atctatcact ggagcagcac ataaacaaac gatcatgaga    2520
aaaggcggta ttgataaaaa aggaaaaact attattatag agcgtttgca tttaaaggat    2580
attaagtttg atgagaatgg tgattttaaa atggttggca agaacaaga tatggcaact     2640 tacgaggcga taaagcaaag atatttggag catggaaaaa actcgaaaaa agcatttgaa    2700
acacctctat acaaacctag taaaaaagga acaggaaatc ttattaaaag agttaaagtt    2760
gaaggacaag ctaaatcttt tgttcgaaga gtaaatgggg gcgtagccca aaatggtgat    2820
ttagtgagag ttgatttatt tgaaaaagat gataaatatt acatggtgcc tatttatgta    2880
ccagataccg tttgttcaga attacccaaa aaagttgtgg caagtagtaa gggttatgag    2940
caatggttaa cactagataa cagctttacg tttaaattta gtttatacccc ttatgattta   3000 gtacggcttg taaaggggga cgaagatcgt ttcttatact ttggtactct cgatatcgat    3060
tcagatcgtc ttaattttaa agatgtaaat aagccatcaa aaagaatga atatcgttat     3120 agccttaaaa caattgagga tttagaaaaa tatgaggtgg gtgttttagg agatttaagg    3180
ttagtaagaa aagaaacacg tagaaatttt cac                                 3213

<210> SEQ ID NO 186
<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG07433.1 E. coli optimized"

<400> SEQUENCE: 186
atgcgcgagc tagattatcg catcggcctg atattggca ctaactcaat aggctggggc      60
gtgatcgaac tgagctggaa taaagaccgc gagcgctatg aaaaggtgcg cattgtggat    120
cagggcgtca gaatgtttga tcgtgcggaa atgccgaaaa ccggtgcatc actggcagaa    180
ccaagacgta tagcacgtag tagtcgccgc cgattaaacc gtaaaagcca gcgcaagaaa    240
aatatccgca acctgctggt tcagcatggc gtcatcaccc aggaagaact ggatagcctg    300
tacccgctga gcaagaaatc aatggacatc tggggcattc gtctggatgg tctgaccgc    360 ctattaaacc actttgaatg ggcccgccta ttaattcatc tggcgcagcg ccgcggcttc    420
aaatcaaacc gcaagagcga attaaaggac accgagaccg gtaaagtgct gtcatcgatc    480
cagctgaatg aaaaacgcct gagcctgtat cgcaccgtgg gcgagatgtg gatgaaagac    540
ccggacttct caaaatacga ccgcaaacgc aacagcccga cgaatacgt gtttagcgtt     600 agccgtgcgg aactggagaa agaaatcgtg accctgtttg cagctcagcg ccgttttcag    660
agcccgtatg cgagcaaaga tctgcaagaa acctacctgc agatctggac ccatcagctg    720
ccgtttgcaa gcggtaacgc gatattaaac aaagtgggct attgcagcct attaaaaggc    780
aaagaacgcc gcatcccgaa agcgacctat acattccagt acttcagcgc gctggaccag    840
gtgaaccgta cccgtctggg tccggatttt cagccgttca ccaaagaaca gcgcgagatc    900
atattaaaca acatgttcca gcgcaccgac tactataaaa agaaaaccat cccggaggtg    960
acatattacg atataaggaa atggctggaa ctggatgaaa ccatccagtt caaaggcctg   1020
aactacgatc cgaacgagga gctgaaaaaa atcgagaaaa aaccgttcat taatctgaaa    1080
gcgttctatg aaatcaacaa agtggtggcg aactacagcg aacgcaccaa tgaaaccttc    1140
```

```
tcaaccctgg attacgatgg catcggctac gcgctgaccg tgtataaaac cgacaaggat    1200
ataaggagct acctgaaatc aagccacaac ctgccgaaac gctgctacga cgaccaatta    1260
atcgaagaac tgctgagcct gagctatact aagttcggcc acctgtcatt aaaagcgatt    1320
aatcacgtgt taagcatcat gcagaaaggc aacacatata agaagcggt ggatcagctg     1380 ggctacgata ccagcggatt aaaaaaagaa aaacgcagca aattcctgcc gccgatcagc    1440
gatgaaatca ccaacccgat cgtgaaacgc gcgctgaccc aggcgcgcaa agtggtgaac    1500
gcgatcatcc gccgccacgg cagcccgcac agcgtgcaca tcgaactggc gcgcgaactg    1560
agcaaaaacc acgatgaacg caccaaaatc gtgagcgcgc aggatgaaaa ctacaaaaag    1620
aacaaaggcg cgatcagcat cctgtcagaa cacggcatcc tgaacccgac cggctacgat    1680
atcgtgcgct acaaactgtg gaaagagcag ggcgaacgct cgcgctacag cctgaaagaa    1740
atcccggcgg ataccttctt caacgagctg aaaaagaac gcaacggcgc cccgatcctg     1800
gaagtggatc acatcctgcc gtacagccag agcttcatcg atagctacca caacaaagtg    1860
ctggtgtaca gcgatgaaaa ccgcaaaaaa ggcaaccgca tcccgtacac ctacttctta    1920
gagaccaaca aagattggga agcgttcgaa cgctacgtgc gcagcaacaa gttcttcagc    1980
aaaaagaagc gcgagtacct gctgaaacgc gcgtacctgc cgcgcgaaag cgaactgatc    2040
aaagaacgcc atcgaacga tacccgctac gcgagcacct tcctgaaaaa cttcatcgaa     2100
cagaacctgc agttcaaaga gcggaagat aacccgcgca aacgccgcgt ccagaccgtg     2160
aacggcgtga tcaccgcgca ttttcgcaaa cgctgggcgt tagaaaaaga tcgccaggaa    2220
acctatctgc atcatgcgat ggatgcgatc atcgtggcgt gcaccgatca tcatatggtg    2280
acccgcgtga ccgaatatta tcagatcaaa gaaagcaaca aaagcgtgaa aaaaccgtat    2340
tttccgatgc cgtgggaagg ctttcgcgat gaactgctga gccatctggc gagccagccg    2400
atcgcgaaaa aaatcagcga agaactgaaa gcgggctatc agagcctgga ttatatcttt    2460
gtgagccgca tgccgaaacg ctcaatcacc ggcgcggcgc ataaacagac catcatgcgc    2520
aaaggcggca tcgataaaaa aggcaaaacc atcatcatcg aacgcctgca tctgaaagat    2580 atcaaattg atgaaaacgg cgatttaaa atggtgggca agaacagga catggcgacc       2640 tacgaagcga tcaaacagcg ctatctggag catggcaaga acagcaaaaa agcgtttgag    2700
accccgctgt acaaaccgag caaaaaaggc accggcaacc tgatcaaacg cgtgaaagtg    2760
gaaggccagg cgaaatcatt tgtgcgcgaa gtgaacggcg gcgtggcgca gaacggcgat    2820
ctggtgcgcg tggatctgtt tgaaaaagat gacaaatatt atatggtgcc gatctatgtg    2880
ccggataccg tgtgtagcga actgccgaaa aaagtggtgg cgagcagcaa aggctatgaa    2940
cagtggctga ccctggataa cagctttacc ttcaaattca gcctgtatcc gtatgatctg    3000
gtgcgcctgg tgaaaggcga tgaagatcgc tttctgtatt ttggcacccct ggacatcgat    3060 tcagatcgcc tgaacttcaa ggacgtgaac aaaccgagca aaagaacga atatcgctat    3120 agcctgaaaa ccattgaaga tctggaaaaa tatgaagtgg gcgtgctggg cgatctgcgc    3180
ctggtgcgca agagacccg ccgcaacttt cat                                  3213

<210> SEQ ID NO 187
<211> LENGTH: 3213
<212> TYPE: DNA
<213> ORGANISM: Bacillus sp.
<220> FEATURE:
<221> NAME/KEY: source
<223> OTHER INFORMATION: /note="APG07513.1 Native Seq"
```

<400> SEQUENCE: 187

```
atgagagagt tggattatcg cataggatta gatattggaa cgaattctat tggctggggt    60
gttattgaat tatcttggaa caaagataga gaacaatatg agaaaacgag aattgtcgac   120
aagggtgttc gtatgtttga taaggctgaa atacctaaga ctggtgcttc tcttgctgaa   180
ccgagacgta tagcgcgctc atcacgtaga aggttaaatc gtaaaagcca gagaaaaaaa   240
gatatacgta atttacttgt tcaacatgaa attattagcc aaaaggaatt gacttcgtta   300
tatcccctgt caaaaagttc aatggatatt tgggatattc gcttagatgg attagatcgc   360
ttgttagacc gttttgaatg ggctcgatta ttaattcatt tagcacaaag acgcggtttt   420
aaatcaaatc gaaagtctga actgaaagat gtggagacag gaaaagtatt atcaagtatt   480
caagtaaatg aaaaacgatt atctctgtac cgtacagtgg gagagatgtg gatgaagaat   540
gcggattgta gtaaatatgg caaaaggcgt aattctccta atgagtatgt attttcggtt   600
agccgtgcag atttagaaaa ggaaattgtg actctatttg aggcgcaaag aaaattccat   660
tcatcatatg catcggttga tttacaaaaa acatatatac aaatttgggc acaccaactt   720
cctttttgctt ctgggaatgc aattgtaaat aaagtaggag attgttcatt attaaaaggt   780
aaagaaaaga gagttccaaa agcaacatat acttttcaat atttcaatac actagatcaa   840
ataaaccgaa cacgattagg gcccaatttc caaccattta cgaaggaaca gagagacata   900
attttagata aaatgtttca acggacagat tattataaaa aaaagacaat acccgaagtt   960
acttactatg atattcggaa atggttagca ctagatgaaa caattcaatt taaaggactt  1020
acctatgacc caaacgaaga gctgaaaaaa atagaaatga accccttttat taatttaaag  1080
ccattctatg aaattaaaaa ggtagttact aattacgcaa aaaaaacaaa tgaggtattc  1140
tcagcattag attatgatac agttgcatac gctttaacag tttataaaac ggacaaagat  1200
attagatctt atttgaagag atctaataat ttatcaaaac gttgctacga tgatcaatta  1260
atagaagagc tattaactct ctcctataca aagtttggtc atttatcatt taaagcaatt  1320
aatcatgtac tgccaattat gcaagaggga aggacttatc aggaagcaat acaccaatta  1380
gggtatgata ccactaatct taaaaaagaa acagaagta tgttcttgcc tattattcca  1440
gatgagataa caaatccaat tgttaaaaga gcgttaactc aagcacgtaa agttgtaaat  1500
gctattatta aagatatgg ttctccaaat tctgttcata ttgaactagc tcgtgagctt  1560
tcgaaaagtc atgacgagag aaaaaaaata atgacagctc atgatgaaaa ttataagaaa  1620
aataaaggag ctgtatcaat tttgatcgat aatggaattt taaatccgac aggatatgat  1680
attgtacgtt ataagttatg gaaagagcaa ggagaacgat gtgcttattc gttaaaaaag  1740
attcctgcta atacgttttt taatgaattg aaaaagagc gaagtggccc tccggttcta  1800
gaggtagatc acattttacc gtatagtcag agtttttattg atagttacca taataaagta  1860
ttagtttatg gggatgaaaa tcaaaaaaag ggaaatcgaa ttccatatac ttttttttca  1920
gaagaagata aggagtggga aagctttgaa agctacgtaa gatcgaatag ttttttttct  1980
aaaaagaagc gcggatattt attgaaaaaa gcttacttgc caagagagag taacttgatt  2040
aaggagcgtc atttaaatga tacccgatat gctagtagct atttgaaaaa cttcattgag  2100
aaaaatttaa aatttaaaga agctgtaggt attacacgaa aaaaatatgt acagacggtt  2160
aacggtgtaa ttcagcccca tctgcgaaaa aggtgggggtt tagaaaaaga taggcaggaa  2220
acatatttgc atcatgcaat ggacgctatt attgttgctt gtacagatca tcatatggtc  2280
```

| actaaagtaa cggagtacta tcaaataaaa gaaggtaata agtcaataaa gaaaccgtat | 2340 |
| tttcctttgc catggatggg atttagagag gaaattttat cacatttaga aagtcagcca | 2400 |
| attgctagaa aaattagtga ggaacttaaa attggatatc aatcacctga ttatatactt | 2460 |
| gtatcgcgaa tgccaaaaag atctgtcact ggatcagctc atgatcagac agtcatgaaa | 2520 |
| aaaggcgata tcgataaaaa aggaaagact attatcataa agcgtgtgca cttaaaggat | 2580 |
| attaagtttg atgagaatgg cgattttaaa atggttggca agaacaaga tttagcaact | 2640 |
| tacgaagcga taaagcaaag atatttagag tatagaaaag aatcgaaaaa agcatttgaa | 2700 |
| acacctttat acaagcctag taaaaaagga aaaggaaacc tcattaaaaa aattaaagta | 2760 |
| gaagtgcaaa ccaaatcttt tgttcgagaa attaatgggg gcgtagctca aaatggtgat | 2820 |
| ttagtaagag tagatttgtt tgaaaaggat aataggtatt atatggtgcc tatttacgta | 2880 |
| gtagatactg ttcgttccga actaccaaat aaagctgtaa caagcagtaa aggctatgag | 2940 |
| caatggttat caatagataa cagctttacg ttcaaattca gtttatatcc ttatgattta | 3000 |
| gtacgacttg taaaaggcga tgaagatcgt tttctatact ttagtactct tgatattaat | 3060 |
| tcggaccgtc ttaattttaa agatgtaaat aagccatcaa agcaagctga atatcgttat | 3120 |
| agtcttaaaa caattgagaa tttagaaaaa tatgagattg tgttttagg tgatttaagg | 3180 |
| ttagtgagac aagaaacacg taaaattttt aaa | 3213 |

<210> SEQ ID NO 188
<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG07513.1 E. coli optimized"

<400> SEQUENCE: 188

| atgcgcgagc tagattatcg catcggcctg gatattggca ctaactcaat aggctggggc | 60 |
| gtgatcgaac tgagctggaa taaagaccgc gagcagtatg aaaagacccg catcgtggat | 120 |
| aaaggcgtgc gcatgttcga caaagcggaa attccgaaaa ccggtgcaag tctggcggaa | 180 |
| ccaagacgta ttgcacgtag tagtcgccgc cgattaaacc gcaaaagtca gcgcaagaag | 240 |
| gatatcagga acctgctggt ccagcatgaa atcatcagcc agaaggaatt aaccagcctg | 300 |
| tacccgctga gcaaatcaag tatggacatc tgggatataa ggctggacgg cctggaccgc | 360 |
| ctgctggatc gttttgaatg ggcccgccta ttaatccatc tggcacagcg ccgtggcttc | 420 |
| aaatcaaacc gcaagagcga attaaaggac gtggagaccg gtaaagtgct gtcaagcatt | 480 |
| caggtgaatg aaaagcgcct gagcctgtat cgcaccgtgg gcgagatgtg atgaaaaac | 540 |
| gcggactgct caaatatgg caaacgccg aacagcccga acgaatacgt gtttagcgtt | 600 |
| agccgtgcgg acctggaaaa agaaatcgtg accctgtttg aggcgcagcg caaattccat | 660 |
| agcagctatg cgagcgtgga tctgcagaaa acatacatcc agatctgggc acatcagctg | 720 |
| ccgtttgcga gcggtaacgc gatcgtgaat aaagtgggct attgcagcct attaaaaggc | 780 |
| aaagaaaaac gcgtgccgaa agcgacctat acattccagt acttcaatac actggaccaa | 840 |
| atcaaccgca cccgcctggg cccgaacttc agccgttca ccaaagaaca gcgcgatata | 900 |
| atcctggata aaatgttcca gcgcaccgac tactataaaa agaaaaccat cccggaggtg | 960 |

```
acatactacg atataaggaa atggctggcg ctggatgaaa ccatccagtt caagggctta    1020
acctacgatc cgaacgagga gctgaaaaag atcgagatga aaccgttcat taatctgaaa    1080
ccgttctatg aaattaaaaa ggtggtaacc aactacgcga agaaaaccaa cgaagtgttc    1140
agcgcgctgg attacgatac cgtggcgtac gcgctgaccg tgtataaaac cgacaaggat    1200
ataaggagct acctgaaacg cagcaataat ctgagcaaac gctgctacga cgaccaatta    1260
atcgaagaac tgctgaccct gagctatact aagttcggcc acctgagctt caaagcgatt    1320
aatcacgtgc tgccaataat gcaggaaggc cgcacctacc aggaagcaat acaccagctg    1380
ggctacgata caaccaacct gaaaaaggaa aataggagca tgttcctgcc aataatcccg    1440
gatgaaatca ccaacccgat cgtgaaacgc gcgctgaccc aggcgcgcaa agtggtgaac    1500
gcaataatcc gccgctacgg ctcaccgaac agcgtgcaca tcgaactggc gcgcgaactg    1560
agcaaaagcc acgatgaacg caaaaagatc atgaccgcgc acgatgaaaa ctacaaaaag    1620
aacaaaggcg cggtgagcat cctgatcgat aacggcatcc tgaacccgac cggctacgat    1680
atcgtgcgct acaaactgtg gaaagaacag ggcgaacgct gcgcgtacag cctgaaaaag    1740
atcccggcga cacccttctt caacgaactg aaaaaggaac gctcaggccc gccggtgctg    1800
gaagtggatc acatcctgcc gtacagccag agcttcatcg atagctacca caacaaagtg    1860
ctggtgtacg gcgacgaaaa ccagaaaaag gcaaccgca tcccgtacac cttcttcagc    1920
gaagaagaca agaatgggga gagcttcgaa agctacgtgc gcagcaacag cttcttcagc    1980
aaaaagaaac gcggctacct gctgaaaaag gcgtacctgc cgcgcgaaag caacttaatc    2040
aaagaacgcc atctgaacga tacccgctac gcgagcagct acctgaaaaa cttcattgag    2100
aaaaacctga aattcaagga agcggtgggc atcacccgca agaagtacgt ccagaccgtg    2160 aacgcgtga tcaccgcgca tctgcgcaaa cgctggggcc tggaaaaaga tcgccaggaa    2220
acctatctgc atcatgcgat ggatgcgatc atcgtggcgt gcaccgatca tcatatggtg    2280
accaaagtga ccgaatatta tcagatcaaa gaaggcaaca aatcaatcaa aaagccgtat    2340
tttccgctgc cgtggatggg cttccgcgaa gaaatcctta gccatctgga aagccagccg    2400
atcgcgcgca aaatcagcga agaactgaaa atcggctatc agagcccgga ttatatcctg    2460
gtgagccgca tgccgaaacg cagcgtgacc ggcagcgcgc atgatcagac cgtgatgaaa    2520
aagggcgata tcgataaaaa gggcaaaacc atcatcatca aacgcgtgca tctgaaagac    2580
atcaaattcg acgaaaacgg cgacttcaaa atggtgggca aggaacagga cttagcgacc    2640
tacgaagcga tcaaacagcg ctacctggaa taccgcaaag agagcaaaaa ggcgtttgaa    2700
accccgctgt acaaaccgag caaaaagggc aagggcaacc tgatcaaaaa gatcaaagtg    2760
gaagtccaga ccaaatcgtt tgtgcgcgag atcaacggcg cgtggcgca aacggcgat    2820 ctggtgcgcg tggatctgtt tgaaaaagat aaccgctatt atatggtgcc gatctacgtg    2880
gtggataccg tgcgcagcga actgccgaac aaagcggtga ccagcagcaa aggctatgaa    2940
cagtggttaa gcatcgataa cagcttcacc ttcaaattca gcctgtaccc gtatgatctg    3000
gtgcgcctgg tgaaaggcga tgaagatcgc ttcctgtatt ttagcaccct ggacatcaac    3060
agcgatcgcc tgaacttcaa agacgtgaac aaaccgagca acaggcgga atatcgctac    3120 agcctgaaga ccatcgagaa cctggagaaa tacgaaattg gcgtgctggg cgatctgcgc    3180
ctggtgcgcc aggaaacccg caaaatcttc aaa                                  3213
```

<210> SEQ ID NO 189
<211> LENGTH: 3216

<212> TYPE: DNA
<213> ORGANISM: Bacillus sp.
<220> FEATURE:
<221> NAME/KEY: source
<223> OTHER INFORMATION: /note="APG08290.1 Native Seq"

<400> SEQUENCE: 189

| | |
|---|---|
| atgagtgagt tggattaccg catagggttg gatattggta cgaattccat tggctggggt | 60 |
| gttattgaat tattttggaa caaggacaga gaacgatatg aaaaagtaag gattgtcgac | 120 |
| aagggcgttc gtatgtttga taaggctgaa atacctaata agggtgcttc tcttgctgaa | 180 |
| ccgagacgta tagcgcgttc atcacgtaga aggttaaatc gcaaaagtca gaggaagaaa | 240 |
| gagatacgta atttacttgt tcaacacgga atgattaccc aagaggaatt ggatttgtta | 300 |
| tatcctcttt caaaaaaatc aatagatatt tgggatattc gtttggatgg attagatcgt | 360 |
| ctgttgaatc atcttgaatg ggctcgatta ttaattcatt tagcacaaag acgtggtttt | 420 |
| aagtcgaatc gaaagtctga attgaaagat gctgagacgg ggaaggtatt atcgagtatt | 480 |
| caagtaaatg aaaaacgact atttctgtac cgtacagtgg gggaaatgtg gataaaagat | 540 |
| gctgagttta gtaagtatga tagaagacgt aattctccta atgagtatgt atttttcggtt | 600 |
| agtcgtgcgg acttagaaaa ggaaattgtt actctatttg aagcacaaag aaagtttcag | 660 |
| tcatcatacg catcgaagaa cttacaagaa acatatttac aaatttgggc acaccaactt | 720 |
| ccttttgctt ctgggaatgc aattttaaac aaagtaggct attgttcatt attgaaaggg | 780 |
| aaagaaagga gaattccgaa agcaacatat acttttcaat atttcagtgc actagatcag | 840 |
| gtgaatcgaa cacgattagg aacctgatttt caaccattta cgcaggaaca gaaagagatt | 900 |
| attttagata aaatgtttca acgtacagat tattataaaa aaaagactat acctgaagtt | 960 |
| agctactatg atatacggaa atggctgagg ttagatgaaa ctattcaatt taaaggactt | 1020 |
| aattatgatc caaacgaaga actgaaaaaa atagaaaaaa aaccatttat taatttaaag | 1080 |
| gcattctatg aaattaaaaa ggtagttgca aattatgctg agagaacaaa tgaggcattt | 1140 |
| tcaacgttag actatgatgc gattgcatat gctttaacag tttataaaac ggacaaagat | 1200 |
| attagatctt atttgaagaa atctaataat ttatcaaaaac gttgctacga cgatcaatta | 1260 |
| atagaagagc tatttactct ctcctataca aagtttggtc atttatcatt taaagcaatt | 1320 |
| aatcatgtac ttccaattat gcaagaggga aggacttatc aagaagcgat acaccaatta | 1380 |
| ggatatgata ccactaatct taaaaaagaa acagaagta tgttcttgcc tcttattcca | 1440 |
| gatgaaataa caaatccaat tgttaaaaga gcgataactc aagcacgtaa agttgtaaac | 1500 |
| gctattatta aagatatgg ttctccaaat tctgttcata ttgaactagc tcgtgagctt | 1560 |
| tctaaaagtc atgacgagag aaagaaaata atgacggctc atgatgaaaa ttataagaaa | 1620 |
| aataaaggag ctatatccat tttgatcgag aatggaattt taaatccgac aggatatgat | 1680 |
| attgtacgtt ataagttatg gaaagagcaa ggagaacgat gtgcttattc gttaaaggag | 1740 |
| attcctccgg atacgttttt taatgaatta aaaaaagaac gaaatggttc tccaattcta | 1800 |
| gaggtagatc acatttttacc gtatagccaa agttttattg atagttatca taataaagta | 1860 |
| ttagtttaca gtgatgaaaa tcgaaacaag ggaaatcgaa ttccatatac ctatttttta | 1920 |
| gagacaaata aggattggga agcttttgaa aggtatgtaa gatcaaataa gcttttttct | 1980 |
| aaaaagaagc gtgagtattt attgaaaaaa acatatttgc caagagagag tgaactaata | 2040 |
| aaggagcgac atttaaatga tacgcgatat gctagtacct ttttgaaaaa cttcattgag | 2100 |
| cagaacttgc aatttaaaga agttgaagtt aatctgcgta aaaaacgtgt gcaaacagtt | 2160 |

-continued

| | |
|---|---|
| aatggtgtaa ttacagcgca ccttcgaaaa agatggggat tagaaaaaaa tagacaggaa | 2220 |
| acatatctgc atcatgcaat ggacgctatc attgttgctt gtacagacca tcatatggtt | 2280 |
| actagaataa cagagtatta tcaaataaaa gaaagtaata aatcagtaaa gaaaccatat | 2340 |
| tttccgatgc catgggaggg ttttagagat gaactcttat cacatttagc gagccagcca | 2400 |
| attgctaaaa aaattagtga ggagcttaaa gctggatatc aatcatctga ttatatattt | 2460 |
| gtgtctcgaa tgccaaaaag atctgtcact ggagcagctc atgatcaaac gattaggaga | 2520 |
| aaaggtggta ttgataaaaa aggaaaaact attattataa agcgtgtgcg cttaaaggat | 2580 |
| attaagtttg atgagaatgg cgattttaaa atggttggaa agaacaaga tttagcaact | 2640 |
| tatgaggcga taaagcaaag atatttggag catagaaaaa actcgaaaaa agcatttgaa | 2700 |
| acacctctat acaagcctag taaaaaaggg acaggaaatc tcatcaaaag agttaaaatt | 2760 |
| gaaggacaaa ctaaagcttt tgttcgagaa gtaaatgggg gagtagccca aaatagtgat | 2820 |
| ttagtaagag ttgatttatt tgaaaaagat gataaatatt acatggtgcc tatttatgta | 2880 |
| ccagataccg tttgttcaga attacccaaa aaagttgtga aaagtggtaa gggttatgag | 2940 |
| caatggctaa cactagataa cagctttacg tttaaatcta gtttataccc ttatgattta | 3000 |
| gtacgtcttg taaaaggtaa tgaagatcgt tttttatact ttggtactct cgatatcgat | 3060 |
| tctgaccgtc ttaattttaa agatgtaaat aagccatcaa acagaatga atatcgttat | 3120 |
| agtcttaaaa caattgagaa tttagaaaaa tatgaggttg gtgttttagg tgatttaagg | 3180 |
| ttagtgaaac aagaaacacg tagaattttt aataga | 3216 |

<210> SEQ ID NO 190
<211> LENGTH: 3216
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: source
<223> OTHER INFORMATION: /note="APG08290.1 E. coli optimized"

<400> SEQUENCE: 190

| | |
|---|---|
| atgagcgagc tagattatcg catcggcctg gatatcggca ctaactcaat aggctggggc | 60 |
| gtgatcgaac tgttctggaa taaagaccgc gagcgctatg aaaaggtgcg catcgtggac | 120 |
| aaaggcgtca ggatgttcga caaagcggag atcccgaata aggtgcatc actggcggaa | 180 |
| ccaagacgta tagcacgtag tagtcgccgc cgattaaacc gcaaaagtca gcgcaagaaa | 240 |
| gagatccgta acctgctggt tcagcatggc atgatcaccc aggaagaact ggatctgctg | 300 |
| tacccgctga gcaagaaatc aatcgacatc tgggatataa ggctggacgg cctggaccgc | 360 |
| ctattaaacc atctggaatg ggcccgccta ttaatccatc tggcgcagcg tagaggcttc | 420 |
| aaatcaaacc gcaagagcga attaaaggac gcggagaccg gtaaagtgct gtcaagcatt | 480 |
| caggtgaatg aaaagcgcct gttcctgtat cgcaccgtgg gcgagatgtg gattaaagac | 540 |
| gcggagttct caaatacga ccgccgtcgc aacagcccga acgaatacgt gtttagcgtt | 600 |
| agccgtgcgg acctggagaa agaaatcgtg accctgtttg aagcgcagcg caaattccaa | 660 |
| tcaagctacg cgagcaagaa cctgcaagag acctacctgc agatttggc acatcagctg | 720 |
| ccgtttgcaa gcggcaacgc gatattaaac aaagtgggct attgcagcct attaaaaggc | 780 |
| aaagaacgcc gcatcccgaa agcgacctat acattccagt acttcagcgc gctggaccag | 840 |

```
gtgaaccgta cccgtctggg ccctgatttt cagccgttta cccaggaaca gaaagaaata    900
atcctggata aaatgttcca gcgcaccgac tactataaaa agaaaaccat cccggaagtg    960
tcatattacg atataaggaa atggctggag ctggatgaga ccatccagtt caagggcctg   1020
aactacgatc cgaacgagga gctgaaaaaa atcgagaaaa aaccgttcat taatctgaaa   1080
gcgttctatg aaattaaaaa agtggtggcg aactacgcgg aacgaaccaa cgaagcattc   1140
agcaccctgg attacgatgc gatcgcgtac gcgttaaccg tgtataaaac cgacaaggat   1200
ataaggagct acctgaaaaa atcaaacaac ctgagcaaac gctgctacga cgaccaatta   1260
atcgaagaac tgttcaccct gagctatact aagttcggcc acctgagctt caaagcgatt   1320
aatcacgtgc tgccaataat gcaggaaggc cgcacctacc aggaagcgat ccaccagctg   1380
ggctacgata ccaccaacct gaaaaaagaa accgcagca tgttcctgcc gctgatcccg   1440
gatgaaatca ccaacccgat cgtgaaacgc gcgatcaccc aggcgcgcaa agtggtgaac   1500
gcgatcatcc gccgctacgg ctcaccgaac agcgtgcaca tcgagctggc gcgcgagctg   1560
agcaaaagcc acgacgagcg caaaaaaatc atgaccgcgc acgacgagaa ctacaagaaa   1620
aacaaaggcg cgatcagcat cctgatcgag aacggcatcc tgaacccgac cggctacgat   1680
atcgtgcgct acaaactgtg gaaagaacag ggtgaacgct gcgcgtacag cctgaaagaa   1740
atcccgccgg ataccttctt caacgaactg aaaaaagaac gcaacggctc accgatcctg   1800
gaagtggatc acatcctgcc gtacagccag agcttcatcg atagctacca caacaaagtg   1860
ctggtgtaca gcgatgaaaa ccgcaacaaa ggcaaccgca tcccgtacac ctacttcctg   1920
gaaaccaaca agattggga gcgttcgaa cgctacgtgc gcagcaacaa actgttcagc   1980
aaaaagaaac gcgaatacct gctgaaaaaa acctacctgc cgcgcgaaag cgaactgatc   2040
aaagaacgcc acttaaacga taccgctac gcgagcacct tcctgaaaaa cttcatcgaa   2100
cagaacctgc agttcaaaga agtggaggtg aacctgcgta aaaagcgcgt ccagaccgtg   2160
aacggcgtga tcaccgcgca tctgcgcaaa cgctggggcc tggaaaaaaa ccgccaggaa   2220
acctatctgc atcatgcgat ggatgcgatc atcgtggcgt gcaccgatca tcatatggtg   2280
acccgcatca ccgaatatta tcagatcaaa gaaagcaaca atcagtgaa aaaaccgtat   2340
tttccgatgc cgtgggaagg cttcgcgat gaactgctga ccatctggc gagccagccg   2400
atcgcgaaaa aaatcagcga agaactgaaa gcgggctatc agagcagcga ttatatcttt   2460
gtgagccgca tgccgaaacg cagcgtgacc ggcgcggcgc atgatcagac catccgccgc   2520
aaaggcggca tcgataaaaa aggcaaaacc atcatcatca aacgcgtgcg cctgaaagat   2580
atcaaatttg atgaaaacgg cgatttaaa atggtgggca agaacagga cttagcgacc   2640
tacgaagcga tcaaacagcg ctatctggag catcgcaaga acagcaaaaa agcgtttgag   2700
accccgctgt acaaaccgag caaaaaaggc accggcaacc tgatcaaacg cgtgaaaatc   2760
gagggccaga ccaaagcgtt tgtgcgcgaa gtgaacggcg gcgtggcgca aacagcgat   2820
ctggtgcgcg tggatctgtt tgaaaaagat gacaaatatt atatggtgcc gatctatgtg   2880
ccggataccg tgtgtagcga actgccgaaa aaagtggtga aagcggcaa aggctatgaa   2940
cagtggttaa ccctggataa cagcttcacc ttcaagagca gcctgtaccc gtatgatctg   3000
gtgcgcctgg tgaaaggcaa cgaagatcgc tttctgtatt ttggcaccct ggacatcgat   3060
agcgatcgcc tgaacttcaa agacgtgaac aaaccgagca gcagaacga ataccgctac   3120
agcctgaaga ccatcgagaa cctggagaaa tatgaagtgg gcgtgctggg cgatctgcgc   3180
```

| ctggtgaaac aggaaacccg ccgcattttt aaccgc | 3216 |

<210> SEQ ID NO 191
<211> LENGTH: 4011
<212> TYPE: DNA
<213> ORGANISM: Enterococcus sp.
<220> FEATURE:
<221> NAME/KEY: source
<223> OTHER INFORMATION: /note="APG05459.1 Native Seq"

<400> SEQUENCE: 191

| atgaagaaag actacgttat tggtctggat atagggacta attctgtcgg ctgggcagtt | 60 |
| atgacagaag actatcagtt ggtgaagaaa aaaatgccta tttatggaaa cactgaaaaa | 120 |
| aagaaaatca gaaaaatttt tggggtgtg cgtttatttg aagaagggca tacagccgaa | 180 |
| gatcgccgat taaaagaac agcacgacga agaattagtc gtcgacggaa tcgtttacgc | 240 |
| tacttacaag ctttttttga agaagcgatg acagctttgg atgaaaactt ttttgctcgt | 300 |
| ttacaagaga gttttttagt gcctgaagat aagaagtggc acagacatcc gattttgct | 360 |
| aagttggaag atgaagtagc ttaccatgaa acgtatccga caatctacca tttacgcaaa | 420 |
| aaattagcag attcatctga gcaagcgat ttacgactaa tttatttggc gttggcacat | 480 |
| attgtcaaat atcgtggaca ttttttaatt gaaggaaaat taagtacaga aaatatttct | 540 |
| gttaaagaac aatttcaaca atttatgatc atttataacc aaacctttgt gaatggagag | 600 |
| agtcgcttag ttagtgcgcc attacctgaa tctgtcttga ttgaggaaga gttgactgaa | 660 |
| aaagcttctc gtactaaaaa atctgaaaaa gtcttacaac aatttcctca agaaaaagct | 720 |
| aatggcttat ttggtcagtt cttaaagcta atggtaggga taaagctga ctttaaaaaa | 780 |
| gttttttggtt tggaagaaga agccaaaata acctacgcta gtgaaagcta tgaagaagat | 840 |
| ttagaaggca ttttagcaaa ggttggggat gaatatagtg acgtgttttt agctgctaaa | 900 |
| aatgtgtacg atgcagttga attatcaacg attttagcag attcggataa aaaaagtcac | 960 |
| gcgaaattat cttctagcat gattgtccgt tttacagaac atcaagaaga tttaaaaaaa | 1020 |
| ttcaaacgat ttattcgtga aaattgtcca gacgaatatg ataatctctt taaaaatgaa | 1080 |
| cagaaagacg gctatgcagg ctacattgca cacgcaggta aggtttcaca gcttaaattt | 1140 |
| taccagtatg ttaagaaaat cattcaagat attgctggag cagaatattt tttagaaaaa | 1200 |
| attgctcaag aaaactttt aagaaagcaa cggaccttg ataatggggt gattcctcat | 1260 |
| caaattcatt ggctgagtt acaagcaatc attcatcgtc aagcggccta ttatccattt | 1320 |
| ttaaaagaaa atcaagaaaa aattgaacaa ctggttacat ttcgaattcc ttattatgtc | 1380 |
| ggaccattat caaaggaga tgcaagtacc ttcgcttggc taaaacgtca aagtgaggaa | 1440 |
| ccaattcgac cttggaacct tcaagaaacc gttgatttgg accaatcagc gacagccttt | 1500 |
| attgaacgaa tgaccaattt tgatacgtat ttaccttctg aaaaagtttt accgaaacat | 1560 |
| agtttgttat atgaaaagtt tatggtattt aatgaattga ccaagatttc ttatacggat | 1620 |
| gatcgaggaa tcaaagccaa ttttcaggt aaagaaaaag aaaaatctt tgattatctg | 1680 |
| tttaagacgc gtcgaaaagt taagaaaag gatatcattc aattctatcg aaacgaatat | 1740 |
| aatacgaga ttgtcacgct tagtggactt gaagaagacc aatttaatgc tagttttagc | 1800 |
| acgtatcagg atttactgaa atgtggttta acaagagctg aattagacca ccctgataat | 1860 |
| gccgaaaaat tggaagatat cataaaaatt ttaactattt ttgaagatcg gcaacgaatt | 1920 |
| cggacgcaac tttccacatt caagggcag ttctcagcag aagtactaaa aaaattagaa | 1980 |

```
cgcaagcact acactggctg gggaagattg tcgaaaaaat taatcaatgg tatctacgat    2040
aaagaatcgg gtaaaacaat tttggactat ttaattaaag atgatggggt ctcaaaacac    2100
tataatcgca attttatgca actgattaat gattcacaat tatctttaaa aaatgctatt    2160
caaaaagcac agtccagtga acatgaagaa acattaagtg aaactgtcaa tgaattagct    2220
ggtagtccag caataaaaaa aggaatttat caaagtttaa aaattgtcga tgaactagtc    2280
gcgattatgg gttatgcgcc caagcggatt gttgtcgaaa tggcacgtga aaatcaaacg    2340
actagcactg gcaagagaag atccatccaa cgcttgaaaa tagttgaaaa agcaatggcc    2400
gaaatcggca gcaatttatt aaaagaacaa ccaacgacta atgaacagtt acgagatacc    2460
cgtcttttcc tttactatat gcaaaatggt aaagatatgt acacgggaga tgaattatcg    2520
cttcatcgtt tatctcacta tgatattgat catattatcc cacaaagctt tatgaaagac    2580
gattcattgg ataacctagt tttagtgggc tctactgaaa atcgagggaa atccgatgat    2640
gtacctagca aggaagttgt taaggatatg aaagcttatt gggagaaatt atatgctgct    2700
ggcttaatta gtcaacggaa attccaacgt ctgaccaagg gggagcaagg tggcttgact    2760
ctcgaagaca aagcgcattt tatccaacga caattagtag aaactcgtca aattaccaaa    2820
aatgttgcag ggatcttaga tcaacgctac aatgctaatt caaagagaa aaaagtccaa    2880 atcatcacct gaaagctag tttaacgagc caatttcgtt cgattttt gg cttgtataaa    2940 gttcgtgaag tgaatgatta tcaccatgga caagatgctt attta aactg tgtggtcgca    3000 accacgttat taaaagttta tcctaattta gcaccagaat ttgtttacgg agaatat cct    3060 aaattccagg cctttaaaga aaataaagcc acggcgaaga ctataattta tacaaatttg    3120
atgcgctttt tcacggaaga tgaaccacgg ttcatgaagg atggcgaaat tctttggagt    3180
aacagttatt taaaaaatat caaaaaagaa ttaaattacc atcaaatgaa tattgtcaaa    3240
aaagtagaag tgcaaaaagg cggtttttca aaagagtcga ttaaacccaa aggaccatcg    3300
aataaattga ttcctgtcaa aaatggtttg gatccccaaa aatatggcgg ttttgatagt    3360
cctgtagttg cttatacagt gttattcacg catgaaaaag gtaaaaaacc tcttattaaa    3420
caggagatac tgggcattac gattatggaa aaaacaaggt ttgaacaaaa tcctattctt    3480
tttttagagg agaaaggctt cctacggcct cgtgtattaa tgaaattgcc taagtataca    3540
ctgtatgaat ttccagaggg gcgcaggcgc ttattagcca gcgctaaaga agcgcaaaaa    3600
gggaaccaga tggttttacc tgaacattta cttacgttac tgtaccatgc gaaacaatgt    3660
ttgttaccaa atcaatcaga aagtttggct tatgtagaac aacatcaacc agaatttcaa    3720
gagattttag agagagtggt tgactttgct gaagtgcata cattagccaa gtcaaaagtc    3780
cagcaaattg tgaaacttt tgaagcaaat caaacagcag atgtgaaaga gattgcggca    3840
tcctttatcc aacttatgca gtttaatgcg atgggcgcac caagtacgtt taaatttttc    3900
caaaaagaca ttgagcgagc acgctacacg tcaatcaaag aaattttttga tgccactatc    3960 atttaccaat cgactacggg actgtatgaa acacgcagaa aggttgtcga c           4011
```

<210> SEQ ID NO 192
<211> LENGTH: 4011
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG05459.1 E. coli optimized"

<400> SEQUENCE: 192

```
atgaaaaagg actacgtgat cggcctagac atcggcacta acagcgttgg ttgggcggtg      60
atgaccgaag attaccagct agtgaagaag aagatgccta tctacggtaa tacagagaag     120
aagaagatta aaagaacttt ctggggcgtg aggctattcg aggagggtca caccgcggag     180
gaccgccgcc tgaagcgcac cgctagacgc gtatttcac gtcgtcgtaa ccgtctgcgt      240
tacctgcaag cattcttcga agaagcaatg accgcgctgg atgaaaactt cttcgctagg     300
ctgcaggagt catttctggt gccggaggat aaaaagtggc accgtcatcc gatcttcgcg     360
aaactagaag acgaggtggc gtaccatgaa acctacccga ctatctacca cctgcgcaaa     420
aagctggcgg atagcagcga acaagcgagc ctgcgattaa tctatctggc gctggcgcac     480
atcgtaaaat acagaggcca cttcctcatc gagggcaaat tatcgaccga aaatattagc     540
gtgaaggagc agttccagca gttcatgatc atctacaacc aaaccttcgt gaacggcgaa     600
tcaaggctgg tgagcgcgcc gctgccggag agcgtattaa ttgaggagga attaaccgag     660
aaagcgagcc gcactaagaa aagcgagaaa gtgcttcagc agttcccgca gaaaaagcg      720
aacggcctgt tcggccagtt cctgaaatta atggtgggca taaagcgga cttcaaaaag     780
gtgttcggcc tggaagagga ggcgaaaata acctacgcga gcgaaagcta cgaggaagac     840
ctggagggca tactagcgaa agtgggcgac gaatacagtg acgtgttcct ggcggctaaa     900
aacgtgtacg acgcggtgga attaagcacc atactagcgg acagcgataa aagagtcac      960
gcgaaattaa gctcaagcat gatcgtgcgc ttcaccgaac accaggaaga cctgaaaaag    1020
ttcaaacgct tcatccgcga aaactgcccg gacgaatacg ataacctgtt caaaaacgaa    1080
cagaaagatg gctacgcggg atacatcgcg cacgcgggca agtgtcaca attaaagttc     1140
taccagtacg tgaagaaaat aatccaggat atcgcgggcg cggaatactt cctggagaaa    1200
atagcgcagg agaacttcct taggaaacag cgcaccttcg acaacggcgt gatcccgcac    1260
caaatacacc tggcggaact acaggcaata attcaccgcc aggcggcata ctacccgttc    1320
ctgaaagaga accaggagaa aatagaacag ctggtgacct tccgcatccc atactacgtg    1380
ggcccgctta gcaaaggcga tgcgagcacc ttcgcgtggc tgaaacgcca gagcgaagaa    1440
ccaatccgcc gtggaacttt acaagaaacc gtggatctgg atcagagcgc gaccgcgttc    1500
atcgaacgca tgaccaactt cgatacatac ctgccgagcg aaaaagtgct gccgaagcat    1560
agcctgctgt atgaaaaatt catggtgttc aacgaactga ccaaaatcag ctacaccgat    1620
gatcgcggca ttaaagcgaa cttcagcggc aaagaaaaag agaaatatat cgattaccta    1680
ttcaaacccc gccgcaaagt gaaaagaaa gacataatac agttctaccg caacgaatac    1740
aacaccgaaa tcgtgaccct gagcggcctg gaagaagatc agttcaacgc gagcttcagc    1800
acctaccagg acttattaaa atgcggcctg acccgcgcgg agcttgacca cccggacaac    1860
gcggaaaaac tggaagatat cattaaaata ctgaccatct tcgaagatcg ccagcgcatc    1920
cgcacccagc tgagcaccct caagggccag ttcagcgcgg aagtgctgaa aagctggaa    1980
cgcaaacatt acaccggctg ggccgcctg agcaaaagc tgatcaacgg catctacgat    2040
aaagaatcag gcaaaaccat cctggactac ctgatcaaag atgacggcgt gagcaaacac    2100
tacaaccgca acttcatgca gctgatcaac gatagccagc tgagcttcaa gaacgcgatc    2160
cagaaagcgc agagcagcga acatgaagaa ccctgagcg aaaccgtgaa cgaactggcg    2220
ggcagcccgg cgatcaaaaa gggcatctat cagagcctga aaatcgtgga tgaattagtg    2280
```

```
gcgatcatgg gctatgcgcc gaaacgcatc gtggtggaaa tggcgcgcga aaaccagacc    2340
accagcaccg gcaaacgccg cagcatccag cgcctgaaaa tcgtggaaaa agcgatggcg    2400
gaaatcggca gcaacctgct gaaagaacag ccgaccacca acgaacagct gcgcgatacc    2460
cgcctgtttc tgtattatat gcagaacggc aaagatatgt ataccggcga tgaactgtca    2520
ctgcatcgcc tcagccatta tgatatcgat catatcatcc cgcagagctt tatgaaagat    2580
gatagcctgg ataacctggt gctggtgggc agcaccgaaa accgcggcaa aagcgatgat    2640
gtgccgagca aagaagtggt gaaagatatg aaagcgtatt gggaaaaact gtatgcggcg    2700
ggcctgatca gccagcgcaa atttcagcgc ctgaccaaag cgaacagggc ggcctgacc     2760 ttagaagata aagcgcattt tatccagcgc cagctggtgg aaacccgcca gatcaccaaa    2820
aacgtggcgg gcatcctgga tcagcgctat aacgcgaaca gcaaagaaaa gaaagtccag    2880
atcatcaccc tgaaagcgag cctgaccagc cagtttcgca gcatctttgg cctgtataaa    2940
gtgcgcgaag tgaacgatta tcatcatggc caggatgcgt atctgaactg cgtggtggcg    3000
accaccttac tgaaagtgta tccgaacctg gcgccggaat ttgtgtatgg cgaatatccg    3060
aaatttcagg cgtttaaaga aaacaaagcg accgcgaaaa ccatcatcta taccaacctg    3120
atgcgcttct ttaccgaaga tgaaccgcgc tttatgaaag atggcgaaat tctgtggagc    3180
aacagctatc tgaaaaacat caaaaaggaa ctgaactacc accagatgaa catcgtgaaa    3240
aaggtggagg tccagaaagg cggcttctca aaggaaagca tcaaaccgaa aggcccgagc    3300
aacaaactga tcccggtgaa aaacggcctg gacccgcaga atatggcgg ctttgatagc    3360 ccggtggtgg cgtataccgt gctgtttacc catgaaaaag gcaaaagcc gctgatcaaa    3420 caggaaattc tgggcatcac catcatggag aaaacccgct ttgaacagaa cccgatcctg    3480
ttcctggaag aaaaaggctt tctgcgcccg cgcgtgctga tgaaactgcc gaaatatacc    3540
ctctatgaat ttccggaagg ccgccgccgc ctgctggcga gcgcgaaaga agcgcagaaa    3600
ggcaaccaga tggtgttacc ggaacatctg ctgaccctgc tgtatcatgc gaaacagtgc    3660
ctgctgccga accagagcga aagcctggcg tatgtggaac agcatcagcc ggaatttcag    3720
gaaattctgg aacgcgtggt ggattttgcg gaagtgcata ccctggcgaa aagcaaagtt    3780
cagcagattg ttaaactgtt tgaagcgaac cagaccgcgg atgtgaaaga aattgcggcg    3840
agctttattc agctgatgca gtttaacgcg atgggcgccc cgagcacctt caaattcttt    3900
cagaaagata ttgaacgcgc gcgctatacc agcattaaag aaattttga tgcgaccatt    3960 atctatcagt caaccaccgg cctgtatgaa acccgccgca agtggtgga t              4011
```

<210> SEQ ID NO 193
<211> LENGTH: 4308
<212> TYPE: DNA
<213> ORGANISM: Enterococcus sp.
<220> FEATURE:
<221> NAME/KEY: source
<223> OTHER INFORMATION: /note="APG04583.1 Native Seq"

<400> SEQUENCE: 193

```
atggctaaaa atatacttgg attagatttg ggaaccaata gtattggttg ggcgttggta      60
cagcaagact ttgaaaacaa agaaggaaat attcttggaa tgggaagtag gattattccg     120
atgtcgcaag atatttagg agaattcggt aagggaatt ctatttctca aactgctgaa       180
cgtactggtt atcgtggtgt ccgtcggtta agagaacgac atttattacg tcgtgagcgt     240
ttgcaccgag ttttgcattt gttgggtttc ttgccaaaac attatgatga aaaaatagat     300
```

```
tttacacaac gttttgggaa attcattaac caagccgaac ctaaattggc ttttgatagt    360
gaatttcttt ttaaagattc tttccatgaa atgttagctg attttaaaca aaatcaacca    420
gagtttttga aagataaaaa tggagaagat tgtttagttc cttatgattg gacgatttat    480
tatttacgta aaaaagcatt aacgcaaaaa attgagaaat atgaattagc ttggttgatt    540
cttaatttta atcaaaaacg tggttattat caattaagag gtgaagaaga gaaagaaaat    600
ccaaataaat tggtgggatt tcattctttg aaaatcgttg atgttattcc cgatgctgaa    660
acaaataaaa aaggagagac ttggtattct ttgcatttag aaaatggttg ggtatatcgc    720
cgttcttcta aaatttcatt agcggattgg aaagataaag ttcgagattt tattgttacg    780
actgatttaa acgatgatgg ttctgaaaaa ttggataaag atggaattgt gaaacgtagc    840
tttcgtgcac caagtgcgga tgattggact ttgttgaaaa agaaaacaga aaaagatatt    900
gataactcta acaaaactgt tggaacttat atttacgaca atcttttatt gaacccaaaa    960
caaaaaaataa aaggaaaaat ggttcgtacc atcgaacgta agttttacaa gcaagaatta   1020
gaacaaattt taaaaactca aaaagaattt cattcagaat tacaaagtga aaatttgcta   1080
caagattgtg ttcgagaatt gtatcgaaat aatgaacaac atcaacaaat gttagaagct   1140
aaagattttg tgcatttgtt cctaaatgat attattttct atcaacgtcc tttgagaagt   1200
caaaaatcca gtatatcgaa ttgtactttg gaatttagaa aatcgaaaaa tgaaaatggt   1260
gaagaagtta ttcatcgttt aaaagtaatt gcaaaatcga atccatatta tcaggaattt   1320
agattgttac aatgggtgca aaatttagca atttatacaa aagatgatga taaaaatgta   1380
acaaacgaat ttctaaagtc tactcaagat tgggaggatt tattgagatg gctacattct   1440
aaaaaagaaa ttaaacagga tgctttaatt aagtttttga ttgaaaagaa aggtttaaaa   1500
ggcaaagctt taactattga agtagcaaaa tatcgttgga attatgttca ggacaaagat   1560
taccctggta atgaaacccg atatttaatt caatctcgtt tggataaagt tgaatatgca   1620
cctaaggatt ttttaactta tgaaaatgaa atggctttgt ggcacatcat ttattcgata   1680
aacgataaaa ttgagtacga aaaagcctta aaatcttttg ccaacaaaaa aggtttggac   1740
gaagtaactt ttgttgaagc gtttaagaaa ttcccgcctt ttaaaagtga ttacggaagt   1800
ttttctgaaa aagcaatcaa gaaattattg cctttgatgc gttttggaac tcaatggaat   1860
tgggataata tcgatcaaaa ttctaaagaa agaattggaa aaatattgac aggcgaatat   1920
gatgaaaaca tcaaaggtcg tgttcgcgaa aaagcaagac atctcaattc tgaaaccgat   1980
tttcaagctt tacctttgtg gttggcgcaa tacgtagttt acggaagaca ttctgaagct   2040
gatattgcag gtaaatggaa ttcggtggat gatttaaagc aatttttaga tgactttaaa   2100
caacattcgc ttcgtaatcc tattgtagag caagtgatta ctgaaacgtt gcgtgcggta   2160
aaagatattt ggaattttta tggaaaaggt gctaaagatt tcttctctga aattcatatc   2220
gagctggggc gtgaaatgaa aaatacggct gatgaacgca agcgtattac tacaatggtt   2280
acggataacg aaaacaccaa tttgcgtatc aaagctttgt tggctgaaat ggctttggat   2340
caaaatgtag ataatgttcg tccatattct ccaatgcaac aagaaatttt gaaaatctat   2400
gaagaaggtg ttttgaatgc tgaagaaaat atcgatgatg atattctgaa aattagtaaa   2460
acggctcaac cttctgctac agatttaaag cgttacaaat tgtggttaga acaaaaatat   2520
cgttcgcctt atacaggtca aatgattcct ttgaataagc tgtttacacc tgaatatgag   2580
attgaacaca taattccgca aagtcgctat tttgatgata gtatgagcaa taaagtgatt   2640
```

```
tgcgaagcag cggtgaataa acttaaagac aatcaaattg gtttggtttt cattaagaat    2700
catcacggag aagttgtgga tttcggaatg ggaaaacaag tgaagatttt ggaagtttcc    2760
gattatgagg attttgtaaa acaaaattac aataaaaaca gaggaaaacg taataagttg    2820
ttattggaag atattcctga gaaaatgatt gaacgtcaac taaatgatac acgttacatc    2880
agcaaatata ttacgcaagt gttatcgaat attgttcgtg atgataaaga aggtagtaaa    2940
gatgatggtg taaattctaa aaatattgtt cctggaaacg gaaaaattac cacaagactt    3000
aaacaagatt ggggattgaa tgacgtttgg aatgatttgg ttttacctcg ttttgaacga    3060
atgaatacat tgactaattc aaatgatttt acatcaaaaa atacacatgg aaaaacaatt    3120
ccaacagttc caattgagtt atccaaaggt ttttctaaaa aacgtatcga tcatcgtcat    3180
cacgcaatgg atgcgttggt aattgcctgt gcaacgagag atcacgtgaa tttgttgaat    3240
aacgaaagtt caaaatcgga tacaaaacgt tatgatttga ataggaaatt aagaaaatac    3300
gagaaagtag cttacaatga tcccaaaaca ggcgaacgaa ttgagaaaga agttccaaaa    3360
gacttcatta aaccttggga gacctttacc gaagatacgc gaactttgtt agaaaatatt    3420
gtaattagtt tcaagcaaaa tctacgagtt atcaataaag caaccaatta ttatgaaaaa    3480
attgagaatg gaaaaaagt aaaagttgaa caaaagggaa taaattgggc tgtaagaaaa    3540
gctttgcata agaaaccgt ttctggacaa gtgcatttgg atagaataaa agttgcaaaa    3600
ggtaaaatat taacggctac tcgtaaaact ttggatgcct cttttaatga aaaaacaatt    3660
gagtcaatta cggatacagg gattcaaaag attttattga attatttaaa atcaaaagat    3720
aacaatccag aggttgcatt ttcaccagaa ggaatagaag aattaaataa aaatattagg    3780
ctatataatg atggaaaagc acatcaacca attttgaaag ttcgtgtttt tgagcaagga    3840
agcaaattta ctttaggtga gacgggaaat aaaaccacta gtttgtagaa gcagcaaaag    3900
ggtactaatc tattttttcgg aatttatgaa gacaaatcag gtaagagaag ctacgaaacc    3960
attccattaa atattgtcat cgaaagacaa aaacaaggtc tgcaagctgt tcccgaaacc    4020
aatgagaaag ggaaacaatt gttgtttacg ttatctccaa atgatttggt ttacgttcct    4080
gaagaaggag tttttgatga gaataatatc aaggtagata ggatttataa ggtagtgagt    4140
ttttctacct atcaatgttt ttttgtaaga aatgatgttt ctacttctgt agttaataag    4200
gttgaatatt ccgctttaaa taaaatggaa aaatctattg acaacataat gataaaagaa    4260
aactgcgtca aactgaatgt agaccgttta ggaaagattt caaaagct                 4308
```

<210> SEQ ID NO 194
<211> LENGTH: 4308
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG04583.1 E. coli optimized"

<400> SEQUENCE: 194

```
atggcgaaga acatactagg cctggatctc ggaaccaaca gcattggttg ggcactggtc     60
cagcaggact tcgagaataa agagggcaac atactaggca tgggcagccg aataatccct    120
atgagtcagg acatactagg cgagttcggc aagggcaaca gcattagcca gaccgcagaa    180
cgtactggtt atcgtggtgt gcgccgttta cgtgaacgtc atctgttacg tcgtgaacgt    240
```

```
ctgcatcgtg ttctgcatct gttaggcttc ctgccgaagc attacgatga aagatcgac      300 ttcacccagc gcttcggcaa gttcattaat caagcggaac caaagctggc gttcgacagc      360
gagttcctgt tcaaggacag cttccatgaa atgctagcgg acttcaagca gaatcaaccg      420
gagttcctga aggataaaaa cggcgaggac tgcctggtgc cgtacgactg gaccatatac      480
tacctgcgca agaaagcact gacccagaag atcgaaaaat acgagctagc gtggctcatc      540
ctgaacttca atcaaaagcg cggatactac cagcttaggg gcgaggagga gaaagagaac      600
ccgaataaac tggtgggctt ccacagcctg aaaatagtgg acgtgatccc ggacgcggaa      660
accaataaaa agggcgagac ctggtactca ctgcatctgg aaaacggctg ggtgtaccgc      720
cgcagcagca aaataagcct ggcggactgg aaagacaaag tgcgcgactt catcgtgacc      780
accgacctga cgatgacgg cagcgaaaaa ctggacaaag acggcatcgt gaaacgcagc      840
tttcgtgcac cgagcgcaga tgattggacc ctattaaaga aaaagaccga aaagacatc      900 gacaacagca ataaaaccgt gggcacctac atctacgaca acctgttatt aaacccgaag      960
cagaaaatca aaggcaaaat ggtgcgcacc atcgaacgaa aattctacaa acaggagctg     1020
gagcagatcc tgaaaaccca aaggaattc cacagcgaac tgcagagcga aaacctgctg     1080
caggattgcg tgcgcgaact gtaccgcaat aatgaacagc accagcagat gctggaagcg     1140
aaagatttcg tgcacctgtt cctgaacgat ataatcttct accagcgccc gctgcgcagc     1200
cagaaatcaa gcatcagcaa ttgcaccctg gaattccgca aaagcaagaa tgaaaacggc     1260
gaagaagtga tccaccgcct gaaagtgatc gcgaaaagca acccatacta ccaggaattc     1320
cgcctgctgc agtgggtcca gaacctggcg atctatacta aagacgacga caagaacgta     1380
accaacgagt tcctgaaatc aacccaggac tgggaagatc tgctgcgctg gctgcatagc     1440
aagaaggaga ttaaacagga cgcgctgatc aagttcctga tcgagaaaaa gggcctgaag     1500
ggcaaagcat tgaccatcga ggtggcaaaa taccgctgga actacgtcca ggacaaagat     1560
tacccgggca atgaaacccg ctacctgatc caatcaaggc tggacaaagt ggaatacgcg     1620
ccgaaagatt tcctgaccta cgagaatgaa atggcgctgt ggcacatcat ctacagcatt     1680
aatgataaaa tcgaatatga aaaagcatta aaatcgttcg cgaataaaaa gggcctggat     1740
gaagtgacct tcgtggaagc attcaaaaag ttcccgccgt tcaaaagcga ttacggcagc     1800
ttcagcgaaa aagcgattaa aaagctgctg ccattaatgc gcttcggcac ccagtggaac     1860
tgggataaca tcgatcaaaa tagcaaagaa cgcatcggca aatactaacg ggcgaatac      1920 gatgaaaata ttaaaggccg cgtgcgcgaa aaagcgcgcc atctgaacag cgaaaccgat     1980
ttccaagcat tgccgctgtg ctggcgcag tacgtggtgt acggccgcca tagcgaagcg     2040
gatatcgcgg gcaaatggaa cagcgtggat gatctgaaac agttcctgga tgatttcaaa     2100
cagcatagcc tgcgcaaccc gatcgtggaa caggtgatca ccgaaaccct gcgcgcggtg     2160
aaagatatct ggaacttcta tggcaaaggc gcgaaagatt tcttcagcga aatacacatc     2220
gaactgggcc gcgaaatgaa aaataccgcg gatgaaagaa aacgcatcac caccatggtg     2280
accgataatg aaaataccaa cttacgcatt aaagcattgc tggcggaaat ggcgctggat     2340
cagaacgtgg ataacgtgcg cccgtatagc ccgatgcagc aggaaatcct gaaaatatat     2400
gaagaaggcg tattaaacgc ggaagaaaat atcgacgatg atatcctgaa aataagcaaa     2460
accgcgcaac aagcgcgac cgatctgaaa cgctataaac tgtggctgga acagaaatat     2520
cgcagcccgt ataccggcca gatgatcccg ctgaacaaac tgtttacccc ggaatatgaa     2580
atcgaacata tcatcccgca gagccgctat tttgatgata gcatgagcaa caaagtgatc     2640
```

| | |
|---|---|
| tgcgaagcgg cggtgaacaa actgaaagat aaccagatcg gcctggtgtt tatcaaaaac | 2700 |
| catcatggcg aagtggtgga tttttggcatg ggcaaacagg tgaaaatcct ggaagtgagc | 2760 |
| gattatgaag attttgtgaa acagaactat aacaaaaacc gcggcaaacg caacaaatta | 2820 |
| ctgctggaag atatcccgga gaaaatgatc gaacgccagc tgaacgatac ccgctatatc | 2880 |
| agcaaatata tcacccaggt gctgagcaac atcgtgcgcg atgataaaga aggcagcaaa | 2940 |
| gatgatggcg tgaacagcaa aaacatcgtg ccgggcaacg gcaaaatcac cacccgcctg | 3000 |
| aaacaggatt ggggcctgaa cgatgtgtgg aacgatctgg tgctgccgcg ctttgaacgc | 3060 |
| atgaacaccc tgaccaacag caacgatttt accagcaaaa acacccatgg caaaaccatt | 3120 |
| ccgaccgtgc cgattgaact gagcaaaggc tttagcaaaa agcgcattga tcatcgccat | 3180 |
| catgcgatgg atgcgctggt gattgcgtgc gcgacccgcg atcatgtgaa cttactgaac | 3240 |
| aacgaaagca gcaaaagcga taccaaacgc tatgatctga accgcaaact gcgcaaatat | 3300 |
| gaaaagtgg cgtataacga tccgaaaacc ggcgaacgca ttgaaaaaga agtgccgaaa | 3360 |
| gattttatta accgtgggga aacctttacc gaagataccc gcaccctgct ggaaaacatt | 3420 |
| gtgattagct ttaaacagaa cctgcgcgtg attaacaaag cgaccaacta ttatgagaaa | 3480 |
| attgaaaacg gcaaaaaggt gaaagtggaa cagaaaggca ttaactgggc ggtgcgcaaa | 3540 |
| gcgctgcata agaaaccgt gagcggccag gtgcatctgg atcgcattaa agtggcgaaa | 3600 |
| ggcaaaattc tgaccgcgac ccgcaaaacc ctggatgcgt cattcaacga gaaaaccatt | 3660 |
| gaaagcatta ccgataccgg cattcagaaa attctgctga actatctgaa agcaaagat | 3720 |
| aacaacccgg aagtggcgtt tagcccggaa ggcattgaag aactgaacaa aaacattcgc | 3780 |
| ctgtataacg atggcaaagc gcatcagccg attctgaaag tgcgcgtgtt tgaacagggc | 3840 |
| agcaaattca ccctgggcga aaccggcaac aaaaccacca aatttgtgga agcggcgaaa | 3900 |
| ggcaccaacc tgttctttgg catctatgaa gataaaagcg gcaaacgcag ctatgaaacc | 3960 |
| attccgctga acattgtgat tgaacgccag aaacaggggcc tgcaagcggt gccggaaacc | 4020 |
| aacgaaaaag gcaaacagct gctgtttacc ctgtcaccga acgatctggt gtatgtgccg | 4080 |
| gaagaaggcg tgtttgatga aaacaacatt aaagtggatc gcatctataa agtggtgagc | 4140 |
| tttagcacct atcagtgctt ctttgtgcgc aacgatgtga gcaccagcgt ggtgaacaaa | 4200 |
| gtggaatata gcgcgctgaa caaaatgaaa aaatcgattg ataacattat gattaaagaa | 4260 |
| aactgcgtga aactgaacgt ggatcgcctg ggcaaaatta gcaaagcg | 4308 |

<210> SEQ ID NO 195
<211> LENGTH: 4368
<212> TYPE: DNA
<213> ORGANISM: Empedobacter sp.
<220> FEATURE:
<221> NAME/KEY: source
<223> OTHER INFORMATION: /note="APG01688.1 Native Seq"

<400> SEQUENCE: 195

| | |
|---|---|
| atgatgatta aaatatact tggattagat ttggggacta actctattgg gtgggcattg | 60 |
| ataaaacaag attttgaaaa taagcatggc gaaattcttg aatgggtag ccggattatt | 120 |
| ccgatgtcac aggatattct gggcgatttt gggaaaggaa attctatttc gcaaaccgct | 180 |
| gatcgtacca atacagaag cgtgagaaga ttacgtgaac gattttattt gaggagagaa | 240 |
| cgactacaca gagttttaca tcttttaaat tttcttccac agcattatgc ttcacaaatt | 300 |
| gattttgaaa aaaaattcgg gaagtttaaa tctgaaactg aacccaaatt ggcatgggaa | 360 |

-continued

```
aattggggtg gaaagttttc attccttttc caaaactctt tcaatgaaat gcttgaagat      420
tttaaagcag ctggacaggg tttaaaaatt ccttacgact ggacaattta ttatctccgt      480
aaaaaagcac tttcacaaaa aattgaaaag gaggaactgg cctggattct tttaaacttt      540
aatcagaaac gaggatatta tcaattgcgt ggtgaggaag aagaagagaa tcctaataag      600
ctggttgaat tttattcttt aaaaattgta gatgttgtag cagatgaacc tcaaaaagga      660
aaatctgata tttggtattc tttgattta gagaatggat gggtttacag acgagcaagc      720
aaaatacccc tatttgactg gaaagataaa acaagagatt ttattgtaac aactgatttg      780
aatgatgaca gaagtgttaa aacagacaaa gaaggaaatg aaaaaagaag tttcagagca      840
ccaagcgaaa acgattggac attggtaaaa aagaaaaccg aacaggaaat cgaccaatct      900
cacaaaaccg ttggaaccta tatctacgaa acacttcttc taaatccgaa acaaaaaatt      960
aaaggaaaat tggttcggac gattgaaaga aaattctata aagatgagct aaaacaaatt     1020
ttagaaaaac aaaaggaatt tcatcaggaa cttaaaaatg atgatttgta taatgattgc     1080
attcgtgagt tgtacagaaa caacgaagca catcagctga ctttgagcaa gaaagatttt     1140
gttcatcttt tgatggatga tcttattttc taccaaagac ctttgagaag ccagaaatca     1200
tctatttcca actgtacgtt agagtttaga aaatataaag atgaaaatgg aatagagcat     1260
acacaatatt taaagccat tccaaaatcc aatccgtatt atcaggaatt tcgtctttgg     1320
caatggatgt ataatctgaa tatttacaga aaggacgatg aagcgaatgt taccaaagaa     1380
tttttaaata cgaacaaaga ttttgaaagt ctgtttgaat ttttaaataa tagaaaagaa     1440
attgagcaaa agccattgat taaatttctt ttggaacaaa aagatatcaa taaaaaattg     1500
cttaacgctg aagcagaaaa atatcgctgg aactatgtag aagacaagaa atatccttgc     1560
aatgaaacca aaacgatgat ttcttctcgt ttggataaag tcgaaaacat ttctgatgat     1620
ttcctgacaa gggacattga gcagaaaatt tggcacatca tctattccgt caatgataaa     1680
atagaatatg aaaaagcttt gaaatctttt gcaactagaa acgatttgga tgaaaactct     1740
tttatcgaag cgtttaagaa attctcgcct tttaaaagtg aatatggttc ttttcggaa     1800 aaagcaatta aaaagttact gccttttaatg cgattgggta aatattggta tgaagatgaa     1860
attgtaaagc atagtgatat ttatttcaaa aatattgaga atcttttggg tgattttca     1920 aatagagaca aaaaaattc tgaagaagac aaagagaaat ggaataaatc tataaatcta     1980
aagttacagg aagagttaaa agattttcaa acagctgaaa tagatttatt tcaaggatta     2040
cgattgcata ttgctcaata ccttgtttat ggaagacatt cagaagcttc aatgattgga     2100
aaatggaatt ccgccgaaga tttagaagaa ttttaaagg attttaaaca gcattcgctt     2160
cgcaacccga ttgtagaaca agtgattaca gaaactttgc gtgttgtaaa agatatttgg     2220
ttgaaatacg gaaatggagc aaaggatttc ttcaatgaaa ttcatattga gttaggaaga     2280
gaaatgaaac ttcccgcaga tgatcgaaaa aaactaacga accagatttc tgaaaacgaa     2340 ataccaatt tccgcatcaa agctctattg gctgaaatga tgaatgacag ttcggtagaa     2400
aatgtccgtc cgttttcgcc gatgcagcaa gaaattttaa aaatttatga agacgatgtt     2460
ttaaaatcag atatagaaat tgaagatgat attctgaaaa tcagcaaaac cgctcaacct     2520
tctccttccg atttgaaacg atataaactt tggttggaac agaaatacaa atcgccttac     2580
acggggcaaa ttattccttt gaataaattg tttacaccag aatacgaaat tgagcacatt     2640
attccgcaga gccgatattt tgatgacagt tttagcaata agtaatttg tgagtctgcg     2700
```

| | |
|---|---|
| gttaataaat tgaaagataa ctacatcgga ctttgaattta ttaagcagtt cggaggaacg | 2760 |
| attattgaac ttggttttgg taaaagcata aaagttttg aaacaaaaga atacgaagat | 2820 |
| ttcgtcaaaa aacattacgc caacaatcaa ggtaaaagaa acaaacttt gatggaagat | 2880 |
| attccagaga aaatgattga acgtcaaatg aacgatacac gatatatcag caaatatatt | 2940 |
| tcgggcgttt tgtctaatat tgttcgggta gaagatggtt cagatgaagg ggtaaattct | 3000 |
| aaaaatattg ttcccggaaa cggaaaaatc accacacagc tgaaacaaga ttggggattg | 3060 |
| aatgatgttt ggaatgattt gatttttacca cgctttgaaa gaatgaacca actcaccaat | 3120 |
| tcaaagtttt ttactgcctg gaatgagaat tatcaaaagt ttttaccaac tgttcctatt | 3180 |
| gaatattcca aagggttttc aaagaaaaga atagaccacc gccatcacgc tttagatgct | 3240 |
| ttggtgattg cctgtgctac aaaagatcac gtgaatttat taaataatca atcggcaaaa | 3300 |
| tcggatacca aacgatacga tttgaaaaag aaatcgatga gtttgaaaa agtagtttac | 3360 |
| aatgatgcca aaacaggaga gaaaatcgaa agggaagtgc caaacaatt tttaaaacct | 3420 |
| tgggaaaatt ttacgctaga tgttaaacat aatttgaaaa ctattattgt aagttttaag | 3480 |
| caaaatcttc gtgttattaa taaagcgact aattattacg aaaagtatgt tgagaaagac | 3540 |
| ggtacaaaaa ataaggaaag agtagagcag accggaacaa actgggcgat taggaaacca | 3600 |
| atgcataaag acacggtttc cggtaaagta gatttaccctt gggtaaaagt cccaaaaggg | 3660 |
| aaaattttaa cagcaacaag gaaaagcctt gatagttcgt ttgacttaaa gtcaataggc | 3720 |
| tctattacgg atacaggaat tcagaaaata ctcaaaaatt atttagcatt taaagacgga | 3780 |
| aatcctgaac tggcttttc accagaagga attgacgatt tgaataaaaa tattgaaaaa | 3840 |
| tacaatgatg gaaaaccgca tcaacccatc aataaagtaa gggttttga attgggaagt | 3900 |
| aaatttcagg taggacaaag tggaaataaa aaagataaat atgtagaagc tgcaaaagga | 3960 |
| actaatctat tctttgctgt ttatgaagat gaaaaaggaa agagaaatta tgaaaccatt | 4020 |
| cctttgaatg aagtgattga aaggcaaaag caaggtttat ctgtggttga tttaaaaggt | 4080 |
| acaaatgatt tctacttatg tccgaatgat tttgtatata ttccatcagg cgacgaactt | 4140 |
| gaaaatataa ataatgttga ttttaaagac attaaaaaag agataaacga aagaatttac | 4200 |
| aaagtagtaa gttttacagg taatagactt tcctgtattc catatatggt tgcaacaacg | 4260 |
| attgttaata aattagagtt tacgcaactt aataaaattg aattcacaaa agaaaaagaa | 4320 |
| atttgtataa aactaaatgt cgatcgttta ggtaacattt caaaagcg | 4368 |

<210> SEQ ID NO 196
<211> LENGTH: 4368
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG01688.1 E. coli optimized"

<400> SEQUENCE: 196

| | |
|---|---|
| atgatgatta aaaatatcct aggcctggac ctgggaacca acagcatcgg ctgggcgctg | 60 |
| attaaacagg acttcgaaaa taagcatggc gagatactag gcatgggcag ccgaataatc | 120 |
| ccgatgagtc aggacatact aggcgacttc ggcaagggca acagcatcag ccagaccgcg | 180 |
| gaccgcacaa aatatcgcag cgtgcgtaga ctgcgcgaac gctttctgtt acgtcgtgaa | 240 |

```
cgtctgcatc gtgttcttca cctattaaac ttcctgccgc agcattacgc tagccagatc    300
gacttcgaga agaagttcgg caagttcaag agcgagaccg aaccaaaact ggcgtgggaa    360
aactggggcg gcaaattcag cttcctattc caaaatagct tcaacgagat gctagaggac    420
ttcaaggcgg cgggtcaggg attaaaaata ccgtacgact ggaccatata ctacctgcgc    480
aagaaagcgc tgagccagaa gatcgagaag gaggagctgg cgtggatact actgaacttt    540
aatcaaaagc gcggatacta ccagctgcgc ggcgaggagg aggaggagaa cccgaataaa    600
ctggtggagt tctacagcct gaaaatagtg gacgtggtgg cggacgagcc gcagaaaggc    660
aaaagcgaca tctggtactc actcatacta gaaaacggct gggtgtatcg ccgcgcgagc    720
aaaataccgc tgttcgactg gaaagataaa acccgcgact tcatcgtgac caccgacctg    780
aacgacgacc gcagcgtgaa aaccgacaaa gaaggcaatg aaaaacgcag ctttcgcgcg    840
ccgagcgaaa acgattggac cctggtgaaa aagaaaccg aacaggaaat cgatcagagc     900
cataaaaccg tgggcacata tatctatgaa acccctgttat taaacccgaa gcagaagatt    960
aaaggcaaac tggtgcgcac catcgaacgc aaattctaca aagacgaatt aaaacagata   1020
ctagaaaaac agaaagaatt ccaccaggaa ttaaagaacg acgacttata taacgattgc   1080
atccgcgaac tgtaccgcaa taatgaagcg caccaattaa ccctgagcaa aaaggatttc   1140
gtgcacttat taatggatga tctgatcttc taccagcgcc cgctgcgcag ccagaaatca   1200
agcatcagca attgcaccct ggaattccgc aaatacaaag atgaaaacgg catcgaacac   1260
acccagtacc tgaaagcgat cccgaaatca aacccatact accaggaatt ccgcctgtgg   1320
cagtggatgt acaacctgaa catctaccgc aaagatgatg aagcgaacgt aaccaaagaa   1380
ttcctgaaca ccaataaaga tttcgaaagc ctgttcgaat tcctgaataa tcgcaaagaa   1440
atcgaacaga aaccattaat caaattcctg ctggaacaga agatattaa taaaaagtta   1500 ttaaacgcgg aagcggaaaa atacagatgg aactacgtgg aagataaaaa gtacccgtgc   1560
aatgaaacca aaaccatgat cagcagccgc ctggataaag tggaaaatat cagcgatgat   1620
ttcctgaccc gcgatatcga acagaaaata tggcatataa tctacagcgt gaacgataaa   1680
atcgaatatg aaaaagcatt aaaatcgttc gcgacccgca acgatctgga tgaaaatagc   1740
ttcatcgaag cattcaaaaa gttcagcccg ttcaaaagcg aatacggcag cttcagcgaa   1800
aaagcgatta aaaagctgct gccattaatg cgcctgggaa atactggta cgaagatgaa    1860 atcgtgaaac acagcgatat ctacttcaaa aacatcgaaa acctgctggg cgatttcagc   1920
aaccgcgata aaaagatcag cgaagaagat aaagaaaaat ggaacaaaag catcaacctg   1980
aaactgcagg aagaactgaa agatttccag accgcggaaa tcgatctgtt ccagggcctg   2040
cgcctgcata tcgcgcagta cctggtgtac ggccgccata gcgaagcgag catgatcggc   2100
aaatggaact cagcggaaga tctggaagaa ttcctgaaag atttcaaaca gcatagcctg   2160
cgcaacccga tcgtggaaca ggtgatcacc gaaaccctgc gcgtggtgaa agatatctgg   2220
ctgaaatatg caacggcgc gaaagatttc tttaacgaaa ttcatatcga actgggccgc    2280
gaaatgaaac tgccggcgga tgatcgcaaa aagctgacca accagatcag cgaaaacgaa   2340
aacaccaact ttcgcatcaa agcgctgctg cggaaatga tgaacgatag cagcgtggaa    2400
aacgtgcgcc cgtttagccc gatgcagcag gaaatcctga aaatctatga agatgatgtg   2460
ctgaaaagcg atatcgaaat cgaagatgat atcttaaaaa tcagcaaaac cgcgcagccg   2520
agcccgagcg atctgaaacg ctataaactg tggctgaaac agaaatataa aagcccgtat   2580
accggccaga tcatcccgct gaacaaactg tttaccccgg aatatgaaat cgaacatatc   2640
```

```
atcccgcaga gccgctattt tgatgatagc tttagcaaca aagtgatctg cgaaagcgcg    2700
gtgaacaaac tgaaagataa ctatatcggc ctggaattca tcaaacagtt tggcggcacc    2760
atcatcgaac tgggctttgg caaaagcatc aaagtgtttg aaaccaaaga atatgaagat    2820
tttgtgaaaa agcattatgc gaacaaccag ggcaaacgca acaaactgtt aatgaaagat    2880
atcccggaga aaatgatcga acgccagatg aacgataccc gctatatcag caaatatatc    2940
agcggcgtgc tgagcaacat cgtgcgcgtg aagatggca gcgatgaagg cgtgaacagc     3000
aaaaacatcg tgccgggcaa cggcaaaatc accacccagc tgaaacagga ttggggcctg    3060
aacgatgtgt ggaacgatct gatcctgccg cgctttgaac gcatgaacca gctgaccaac    3120
agcaaagtgt ttaccgcgtg aacgaaaac tatcagaaat tctgccgac cgtgccgatt       3180 gaatatagca aaggctttag caaaaagcgc attgatcatc gccatcatgc gctggatgcg    3240
ttagtgattg cgtgcgcgac caaagatcat gtgaacctgc tgaacaacca gagcgcgaaa    3300
agcgatacca aacgctatga tctgaaaaag aaaagcatga aatttgaaaa agtggtgtat    3360
aacgatgcga aaccggcga gaaaattgaa cgcgaagtgc cgaaacagtt tctgaaaccg     3420
tgggaaaact ttacccctgga tgtgaaacat aacctggaaa ccattattgt gagctttaaa    3480
cagaacctgc gcgtgattaa caaagcgacc aactattatg aaaaatatgt ggaaaaagat    3540
ggcaccaaaa acaaagaacg cgtggaacag accggcacca actgggcgat cgcaaaccg     3600 atgcataaag ataccgtgtc aggcaaagtg gatctgccgt gggtgaaagt gccgaaaggc    3660
aaaattctga ccgcgacccg caaaagcctg gatagcagct ttgatctgaa aagcattggc    3720
agcattaccg ataccggcat tcagaaaatt ctgaaaaact atctggcgtt taaagatggc    3780
aacccggaac tggcgtttag cccggaaggc attgatgatc tgaacaaaaa cattgaaaaa    3840
tataacgatg gcaaaccgca tcagccgatt aacaaagtgc gcgtgtttga actgggcagc    3900
aaatttcagg tgggccagag cggcaacaaa aaggacaaat atgtggaagc ggcgaaaggc    3960
accaacctgt tctttgcggt gtatgaagat gaaaaaggca aacgcaacta tgaaaccatc    4020
ccgttaaacg aagtgattga acgccagaaa cagggcctga gcgtggtgga tctgaaaggc    4080
accaacgatt tttatctgtg cccgaacgat tttgtgtata ttccgagcgg cgatgaactg    4140
gaaaacatta caacgtgga ttttaaagat attaaaaagg aaattaacga acgcatctat     4200
aaagtggtga gctttaccgg caaccgcctg agctgcattc cgtatatggt ggcgaccacc    4260
attgtgaaca aactggaatt cacccagctg aacaaaattg aattcaccaa agaaaaagaa    4320
atttgcatta aactgaacgt ggatcgcctg ggcaacatta gcaaagcg                  4368
```

<210> SEQ ID NO 197
<211> LENGTH: 25
<212> TYPE: DNA
<213> ORGANISM: Homo sapiens
<220> FEATURE:
<221> NAME/KEY: source
<223> OTHER INFORMATION: /note="target seq for Ataxia-telangiectasia
      syndrome"

<400> SEQUENCE: 197

```
gaattattcc agaaagccaa agtag                                             25
```

<210> SEQ ID NO 198
<211> LENGTH: 20
<212> TYPE: DNA
<213> ORGANISM: Homo sapiens
<220> FEATURE:

```
<221> NAME/KEY: source
<223> OTHER INFORMATION: /note="target seq for Very long chain acyl-CoA
      dehydrogenase deficiency"

<400> SEQUENCE: 198
ggcttcatga aggtacagga                                                    20

<210> SEQ ID NO 199
<211> LENGTH: 25
<212> TYPE: DNA
<213> ORGANISM: Homo sapiens
<220> FEATURE:
<221> NAME/KEY: source
<223> OTHER INFORMATION: /note="target seq for Abnormality of T cell
      physiology"

<400> SEQUENCE: 199
ggtgtgctca ccagaatgga gtaca                                              25

<210> SEQ ID NO 200
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 200
gcagatcatt ggggtggatc ccgaa                                              25

<210> SEQ ID NO 201
<211> LENGTH: 25
<212> TYPE: DNA
<213> ORGANISM: Homo sapiens
<220> FEATURE:
<221> NAME/KEY: source
<223> OTHER INFORMATION: /note="target seq for 3-Oxo-5 alpha-steroid
      delta 4-dehydrogenase deficiency"

<400> SEQUENCE: 201
ggctgcaagc ttttcaccac cayag                                              25

<210> SEQ ID NO 202
<211> LENGTH: 25
<212> TYPE: DNA
<213> ORGANISM: Homo sapiens
<220> FEATURE:
<221> NAME/KEY: source
<223> OTHER INFORMATION: /note="target seq for Acute myeloid leukemia"

<400> SEQUENCE: 202
gggcggcatg aaccggaggc ccatc                                              25

<210> SEQ ID NO 203
<211> LENGTH: 20
<212> TYPE: DNA
<213> ORGANISM: Homo sapiens
<220> FEATURE:
<221> NAME/KEY: source
<223> OTHER INFORMATION: /note="target seq for Acute myeloid leukemia"

<400> SEQUENCE: 203
gcatgggcgg catgaaccgg                                                    20

<210> SEQ ID NO 204
<211> LENGTH: 20
<212> TYPE: DNA
```

```
<213> ORGANISM: Homo sapiens
<220> FEATURE:
<221> NAME/KEY: source
<223> OTHER INFORMATION: /note="target seq for Cutaneous malignant
      melanoma 3"

<400> SEQUENCE: 204
gtggccactg tggggatcac                                              20

<210> SEQ ID NO 205
<211> LENGTH: 20
<212> TYPE: DNA
<213> ORGANISM: Homo sapiens
<220> FEATURE:
<221> NAME/KEY: source
<223> OTHER INFORMATION: /note="target seq for Alpha-1-antitrypsin
      deficiency"

<400> SEQUENCE: 205
gtgctgacca tcgacgagaa                                              20

<210> SEQ ID NO 206
<211> LENGTH: 20
<212> TYPE: DNA
<213> ORGANISM: Homo sapiens
<220> FEATURE:
<221> NAME/KEY: source
<223> OTHER INFORMATION: /note="target seq for Charcot-Marie-Tooth
      disease, type 2"

<400> SEQUENCE: 206
ggcgagctgc atgatctgcg                                              20

<210> SEQ ID NO 207
<211> LENGTH: 25
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 207
gcacatgacg gaggttgtga ggcgc                                        25

<210> SEQ ID NO 208
<211> LENGTH: 25
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 208
gaggttgtga ggcactgccc ccacc                                        25

<210> SEQ ID NO 209
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 209
gcagcatccg gctgcaggta                                              20
```

<210> SEQ ID NO 210
<211> LENGTH: 25
<212> TYPE: DNA
<213> ORGANISM: Homo sapiens
<220> FEATURE:
<221> NAME/KEY: source
<223> OTHER INFORMATION: /note="target seq for Brugada syndrome"

<400> SEQUENCE: 210 ggccaaggggg atccgcacgc tgctc                                          25

<210> SEQ ID NO 211
<211> LENGTH: 20
<212> TYPE: DNA
<213> ORGANISM: Homo sapiens
<220> FEATURE:
<221> NAME/KEY: source
<223> OTHER INFORMATION: /note="target seq for Brugada syndrome"

<400> SEQUENCE: 211
gcctgatgac gcaggactgc                                                 20

<210> SEQ ID NO 212
<211> LENGTH: 20
<212> TYPE: DNA
<213> ORGANISM: Homo sapiens
<220> FEATURE:
<221> NAME/KEY: source
<223> OTHER INFORMATION: /note="target seq for GRACILE syndrome"

<400> SEQUENCE: 212
ggtacgaagt ctcgacactg                                                 20

<210> SEQ ID NO 213
<211> LENGTH: 20
<212> TYPE: DNA
<213> ORGANISM: Homo sapiens
<220> FEATURE:
<221> NAME/KEY: source
<223> OTHER INFORMATION: /note="target seq for Enhanced s-cone syndrome"

<400> SEQUENCE: 213
ggcattggcg gtggacccca                                                 20

<210> SEQ ID NO 214
<211> LENGTH: 25
<212> TYPE: DNA
<213> ORGANISM: Homo sapiens
<220> FEATURE:
<221> NAME/KEY: source
<223> OTHER INFORMATION: /note="target seq for Charcot-Marie-Tooth
      disease, type 2"

<400> SEQUENCE: 214
gaagaacagg ttctggacgt caaag                                           25

<210> SEQ ID NO 215
<211> LENGTH: 20
<212> TYPE: DNA
<213> ORGANISM: Homo sapiens
<220> FEATURE:
<221> NAME/KEY: source
<223> OTHER INFORMATION: /note="target seq for Charcot-Marie-Tooth
      disease, type 2"

<400> SEQUENCE: 215
gaacaggttc tggacgtcaa                                          20

<210> SEQ ID NO 216
<211> LENGTH: 20
<212> TYPE: DNA
<213> ORGANISM: Homo sapiens
<220> FEATURE:
<221> NAME/KEY: source
<223> OTHER INFORMATION: /note="target seq for Arylsulfatase a, allele
      a"

<400> SEQUENCE: 216
gacaggtcat agagcagcgg                                          20

<210> SEQ ID NO 217
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial
      hypercholesterolemia"

<400> SEQUENCE: 217
gaacgtggtc gctctggaca                                          20

<210> SEQ ID NO 218
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial
      hypercholesterolemia"

<400> SEQUENCE: 218
gaacgtggtc gctctggaca                                          20

<210> SEQ ID NO 219
<211> LENGTH: 25
<212> TYPE: DNA
<213> ORGANISM: Homo sapiens
<220> FEATURE:
<221> NAME/KEY: source
<223> OTHER INFORMATION: /note="target seq for HEMOGLOBIN ARLINGTON
      PARK"

<400> SEQUENCE: 219
ggtgcatctg actcctgagg agaag                                    25

<210> SEQ ID NO 220
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial hypertrophic
      cardiomyopathy 1"

<400> SEQUENCE: 220
gaagtccgag gctcgccgca                                          20

<210> SEQ ID NO 221
<211> LENGTH: 20
<212> TYPE: DNA
<213> ORGANISM: Homo sapiens
<220> FEATURE:
<221> NAME/KEY: source

```
<223> OTHER INFORMATION: /note="target seq for Cardiovascular phenotype"

<400> SEQUENCE: 221
gtcaaggtca tcggtgaggc                                              20

<210> SEQ ID NO 222
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 222
ggtcatcagt gaggccggcc ggggt                                        25

<210> SEQ ID NO 223
<211> LENGTH: 25
<212> TYPE: DNA
<213> ORGANISM: Homo sapiens
<220> FEATURE:
<221> NAME/KEY: source
<223> OTHER INFORMATION: /note="target seq for Brugada syndrome"

<400> SEQUENCE: 223
gtctcagcct tacgcacctt ccgag                                        25

<210> SEQ ID NO 224
<211> LENGTH: 25
<212> TYPE: DNA
<213> ORGANISM: Homo sapiens
<220> FEATURE:
<221> NAME/KEY: source
<223> OTHER INFORMATION: /note="target seq for Brugada syndrome"

<400> SEQUENCE: 224
gcaccttcca agtcctccgg gccct                                        25

<210> SEQ ID NO 225
<211> LENGTH: 26
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 225
gaagccagcc cctcagggca actgac                                       26

<210> SEQ ID NO 226
<211> LENGTH: 20
<212> TYPE: DNA
<213> ORGANISM: Homo sapiens
<220> FEATURE:
<221> NAME/KEY: source
<223> OTHER INFORMATION: /note="target seq for Deficiency of butyryl-CoA
      dehydrogenase"

<400> SEQUENCE: 226
ggcgactcat gggttctgaa                                              20

<210> SEQ ID NO 227
<211> LENGTH: 25
<212> TYPE: DNA
<213> ORGANISM: Homo sapiens
<220> FEATURE:
```

```
<221> NAME/KEY: source
<223> OTHER INFORMATION: /note="target seq for Deficiency of butyryl-CoA
      dehydrogenase"

<400> SEQUENCE: 227
gcgactcacg ggttctgaat ggaac                                25

<210> SEQ ID NO 228
<211> LENGTH: 20
<212> TYPE: DNA
<213> ORGANISM: Homo sapiens
<220> FEATURE:
<221> NAME/KEY: source
<223> OTHER INFORMATION: /note="target seq for Benign scapuloperoneal
      muscular dystrophy with cardiomyopathy"

<400> SEQUENCE: 228
ggaactgcgg gcccagcatg                                      20

<210> SEQ ID NO 229
<211> LENGTH: 20
<212> TYPE: DNA
<213> ORGANISM: Homo sapiens
<220> FEATURE:
<221> NAME/KEY: source
<223> OTHER INFORMATION: /note="target seq for Benign scapuloperoneal
      muscular dystrophy with cardiomyopathy"

<400> SEQUENCE: 229
ggacgagtac caggagcttc                                      20

<210> SEQ ID NO 230
<211> LENGTH: 20
<212> TYPE: DNA
<213> ORGANISM: Homo sapiens
<220> FEATURE:
<221> NAME/KEY: source
<223> OTHER INFORMATION: /note="target seq for Cone-rod dystrophy 6"

<400> SEQUENCE: 230
ggatctgatc cgggagcgca                                      20

<210> SEQ ID NO 231
<211> LENGTH: 25
<212> TYPE: DNA
<213> ORGANISM: Homo sapiens
<220> FEATURE:
<221> NAME/KEY: source
<223> OTHER INFORMATION: /note="target seq for Cone-rod dystrophy 6"

<400> SEQUENCE: 231
gaatgcacta tgttctattc catcc                                25

<210> SEQ ID NO 232
<211> LENGTH: 25
<212> TYPE: DNA
<213> ORGANISM: Homo sapiens
<220> FEATURE:
<221> NAME/KEY: source
<223> OTHER INFORMATION: /note="target seq for Stargardt disease 1"

<400> SEQUENCE: 232
gagctgctca caggacgaga acatc                                25

<210> SEQ ID NO 233
<211> LENGTH: 20
<212> TYPE: DNA
```

-continued

```
<213> ORGANISM: Homo sapiens
<220> FEATURE:
<221> NAME/KEY: source
<223> OTHER INFORMATION: /note="target seq for Leber congenital
      amaurosis 2"

<400> SEQUENCE: 233
gtctatccag taagtatctc                                             20

<210> SEQ ID NO 234
<211> LENGTH: 20
<212> TYPE: DNA
<213> ORGANISM: Homo sapiens
<220> FEATURE:
<221> NAME/KEY: source
<223> OTHER INFORMATION: /note="target seq for Cone-rod dystrophy 3"

<400> SEQUENCE: 234
ggtacgtcca tgccacaccc                                             20

<210> SEQ ID NO 235
<211> LENGTH: 20
<212> TYPE: DNA
<213> ORGANISM: Homo sapiens
<220> FEATURE:
<221> NAME/KEY: source
<223> OTHER INFORMATION: /note="target seq for Nonsyndromic
      Oculocutaneous Albinism"

<400> SEQUENCE: 235
ggacctttac ggcgtaatcc                                             20

<210> SEQ ID NO 236
<211> LENGTH: 20
<212> TYPE: DNA
<213> ORGANISM: Homo sapiens
<220> FEATURE:
<221> NAME/KEY: source
<223> OTHER INFORMATION: /note="target seq for Phenylketonuria"

<400> SEQUENCE: 236
gtcatccttt ggtgaattac                                             20

<210> SEQ ID NO 237
<211> LENGTH: 25
<212> TYPE: DNA
<213> ORGANISM: Homo sapiens
<220> FEATURE:
<221> NAME/KEY: source
<223> OTHER INFORMATION: /note="target seq for Phenylketonuria"

<400> SEQUENCE: 237
gtattacgtg gcagagagtt ttaat                                       25

<210> SEQ ID NO 238
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 1"

<400> SEQUENCE: 238
ggacgctctt gtattatctg                                             20

<210> SEQ ID NO 239
```

```
<211> LENGTH: 25
<212> TYPE: DNA
<213> ORGANISM: Homo sapiens
<220> FEATURE:
<221> NAME/KEY: source
<223> OTHER INFORMATION: /note="target seq for Hyperphenylalaninemia,
      non-pku"

<400> SEQUENCE: 239
gcccttctca gttcgctacg accca                                              25

<210> SEQ ID NO 240
<211> LENGTH: 20
<212> TYPE: DNA
<213> ORGANISM: Homo sapiens
<220> FEATURE:
<221> NAME/KEY: source
<223> OTHER INFORMATION: /note="target seq for Hyperphenylalaninemia,
      non-pku"

<400> SEQUENCE: 240
gctacgaccc atacacccaa                                                    20

<210> SEQ ID NO 241
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 241
gcgctatgtt ctattccatc                                                    20

<210> SEQ ID NO 242
<211> LENGTH: 25
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 242
ggggctggta ttcatgaaag gcaac                                              25

<210> SEQ ID NO 243
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 243
gcgctatgtt ctattccatc                                                    20

<210> SEQ ID NO 244
<211> LENGTH: 25
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 244
```

```
gtgttctcag gttatcggta agttt                                               25
```

<210> SEQ ID NO 245
<211> LENGTH: 25
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 245

```
ggaaatgctg ttagtcggta tgtcg                                               25
```

<210> SEQ ID NO 246
<211> LENGTH: 25
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 246

```
ggaaatgctg ttagtcagta tgtcg                                               25
```

<210> SEQ ID NO 247
<211> LENGTH: 20
<212> TYPE: DNA
<213> ORGANISM: Homo sapiens
<220> FEATURE:
<221> NAME/KEY: source
<223> OTHER INFORMATION: /note="target seq for Anterior segment
      dysgenesis 6"

<400> SEQUENCE: 247

```
gtggccactg atcggaaacg                                                     20
```

<210> SEQ ID NO 248
<211> LENGTH: 25
<212> TYPE: DNA
<213> ORGANISM: Homo sapiens
<220> FEATURE:
<221> NAME/KEY: source
<223> OTHER INFORMATION: /note="target seq for Brugada syndrome"

<400> SEQUENCE: 248

```
gaacctgatc ctggccgtgg tcgca                                               25
```

<210> SEQ ID NO 249
<211> LENGTH: 20
<212> TYPE: DNA
<213> ORGANISM: Homo sapiens
<220> FEATURE:
<221> NAME/KEY: source
<223> OTHER INFORMATION: /note="target seq for Brugada syndrome"

<400> SEQUENCE: 249

```
gatcctggcc gtggtcgcaa                                                     20
```

<210> SEQ ID NO 250
<211> LENGTH: 25
<212> TYPE: DNA
<213> ORGANISM: Homo sapiens
<220> FEATURE:
<221> NAME/KEY: source
<223> OTHER INFORMATION: /note="target seq for Ornithine carbamoyltransferase deficiency"

<400> SEQUENCE: 250
gaagggccat gaccttctca ctcta                                          25

<210> SEQ ID NO 251
<211> LENGTH: 25
<212> TYPE: DNA
<213> ORGANISM: Homo sapiens
<220> FEATURE:
<221> NAME/KEY: source
<223> OTHER INFORMATION: /note="target seq for Osteogenesis imperfecta
      type I"

<400> SEQUENCE: 251
ggtgctcgag gattgcccgg aacag                                          25

<210> SEQ ID NO 252
<211> LENGTH: 25
<212> TYPE: DNA
<213> ORGANISM: Homo sapiens
<220> FEATURE:
<221> NAME/KEY: source
<223> OTHER INFORMATION: /note="target seq for Osteogenesis imperfecta
      type I"

<400> SEQUENCE: 252
gctcgaggat tgcccggaac agctg                                          25

<210> SEQ ID NO 253
<211> LENGTH: 25
<212> TYPE: DNA
<213> ORGANISM: Homo sapiens
<220> FEATURE:
<221> NAME/KEY: source
<223> OTHER INFORMATION: /note="target seq for Constipation"

<400> SEQUENCE: 253
gattccagtt aaatggatgg caatt                                          25

<210> SEQ ID NO 254
<211> LENGTH: 25
<212> TYPE: DNA
<213> ORGANISM: Homo sapiens
<220> FEATURE:
<221> NAME/KEY: source
<223> OTHER INFORMATION: /note="target seq for Dopamine beta hydroxylase
      deficiency"

<400> SEQUENCE: 254
ggacactgcc tattttgcgg tgagt                                          25

<210> SEQ ID NO 255
<211> LENGTH: 25
<212> TYPE: DNA
<213> ORGANISM: Homo sapiens
<220> FEATURE:
<221> NAME/KEY: source
<223> OTHER INFORMATION: /note="target seq for Cystic fibrosis"

<400> SEQUENCE: 255
gacttcatcc aggtatgtaa aaata                                          25

<210> SEQ ID NO 256
<211> LENGTH: 25
<212> TYPE: DNA
<213> ORGANISM: Homo sapiens

```
<220> FEATURE:
<221> NAME/KEY: source
<223> OTHER INFORMATION: /note="target seq for Phenylketonuria"

<400> SEQUENCE: 256
gatgtaaacc tgacccacac tgaat                                              25

<210> SEQ ID NO 257
<211> LENGTH: 20
<212> TYPE: DNA
<213> ORGANISM: Homo sapiens
<220> FEATURE:
<221> NAME/KEY: source
<223> OTHER INFORMATION: /note="target seq for Deficiency of
      UDPglucose-hexose-1-phosphate uridylyltransferase"

<400> SEQUENCE: 257
gagcccctga caccottacc                                                    20

<210> SEQ ID NO 258
<211> LENGTH: 20
<212> TYPE: DNA
<213> ORGANISM: Homo sapiens
<220> FEATURE:
<221> NAME/KEY: source
<223> OTHER INFORMATION: /note="target seq for Amyloid Cardiomyopathy,
      Transthyretin-related"

<400> SEQUENCE: 258
gtcaccaatc ccaaggaatg                                                    20

<210> SEQ ID NO 259
<211> LENGTH: 25
<212> TYPE: DNA
<213> ORGANISM: Homo sapiens
<220> FEATURE:
<221> NAME/KEY: source
<223> OTHER INFORMATION: /note="target seq for Carbohydrate-deficient
      glycoprotein syndrome type I"

<400> SEQUENCE: 259
ggctactcca tgacagcgcc tgagg                                              25

<210> SEQ ID NO 260
<211> LENGTH: 25
<212> TYPE: DNA
<213> ORGANISM: Homo sapiens
<220> FEATURE:
<221> NAME/KEY: source
<223> OTHER INFORMATION: /note="target seq for Metachromatic
      leukodystrophy"

<400> SEQUENCE: 260
gcatcccgta ctcccacgac cagat                                              25

<210> SEQ ID NO 261
<211> LENGTH: 25
<212> TYPE: DNA
<213> ORGANISM: Homo sapiens
<220> FEATURE:
<221> NAME/KEY: source
<223> OTHER INFORMATION: /note="target seq for Smith-Lemli-Opitz
      syndrome"

<400> SEQUENCE: 261
gttcttcaat gggcgccccg ggatc                                              25
```

```
<210> SEQ ID NO 262
<211> LENGTH: 20
<212> TYPE: DNA
<213> ORGANISM: Homo sapiens
<220> FEATURE:
<221> NAME/KEY: source
<223> OTHER INFORMATION: /note="target seq for Deafness, autosomal
      recessive 1A"

<400> SEQUENCE: 262
gcaggtgagc ccgccggccc                                             20

<210> SEQ ID NO 263
<211> LENGTH: 25
<212> TYPE: DNA
<213> ORGANISM: Homo sapiens
<220> FEATURE:
<221> NAME/KEY: source
<223> OTHER INFORMATION: /note="target seq for Congenital omphalocele"

<400> SEQUENCE: 263
gccagcgctc ctagtggcca tgcac                                       25

<210> SEQ ID NO 264
<211> LENGTH: 25
<212> TYPE: DNA
<213> ORGANISM: Homo sapiens
<220> FEATURE:
<221> NAME/KEY: source
<223> OTHER INFORMATION: /note="target seq for Congenital omphalocele"

<400> SEQUENCE: 264
gcgctcctag tggccatgca cgtgg                                       25

<210> SEQ ID NO 265
<211> LENGTH: 20
<212> TYPE: DNA
<213> ORGANISM: Homo sapiens
<220> FEATURE:
<221> NAME/KEY: source
<223> OTHER INFORMATION: /note="target seq for Congenital omphalocele"

<400> SEQUENCE: 265
gtccacgcca gcgctcctag                                             20

<210> SEQ ID NO 266
<211> LENGTH: 20
<212> TYPE: DNA
<213> ORGANISM: Homo sapiens
<220> FEATURE:
<221> NAME/KEY: source
<223> OTHER INFORMATION: /note="target seq for Congenital omphalocele"

<400> SEQUENCE: 266
gctcctagtg gccatgcacg                                             20

<210> SEQ ID NO 267
<211> LENGTH: 25
<212> TYPE: DNA
<213> ORGANISM: Homo sapiens
<220> FEATURE:
<221> NAME/KEY: source
<223> OTHER INFORMATION: /note="target seq for Congenital myotonia,
      autosomal dominant form"

<400> SEQUENCE: 267
gagaggattc tttgcagcca cgttc                                       25
```

```
<210> SEQ ID NO 268
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 1"

<400> SEQUENCE: 268
ggtgacccga gagtgggtgt                                              20

<210> SEQ ID NO 269
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast and/or ovarian
      cancer"

<400> SEQUENCE: 269
gatgcctgga cagaggacaa                                              20

<210> SEQ ID NO 270
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 1"

<400> SEQUENCE: 270
ggacaatggc ttccatggta                                              20

<210> SEQ ID NO 271
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 1"

<400> SEQUENCE: 271
gggctagaaa tctgttgcta                                              20

<210> SEQ ID NO 272
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 1"

<400> SEQUENCE: 272
ggtgacccga gagtgggtgt                                              20

<210> SEQ ID NO 273
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 1"
```

```
<400> SEQUENCE: 273
gattctgcaa ctttcaattg                                               20

<210> SEQ ID NO 274
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 1"

<400> SEQUENCE: 274
ggacaatggc ttccatggta                                               20

<210> SEQ ID NO 275
<211> LENGTH: 25
<212> TYPE: DNA
<213> ORGANISM: Homo sapiens
<220> FEATURE:
<221> NAME/KEY: source
<223> OTHER INFORMATION: /note="target seq for Inborn genetic diseases"

<400> SEQUENCE: 275
gaaagcccga cttatagcca gtaat                                         25

<210> SEQ ID NO 276
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 2"

<400> SEQUENCE: 276
gattacatga acaaatgggc                                               20

<210> SEQ ID NO 277
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 2"

<400> SEQUENCE: 277
gattacatga acaaatgggc                                               20

<210> SEQ ID NO 278
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 2"

<400> SEQUENCE: 278
gactggaaaa ggaatacagt                                               20

<210> SEQ ID NO 279
<211> LENGTH: 25
<212> TYPE: DNA
<213> ORGANISM: Homo sapiens
```

```
<220> FEATURE:
<221> NAME/KEY: source
<223> OTHER INFORMATION: /note="target seq for Breast and/or ovarian
      cancer"

<400> SEQUENCE: 279
gttggctgat ggtggatggc tcata                                              25

<210> SEQ ID NO 280
<211> LENGTH: 25
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 2"

<400> SEQUENCE: 280
gttggctgat ggtggatggc tcata                                              25

<210> SEQ ID NO 281
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 2"

<400> SEQUENCE: 281
ggtcagaaga ttattcttca                                                    20

<210> SEQ ID NO 282
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 2"

<400> SEQUENCE: 282
ggcttctagt ctcttttgtt                                                    20

<210> SEQ ID NO 283
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 2"

<400> SEQUENCE: 283
ggcttctagt ctcttttgtt                                                    20

<210> SEQ ID NO 284
<211> LENGTH: 20
<212> TYPE: DNA
<213> ORGANISM: Homo sapiens
<220> FEATURE:
<221> NAME/KEY: source
<223> OTHER INFORMATION: /note="target seq for Smith-Lemli-Opitz
      syndrome"

<400> SEQUENCE: 284
gttgcgattt tgcagccatt                                                    20
```

```
<210> SEQ ID NO 285
<211> LENGTH: 25
<212> TYPE: DNA
<213> ORGANISM: Homo sapiens
<220> FEATURE:
<221> NAME/KEY: source
<223> OTHER INFORMATION: /note="target seq for Alport syndrome 1,
      X-linked recessive"

<400> SEQUENCE: 285
ggcctatggg tccccctggt ttcgg                                              25

<210> SEQ ID NO 286
<211> LENGTH: 20
<212> TYPE: DNA
<213> ORGANISM: Homo sapiens
<220> FEATURE:
<221> NAME/KEY: source
<223> OTHER INFORMATION: /note="target seq for Acute neuronopathic
      Gaucher's disease"

<400> SEQUENCE: 286
ggcatcaggt gagtgagtca                                                    20

<210> SEQ ID NO 287
<211> LENGTH: 20
<212> TYPE: DNA
<213> ORGANISM: Homo sapiens
<220> FEATURE:
<221> NAME/KEY: source
<223> OTHER INFORMATION: /note="target seq for Gonadotropin deficiency"

<400> SEQUENCE: 287
gtaactctcc agcataccat                                                    20

<210> SEQ ID NO 288
<211> LENGTH: 20
<212> TYPE: DNA
<213> ORGANISM: Homo sapiens
<220> FEATURE:
<221> NAME/KEY: source
<223> OTHER INFORMATION: /note="target seq for Distal arthrogryposis
      type 1A"

<400> SEQUENCE: 288
gaagctggag gaggccgaga                                                    20

<210> SEQ ID NO 289
<211> LENGTH: 20
<212> TYPE: DNA
<213> ORGANISM: Homo sapiens
<220> FEATURE:
<221> NAME/KEY: source
<223> OTHER INFORMATION: /note="target seq for Distal arthrogryposis
      type 1A"

<400> SEQUENCE: 289
gctggaggag gccgagaagg                                                    20

<210> SEQ ID NO 290
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"
```

```
<400> SEQUENCE: 290
gctgccacct tcagggcctc                                               20

<210> SEQ ID NO 291
<211> LENGTH: 20
<212> TYPE: DNA
<213> ORGANISM: Homo sapiens
<220> FEATURE:
<221> NAME/KEY: source
<223> OTHER INFORMATION: /note="target seq for Inborn genetic diseases"

<400> SEQUENCE: 291
gataaacttc ttgaagagga                                               20

<210> SEQ ID NO 292
<211> LENGTH: 25
<212> TYPE: DNA
<213> ORGANISM: Homo sapiens
<220> FEATURE:
<221> NAME/KEY: source
<223> OTHER INFORMATION: /note="target seq for Death in early adulthood"

<400> SEQUENCE: 292
gtgttctcca tgttcgaaca gaccc                                         25

<210> SEQ ID NO 293
<211> LENGTH: 20
<212> TYPE: DNA
<213> ORGANISM: Homo sapiens
<220> FEATURE:
<221> NAME/KEY: source
<223> OTHER INFORMATION: /note="target seq for Death in early adulthood"

<400> SEQUENCE: 293
gttcgaacag acccaaatcc                                               20

<210> SEQ ID NO 294
<211> LENGTH: 20
<212> TYPE: DNA
<213> ORGANISM: Homo sapiens
<220> FEATURE:
<221> NAME/KEY: source
<223> OTHER INFORMATION: /note="target seq for Severe autosomal
        recessive muscular dystrophy of childhood - North African type"

<400> SEQUENCE: 294
gaaatctgtg tgtgtccaga                                               20

<210> SEQ ID NO 295
<211> LENGTH: 20
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 295
ggtcatcatt gagagcgacc                                               20

<210> SEQ ID NO 296
<211> LENGTH: 20
<212> TYPE: DNA
<213> ORGANISM: Homo sapiens
<220> FEATURE:
<221> NAME/KEY: source
<223> OTHER INFORMATION: /note="target seq for Carbohydrate-deficient
        glycoprotein syndrome type I"
```

```
<400> SEQUENCE: 296
gaatgctgaa gatgatcgac                                              20

<210> SEQ ID NO 297
<211> LENGTH: 20
<212> TYPE: DNA
<213> ORGANISM: Homo sapiens
<220> FEATURE:
<221> NAME/KEY: source
<223> OTHER INFORMATION: /note="target seq for Charcot-Marie-Tooth
      disease, type I"

<400> SEQUENCE: 297
gaatgctgaa gatgatcgac                                              20

<210> SEQ ID NO 298
<211> LENGTH: 25
<212> TYPE: DNA
<213> ORGANISM: Homo sapiens
<220> FEATURE:
<221> NAME/KEY: source
<223> OTHER INFORMATION: /note="target seq for Inborn genetic diseases"

<400> SEQUENCE: 298
gctcagtaca ccaccgtcgg ccgca                                        25

<210> SEQ ID NO 299
<211> LENGTH: 20
<212> TYPE: DNA
<213> ORGANISM: Homo sapiens
<220> FEATURE:
<221> NAME/KEY: source
<223> OTHER INFORMATION: /note="target seq for Inborn genetic diseases"

<400> SEQUENCE: 299
gtacaccacc gtcggccgca                                              20

<210> SEQ ID NO 300
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial Mediterranean
      fever"

<400> SEQUENCE: 300
ggacacgtga tggagggaag aacac                                        25

<210> SEQ ID NO 301
<211> LENGTH: 25
<212> TYPE: DNA
<213> ORGANISM: Homo sapiens
<220> FEATURE:
<221> NAME/KEY: source
<223> OTHER INFORMATION: /note="target seq for Deafness, autosomal
      recessive 2"

<400> SEQUENCE: 301
ggacctttgt caatgggaca cggac                                        25

<210> SEQ ID NO 302
<211> LENGTH: 25
<212> TYPE: DNA
<213> ORGANISM: Homo sapiens
<220> FEATURE:
```

```
<221> NAME/KEY: source
<223> OTHER INFORMATION: /note="target seq for Deafness, autosomal
      recessive 2"

<400> SEQUENCE: 302
ggacctttgt caatgggaca cagac                                             25

<210> SEQ ID NO 303
<211> LENGTH: 25
<212> TYPE: DNA
<213> ORGANISM: Homo sapiens
<220> FEATURE:
<221> NAME/KEY: source
<223> OTHER INFORMATION: /note="target seq for Deafness, X-linked 2"

<400> SEQUENCE: 303
gcgctcctag tggccatgca cgtgg                                             25

<210> SEQ ID NO 304
<211> LENGTH: 25
<212> TYPE: DNA
<213> ORGANISM: Homo sapiens
<220> FEATURE:
<221> NAME/KEY: source
<223> OTHER INFORMATION: /note="target seq for Enlarged vestibular
      aqueduct"

<400> SEQUENCE: 304
gccaccactg ctctttcccg cacgg                                             25

<210> SEQ ID NO 305
<211> LENGTH: 20
<212> TYPE: DNA
<213> ORGANISM: Homo sapiens
<220> FEATURE:
<221> NAME/KEY: source
<223> OTHER INFORMATION: /note="target seq for Congenital sensorineural
      hearing impairment"

<400> SEQUENCE: 305
gtggtcatta acacaaactc                                                   20

<210> SEQ ID NO 306
<211> LENGTH: 20
<212> TYPE: DNA
<213> ORGANISM: Homo sapiens
<220> FEATURE:
<221> NAME/KEY: source
<223> OTHER INFORMATION: /note="target seq for Deficiency of
      UDPglucose-hexose-1-phosphate uridylyltransferase"

<400> SEQUENCE: 306
gccagatatt gcccagcgtg                                                   20

<210> SEQ ID NO 307
<211> LENGTH: 20
<212> TYPE: DNA
<213> ORGANISM: Homo sapiens
<220> FEATURE:
<221> NAME/KEY: source
<223> OTHER INFORMATION: /note="target seq for Very long chain acyl-CoA
      dehydrogenase deficiency"

<400> SEQUENCE: 307
gccactaatc gtacccagtt                                                   20

<210> SEQ ID NO 308
```

```
<211> LENGTH: 20
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 308
gatattccac tggtggtcga                                              20

<210> SEQ ID NO 309
<211> LENGTH: 20
<212> TYPE: DNA
<213> ORGANISM: Homo sapiens
<220> FEATURE:
<221> NAME/KEY: source
<223> OTHER INFORMATION: /note="target seq for Pyruvate kinase
      deficiency of red cells"

<400> SEQUENCE: 309
ggaagactcc tgggcataag                                              20

<210> SEQ ID NO 310
<211> LENGTH: 25
<212> TYPE: DNA
<213> ORGANISM: Homo sapiens
<220> FEATURE:
<221> NAME/KEY: source
<223> OTHER INFORMATION: /note="target seq for Autosomal dominant
      progressive external ophthalmoplegia with mitochondrial DNA
      deletions 1"

<400> SEQUENCE: 310
gaagtcgttg atggatctgg ccaat                                        25

<210> SEQ ID NO 311
<211> LENGTH: 20
<212> TYPE: DNA
<213> ORGANISM: Homo sapiens
<220> FEATURE:
<221> NAME/KEY: source
<223> OTHER INFORMATION: /note="target seq for Very long chain acyl-CoA
      dehydrogenase deficiency"

<400> SEQUENCE: 311
gaagatcaca gcttttgtgg                                              20

<210> SEQ ID NO 312
<211> LENGTH: 20
<212> TYPE: DNA
<213> ORGANISM: Homo sapiens
<220> FEATURE:
<221> NAME/KEY: source
<223> OTHER INFORMATION: /note="target seq for Cystinosis, ocular
      nonnephropathic"

<400> SEQUENCE: 312
gtccatctcc ttctaccctc                                              20

<210> SEQ ID NO 313
<211> LENGTH: 20
<212> TYPE: DNA
<213> ORGANISM: Homo sapiens
<220> FEATURE:
<221> NAME/KEY: source
<223> OTHER INFORMATION: /note="target seq for Pyruvate kinase
      deficiency of red cells"

<400> SEQUENCE: 313
```

```
gctcagccca gcttctgtct                                              20

<210> SEQ ID NO 314
<211> LENGTH: 25
<212> TYPE: DNA
<213> ORGANISM: Homo sapiens
<220> FEATURE:
<221> NAME/KEY: source
<223> OTHER INFORMATION: /note="target seq for Distal myopathy, Tateyama
      type"

<400> SEQUENCE: 314
gattgacctg gtgaaccaag acccc                                        25

<210> SEQ ID NO 315
<211> LENGTH: 25
<212> TYPE: DNA
<213> ORGANISM: Homo sapiens
<220> FEATURE:
<221> NAME/KEY: source
<223> OTHER INFORMATION: /note="target seq for Malignant hyperthermia,
      susceptibility to, 1"

<400> SEQUENCE: 315
ggccctgcgg atccgcgcca tcctc                                        25

<210> SEQ ID NO 316
<211> LENGTH: 25
<212> TYPE: DNA
<213> ORGANISM: Homo sapiens
<220> FEATURE:
<221> NAME/KEY: source
<223> OTHER INFORMATION: /note="target seq for Malignant hyperthermia,
      susceptibility to, 1"

<400> SEQUENCE: 316
ggatccgcgc catcctccgc tccct                                        25

<210> SEQ ID NO 317
<211> LENGTH: 25
<212> TYPE: DNA
<213> ORGANISM: Homo sapiens
<220> FEATURE:
<221> NAME/KEY: source
<223> OTHER INFORMATION: /note="target seq for Myopathy, Central Core"

<400> SEQUENCE: 317
ggtctgatca tcgacgcttt tggtg                                        25

<210> SEQ ID NO 318
<211> LENGTH: 20
<212> TYPE: DNA
<213> ORGANISM: Homo sapiens
<220> FEATURE:
<221> NAME/KEY: source
<223> OTHER INFORMATION: /note="target seq for Myopathy, Central Core"

<400> SEQUENCE: 318
ggtctgatca tcgacgcttt                                              20

<210> SEQ ID NO 319
<211> LENGTH: 25
<212> TYPE: DNA
<213> ORGANISM: Homo sapiens
<220> FEATURE:
<221> NAME/KEY: source
<223> OTHER INFORMATION: /note="target seq for Myopathy, Central Core"
```

<400> SEQUENCE: 319
gatcatcgac acttttggtg agctc                                    25

<210> SEQ ID NO 320
<211> LENGTH: 25
<212> TYPE: DNA
<213> ORGANISM: Homo sapiens
<220> FEATURE:
<221> NAME/KEY: source
<223> OTHER INFORMATION: /note="target seq for Malignant hyperthermia,
      susceptibility to, 1"

<400> SEQUENCE: 320
ggcggaggca ttggggacga gatcg                                    25

<210> SEQ ID NO 321
<211> LENGTH: 20
<212> TYPE: DNA
<213> ORGANISM: Homo sapiens
<220> FEATURE:
<221> NAME/KEY: source
<223> OTHER INFORMATION: /note="target seq for Ceroid lipofuscinosis
      neuronal 2"

<400> SEQUENCE: 321
gtgacagtgg ggccgggtgt                                          20

<210> SEQ ID NO 322
<211> LENGTH: 25
<212> TYPE: DNA
<213> ORGANISM: Homo sapiens
<220> FEATURE:
<221> NAME/KEY: source
<223> OTHER INFORMATION: /note="target seq for Ceroid lipofuscinosis
      neuronal 2"

<400> SEQUENCE: 322
ggggccgggt attggtctgt ctctg                                    25

<210> SEQ ID NO 323
<211> LENGTH: 25
<212> TYPE: DNA
<213> ORGANISM: Homo sapiens
<220> FEATURE:
<221> NAME/KEY: source
<223> OTHER INFORMATION: /note="target seq for Niemann-Pick disease type
      C1"

<400> SEQUENCE: 323
ggatcgacga ttatttcgac tgggt                                    25

<210> SEQ ID NO 324
<211> LENGTH: 25
<212> TYPE: DNA
<213> ORGANISM: Homo sapiens
<220> FEATURE:
<221> NAME/KEY: source
<223> OTHER INFORMATION: /note="target seq for Glutaric aciduria, type
      1"

<400> SEQUENCE: 324
gagtatcacg tgatccggca cgcca                                    25

<210> SEQ ID NO 325
<211> LENGTH: 25
<212> TYPE: DNA

```
<213> ORGANISM: Homo sapiens
<220> FEATURE:
<221> NAME/KEY: source
<223> OTHER INFORMATION: /note="target seq for CAPN3-Related Disorders"

<400> SEQUENCE: 325
gccctgatgc agaagaaccg gcgga                                              25

<210> SEQ ID NO 326
<211> LENGTH: 20
<212> TYPE: DNA
<213> ORGANISM: Homo sapiens
<220> FEATURE:
<221> NAME/KEY: source
<223> OTHER INFORMATION: /note="target seq for CAPN3-Related Disorders"

<400> SEQUENCE: 326
gatgcagaag aaccggcgga                                                    20

<210> SEQ ID NO 327
<211> LENGTH: 20
<212> TYPE: DNA
<213> ORGANISM: Homo sapiens
<220> FEATURE:
<221> NAME/KEY: source
<223> OTHER INFORMATION: /note="target seq for Glycogen storage disease,
      type II"

<400> SEQUENCE: 327
gtcccagaac agctcccctc                                                    20

<210> SEQ ID NO 328
<211> LENGTH: 25
<212> TYPE: DNA
<213> ORGANISM: Homo sapiens
<220> FEATURE:
<221> NAME/KEY: source
<223> OTHER INFORMATION: /note="target seq for Nonsyndromic
      Oculocutaneous Albinism"

<400> SEQUENCE: 328
gtacagggat ctgccaacga tccta                                              25

<210> SEQ ID NO 329
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial
      hypercholesterolemia"

<400> SEQUENCE: 329
gcgaagatgg ctcggatgag                                                    20

<210> SEQ ID NO 330
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial
      hypercholesterolemia"

<400> SEQUENCE: 330
gagtggccgc agcgctgtag                                                    20
```

```
<210> SEQ ID NO 331
<211> LENGTH: 20
<212> TYPE: DNA
<213> ORGANISM: Homo sapiens
<220> FEATURE:
<221> NAME/KEY: source
<223> OTHER INFORMATION: /note="target seq for Deafness, autosomal
      recessive 7"

<400> SEQUENCE: 331
ggtctcaagc tctctcttcg                                              20

<210> SEQ ID NO 332
<211> LENGTH: 20
<212> TYPE: DNA
<213> ORGANISM: Homo sapiens
<220> FEATURE:
<221> NAME/KEY: source
<223> OTHER INFORMATION: /note="target seq for Chronic infantile
      neurological, cutaneous and articular syndrome"

<400> SEQUENCE: 332
gacggcttcg atgagctgca                                              20

<210> SEQ ID NO 333
<211> LENGTH: 20
<212> TYPE: DNA
<213> ORGANISM: Homo sapiens
<220> FEATURE:
<221> NAME/KEY: source
<223> OTHER INFORMATION: /note="target seq for Eichsfeld type congenital
      muscular dystrophy"

<400> SEQUENCE: 333
gactctccgg gagactgtcc                                              20

<210> SEQ ID NO 334
<211> LENGTH: 20
<212> TYPE: DNA
<213> ORGANISM: Homo sapiens
<220> FEATURE:
<221> NAME/KEY: source
<223> OTHER INFORMATION: /note="target seq for Inborn genetic diseases"

<400> SEQUENCE: 334
gctcaaaagt ggatgagcgc                                              20

<210> SEQ ID NO 335
<211> LENGTH: 20
<212> TYPE: DNA
<213> ORGANISM: Homo sapiens
<220> FEATURE:
<221> NAME/KEY: source
<223> OTHER INFORMATION: /note="target seq for Hyperkalemic Periodic
      Paralysis Type 1"

<400> SEQUENCE: 335
gcagctgcgg gtcttcaagc                                              20

<210> SEQ ID NO 336
<211> LENGTH: 20
<212> TYPE: DNA
<213> ORGANISM: Homo sapiens
<220> FEATURE:
<221> NAME/KEY: source
<223> OTHER INFORMATION: /note="target seq for Inclusion body myopathy
      2"

<400> SEQUENCE: 336
```
ggacgtggat gtggtggttt                                          20

<210> SEQ ID NO 337
<211> LENGTH: 25
<212> TYPE: DNA
<213> ORGANISM: Homo sapiens
<220> FEATURE:
<221> NAME/KEY: source
<223> OTHER INFORMATION: /note="target seq for Severe APG05083.1,
      APG07433.1, APG07513.1, APG08290.1 immunodeficiency due to ADA
      Deficiency"

<400> SEQUENCE: 337
gaagagcggc attcaccgta ctgtc                                    25

<210> SEQ ID NO 338
<211> LENGTH: 25
<212> TYPE: DNA
<213> ORGANISM: Homo sapiens
<220> FEATURE:
<221> NAME/KEY: source
<223> OTHER INFORMATION: /note="target seq for Severe APG05083.1,
      APG07433.1, APG07513.1, APG08290.1 immunodeficiency due to ADA
      Deficiency"

<400> SEQUENCE: 338
gcggtacagt ccgcacctgc tggcc                                    25

<210> SEQ ID NO 339
<211> LENGTH: 20
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 339
gtgtccgagc agcgccactg                                          20

<210> SEQ ID NO 340
<211> LENGTH: 20
<212> TYPE: DNA
<213> ORGANISM: Homo sapiens
<220> FEATURE:
<221> NAME/KEY: source
<223> OTHER INFORMATION: /note="target seq for Cystic fibrosis"

<400> SEQUENCE: 340
ggacacttcg tgccttcgga                                          20

<210> SEQ ID NO 341
<211> LENGTH: 20
<212> TYPE: DNA
<213> ORGANISM: Homo sapiens
<220> FEATURE:
<221> NAME/KEY: source
<223> OTHER INFORMATION: /note="target seq for Cystic fibrosis"

<400> SEQUENCE: 341
ggacacttcg tgccttcgga                                          20

<210> SEQ ID NO 342
<211> LENGTH: 25
<212> TYPE: DNA
<213> ORGANISM: Homo sapiens
<220> FEATURE:
<221> NAME/KEY: source

```
<223> OTHER INFORMATION: /note="target seq for Adrenocortical carcinoma,
      pediatric"

<400> SEQUENCE: 342
gggcgtgagc acttcgagat gttcc                                              25

<210> SEQ ID NO 343
<211> LENGTH: 20
<212> TYPE: DNA
<213> ORGANISM: Homo sapiens
<220> FEATURE:
<221> NAME/KEY: source
<223> OTHER INFORMATION: /note="target seq for Fumarase deficiency"

<400> SEQUENCE: 343
gattggacgt actcatactc                                                    20

<210> SEQ ID NO 344
<211> LENGTH: 20
<212> TYPE: DNA
<213> ORGANISM: Homo sapiens
<220> FEATURE:
<221> NAME/KEY: source
<223> OTHER INFORMATION: /note="target seq for Adenocarcinoma of
      prostate"

<400> SEQUENCE: 344
gaacactgtc cattggcatg                                                    20

<210> SEQ ID NO 345
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial hypertrophic
      cardiomyopathy 1"

<400> SEQUENCE: 345
gcatcctcta cggggacttc                                                    20

<210> SEQ ID NO 346
<211> LENGTH: 25
<212> TYPE: DNA
<213> ORGANISM: Homo sapiens
<220> FEATURE:
<221> NAME/KEY: source
<223> OTHER INFORMATION: /note="target seq for Adult hypophosphatasia"

<400> SEQUENCE: 346
gacaacgaga tgcccctga ggcct                                               25

<210> SEQ ID NO 347
<211> LENGTH: 25
<212> TYPE: DNA
<213> ORGANISM: Homo sapiens
<220> FEATURE:
<221> NAME/KEY: source
<223> OTHER INFORMATION: /note="target seq for Adult hypophosphatasia"

<400> SEQUENCE: 347
ggtactcaga caacaagatg ccccc                                              25

<210> SEQ ID NO 348
<211> LENGTH: 25
<212> TYPE: DNA
<213> ORGANISM: Homo sapiens
```

```
<220> FEATURE:
<221> NAME/KEY: source
<223> OTHER INFORMATION: /note="target seq for Adult hypophosphatasia"

<400> SEQUENCE: 348
gacaacaaga tgcccctga ggcct                                              25

<210> SEQ ID NO 349
<211> LENGTH: 25
<212> TYPE: DNA
<213> ORGANISM: Homo sapiens
<220> FEATURE:
<221> NAME/KEY: source
<223> OTHER INFORMATION: /note="target seq for Inborn genetic diseases"

<400> SEQUENCE: 349
gccttcttgg acaacgtcac cacca                                             25

<210> SEQ ID NO 350
<211> LENGTH: 25
<212> TYPE: DNA
<213> ORGANISM: Homo sapiens
<220> FEATURE:
<221> NAME/KEY: source
<223> OTHER INFORMATION: /note="target seq for Inborn genetic diseases"

<400> SEQUENCE: 350
ggtttgccat ccgaggggta gtgct                                             25

<210> SEQ ID NO 351
<211> LENGTH: 20
<212> TYPE: DNA
<213> ORGANISM: Homo sapiens
<220> FEATURE:
<221> NAME/KEY: source
<223> OTHER INFORMATION: /note="target seq for Crouzon syndrome"

<400> SEQUENCE: 351
gcaaatgcct ccacagtggt                                                   20

<210> SEQ ID NO 352
<211> LENGTH: 20
<212> TYPE: DNA
<213> ORGANISM: Homo sapiens
<220> FEATURE:
<221> NAME/KEY: source
<223> OTHER INFORMATION: /note="target seq for Propionyl-CoA carboxylase
      deficiency"

<400> SEQUENCE: 352
gacatcatag gcacctccat                                                   20

<210> SEQ ID NO 353
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 353
ggtggaaggg atcggctacg acttc                                             25

<210> SEQ ID NO 354
<211> LENGTH: 25
<212> TYPE: DNA
<213> ORGANISM: Homo sapiens
```

```
<220> FEATURE:
<221> NAME/KEY: source
<223> OTHER INFORMATION: /note="target seq for Dysostosis multiplex"

<400> SEQUENCE: 354
ggagcagctc tgggccgaag tgtcg                                          25

<210> SEQ ID NO 355
<211> LENGTH: 20
<212> TYPE: DNA
<213> ORGANISM: Homo sapiens
<220> FEATURE:
<221> NAME/KEY: source
<223> OTHER INFORMATION: /note="target seq for Multiple sulfatase
      deficiency"

<400> SEQUENCE: 355
ggcgactcct ttgtctttga                                                20

<210> SEQ ID NO 356
<211> LENGTH: 20
<212> TYPE: DNA
<213> ORGANISM: Homo sapiens
<220> FEATURE:
<221> NAME/KEY: source
<223> OTHER INFORMATION: /note="target seq for Bifunctional peroxisomal
      enzyme deficiency"

<400> SEQUENCE: 356
ggtggtactg gtcaccggcg                                                20

<210> SEQ ID NO 357
<211> LENGTH: 25
<212> TYPE: DNA
<213> ORGANISM: Homo sapiens
<220> FEATURE:
<221> NAME/KEY: source
<223> OTHER INFORMATION: /note="target seq for Bifunctional peroxisomal
      enzyme deficiency"

<400> SEQUENCE: 357
gtactggtca ccagcgcggg ggcag                                          25

<210> SEQ ID NO 358
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 358
ggaaacttgt aagggcttcg                                                20

<210> SEQ ID NO 359
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 359
gtgcagacat tgacgaatgc cgcat                                          25

<210> SEQ ID NO 360
```

-continued

```
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 360
gacattgacg aatgccgcat atctc                                          25

<210> SEQ ID NO 361
<211> LENGTH: 20
<212> TYPE: DNA
<213> ORGANISM: Homo sapiens
<220> FEATURE:
<221> NAME/KEY: source
<223> OTHER INFORMATION: /note="target seq for Limb-girdle muscular
      dystrophy, type 2L"

<400> SEQUENCE: 361
gcatagtagt aaactagacg                                                20

<210> SEQ ID NO 362
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial
      hypercholesterolemia"

<400> SEQUENCE: 362
gcatcgatgt caacgagggc aaccg                                          25

<210> SEQ ID NO 363
<211> LENGTH: 20
<212> TYPE: DNA
<213> ORGANISM: Homo sapiens
<220> FEATURE:
<221> NAME/KEY: source
<223> OTHER INFORMATION: /note="target seq for Spastic Paraplegia,
      Recessive"

<400> SEQUENCE: 363
gcactgctgc tcggcccccc                                                20

<210> SEQ ID NO 364
<211> LENGTH: 20
<212> TYPE: DNA
<213> ORGANISM: Homo sapiens
<220> FEATURE:
<221> NAME/KEY: source
<223> OTHER INFORMATION: /note="target seq for Isovaleryl-CoA
      dehydrogenase deficiency"

<400> SEQUENCE: 364
ggagcagtgg ggctcagtta                                                20

<210> SEQ ID NO 365
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial
      hypercholesterolemia"

<400> SEQUENCE: 365
```
gaggagctgc ctcacaggtg                                              20

<210> SEQ ID NO 366
<211> LENGTH: 20
<212> TYPE: DNA
<213> ORGANISM: Homo sapiens
<220> FEATURE:
<221> NAME/KEY: source
<223> OTHER INFORMATION: /note="target seq for Biotinidase deficiency"

<400> SEQUENCE: 366
gctccagcgc ctgagttgta                                              20

<210> SEQ ID NO 367
<211> LENGTH: 20
<212> TYPE: DNA
<213> ORGANISM: Homo sapiens
<220> FEATURE:
<221> NAME/KEY: source
<223> OTHER INFORMATION: /note="target seq for Biotinidase deficiency"

<400> SEQUENCE: 367
gcctgagttg tatggccatc                                              20

<210> SEQ ID NO 368
<211> LENGTH: 25
<212> TYPE: DNA
<213> ORGANISM: Homo sapiens
<220> FEATURE:
<221> NAME/KEY: source
<223> OTHER INFORMATION: /note="target seq for Leber congenital
      amaurosis"

<400> SEQUENCE: 368
gcataatttg tacagctcta agagt                                        25

<210> SEQ ID NO 369
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial hyperinsulinism"

<400> SEQUENCE: 369
ggtggctgag cccagcccgg ccccc                                        25

<210> SEQ ID NO 370
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial cancer of
      breast"

<400> SEQUENCE: 370
ggatgcttgg cagtgggaaa aactt                                        25

<210> SEQ ID NO 371
<211> LENGTH: 20
<212> TYPE: DNA
<213> ORGANISM: Homo sapiens
<220> FEATURE:
<221> NAME/KEY: source
<223> OTHER INFORMATION: /note="target seq for Cohen syndrome"

<400> SEQUENCE: 371
ggaggtctac tacaggtctg                                              20

<210> SEQ ID NO 372
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 372
gctccctctg tactgtgcag gagtc                                        25

<210> SEQ ID NO 373
<211> LENGTH: 20
<212> TYPE: DNA
<213> ORGANISM: Homo sapiens
<220> FEATURE:
<221> NAME/KEY: source
<223> OTHER INFORMATION: /note="target seq for Wilson disease"

<400> SEQUENCE: 373
ggcaatgaac acaaagagca                                              20

<210> SEQ ID NO 374
<211> LENGTH: 25
<212> TYPE: DNA
<213> ORGANISM: Homo sapiens
<220> FEATURE:
<221> NAME/KEY: source
<223> OTHER INFORMATION: /note="target seq for Wilson disease"

<400> SEQUENCE: 374
gccctggatg ggctcagcgg ccatg                                        25

<210> SEQ ID NO 375
<211> LENGTH: 20
<212> TYPE: DNA
<213> ORGANISM: Homo sapiens
<220> FEATURE:
<221> NAME/KEY: source
<223> OTHER INFORMATION: /note="target seq for Wilson disease"

<400> SEQUENCE: 375
gcagccctgg atgggctcag                                              20

<210> SEQ ID NO 376
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial
    hypercholesterolemia"

<400> SEQUENCE: 376
gtggcccagc gaagatgcga                                              20

<210> SEQ ID NO 377
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial
    hypercholesterolemia"

-continued

<400> SEQUENCE: 377
gaagatgcga aggtgatttc                    20

<210> SEQ ID NO 378
<211> LENGTH: 20
<212> TYPE: DNA
<213> ORGANISM: Homo sapiens
<220> FEATURE:
<221> NAME/KEY: source
<223> OTHER INFORMATION: /note="target seq for Floating-Harbor syndrome"

<400> SEQUENCE: 378
gctgaagctg gagtgggtcg                    20

<210> SEQ ID NO 379
<211> LENGTH: 25
<212> TYPE: DNA
<213> ORGANISM: Homo sapiens
<220> FEATURE:
<221> NAME/KEY: source
<223> OTHER INFORMATION: /note="target seq for Congenital long QT syndrome"

<400> SEQUENCE: 379
gatgctacac gtcgaccgcc aggga                    25

<210> SEQ ID NO 380
<211> LENGTH: 20
<212> TYPE: DNA
<213> ORGANISM: Homo sapiens
<220> FEATURE:
<221> NAME/KEY: source
<223> OTHER INFORMATION: /note="target seq for Congenital long QT syndrome"

<400> SEQUENCE: 380
gatgctacac gtcgaccgcc                    20

<210> SEQ ID NO 381
<211> LENGTH: 25
<212> TYPE: DNA
<213> ORGANISM: Homo sapiens
<220> FEATURE:
<221> NAME/KEY: source
<223> OTHER INFORMATION: /note="target seq for Andersen Tawil syndrome"

<400> SEQUENCE: 381
gaggaagaga tcaaggtcct ttcca                    25

<210> SEQ ID NO 382
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 382
gagctgataa ccaccctgta catcg                    25

<210> SEQ ID NO 383
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial hypercholesterolemia"

<400> SEQUENCE: 383
ggaaaactgc ggtatgggcg                                           20

<210> SEQ ID NO 384
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 384
gtatttgaag gtctcctccg gggtc                                     25

<210> SEQ ID NO 385
<211> LENGTH: 20
<212> TYPE: DNA
<213> ORGANISM: Homo sapiens
<220> FEATURE:
<221> NAME/KEY: source
<223> OTHER INFORMATION: /note="target seq for Gastrointestinal stroma
      tumor"

<400> SEQUENCE: 385
gagggctaaa gtgggctcgg                                           20

<210> SEQ ID NO 386
<211> LENGTH: 20
<212> TYPE: DNA
<213> ORGANISM: Homo sapiens
<220> FEATURE:
<221> NAME/KEY: source
<223> OTHER INFORMATION: /note="target seq for Dyskeratosis congenita"

<400> SEQUENCE: 386
gctgccaagc ctgctggcaa                                           20

<210> SEQ ID NO 387
<211> LENGTH: 25
<212> TYPE: DNA
<213> ORGANISM: Homo sapiens
<220> FEATURE:
<221> NAME/KEY: source
<223> OTHER INFORMATION: /note="target seq for Dyskeratosis congenita"

<400> SEQUENCE: 387
gccctgcctg tgacttccag cactg                                     25

<210> SEQ ID NO 388
<211> LENGTH: 25
<212> TYPE: DNA
<213> ORGANISM: Homo sapiens
<220> FEATURE:
<221> NAME/KEY: source
<223> OTHER INFORMATION: /note="target seq for Glycogen storage disease
      IIIa"

<400> SEQUENCE: 388
gatgagtaga acagaaaaat acaag                                     25

<210> SEQ ID NO 389
<211> LENGTH: 25
<212> TYPE: DNA
<213> ORGANISM: Homo sapiens
<220> FEATURE:

```
<221> NAME/KEY: source
<223> OTHER INFORMATION: /note="target seq for Dilated cardiomyopathy
      1DD"

<400> SEQUENCE: 389
gtctcgtagt ccggtgagcc ggtca                                         25

<210> SEQ ID NO 390
<211> LENGTH: 20
<212> TYPE: DNA
<213> ORGANISM: Homo sapiens
<220> FEATURE:
<221> NAME/KEY: source
<223> OTHER INFORMATION: /note="target seq for Renal carnitine transport
      defect"

<400> SEQUENCE: 390
gtggccatgg aatagcgccg                                               20

<210> SEQ ID NO 391
<211> LENGTH: 25
<212> TYPE: DNA
<213> ORGANISM: Homo sapiens
<220> FEATURE:
<221> NAME/KEY: source
<223> OTHER INFORMATION: /note="target seq for Baraitser-Winter syndrome
      1"

<400> SEQUENCE: 391
gatcctcacc gagcgcggct acagc                                         25

<210> SEQ ID NO 392
<211> LENGTH: 25
<212> TYPE: DNA
<213> ORGANISM: Homo sapiens
<220> FEATURE:
<221> NAME/KEY: source
<223> OTHER INFORMATION: /note="target seq for Very long chain acyl-CoA
      dehydrogenase deficiency"

<400> SEQUENCE: 392
gggcatgcat gaccttggcg tgggc                                         25

<210> SEQ ID NO 393
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial
      hypercholesterolemia"

<400> SEQUENCE: 393
gtcagatttg tccttgcagt                                               20

<210> SEQ ID NO 394
<211> LENGTH: 20
<212> TYPE: DNA
<213> ORGANISM: Homo sapiens
<220> FEATURE:
<221> NAME/KEY: source
<223> OTHER INFORMATION: /note="target seq for Limb-girdle muscular
      dystrophy, type 2A"

<400> SEQUENCE: 394
gtacggggtt gctctgccgg                                               20
```

```
<210> SEQ ID NO 395
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial
      hypercholesterolemia"

<400> SEQUENCE: 395
gacagtagcc cctgctcggc cttcg                                             25

<210> SEQ ID NO 396
<211> LENGTH: 20
<212> TYPE: DNA
<213> ORGANISM: Homo sapiens
<220> FEATURE:
<221> NAME/KEY: source
<223> OTHER INFORMATION: /note="target seq for Aortic aneurysm, familial
      thoracic 6"

<400> SEQUENCE: 396
gccccatgcc atcatgcgtc                                                   20

<210> SEQ ID NO 397
<211> LENGTH: 25
<212> TYPE: DNA
<213> ORGANISM: Homo sapiens
<220> FEATURE:
<221> NAME/KEY: source
<223> OTHER INFORMATION: /note="target seq for Acromicric dysplasia"

<400> SEQUENCE: 397
gctttgtcat cgacatttat accgg                                             25

<210> SEQ ID NO 398
<211> LENGTH: 25
<212> TYPE: DNA
<213> ORGANISM: Homo sapiens
<220> FEATURE:
<221> NAME/KEY: source
<223> OTHER INFORMATION: /note="target seq for Charcot-Marie-Tooth
      disease type 2C"

<400> SEQUENCE: 398
ggcggacatg cggcaccagg actcg                                             25

<210> SEQ ID NO 399
<211> LENGTH: 25
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 2"

<400> SEQUENCE: 399
gtgtaactgt atacgtatgg cgttt                                             25

<210> SEQ ID NO 400
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 1"

<400> SEQUENCE: 400
```

```
gatgcctgga cagaggacaa                                              20

<210> SEQ ID NO 401
<211> LENGTH: 25
<212> TYPE: DNA
<213> ORGANISM: Homo sapiens
<220> FEATURE:
<221> NAME/KEY: source
<223> OTHER INFORMATION: /note="target seq for Charcot-Marie-Tooth
      disease type 2C"

<400> SEQUENCE: 401
gcctaactga tgaggagttt cgagg                                        25

<210> SEQ ID NO 402
<211> LENGTH: 25
<212> TYPE: DNA
<213> ORGANISM: Homo sapiens
<220> FEATURE:
<221> NAME/KEY: source
<223> OTHER INFORMATION: /note="target seq for Charcot-Marie-Tooth
      disease type 2C"

<400> SEQUENCE: 402
gcctaactga tgaggagttt caagg                                        25

<210> SEQ ID NO 403
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 403
gagcgctgct cagatagcga                                              20

<210> SEQ ID NO 404
<211> LENGTH: 25
<212> TYPE: DNA
<213> ORGANISM: Homo sapiens
<220> FEATURE:
<221> NAME/KEY: source
<223> OTHER INFORMATION: /note="target seq for Early infantile epileptic
      encephalopathy"

<400> SEQUENCE: 404
gatgatccgc atggaccggc gggga                                        25

<210> SEQ ID NO 405
<211> LENGTH: 20
<212> TYPE: DNA
<213> ORGANISM: Homo sapiens
<220> FEATURE:
<221> NAME/KEY: source
<223> OTHER INFORMATION: /note="target seq for Early infantile epileptic
      encephalopathy"

<400> SEQUENCE: 405
ggatgatccg catggaccgg                                              20

<210> SEQ ID NO 406
<211> LENGTH: 25
<212> TYPE: DNA
<213> ORGANISM: Homo sapiens
<220> FEATURE:
```

```
<221> NAME/KEY: source
<223> OTHER INFORMATION: /note="target seq for Early infantile epileptic
      encephalopathy"

<400> SEQUENCE: 406
gcggatgatc cgcatggacc agcgg                                              25

<210> SEQ ID NO 407
<211> LENGTH: 20
<212> TYPE: DNA
<213> ORGANISM: Homo sapiens
<220> FEATURE:
<221> NAME/KEY: source
<223> OTHER INFORMATION: /note="target seq for Acromicric dysplasia"

<400> SEQUENCE: 407
gtacgtgatc catcctaggt                                                    20

<210> SEQ ID NO 408
<211> LENGTH: 25
<212> TYPE: DNA
<213> ORGANISM: Homo sapiens
<220> FEATURE:
<221> NAME/KEY: source
<223> OTHER INFORMATION: /note="target seq for Hypertrophic
      cardiomyopathy"

<400> SEQUENCE: 408
gacaccacgg tctccctcaa gtggc                                              25

<210> SEQ ID NO 409
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 409
gctgtccggg gtagccccaa gatag                                              25

<210> SEQ ID NO 410
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 410
gtccacggtg aggggggccct ggtgt                                             25

<210> SEQ ID NO 411
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 411
gcctagactg caggacacag ggact                                              25

<210> SEQ ID NO 412
<211> LENGTH: 25
<212> TYPE: DNA
<213> ORGANISM: Homo sapiens
```

```
<220> FEATURE:
<221> NAME/KEY: source
<223> OTHER INFORMATION: /note="target seq for Familial hypertrophic
      cardiomyopathy 1"

<400> SEQUENCE: 412
gcatctgcag acatagagac ctgtg                                            25

<210> SEQ ID NO 413
<211> LENGTH: 20
<212> TYPE: DNA
<213> ORGANISM: Homo sapiens
<220> FEATURE:
<221> NAME/KEY: source
<223> OTHER INFORMATION: /note="target seq for Benign scapuloperoneal
      muscular dystrophy with cardiomyopathy"

<400> SEQUENCE: 413
gccctccaag agcttgcggt                                                  20

<210> SEQ ID NO 414
<211> LENGTH: 25
<212> TYPE: DNA
<213> ORGANISM: Homo sapiens
<220> FEATURE:
<221> NAME/KEY: source
<223> OTHER INFORMATION: /note="target seq for Glycogen storage disease,
      type II"

<400> SEQUENCE: 414
ggccctcacc ctgcgctacg cactc                                            25

<210> SEQ ID NO 415
<211> LENGTH: 25
<212> TYPE: DNA
<213> ORGANISM: Homo sapiens
<220> FEATURE:
<221> NAME/KEY: source
<223> OTHER INFORMATION: /note="target seq for Diffuse mesangial
      sclerosis"

<400> SEQUENCE: 415
gtttaggcac ttgttttacc tgtat                                            25

<210> SEQ ID NO 416
<211> LENGTH: 20
<212> TYPE: DNA
<213> ORGANISM: Homo sapiens
<220> FEATURE:
<221> NAME/KEY: source
<223> OTHER INFORMATION: /note="target seq for Colobomatous
      microphthalmia"

<400> SEQUENCE: 416
gggtcgaggc ggacgccata                                                  20

<210> SEQ ID NO 417
<211> LENGTH: 20
<212> TYPE: DNA
<213> ORGANISM: Homo sapiens
<220> FEATURE:
<221> NAME/KEY: source
<223> OTHER INFORMATION: /note="target seq for Ataxia-telangiectasia
      syndrome"

<400> SEQUENCE: 417
gtaaatacat atttactact                                                  20
```

<210> SEQ ID NO 418
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial cancer of breast"

<400> SEQUENCE: 418
ggctacagca cacagctcgt                                              20

<210> SEQ ID NO 419
<211> LENGTH: 25
<212> TYPE: DNA
<213> ORGANISM: Homo sapiens
<220> FEATURE:
<221> NAME/KEY: source
<223> OTHER INFORMATION: /note="target seq for Limb-girdle muscular dystrophy, type 2A"

<400> SEQUENCE: 419
gctacgagat gcaaaatgca gtcaa                                        25

<210> SEQ ID NO 420
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary cancer-predisposing syndrome"

<400> SEQUENCE: 420
gccgcttacc aaaaggagta                                              20

<210> SEQ ID NO 421
<211> LENGTH: 25
<212> TYPE: DNA
<213> ORGANISM: Homo sapiens
<220> FEATURE:
<221> NAME/KEY: source
<223> OTHER INFORMATION: /note="target seq for Asymmetric septal hypertrophy"

<400> SEQUENCE: 421
gtgctgcagg ttgttggtgc atggc                                        25

<210> SEQ ID NO 422
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary cancer-predisposing syndrome"

<400> SEQUENCE: 422
gtaattctat aactccttag                                              20

<210> SEQ ID NO 423
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial hypertrophic cardiomyopathy 2"

<400> SEQUENCE: 423
gctaaagtca ccgggcgctg gaaat         25

<210> SEQ ID NO 424
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial hypertrophic
      cardiomyopathy 2"

<400> SEQUENCE: 424
ggctaaagtc accgggcgct agaaa         25

<210> SEQ ID NO 425
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial hypertrophic
      cardiomyopathy 2"

<400> SEQUENCE: 425
gctaaagtca ccgggcgcta gaaat         25

<210> SEQ ID NO 426
<211> LENGTH: 25
<212> TYPE: DNA
<213> ORGANISM: Homo sapiens
<220> FEATURE:
<221> NAME/KEY: source
<223> OTHER INFORMATION: /note="target seq for Erythrocytosis, familial,
      2"

<400> SEQUENCE: 426
gaaagagcaa tgcctccagg ttgtc         25

<210> SEQ ID NO 427
<211> LENGTH: 25
<212> TYPE: DNA
<213> ORGANISM: Homo sapiens
<220> FEATURE:
<221> NAME/KEY: source
<223> OTHER INFORMATION: /note="target seq for Death in infancy"

<400> SEQUENCE: 427
gtattggaat ccggagcatc cacgt         25

<210> SEQ ID NO 428
<211> LENGTH: 20
<212> TYPE: DNA
<213> ORGANISM: Homo sapiens
<220> FEATURE:
<221> NAME/KEY: source
<223> OTHER INFORMATION: /note="target seq for Muscular Diseases"

<400> SEQUENCE: 428
gcatcttccg gatctttgag         20

<210> SEQ ID NO 429
<211> LENGTH: 25
<212> TYPE: DNA
<213> ORGANISM: Homo sapiens
<220> FEATURE:

```
<221> NAME/KEY: source
<223> OTHER INFORMATION: /note="target seq for Familial
      hypercholesterolemia"

<400> SEQUENCE: 429
gctgcgagca tggggccctg aggct                                              25

<210> SEQ ID NO 430
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial cancer of
      breast"

<400> SEQUENCE: 430
ggcagcgtta cccagtccga                                                    20

<210> SEQ ID NO 431
<211> LENGTH: 25
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 431
gtgtaggcaa cttctatagc cacag                                              25

<210> SEQ ID NO 432
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial
      hypercholesterolemia"

<400> SEQUENCE: 432
ggaactcccg ccaagatcaa gaaag                                              25

<210> SEQ ID NO 433
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial
      hypercholesterolemia"

<400> SEQUENCE: 433
gcggctgcca gtatctgtgc ctccc                                              25

<210> SEQ ID NO 434
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial
      hypercholesterolemia"

<400> SEQUENCE: 434
gaatgatctg caggtgagcg tcgcc                                              25
```

```
<210> SEQ ID NO 435
<211> LENGTH: 25
<212> TYPE: DNA
<213> ORGANISM: Homo sapiens
<220> FEATURE:
<221> NAME/KEY: source
<223> OTHER INFORMATION: /note="target seq for Inclusion body myopathy
      2"

<400> SEQUENCE: 435
gtgctgtagt gcaccaatgt aatct                                              25

<210> SEQ ID NO 436
<211> LENGTH: 20
<212> TYPE: DNA
<213> ORGANISM: Homo sapiens
<220> FEATURE:
<221> NAME/KEY: source
<223> OTHER INFORMATION: /note="target seq for Ataxia-telangiectasia
      syndrome"

<400> SEQUENCE: 436
gctttgatgt taacaatcgc                                                    20

<210> SEQ ID NO 437
<211> LENGTH: 25
<212> TYPE: DNA
<213> ORGANISM: Homo sapiens
<220> FEATURE:
<221> NAME/KEY: source
<223> OTHER INFORMATION: /note="target seq for Benign familial
      neonatal-infantile seizures"

<400> SEQUENCE: 437
gtcagttctc cgatcattcc agctg                                              25

<210> SEQ ID NO 438
<211> LENGTH: 20
<212> TYPE: DNA
<213> ORGANISM: Homo sapiens
<220> FEATURE:
<221> NAME/KEY: source
<223> OTHER INFORMATION: /note="target seq for Marfan Syndrome/Loeys-
      Dietz Syndrome/Familial Thoracic Aortic Aneurysms and
      Dissections"

<400> SEQUENCE: 438
gtatctccat tgtctcctcg                                                    20

<210> SEQ ID NO 439
<211> LENGTH: 25
<212> TYPE: DNA
<213> ORGANISM: Homo sapiens
<220> FEATURE:
<221> NAME/KEY: source
<223> OTHER INFORMATION: /note="target seq for Dilated cardiomyopathy
      1G"

<400> SEQUENCE: 439
gtttcagatt cccctggccc acgtg                                              25

<210> SEQ ID NO 440
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial
      hypercholesterolemia"
```

-continued

<400> SEQUENCE: 440
gcggtgagtc tcggtgcagg                                           20

<210> SEQ ID NO 441
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer,
      familial 2"

<400> SEQUENCE: 441
gatacagtat taattgactg                                           20

<210> SEQ ID NO 442
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial
      hypercholesterolemia"

<400> SEQUENCE: 442
gcgagtgcat ccactccagc                                           20

<210> SEQ ID NO 443
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial
      hypercholesterolemia"

<400> SEQUENCE: 443
ggctacaagt gccagtgtga ggaag                                     25

<210> SEQ ID NO 444
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial
      hypercholesterolemia"

<400> SEQUENCE: 444
gggtggctac aagtgccagc gtgag                                     25

<210> SEQ ID NO 445
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial
      hypercholesterolemia"

<400> SEQUENCE: 445
gtacaccagc ctcaccccca acctg                                     25

<210> SEQ ID NO 446
<211> LENGTH: 25
<212> TYPE: DNA

```
<213> ORGANISM: Homo sapiens
<220> FEATURE:
<221> NAME/KEY: source
<223> OTHER INFORMATION: /note="target seq for Familial cancer of
      breast"

<400> SEQUENCE: 446
gcctgcccga tagacgagcc tcccg                                           25

<210> SEQ ID NO 447
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary hemorrhagic
      telangiectasia type 2"

<400> SEQUENCE: 447
gatccgcagc gcggtgagtc                                                 20

<210> SEQ ID NO 448
<211> LENGTH: 3
<212> TYPE: DNA
<213> ORGANISM: Streptococcus pyogenes
<220> FEATURE:
<221> NAME/KEY: source
<223> OTHER INFORMATION: /note="SpyCas9 PAM"
<220> FEATURE:
<221> NAME/KEY: modified_base
<222> LOCATION: (1)..(1)
<223> OTHER INFORMATION: a, c, t, g, unknown or other

<400> SEQUENCE: 448 ngg                                                                    3

<210> SEQ ID NO 449
<211> LENGTH: 5
<212> TYPE: DNA
<213> ORGANISM: Staphylococcus aureus
<220> FEATURE:
<221> NAME/KEY: source
<223> OTHER INFORMATION: /note="SauCas9"
<220> FEATURE:
<221> NAME/KEY: modified_base
<222> LOCATION: (1)..(1)
<223> OTHER INFORMATION: a, c, t, g, unknown or other

<400> SEQUENCE: 449 ngrrt                                                                  5

<210> SEQ ID NO 450
<211> LENGTH: 415
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="ADAT"

<400> SEQUENCE: 450

Met Ala Lys Arg Pro Ala Ala Thr Lys Lys Ala Gly Gln Ala Lys Lys
1               5                   10                  15

Lys Lys Ser Glu Val Glu Phe Ser His Glu Tyr Trp Met Arg His Ala
            20                  25                  30
```

Leu Thr Leu Ala Lys Arg Ala Trp Asp Glu Arg Glu Val Pro Val Gly
             35                  40                  45

Ala Val Leu Val His Asn Asn Arg Val Ile Gly Glu Gly Trp Asn Arg
 50                  55                  60

Pro Ile Gly Arg His Asp Pro Thr Ala His Ala Glu Ile Met Ala Leu
 65                  70                  75                  80

Arg Gln Gly Gly Leu Val Met Gln Asn Tyr Arg Leu Ile Asp Ala Thr
                 85                  90                  95

Leu Tyr Val Thr Leu Glu Pro Cys Val Met Cys Ala Gly Ala Met Ile
            100                 105                 110

His Ser Arg Ile Gly Arg Val Val Phe Gly Ala Arg Asp Ala Lys Thr
            115                 120                 125

Gly Ala Ala Gly Ser Leu Met Asp Val Leu His His Pro Gly Met Asn
130                 135                 140

His Arg Val Glu Ile Thr Glu Gly Ile Leu Ala Asp Glu Cys Ala Ala
145                 150                 155                 160

Leu Leu Ser Asp Phe Phe Arg Met Arg Arg Gln Glu Ile Lys Ala Gln
                165                 170                 175

Lys Lys Ala Gln Ser Ser Thr Asp Ser Gly Gly Ser Ser Gly Gly Ser
            180                 185                 190

Ser Gly Ser Glu Thr Pro Gly Thr Ser Glu Ser Ala Thr Pro Glu Ser
            195                 200                 205

Ser Gly Gly Ser Ser Gly Gly Ser Ser Glu Val Glu Phe Ser His Glu
            210                 215                 220

Tyr Trp Met Arg His Ala Leu Thr Leu Ala Lys Arg Ala Arg Asp Glu
225                 230                 235                 240

Arg Glu Val Pro Val Gly Ala Val Leu Val Leu Asn Asn Arg Val Ile
                245                 250                 255

Gly Glu Gly Trp Asn Arg Ala Ile Gly Leu His Asp Pro Thr Ala His
            260                 265                 270

Ala Glu Ile Met Ala Leu Arg Gln Gly Gly Leu Val Met Gln Asn Tyr
            275                 280                 285

Arg Leu Ile Asp Ala Thr Leu Tyr Val Thr Phe Glu Pro Cys Val Met
290                 295                 300

Cys Ala Gly Ala Met Ile His Ser Arg Ile Gly Arg Val Val Phe Gly
305                 310                 315                 320

Val Arg Asn Ala Lys Thr Gly Ala Ala Gly Ser Leu Met Asp Val Leu
                325                 330                 335

His Tyr Pro Gly Met Asn His Arg Val Glu Ile Thr Glu Gly Ile Leu
            340                 345                 350

Ala Asp Glu Cys Ala Ala Leu Leu Cys Tyr Phe Phe Arg Met Pro Arg
            355                 360                 365

Gln Val Phe Asn Ala Gln Lys Lys Ala Gln Ser Ser Thr Asp Ser Gly
370                 375                 380

Gly Ser Ser Gly Gly Ser Ser Gly Ser Glu Thr Pro Gly Thr Ser Glu
385                 390                 395                 400

Ser Ala Thr Pro Glu Ser Ser Gly Gly Ser Ser Gly Gly Ser Ser
            405                 410                 415

<210> SEQ ID NO 451
<211> LENGTH: 1494
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"
<220> FEATURE:
<221> NAME/KEY: source
<223> OTHER INFORMATION: /note="Nuc-ADAT-Linker-dAPG08290.1-Linker-SV40"

<400> SEQUENCE: 451

```
Met Ala Lys Arg Pro Ala Ala Thr Lys Lys Ala Gly Gln Ala Lys Lys
1               5                   10                  15

Lys Lys Ser Glu Val Glu Phe Ser His Glu Tyr Trp Met Arg His Ala
            20                  25                  30

Leu Thr Leu Ala Lys Arg Ala Trp Asp Glu Arg Glu Val Pro Val Gly
        35                  40                  45

Ala Val Leu Val His Asn Asn Arg Val Ile Gly Glu Gly Trp Asn Arg
    50                  55                  60

Pro Ile Gly Arg His Asp Pro Thr Ala His Ala Glu Ile Met Ala Leu
65                  70                  75                  80

Arg Gln Gly Gly Leu Val Met Gln Asn Tyr Arg Leu Ile Asp Ala Thr
                85                  90                  95

Leu Tyr Val Thr Leu Glu Pro Cys Val Met Cys Ala Gly Ala Met Ile
            100                 105                 110

His Ser Arg Ile Gly Arg Val Val Phe Gly Ala Arg Asp Ala Lys Thr
        115                 120                 125

Gly Ala Ala Gly Ser Leu Met Asp Val Leu His His Pro Gly Met Asn
    130                 135                 140

His Arg Val Glu Ile Thr Glu Gly Ile Leu Ala Asp Glu Cys Ala Ala
145                 150                 155                 160

Leu Leu Ser Asp Phe Phe Arg Met Arg Arg Gln Glu Ile Lys Ala Gln
                165                 170                 175

Lys Lys Ala Gln Ser Ser Thr Asp Ser Gly Ser Ser Gly Gly Ser
            180                 185                 190

Ser Gly Ser Glu Thr Pro Gly Thr Ser Glu Ser Ala Thr Pro Glu Ser
        195                 200                 205

Ser Gly Gly Ser Ser Gly Gly Ser Ser Glu Val Glu Phe Ser His Glu
    210                 215                 220

Tyr Trp Met Arg His Ala Leu Thr Leu Ala Lys Arg Ala Arg Asp Glu
225                 230                 235                 240

Arg Glu Val Pro Val Gly Ala Val Leu Val Leu Asn Asn Arg Val Ile
                245                 250                 255

Gly Glu Gly Trp Asn Arg Ala Ile Gly Leu His Asp Pro Thr Ala His
            260                 265                 270

Ala Glu Ile Met Ala Leu Arg Gln Gly Gly Leu Val Met Gln Asn Tyr
        275                 280                 285

Arg Leu Ile Asp Ala Thr Leu Tyr Val Thr Phe Glu Pro Cys Val Met
    290                 295                 300

Cys Ala Gly Ala Met Ile His Ser Arg Ile Gly Arg Val Val Phe Gly
305                 310                 315                 320

Val Arg Asn Ala Lys Thr Gly Ala Ala Gly Ser Leu Met Asp Val Leu
                325                 330                 335

His Tyr Pro Gly Met Asn His Arg Val Glu Ile Thr Glu Gly Ile Leu
            340                 345                 350

Ala Asp Glu Cys Ala Ala Leu Leu Cys Tyr Phe Phe Arg Met Pro Arg
        355                 360                 365

Gln Val Phe Asn Ala Gln Lys Lys Ala Gln Ser Ser Thr Asp Ser Gly
    370                 375                 380
```

```
Gly Ser Ser Gly Gly Ser Gly Ser Glu Thr Pro Gly Thr Ser Glu
385                 390                 395                 400
Ser Ala Thr Pro Glu Ser Ser Gly Gly Ser Ser Gly Gly Ser Ser Met
            405                 410                 415
Ser Glu Leu Asp Tyr Arg Ile Gly Leu Ala Ile Gly Thr Asn Ser Ile
        420                 425                 430
Gly Trp Gly Val Ile Glu Leu Phe Trp Asn Lys Asp Arg Glu Arg Tyr
    435                 440                 445
Glu Lys Val Arg Ile Val Asp Lys Gly Val Arg Met Phe Asp Lys Ala
    450                 455                 460
Glu Ile Pro Asn Lys Gly Ala Ser Leu Ala Glu Pro Arg Arg Ile Ala
465                 470                 475                 480
Arg Ser Ser Arg Arg Arg Leu Asn Arg Lys Ser Gln Arg Lys Lys Glu
            485                 490                 495
Ile Arg Asn Leu Leu Val Gln His Gly Met Ile Thr Gln Glu Glu Leu
        500                 505                 510
Asp Leu Leu Tyr Pro Leu Ser Lys Lys Ser Ile Asp Ile Trp Asp Ile
        515                 520                 525
Arg Leu Asp Gly Leu Asp Arg Leu Leu Asn His Leu Glu Trp Ala Arg
    530                 535                 540
Leu Leu Ile His Leu Ala Gln Arg Arg Gly Phe Lys Ser Asn Arg Lys
545                 550                 555                 560
Ser Glu Leu Lys Asp Ala Glu Thr Gly Lys Val Leu Ser Ser Ile Gln
            565                 570                 575
Val Asn Glu Lys Arg Leu Phe Leu Tyr Arg Thr Val Gly Glu Met Trp
        580                 585                 590
Ile Lys Asp Ala Glu Phe Ser Lys Tyr Asp Arg Arg Asn Ser Pro
    595                 600                 605
Asn Glu Tyr Val Phe Ser Val Ser Arg Ala Asp Leu Glu Lys Glu Ile
        610                 615                 620
Val Thr Leu Phe Glu Ala Gln Arg Lys Phe Gln Ser Ser Tyr Ala Ser
625                 630                 635                 640
Lys Asn Leu Gln Glu Thr Tyr Leu Gln Ile Trp Ala His Gln Leu Pro
            645                 650                 655
Phe Ala Ser Gly Asn Ala Ile Leu Asn Lys Val Gly Tyr Cys Ser Leu
        660                 665                 670
Leu Lys Gly Lys Glu Arg Arg Ile Pro Lys Ala Thr Tyr Thr Phe Gln
    675                 680                 685
Tyr Phe Ser Ala Leu Asp Gln Val Asn Arg Thr Arg Leu Gly Pro Asp
    690                 695                 700
Phe Gln Pro Phe Thr Gln Glu Gln Lys Glu Ile Ile Leu Asp Lys Met
705                 710                 715                 720
Phe Gln Arg Thr Asp Tyr Tyr Lys Lys Thr Ile Pro Glu Val Ser
            725                 730                 735
Tyr Tyr Asp Ile Arg Lys Trp Leu Glu Leu Asp Glu Thr Ile Gln Phe
        740                 745                 750
Lys Gly Leu Asn Tyr Asp Pro Asn Glu Glu Leu Lys Lys Ile Glu Lys
    755                 760                 765
Lys Pro Phe Ile Asn Leu Lys Ala Phe Tyr Glu Ile Lys Lys Val Val
    770                 775                 780
Ala Asn Tyr Ala Glu Arg Thr Asn Glu Ala Phe Ser Thr Leu Asp Tyr
785                 790                 795                 800
```

-continued

Asp Ala Ile Ala Tyr Ala Leu Thr Val Tyr Lys Thr Asp Lys Asp Ile
                805                 810                 815

Arg Ser Tyr Leu Lys Lys Ser Asn Asn Leu Ser Lys Arg Cys Tyr Asp
            820                 825                 830

Asp Gln Leu Ile Glu Glu Leu Phe Thr Leu Ser Tyr Thr Lys Phe Gly
        835                 840                 845

His Leu Ser Phe Lys Ala Ile Asn His Val Leu Pro Ile Met Gln Glu
850                 855                 860

Gly Arg Thr Tyr Gln Glu Ala Ile His Gln Leu Gly Tyr Asp Thr Thr
865                 870                 875                 880

Asn Leu Lys Lys Glu Asn Arg Ser Met Phe Leu Pro Leu Ile Pro Asp
                885                 890                 895

Glu Ile Thr Asn Pro Ile Val Lys Arg Ala Ile Thr Gln Ala Arg Lys
            900                 905                 910

Val Val Asn Ala Ile Ile Arg Arg Tyr Gly Ser Pro Asn Ser Val His
        915                 920                 925

Ile Ala Leu Ala Arg Glu Leu Ser Lys Ser His Asp Glu Arg Lys Lys
930                 935                 940

Ile Met Thr Ala His Asp Glu Asn Tyr Lys Lys Asn Lys Gly Ala Ile
945                 950                 955                 960

Ser Ile Leu Ile Glu Asn Gly Ile Leu Asn Pro Thr Gly Tyr Asp Ile
                965                 970                 975

Val Arg Tyr Lys Leu Trp Lys Glu Gln Gly Glu Arg Cys Ala Tyr Ser
            980                 985                 990

Leu Lys Glu Ile Pro Pro Asp Thr Phe Phe Asn Glu Leu Lys Lys Glu
        995                 1000                1005

Arg Asn Gly Ser Pro Ile Leu Glu Val Asp His Ile Leu Pro Tyr
    1010                1015                1020

Ser Gln Ser Phe Ile Asp Ser Tyr His Asn Lys Val Leu Val Tyr
    1025                1030                1035

Ser Asp Glu Asn Arg Asn Lys Gly Asn Arg Ile Pro Tyr Thr Tyr
    1040                1045                1050

Phe Leu Glu Thr Asn Lys Asp Trp Glu Ala Phe Glu Arg Tyr Val
    1055                1060                1065

Arg Ser Asn Lys Leu Phe Ser Lys Lys Lys Arg Glu Tyr Leu Leu
    1070                1075                1080

Lys Lys Thr Tyr Leu Pro Arg Glu Ser Glu Leu Ile Lys Glu Arg
    1085                1090                1095

His Leu Asn Asp Thr Arg Tyr Ala Ser Thr Phe Leu Lys Asn Phe
    1100                1105                1110

Ile Glu Gln Asn Leu Gln Phe Lys Glu Val Glu Val Asn Leu Arg
    1115                1120                1125

Lys Lys Arg Val Gln Thr Val Asn Gly Val Ile Thr Ala His Leu
    1130                1135                1140

Arg Lys Arg Trp Gly Leu Glu Lys Asn Arg Gln Glu Thr Tyr Leu
    1145                1150                1155

His His Ala Met Asp Ala Ile Ile Val Ala Cys Thr Asp His His
    1160                1165                1170

Met Val Thr Arg Ile Thr Glu Tyr Tyr Gln Ile Lys Glu Ser Asn
    1175                1180                1185

Lys Ser Val Lys Lys Pro Tyr Phe Pro Met Pro Trp Glu Gly Phe
    1190                1195                1200

Arg Asp Glu Leu Leu Ser His Leu Ala Ser Gln Pro Ile Ala Lys

```
            1205                1210                1215

Lys Ile Ser Glu Glu Leu Lys Ala Gly Tyr Gln Ser Ser Asp Tyr
            1220                1225                1230

Ile Phe Val Ser Arg Met Pro Lys Arg Ser Val Thr Gly Ala Ala
            1235                1240                1245

His Asp Gln Thr Ile Arg Arg Lys Gly Gly Ile Asp Lys Lys Gly
            1250                1255                1260

Lys Thr Ile Ile Ile Lys Arg Val Arg Leu Lys Asp Ile Lys Phe
            1265                1270                1275

Asp Glu Asn Gly Asp Phe Lys Met Val Gly Lys Glu Gln Asp Leu
            1280                1285                1290

Ala Thr Tyr Glu Ala Ile Lys Gln Arg Tyr Leu Glu His Arg Lys
            1295                1300                1305

Asn Ser Lys Lys Ala Phe Glu Thr Pro Leu Tyr Lys Pro Ser Lys
            1310                1315                1320

Lys Gly Thr Gly Asn Leu Ile Lys Arg Val Lys Ile Glu Gly Gln
            1325                1330                1335

Thr Lys Ala Phe Val Arg Glu Val Asn Gly Gly Val Ala Gln Asn
            1340                1345                1350

Ser Asp Leu Val Arg Val Asp Leu Phe Glu Lys Asp Asp Lys Tyr
            1355                1360                1365

Tyr Met Val Pro Ile Tyr Val Pro Asp Thr Val Cys Ser Glu Leu
            1370                1375                1380

Pro Lys Lys Val Val Lys Ser Gly Lys Gly Tyr Glu Gln Trp Leu
            1385                1390                1395

Thr Leu Asp Asn Ser Phe Thr Phe Lys Ser Ser Leu Tyr Pro Tyr
            1400                1405                1410

Asp Leu Val Arg Leu Val Lys Gly Asn Glu Asp Arg Phe Leu Tyr
            1415                1420                1425

Phe Gly Thr Leu Asp Ile Asp Ser Asp Arg Leu Asn Phe Lys Asp
            1430                1435                1440

Val Asn Lys Pro Ser Lys Gln Asn Glu Tyr Arg Tyr Ser Leu Lys
            1445                1450                1455

Thr Ile Glu Asn Leu Glu Lys Tyr Glu Val Gly Val Leu Gly Asp
            1460                1465                1470

Leu Arg Leu Val Lys Gln Glu Thr Arg Arg Ile Phe Asn Arg Pro
            1475                1480                1485

Lys Lys Lys Arg Lys Val
            1490

<210> SEQ ID NO 452
<211> LENGTH: 1494
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Nuc-ADAT-Linker-nAPG08290.1-Linker-SV40"

<400> SEQUENCE: 452

Met Ala Lys Arg Pro Ala Ala Thr Lys Ala Gly Gln Ala Lys Lys
1               5                   10                  15

Lys Lys Ser Glu Val Glu Phe Ser His Glu Tyr Trp Met Arg His Ala
                20                  25                  30
```

-continued

```
Leu Thr Leu Ala Lys Arg Ala Trp Asp Glu Arg Glu Val Pro Val Gly
            35                  40                  45

Ala Val Leu Val His Asn Asn Arg Val Ile Gly Glu Gly Trp Asn Arg
 50                  55                  60

Pro Ile Gly Arg His Asp Pro Thr Ala His Ala Glu Ile Met Ala Leu
 65                  70                  75                  80

Arg Gln Gly Gly Leu Val Met Gln Asn Tyr Arg Leu Ile Asp Ala Thr
                85                  90                  95

Leu Tyr Val Thr Leu Glu Pro Cys Val Met Cys Ala Gly Ala Met Ile
                100                 105                 110

His Ser Arg Ile Gly Arg Val Val Phe Gly Ala Arg Asp Ala Lys Thr
            115                 120                 125

Gly Ala Ala Gly Ser Leu Met Asp Val Leu His His Pro Gly Met Asn
130                 135                 140

His Arg Val Glu Ile Thr Glu Gly Ile Leu Ala Asp Glu Cys Ala Ala
145                 150                 155                 160

Leu Leu Ser Asp Phe Phe Arg Met Arg Arg Gln Glu Ile Lys Ala Gln
                165                 170                 175

Lys Lys Ala Gln Ser Ser Thr Asp Ser Gly Gly Ser Gly Gly Ser
            180                 185                 190

Ser Gly Ser Glu Thr Pro Gly Thr Ser Glu Ser Ala Thr Pro Glu Ser
            195                 200                 205

Ser Gly Gly Ser Ser Gly Gly Ser Ser Glu Val Glu Phe Ser His Glu
            210                 215                 220

Tyr Trp Met Arg His Ala Leu Thr Leu Ala Lys Arg Ala Arg Asp Glu
225                 230                 235                 240

Arg Glu Val Pro Val Gly Ala Val Leu Val Leu Asn Asn Arg Val Ile
                245                 250                 255

Gly Glu Gly Trp Asn Arg Ala Ile Gly Leu His Asp Pro Thr Ala His
            260                 265                 270

Ala Glu Ile Met Ala Leu Arg Gln Gly Gly Leu Val Met Gln Asn Tyr
                275                 280                 285

Arg Leu Ile Asp Ala Thr Leu Tyr Val Thr Phe Glu Pro Cys Val Met
            290                 295                 300

Cys Ala Gly Ala Met Ile His Ser Arg Ile Gly Arg Val Val Phe Gly
305                 310                 315                 320

Val Arg Asn Ala Lys Thr Gly Ala Ala Gly Ser Leu Met Asp Val Leu
                325                 330                 335

His Tyr Pro Gly Met Asn His Arg Val Glu Ile Thr Glu Gly Ile Leu
            340                 345                 350

Ala Asp Glu Cys Ala Ala Leu Leu Cys Tyr Phe Phe Arg Met Pro Arg
            355                 360                 365

Gln Val Phe Asn Ala Gln Lys Lys Ala Gln Ser Ser Thr Asp Ser Gly
            370                 375                 380

Gly Ser Ser Gly Gly Ser Gly Ser Glu Thr Pro Gly Thr Ser Glu
385                 390                 395                 400

Ser Ala Thr Pro Glu Ser Ser Gly Gly Ser Ser Gly Gly Ser Ser Met
                405                 410                 415

Ser Glu Leu Asp Tyr Arg Ile Gly Leu Ala Ile Gly Thr Asn Ser Ile
                420                 425                 430

Gly Trp Gly Val Ile Glu Leu Phe Trp Asn Lys Asp Arg Glu Arg Tyr
            435                 440                 445
```

-continued

```
Glu Lys Val Arg Ile Val Asp Lys Gly Val Arg Met Phe Asp Lys Ala
    450                 455                 460
Glu Ile Pro Asn Lys Gly Ala Ser Leu Ala Glu Pro Arg Arg Ile Ala
465                 470                 475                 480
Arg Ser Ser Arg Arg Leu Asn Arg Lys Ser Gln Arg Lys Lys Glu
                485                 490                 495
Ile Arg Asn Leu Leu Val Gln His Gly Met Ile Thr Gln Glu Glu Leu
            500                 505                 510
Asp Leu Leu Tyr Pro Leu Ser Lys Ser Ile Asp Ile Trp Asp Ile
        515                 520                 525
Arg Leu Asp Gly Leu Asp Arg Leu Leu Asn His Leu Glu Trp Ala Arg
530                 535                 540
Leu Leu Ile His Leu Ala Gln Arg Arg Gly Phe Lys Ser Asn Arg Lys
545                 550                 555                 560
Ser Glu Leu Lys Asp Ala Glu Thr Gly Lys Val Leu Ser Ser Ile Gln
                565                 570                 575
Val Asn Glu Lys Arg Leu Phe Leu Tyr Arg Thr Val Gly Glu Met Trp
            580                 585                 590
Ile Lys Asp Ala Glu Phe Ser Lys Tyr Asp Arg Arg Asn Ser Pro
        595                 600                 605
Asn Glu Tyr Val Phe Ser Val Ser Arg Ala Asp Leu Glu Lys Glu Ile
    610                 615                 620
Val Thr Leu Phe Glu Ala Gln Arg Lys Phe Gln Ser Ser Tyr Ala Ser
625                 630                 635                 640
Lys Asn Leu Gln Glu Thr Tyr Leu Gln Ile Trp Ala His Gln Leu Pro
                645                 650                 655
Phe Ala Ser Gly Asn Ala Ile Leu Asn Lys Val Gly Tyr Cys Ser Leu
            660                 665                 670
Leu Lys Gly Lys Glu Arg Arg Ile Pro Lys Ala Thr Tyr Thr Phe Gln
        675                 680                 685
Tyr Phe Ser Ala Leu Asp Gln Val Asn Arg Thr Arg Leu Gly Pro Asp
    690                 695                 700
Phe Gln Pro Phe Thr Gln Glu Gln Lys Glu Ile Ile Leu Asp Lys Met
705                 710                 715                 720
Phe Gln Arg Thr Asp Tyr Tyr Lys Lys Thr Ile Pro Glu Val Ser
                725                 730                 735
Tyr Tyr Asp Ile Arg Lys Trp Leu Glu Leu Asp Glu Thr Ile Gln Phe
            740                 745                 750
Lys Gly Leu Asn Tyr Asp Pro Asn Glu Glu Leu Lys Lys Ile Glu Lys
        755                 760                 765
Lys Pro Phe Ile Asn Leu Lys Ala Phe Tyr Glu Ile Lys Lys Val Val
770                 775                 780
Ala Asn Tyr Ala Glu Arg Thr Asn Glu Ala Phe Ser Thr Leu Asp Tyr
785                 790                 795                 800
Asp Ala Ile Ala Tyr Ala Leu Thr Val Tyr Lys Thr Asp Lys Asp Ile
            805                 810                 815
Arg Ser Tyr Leu Lys Lys Ser Asn Asn Leu Ser Lys Arg Cys Tyr Asp
        820                 825                 830
Asp Gln Leu Ile Glu Glu Leu Phe Thr Leu Ser Tyr Thr Lys Phe Gly
    835                 840                 845
His Leu Ser Phe Lys Ala Ile Asn His Val Leu Pro Ile Met Gln Glu
850                 855                 860
Gly Arg Thr Tyr Gln Glu Ala Ile His Gln Leu Gly Tyr Asp Thr Thr
```

```
                865                 870                 875                 880
Asn Leu Lys Lys Glu Asn Arg Ser Met Phe Leu Pro Leu Ile Pro Asp
                    885                 890                 895
Glu Ile Thr Asn Pro Ile Val Lys Arg Ala Ile Thr Gln Ala Arg Lys
                    900                 905                 910
Val Val Asn Ala Ile Ile Arg Arg Tyr Gly Ser Pro Asn Ser Val His
                    915                 920                 925
Ile Glu Leu Ala Arg Glu Leu Ser Lys Ser His Asp Glu Arg Lys Lys
                    930                 935                 940
Ile Met Thr Ala His Asp Glu Asn Tyr Lys Lys Asn Lys Gly Ala Ile
945                 950                 955                 960
Ser Ile Leu Ile Glu Asn Gly Ile Leu Asn Pro Thr Gly Tyr Asp Ile
                    965                 970                 975
Val Arg Tyr Lys Leu Trp Lys Glu Gln Gly Gly Arg Cys Ala Tyr Ser
                    980                 985                 990
Leu Lys Glu Ile Pro Pro Asp Thr Phe Phe Asn Glu Leu Lys Lys Glu
                    995                 1000                1005
Arg Asn Gly Ser Pro Ile Leu Glu Val Asp His Ile Leu Pro Tyr
                    1010                1015                1020
Ser Gln Ser Phe Ile Asp Ser Tyr His Asn Lys Val Leu Val Tyr
                    1025                1030                1035
Ser Asp Glu Asn Arg Asn Lys Gly Asn Arg Ile Pro Tyr Thr Tyr
                    1040                1045                1050
Phe Leu Glu Thr Asn Lys Asp Trp Glu Ala Phe Glu Arg Tyr Val
                    1055                1060                1065
Arg Ser Asn Lys Leu Phe Ser Lys Lys Arg Glu Tyr Leu Leu
                    1070                1075                1080
Lys Lys Thr Tyr Leu Pro Arg Glu Ser Glu Leu Ile Lys Glu Arg
                    1085                1090                1095
His Leu Asn Asp Thr Arg Tyr Ala Ser Thr Phe Leu Lys Asn Phe
                    1100                1105                1110
Ile Glu Gln Asn Leu Gln Phe Lys Glu Val Glu Val Asn Leu Arg
                    1115                1120                1125
Lys Lys Arg Val Gln Thr Val Asn Gly Val Ile Thr Ala His Leu
                    1130                1135                1140
Arg Lys Arg Trp Gly Leu Glu Lys Asn Arg Gln Glu Thr Tyr Leu
                    1145                1150                1155
His His Ala Met Asp Ala Ile Ile Val Ala Cys Thr Asp His His
                    1160                1165                1170
Met Val Thr Arg Ile Thr Glu Tyr Tyr Gln Ile Lys Glu Ser Asn
                    1175                1180                1185
Lys Ser Val Lys Lys Pro Tyr Phe Pro Met Pro Trp Glu Gly Phe
                    1190                1195                1200
Arg Asp Glu Leu Leu Ser His Leu Ala Ser Gln Pro Ile Ala Lys
                    1205                1210                1215
Lys Ile Ser Glu Glu Leu Lys Ala Gly Tyr Gln Ser Ser Asp Tyr
                    1220                1225                1230
Ile Phe Val Ser Arg Met Pro Lys Arg Ser Val Thr Gly Ala Ala
                    1235                1240                1245
His Asp Gln Thr Ile Arg Arg Lys Gly Gly Ile Asp Lys Lys Gly
                    1250                1255                1260
Lys Thr Ile Ile Ile Lys Arg Val Arg Leu Lys Asp Ile Lys Phe
                    1265                1270                1275
```

-continued

```
Asp Glu Asn Gly Asp Phe Lys Met Val Gly Lys Glu Gln Asp Leu
    1280            1285                1290
Ala Thr Tyr Glu Ala Ile Lys Gln Arg Tyr Leu Glu His Arg Lys
    1295            1300                1305
Asn Ser Lys Lys Ala Phe Glu Thr Pro Leu Tyr Lys Pro Ser Lys
    1310            1315                1320
Lys Gly Thr Gly Asn Leu Ile Lys Arg Val Lys Ile Glu Gly Gln
    1325            1330                1335
Thr Lys Ala Phe Val Arg Glu Val Asn Gly Gly Val Ala Gln Asn
    1340            1345                1350
Ser Asp Leu Val Arg Val Asp Leu Phe Glu Lys Asp Asp Lys Tyr
    1355            1360                1365
Tyr Met Val Pro Ile Tyr Val Pro Asp Thr Val Cys Ser Glu Leu
    1370            1375                1380
Pro Lys Lys Val Val Lys Ser Gly Lys Gly Tyr Glu Gln Trp Leu
    1385            1390                1395
Thr Leu Asp Asn Ser Phe Thr Phe Lys Ser Ser Leu Tyr Pro Tyr
    1400            1405                1410
Asp Leu Val Arg Leu Val Lys Gly Asn Glu Asp Arg Phe Leu Tyr
    1415            1420                1425
Phe Gly Thr Leu Asp Ile Asp Ser Asp Arg Leu Asn Phe Lys Asp
    1430            1435                1440
Val Asn Lys Pro Ser Lys Gln Asn Glu Tyr Arg Tyr Ser Leu Lys
    1445            1450                1455
Thr Ile Glu Asn Leu Glu Lys Tyr Glu Val Gly Val Leu Gly Asp
    1460            1465                1470
Leu Arg Leu Val Lys Gln Glu Thr Arg Arg Ile Phe Asn Arg Pro
    1475            1480                1485
Lys Lys Lys Arg Lys Val
    1490

<210> SEQ ID NO 453
<211> LENGTH: 25
<212> TYPE: DNA
<213> ORGANISM: Homo sapiens
<220> FEATURE:
<221> NAME/KEY: source
<223> OTHER INFORMATION: /note="Hurler target 1"

<400> SEQUENCE: 453
ggagcagctc taggccgaag tgtcg                                        25

<210> SEQ ID NO 454
<211> LENGTH: 25
<212> TYPE: DNA
<213> ORGANISM: Homo sapiens
<220> FEATURE:
<221> NAME/KEY: source
<223> OTHER INFORMATION: /note="Hurler target 2"

<400> SEQUENCE: 454
taggccgaag tgtcgcaggc cggga                                        25

<210> SEQ ID NO 455
<211> LENGTH: 25
<212> TYPE: DNA
<213> ORGANISM: Homo sapiens
<220> FEATURE:
<221> NAME/KEY: source
```

<223> OTHER INFORMATION: /note="Hurler target 3"

<400> SEQUENCE: 455
gctctaggcc gaagtgtcgc aggcc        25

<210> SEQ ID NO 456
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA Hurler target 1"

<400> SEQUENCE: 456
ggagcagctc taggccgaag tgtcggtcat agttccatga aagccaaaag tggctttgat    60
gtttctatga taagggtttc ggcccgtggc gtcgggatc gcctgcccat tccgatgggc   120
ttctccccat ttatt                                                    135

<210> SEQ ID NO 457
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA Hurler target 2"

<400> SEQUENCE: 457
taggccgaag tgtcgcaggc cgggagtcat agttccatga aagccaaaag tggctttgat    60
gtttctatga taagggtttc ggcccgtggc gtcgggatc gcctgcccat tccgatgggc   120
ttctccccat ttatt                                                    135

<210> SEQ ID NO 458
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA Hurler target 3"

<400> SEQUENCE: 458
ggcctgcgac acttcggcct agagcgtcat agttccatga aagccaaaag tggctttgat    60
gtttctatga taagggtttc ggcccgtggc gtcgggatc gcctgcccat tccgatgggc   120
ttctccccat ttatt                                                    135

<210> SEQ ID NO 459
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:

<221> NAME/KEY: source
<223> OTHER INFORMATION: /note="Hurler Forward Amplification Primer"

<400> SEQUENCE: 459
gactccttca ccaag                                                    15

<210> SEQ ID NO 460
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Hurler Reverse Amplification Primer"

<400> SEQUENCE: 460
gtagatcagc accg                                                     14

<210> SEQ ID NO 461
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Hurler Wild Type Probe"

<400> SEQUENCE: 461
ctctgggccg aagt                                                     14

<210> SEQ ID NO 462
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Hurler W402X Probe-beta"

<400> SEQUENCE: 462
ctctaggccg aagt                                                     14

<210> SEQ ID NO 463
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Hurler NGS forward"

<400> SEQUENCE: 463
acttcctcca gcc                                                      13

<210> SEQ ID NO 464
<211> LENGTH: 13
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Hurler NGS Reverse"

<400> SEQUENCE: 464 gaacccggc tta                                                          13

<210> SEQ ID NO 465
<211> LENGTH: 31
<212> TYPE: DNA
<213> ORGANISM: Homo sapiens
<220> FEATURE:
<221> NAME/KEY: source
<223> OTHER INFORMATION: /note="Human W402X"

<400> SEQUENCE: 465
ggagcagctc taggccgaag tgtcgcaggc c                                     31

<210> SEQ ID NO 466
<211> LENGTH: 31
<212> TYPE: DNA
<213> ORGANISM: Mus musculus
<220> FEATURE:
<221> NAME/KEY: source
<223> OTHER INFORMATION: /note="Mouse W392X"

<400> SEQUENCE: 466
agaacaactc taggcagagg tctcaaaggc t                                     31

<210> SEQ ID NO 467
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="humanized mouse"

<400> SEQUENCE: 467
ggagcagctc taggccgaag tgtcgcaggc c                                     31

<210> SEQ ID NO 468
<211> LENGTH: 25
<212> TYPE: DNA
<213> ORGANISM: Homo sapiens
<220> FEATURE:
<221> NAME/KEY: source
<223> OTHER INFORMATION: /note="FRDA target 1"

<400> SEQUENCE: 468
atcacctgag gtccggagtt caaga                                            25

<210> SEQ ID NO 469
<211> LENGTH: 25
<212> TYPE: DNA
<213> ORGANISM: Homo sapiens
<220> FEATURE:
<221> NAME/KEY: source
<223> OTHER INFORMATION: /note="FRDA target 2"

<400> SEQUENCE: 469
```
gtcttgaact ccggacctca ggtga                                           25

<210> SEQ ID NO 470
<211> LENGTH: 25
<212> TYPE: DNA
<213> ORGANISM: Homo sapiens
<220> FEATURE:
<221> NAME/KEY: source
<223> OTHER INFORMATION: /note="FRDA target 3"

<400> SEQUENCE: 470
tgaactccgg acctcaggtg atcca                                           25

<210> SEQ ID NO 471
<211> LENGTH: 25
<212> TYPE: DNA
<213> ORGANISM: Homo sapiens
<220> FEATURE:
<221> NAME/KEY: source
<223> OTHER INFORMATION: /note="FRDA target 4"

<400> SEQUENCE: 471
gaaaagttag ccgggcgtgg tgtcg                                           25

<210> SEQ ID NO 472
<211> LENGTH: 500
<212> TYPE: DNA
<213> ORGANISM: Artificial Sequence
<220> FEATURE:
<223> OTHER INFORMATION: /note="Description of Artificial Sequence:
      Synthetic polynucleotide"
<220> FEATURE:
<221> NAME/KEY: source
<223> OTHER INFORMATION: /note="BCL11A enhancer region"

<400> SEQUENCE: 472
aaaaatggac aattatgagg aggggagagt gcagacaggg gaagcttcac ctcctttaca     60
attttgggag tccacacggc atggcataca aattatttca ttcccattga gaaataaaat   120
ccaattctcc atcaccaaga gagccttccg aaagaggccc ccctgggcaa acggccaccg   180
atggagaggt ctgccagtcc tcttctaccc cacccacgcc cccaccctaa tcagaggcca   240
aacccttcct ggagcctgtg ataaaagcaa ctgttagctt gcactagact agcttcaaag   300
ttgtattgac cctggtgtgt tatgtctaag agtagatgcc atatctcttt tctggcctat   360
gttattacct gtatggactt tgcactggaa tcagctatct gctcttactt atgcacacct   420
ggggcataga gccagccctg tatcgctttt cagccatctc actacagata actcccaagt   480
cctgtctagc tgccttcctt                                                500

<210> SEQ ID NO 473
<211> LENGTH: 26
<212> TYPE: DNA
<213> ORGANISM: Homo sapiens
<220> FEATURE:
<221> NAME/KEY: source
<223> OTHER INFORMATION: /note="SCD target seq 1"

<400> SEQUENCE: 473
gcactagact agcttcaaag ttgtag                                          26

<210> SEQ ID NO 474
<211> LENGTH: 26
<212> TYPE: DNA

<213> ORGANISM: Homo sapiens
<220> FEATURE:
<221> NAME/KEY: source
<223> OTHER INFORMATION: /note="SCD target seq 2"

<400> SEQUENCE: 474
cctaatcaga ggccaaaccc ttcctg                                              26

<210> SEQ ID NO 475
<211> LENGTH: 26
<212> TYPE: DNA
<213> ORGANISM: Homo sapiens
<220> FEATURE:
<221> NAME/KEY: source
<223> OTHER INFORMATION: /note="SCD target seq 3"

<400> SEQUENCE: 475
caagctaaca gttgctttta tcacag                                              26

<210> SEQ ID NO 476
<211> LENGTH: 26
<212> TYPE: DNA
<213> ORGANISM: Homo sapiens
<220> FEATURE:
<221> NAME/KEY: source
<223> OTHER INFORMATION: /note="SCD target seq 4"

<400> SEQUENCE: 476
gcactagact agcttcaaag ttgtag                                              26

<210> SEQ ID NO 477
<211> LENGTH: 26
<212> TYPE: DNA
<213> ORGANISM: Homo sapiens
<220> FEATURE:
<221> NAME/KEY: source
<223> OTHER INFORMATION: /note="SCD target seq 5"

<400> SEQUENCE: 477
cctaatcaga ggccaaaccc ttcctg                                              26

<210> SEQ ID NO 478
<211> LENGTH: 26
<212> TYPE: DNA
<213> ORGANISM: Homo sapiens
<220> FEATURE:
<221> NAME/KEY: source
<223> OTHER INFORMATION: /note="SCD target seq 6"

<400> SEQUENCE: 478
caagctaaca gttgctttta tcacag                                              26

<210> SEQ ID NO 479
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="RelA FWD"

<400> SEQUENCE: 479
cttagtttca ccgcaggttc ta                                                  22

```
<210> SEQ ID NO 480
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="RelA REV"

<400> SEQUENCE: 480
ctgtgcactc aacactgatc ta                                            22

<210> SEQ ID NO 481
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="AurkB FWD"

<400> SEQUENCE: 481
cccagcccta ggttgtttat t                                             21

<210> SEQ ID NO 482
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="AurkB REV"

<400> SEQUENCE: 482
ctggctacat cttccttgac tac                                           23

<210> SEQ ID NO 483
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="HPRT1 FWD"

<400> SEQUENCE: 483
gtggcagaag cagtgagtaa                                               20

<210> SEQ ID NO 484
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="HPRT1 REV"
```

```
<400> SEQUENCE: 484
tcccatctag gcactaggta aa                                                  22

<210> SEQ ID NO 485
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 134, Guide 135, Guide 136,
      Guide 137"

<400> SEQUENCE: 485
gtctcgtggg ctcggagatg tgtataagag acagacaatt ctcctgcctc agcc              54

<210> SEQ ID NO 486
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 134, Guide 135, Guide 136,
      Guide 137"

<400> SEQUENCE: 486
tcgtcggcag cgtcagatgt gtataagaga cagactgcca tgggaagaag gtg               53

<210> SEQ ID NO 487
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 138, Guide 139, Guide 140,
      Guide 141"

<400> SEQUENCE: 487
gtctcgtggg ctcggagatg tgtataagag acagacaatt ctcctgcctc agcc              54

<210> SEQ ID NO 488
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 138, Guide 139, Guide 140,
      Guide 141"

<400> SEQUENCE: 488
tcgtcggcag cgtcagatgt gtataagaga cagactgcca tgggaagaag gtg               53

<210> SEQ ID NO 489
```

```
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 142, Guide 143, Guide 144,
      Guide 145"

<400> SEQUENCE: 489
tcgtcggcag cgtcagatgt gtataagaga caggagctgc acatttgacg agc            53

<210> SEQ ID NO 490
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 142, Guide 143, Guide 144,
      Guide 145"

<400> SEQUENCE: 490
gtctcgtggg ctcggagatg tgtataagag acagattaca ggtgtgagcc acgg           54

<210> SEQ ID NO 491
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 164, Guide 165, Guide 166,
      Guide 167"

<400> SEQUENCE: 491
tcgtcggcag cgtcagatgt gtataagaga cagctgacct caggtgatac gcc            53

<210> SEQ ID NO 492
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 164, Guide 165, Guide 166,
      Guide 167"

<400> SEQUENCE: 492
gtctcgtggg ctcggagatg tgtataagag acagctttgg gaggctgaga cagg           54

<210> SEQ ID NO 493
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="REV_Guide 168, Guide 169, Guide 170,
      Guide 171"

<400> SEQUENCE: 493
tcgtcggcag cgtcagatgt gtataagaga cagtgctcta ttgtccaggc tgg           53

<210> SEQ ID NO 494
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 168, Guide 169, Guide 170,
      Guide 171"

<400> SEQUENCE: 494
gtctcgtggg ctcggagatg tgtataagag acagtccagc aggtcagcaa agaa          54

<210> SEQ ID NO 495
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 172, Guide 173, Guide 174,
      Guide 175"

<400> SEQUENCE: 495
tcgtcggcag cgtcagatgt gtataagaga caggcagtat aactggccag cct           53

<210> SEQ ID NO 496
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 172, Guide 173, Guide 174,
      Guide 175"

<400> SEQUENCE: 496
gtctcgtggg ctcggagatg tgtataagag acagtcagtt gaggagttca gcttaa        56

<210> SEQ ID NO 497
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 185, Guide 186, Guide 187,
      Guide 188"

<400> SEQUENCE: 497
```
tcgtcggcag cgtcagatgt gtataagaga cagtggcccc tatgtggaga tca    53

<210> SEQ ID NO 498
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 185, Guide 186, Guide 187,
      Guide 188"

<400> SEQUENCE: 498
gtctcgtggg ctcggagatg tgtataagag acagggcaga gctcagcctc atag    54

<210> SEQ ID NO 499
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 189, Guide 190, Guide 191,
      Guide 192"

<400> SEQUENCE: 499
tcgtcggcag cgtcagatgt gtataagaga cagatatccc cacttcccct gct    53

<210> SEQ ID NO 500
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 189, Guide 190, Guide 191,
      Guide 192"

<400> SEQUENCE: 500
gtctcgtggg ctcggagatg tgtataagag acagcacctc aaggacagct ctgg    54

<210> SEQ ID NO 501
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 193, Guide 194, Guide 195,
      Guide 196"

<400> SEQUENCE: 501
tcgtcggcag cgtcagatgt gtataagaga cagatatccc cacttcccct gct    53

<210> SEQ ID NO 502
<211> LENGTH: 54
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 193, Guide 194, Guide 195,
      Guide 196"

<400> SEQUENCE: 502
gtctcgtggg ctcggagatg tgtataagag acagcacctc aaggacagct ctgg         54

<210> SEQ ID NO 503
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 146"

<400> SEQUENCE: 503
gtctcgtggg ctcggagatg tgtataagag acagacaatt ctcctgcctc agcc         54

<210> SEQ ID NO 504
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 146"

<400> SEQUENCE: 504
tcgtcggcag cgtcagatgt gtataagaga cagactgcca tgggaagaag gtg          53

<210> SEQ ID NO 505
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 147"

<400> SEQUENCE: 505
gtctcgtggg ctcggagatg tgtataagag acagacaatt ctcctgcctc agcc         54

<210> SEQ ID NO 506
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 147"

<400> SEQUENCE: 506
```
tcgtcggcag cgtcagatgt gtataagaga cagactgcca tgggaagaag gtg         53

<210> SEQ ID NO 507
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 148"

<400> SEQUENCE: 507
tcgtcggcag cgtcagatgt gtataagaga cagactgcca tgggaagaag gtg         53

<210> SEQ ID NO 508
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 148"

<400> SEQUENCE: 508
gtctcgtggg ctcggagatg tgtataagag acagacaatt ctcctgcctc agcc        54

<210> SEQ ID NO 509
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 176"

<400> SEQUENCE: 509
tcgtcggcag cgtcagatgt gtataagaga caggtagctc actgcagcct caa         53

<210> SEQ ID NO 510
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 176"

<400> SEQUENCE: 510
gtctcgtggg ctcggagatg tgtataagag acagtgggtg atgaacatac gggt        54

<210> SEQ ID NO 511
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

```
<220> FEATURE:
<221> NAME/KEY: source
<223> OTHER INFORMATION: /note="REV_Guide 177"

<400> SEQUENCE: 511
tcgtcggcag cgtcagatgt gtataagaga cagtcagact gaagagctat tgtgtga      57

<210> SEQ ID NO 512
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 177"

<400> SEQUENCE: 512
gtctcgtggg ctcggagatg tgtataagag acagccccac aaaccgatgt agct         54

<210> SEQ ID NO 513
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 209"

<400> SEQUENCE: 513
tcgtcggcag cgtcagatgt gtataagaga cagtggagtg cagtggtgtg atc          53

<210> SEQ ID NO 514
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 209"

<400> SEQUENCE: 514
gtctcgtggg ctcggagatg tgtataagag acagttgagg ctgcagtgag ctac         54

<210> SEQ ID NO 515
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 197"

<400> SEQUENCE: 515
tcgtcggcag cgtcagatgt gtataagaga cagtggcccc tatgtggaga tca          53

<210> SEQ ID NO 516
<211> LENGTH: 54
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 197"

<400> SEQUENCE: 516
gtctcgtggg ctcggagatg tgtataagag acagggcaga gctcagcctc atag            54

<210> SEQ ID NO 517
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 198"

<400> SEQUENCE: 517
tcgtcggcag cgtcagatgt gtataagaga cagccaagcc gaccaaacaa gtg             53

<210> SEQ ID NO 518
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 198"

<400> SEQUENCE: 518
gtctcgtggg ctcggagatg tgtataagag acaggatgcg ctgactgata gcct            54

<210> SEQ ID NO 519
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 199"

<400> SEQUENCE: 519
tcgtcggcag cgtcagatgt gtataagaga cagtggcccc tatgtggaga tca             53

<210> SEQ ID NO 520
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 199"

<400> SEQUENCE: 520
```
gtctcgtggg ctcggagatg tgtataagag acagggcaga gctcagcctc atag    54

<210> SEQ ID NO 521
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="FWD_Guide 149"

<400> SEQUENCE: 521
gtctcgtggg ctcggagatg tgtataagag acagggtaag gggaaactgg aggc    54

<210> SEQ ID NO 522
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="REV_Guide 149"

<400> SEQUENCE: 522
tcgtcggcag cgtcagatgt gtataagaga cagtccactt tctaagcagg cgg    53

<210> SEQ ID NO 523
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="FWD_Guide 150"

<400> SEQUENCE: 523
gtctcgtggg ctcggagatg tgtataagag acaggtgggc tggatttcg atct    54

<210> SEQ ID NO 524
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="REV_Guide 150"

<400> SEQUENCE: 524
tcgtcggcag cgtcagatgt gtataagaga cagatgaaca ggcaggaagt cgg    53

<210> SEQ ID NO 525
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"
<220> FEATURE:
<221> NAME/KEY: source
<223> OTHER INFORMATION: /note="REV_Guide 151"

<400> SEQUENCE: 525
tcgtcggcag cgtcagatgt gtataagaga cagcggttct gagttgcctt cct          53

<210> SEQ ID NO 526
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 151"

<400> SEQUENCE: 526
gtctcgtggg ctcggagatg tgtataagag acagggtaag gggaaactgg aggc          54

<210> SEQ ID NO 527
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 179"

<400> SEQUENCE: 527
tcgtcggcag cgtcagatgt gtataagaga cagtcagtgg tccacatgca agt          53

<210> SEQ ID NO 528
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 179"

<400> SEQUENCE: 528
gtctcgtggg ctcggagatg tgtataagag acagaaggca agttgatcgc tcga          54

<210> SEQ ID NO 529
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 180"

<400> SEQUENCE: 529
tcgtcggcag cgtcagatgt gtataagaga cagagtggtt ctgttgcaca cgt          53

<210> SEQ ID NO 530

```
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 180"

<400> SEQUENCE: 530
gtctcgtggg ctcggagatg tgtataagag acagtcgctt aagcccagga gttc          54

<210> SEQ ID NO 531
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 181"

<400> SEQUENCE: 531
tcgtcggcag cgtcagatgt gtataagaga cagtctggct gatccgtact aatcc         55

<210> SEQ ID NO 532
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 181"

<400> SEQUENCE: 532
gtctcgtggg ctcggagatg tgtataagag acagtaggct caagggatgc tcct          54

<210> SEQ ID NO 533
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 200"

<400> SEQUENCE: 533
tcgtcggcag cgtcagatgt gtataagaga cagccagagc tgtccttgag gtg           53

<210> SEQ ID NO 534
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 200"
```

```
<400> SEQUENCE: 534
gtctcgtggg ctcggagatg tgtataagag acaggtccat acccaccttg gcaa          54

<210> SEQ ID NO 535
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 201"

<400> SEQUENCE: 535
tcgtcggcag cgtcagatgt gtataagaga cagccaagcc gaccaaacaa gtg           53

<210> SEQ ID NO 536
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 201"

<400> SEQUENCE: 536
gtctcgtggg ctcggagatg tgtataagag acaggatgcg ctgactgata gcct          54

<210> SEQ ID NO 537
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 202"

<400> SEQUENCE: 537
tcgtcggcag cgtcagatgt gtataagaga cagaggctat cagtcagcgc atc           53

<210> SEQ ID NO 538
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 202"

<400> SEQUENCE: 538
gtctcgtggg ctcggagatg tgtataagag acagagcagg ggaagtgggg atat          54

<210> SEQ ID NO 539
<211> LENGTH: 54
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 152"

<400> SEQUENCE: 539
gtctcgtggg ctcggagatg tgtataagag acagattaca ggtgtgagcc acgg         54

<210> SEQ ID NO 540
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 152"

<400> SEQUENCE: 540
tcgtcggcag cgtcagatgt gtataagaga caggagctgc acatttgacg agc          53

<210> SEQ ID NO 541
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 153"

<400> SEQUENCE: 541
gtctcgtggg ctcggagatg tgtataagag acagacaatt ctcctgcctc agcc         54

<210> SEQ ID NO 542
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 153"

<400> SEQUENCE: 542
tcgtcggcag cgtcagatgt gtataagaga cagactgcca tgggaagaag gtg          53

<210> SEQ ID NO 543
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 154"

<400> SEQUENCE: 543
gtctcgtggg ctcggagatg tgtataagag acagattaca ggtgtgagcc acgg         54
```

-continued

```
<210> SEQ ID NO 544
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 154"

<400> SEQUENCE: 544
tcgtcggcag cgtcagatgt gtataagaga caggagctgc acatttgacg agc          53

<210> SEQ ID NO 545
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 182"

<400> SEQUENCE: 545
gtctcgtggg ctcggagatg tgtataagag acagtgggtg atgaacatac gggt          54

<210> SEQ ID NO 546
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 182"

<400> SEQUENCE: 546
tcgtcggcag cgtcagatgt gtataagaga caggtagctc actgcagcct caa           53

<210> SEQ ID NO 547
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 183"

<400> SEQUENCE: 547
gtctcgtggg ctcggagatg tgtataagag acagtgcctg tagtcccagc tact          54

<210> SEQ ID NO 548
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 183"
```

<400> SEQUENCE: 548
tcgtcggcag cgtcagatgt gtataagaga cagtcagctc agtgcaacct ctg    53

<210> SEQ ID NO 549
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 184"

<400> SEQUENCE: 549
gtctcgtggg ctcggagatg tgtataagag acagctttgg gaggctgaga cagg    54

<210> SEQ ID NO 550
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 184"

<400> SEQUENCE: 550
tcgtcggcag cgtcagatgt gtataagaga cagctgacct caggtgatac gcc    53

<210> SEQ ID NO 551
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 203"

<400> SEQUENCE: 551
gtctcgtggg ctcggagatg tgtataagag acaggatgcg ctgactgata gcct    54

<210> SEQ ID NO 552
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 203"

<400> SEQUENCE: 552
tcgtcggcag cgtcagatgt gtataagaga cagccaagcc gaccaaacaa gtg    53

<210> SEQ ID NO 553
<211> LENGTH: 54
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 204"

<400> SEQUENCE: 553
gtctcgtggg ctcggagatg tgtataagag acagcacctc aaggacagct ctgg      54

<210> SEQ ID NO 554
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 204"

<400> SEQUENCE: 554
tcgtcggcag cgtcagatgt gtataagaga cagatatccc cacttcccct gct       53

<210> SEQ ID NO 555
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 205"

<400> SEQUENCE: 555
gtctcgtggg ctcggagatg tgtataagag acagggcaga gctcagcctc atag      54

<210> SEQ ID NO 556
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 205"

<400> SEQUENCE: 556
tcgtcggcag cgtcagatgt gtataagaga cagtggcccc tatgtggaga tca       53

<210> SEQ ID NO 557
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="seq in base of hairpin stem of tracrRNA"
<220> FEATURE:
<221> NAME/KEY: modified_base
<222> LOCATION: (2)..(2)
<223> OTHER INFORMATION: a, c, u, g, unknown or other
<220> FEATURE:
```

```
<221> NAME/KEY: modified_base
<222> LOCATION: (4)..(5)
<223> OTHER INFORMATION: a, c, u, g, unknown or other

<400> SEQUENCE: 557 unannu                                                                    6

<210> SEQ ID NO 558
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="seq in base of hairpin stem of tracrRNA"
<220> FEATURE:
<221> NAME/KEY: modified_base
<222> LOCATION: (2)..(2)
<223> OTHER INFORMATION: a, c, u, g, unknown or other
<220> FEATURE:
<221> NAME/KEY: modified_base
<222> LOCATION: (4)..(5)
<223> OTHER INFORMATION: a, c, u, g, unknown or other

<400> SEQUENCE: 558 unanna                                                                    6

<210> SEQ ID NO 559
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="sequence 2 for cleavage site assay"

<400> SEQUENCE: 559
ccatgatata gacgttgtgg ctgttgtagt                                         30

<210> SEQ ID NO 560
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 560

His His His His His His
1               5

<210> SEQ ID NO 561
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 10xHis tag"

<400> SEQUENCE: 561

His His His His His His His His His His
1               5                   10
```

<210> SEQ ID NO 562
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 562
cctgggtgtg aggctgggcc attaaaacct ctcc                              34

<210> SEQ ID NO 563
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
cctgaaaacc tctcc                                                   15

<210> SEQ ID NO 564
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
cctgggtgtg agctgggcca ttaaaacctc tcc                               33

<210> SEQ ID NO 565
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
cctgggccat taaaacctct cc                                           22

<210> SEQ ID NO 566
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
cctggctctc c                                                       11

<210> SEQ ID NO 567
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 567
cgggccatta aaacctctcc                                              20

<210> SEQ ID NO 568
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568
cctgggtgtg aggccagacc tgggccatta aaacctctcc                        40

<210> SEQ ID NO 569
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
cctgggtgtg aggggaagct gacgtccttt ccatggctgc tcgcctgtgt tgccaccgct   60
gggccattaa aacctctcc                                               79

<210> SEQ ID NO 570
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 570
cctgggtgtg acctgggcca ttaaaacctc tcc                               33

<210> SEQ ID NO 571
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
cctgggtgtg aggactgggc cattaaaacc tctcc                             35

<210> SEQ ID NO 572
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
agttggcaga tgctctaatg tactgccatg ggaa                              34

```
<210> SEQ ID NO 573
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 573
agttggcaga tgcaatgtac tgccatggga a                              31

<210> SEQ ID NO 574
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
agttggcaga tgcatgtact gccatgggaa                                30

<210> SEQ ID NO 575
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
agttggcaga tgctatgtac tgccatggga a                              31

<210> SEQ ID NO 576
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 576
agttggcaga tgctaatgta ctgccatggg aa                             32

<210> SEQ ID NO 577
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
agttggcaga tgctatgtaa tgccatggga a                              31

<210> SEQ ID NO 578
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 578
agttggcaga tgctctatgt actgccatgg gaa                              33

<210> SEQ ID NO 579
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 579
cgacctgaat gctgtgcggc gctctggctt cattcaatc                        39

<210> SEQ ID NO 580
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
cgacctgaat gctgtgcggc tctgcttcca ggtga                            35

<210> SEQ ID NO 581
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
cgacctgaat gctgtgcggc atctgcttcc aggtga                           36

<210> SEQ ID NO 582
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 582
cgacctgaat gctgcttcca ggtga                                       25

<210> SEQ ID NO 583
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
cgacctgaat gcttctgctt ccaggtga                                    28

<210> SEQ ID NO 584
<211> LENGTH: 22
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 584
cgacctgaat gcttccaggt ga                                               22

<210> SEQ ID NO 585
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585
gcgtggggac tacgacctga atgctgtgcg gctct                                 35

<210> SEQ ID NO 586
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
gcgacctgaa tgctgtgcgg ctct                                             24

<210> SEQ ID NO 587
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
gcgtggggac tacgagctgt gcggctct                                         28

<210> SEQ ID NO 588
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 588
gcgtggggac tgaatgctgt gcggctct                                         28

<210> SEQ ID NO 589
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
gcgtggggac tcctgaatgc tgtgcggctc t                                     31
```

```
<210> SEQ ID NO 590
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
gcgtggggac tacgaacctg aatgctgtgc ggctct                                 36

<210> SEQ ID NO 591
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
gcgtggggac tacgaatgct gtgcggctct                                        30

<210> SEQ ID NO 592
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
gcgtggggac tacctgaatg ctgtgcggct ct                                     32

<210> SEQ ID NO 593
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
gcgtgaatgc tgtgcggctc t                                                 21

<210> SEQ ID NO 594
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
gcgacctgac tgctgtgcgg ctct                                              24

<210> SEQ ID NO 595
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 595
gcgtggggac tacgcctgaa tgctgtgcgg ctct    34

<210> SEQ ID NO 596
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596
atggaggagt tggcagatgc tctaatgtac tgccatggga ag    42

<210> SEQ ID NO 597
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
atggaggagt tggcagatgc taatgtactg ccatgggaag    40

<210> SEQ ID NO 598
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
atggaggagt tggcagatgt actgccatgg gaag    34

<210> SEQ ID NO 599
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599
atgtactgcc atgggaag    18

<210> SEQ ID NO 600
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
atggaggagt tggtgtactg ccatgggaag    30

<210> SEQ ID NO 601
<211> LENGTH: 43
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 601
atggaggagt tggcagatgc tctaaatgta ctgccatggg aag                43

<210> SEQ ID NO 602
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
atggaggagt tggcagatgc tcttctaatg tactgccatg ggaag              45

<210> SEQ ID NO 603
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
atggaggagt tggcagatgc cctctaatgt actgccatgg gaag               44

<210> SEQ ID NO 604
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604
atggaggagt tggcagataa tgtactgcca tgggaagaag                    40

<210> SEQ ID NO 605
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
atggcgtact gccatgggaa gaag                                     24

<210> SEQ ID NO 606
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 606
atggaggagt tggcagatgc ttctaatgta ctgccatggg aagaag             46
```

<210> SEQ ID NO 607
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 607
atggaggagt tggcatctgc catgggaaga ag                                      32

<210> SEQ ID NO 608
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 608
atggaggagt tggcagatgc aatgtactgc catgggaaga ag                            42

<210> SEQ ID NO 609
<211> LENGTH: 124
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 609
atggaggagt tggcagatgc caaactgaaa aacaaatcaa agcactctta ttgagtgctg         60
gcgatccccg acgccacggg ccgaaaccct tatcatagaa actctaatgt actgccatgg       120
gaag                                                                    124

<210> SEQ ID NO 610
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 610
atggaggagt tggcagatgc tgcttatata gacctcccac cgtacacgcc taccgcccat         60
tttctaatgt actgccatgg gaag                                                84

<210> SEQ ID NO 611
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 611
atggaggagt tgtctaatgt actgccatgg gaag                                    34

<210> SEQ ID NO 612

```
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 612
ctgccatggg aagaag                                                      16

<210> SEQ ID NO 613
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
atggaggagt tggcagatgc gcggctgttc ctgtacagaa ccgtgggcga gatgtggatc      60
aaggatgctc taatgtactg ccatgggaag                                       90

<210> SEQ ID NO 614
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
atggaggagt tggcagatgc ctaatgtact gccatgggaa g                          41

<210> SEQ ID NO 615
<211> LENGTH: 97
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
atggaggagt tggcagatgc tgtcatgatc tttttccgct cgtcgtggga cttgctcagt      60
tctctggcca gctcgtctaa tgtactgcca tgggaag                               97

<210> SEQ ID NO 616
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
atggaggagt tggcagatgc tctatgtact gccatgggaa g                          41

<210> SEQ ID NO 617
<211> LENGTH: 32
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 617
cagggacagt gcgcatctcc ctggtcacca ag                              32

<210> SEQ ID NO 618
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 618
cagggacagt caccaag                                               17

<210> SEQ ID NO 619
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
cagggacagt gcgcatctcc tggtcaccaa g                               31

<210> SEQ ID NO 620
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620
cagggacagt gcgcatctct ggtcaccaag                                 30

<210> SEQ ID NO 621
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 621
cagggacagt gcgcatctcc tctggtcacc aag                             33

<210> SEQ ID NO 622
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 622
cagggacagt gcgcatcctg gtcaccaag                                  29

<210> SEQ ID NO 623
```

```
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 623
cagggacggt caccaag                                                    17

<210> SEQ ID NO 624
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 624
cggggacagg gcgcatctcc tggtcaccaa g                                    31

<210> SEQ ID NO 625
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
cgacctgaat gctgtgcggc tctgcttcca gg                                   32

<210> SEQ ID NO 626
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
cgacctgaat gctgtgcggc atctgcttcc agg                                  33

<210> SEQ ID NO 627
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
cgacctgaat gctgtgcggc ttctgcttcc agg                                  33

<210> SEQ ID NO 628
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 628
```

```
cgacctgaat gctgtgtctg cttccagg                                              28

<210> SEQ ID NO 629
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
cgacctgcat gctgtgcggc atctgcttcc agg                                        33

<210> SEQ ID NO 630
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 630
cgacctgcat gctgtgcggc ttctgcttcc agg                                        33

<210> SEQ ID NO 631
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
cgacctgcat gctgtgtctg cttccagg                                              28

<210> SEQ ID NO 632
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
cgacctgaat gctgtgcgac atctgcttcc agg                                        33

<210> SEQ ID NO 633
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
tggggactac gacctgaatg ctgtgcggct ct                                         32

<210> SEQ ID NO 634
<211> LENGTH: 27
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 634
tggggactac gaatgctgtg cggctct                                          27

<210> SEQ ID NO 635
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 635
tggggactac gagcaggcag aagtatgcaa agcatgcatc tcaattcctg aatgctgtgc      60
ggctct                                                                66

<210> SEQ ID NO 636
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 636
tggggactac gaagaaggcg atagaaggcc atgcgctgcg aatcgggagc ggcctgaatg      60
ctgtgcggct ct                                                         72

<210> SEQ ID NO 637
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 637
tggggactac gatgactcgc tgcgctcggt cgttcggctg cggcgagcgg tatcagctca      60
ctcaaaggcg gtaatacggc ctgaatgctg tgcggctct                             99

<210> SEQ ID NO 638
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
tggggtgcgg ctct                                                        14

<210> SEQ ID NO 639
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 639
tggggactac gactgctgtg cggctct                                          27

<210> SEQ ID NO 640
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640
cgacctgaat gctgtgcggc gctctggctt cattcaatc                             39

<210> SEQ ID NO 641
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 641
cgacctgaat gctgtgcggc tctgcttcca ggtga                                 35

<210> SEQ ID NO 642
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 642
cgacctgaat gctgtgcggc atctgcttcc aggtga                                36

<210> SEQ ID NO 643
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643
cgacctgaat gctgcttcca ggtga                                            25

<210> SEQ ID NO 644
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 644
cgacctgaat gcttctgctt ccaggtga                                         28

<210> SEQ ID NO 645
<211> LENGTH: 22
<212> TYPE: DNA
```

<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 645
cgacctgaat gcttccaggt ga        22

<210> SEQ ID NO 646
<211> LENGTH: 4
<212> TYPE: PRT
<213> ORGANISM: Homo sapiens

<400> SEQUENCE: 646

Glu Glu Gln Leu
1

<210> SEQ ID NO 647
<211> LENGTH: 6
<212> TYPE: PRT
<213> ORGANISM: Homo sapiens

<400> SEQUENCE: 647

Ala Glu Val Ser Gln Ala
1               5

<210> SEQ ID NO 648
<211> LENGTH: 4
<212> TYPE: PRT
<213> ORGANISM: Mus musculus

<400> SEQUENCE: 648

Gly Glu Gln Leu
1

<210> SEQ ID NO 649
<211> LENGTH: 6
<212> TYPE: PRT
<213> ORGANISM: Mus musculus

<400> SEQUENCE: 649

Ala Glu Val Ser Lys Ala
1               5

<210> SEQ ID NO 650
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 650

Gly Glu Gln Leu
1

<210> SEQ ID NO 651
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

```
<400> SEQUENCE: 651

Ala Glu Val Ser Gln Ala
1               5
```